United States Patent
Jennewein et al.

(10) Patent No.: US 11,046,985 B2
(45) Date of Patent: Jun. 29, 2021

(54) PRODUCTION OF HUMAN MILK OLIGOSACCHARIDES IN MICROBIAL HOSTS WITH ENGINEERED IMPORT/EXPORT

(71) Applicant: Jennewein Biotechnologie GmbH, Rheinbreitbach (DE)

(72) Inventors: Stefan Jennewein, Bad Honnef (DE); Dirk Wartenberg, Bonn (DE)

(73) Assignee: Jennewein Biotechnologie GmbH

( * ) Notice: Subject to any disclaimer, the term of this patent is extended or adjusted under 35 U.S.C. 154(b) by 85 days.

(21) Appl. No.: 15/758,653

(22) PCT Filed: Sep. 12, 2016

(86) PCT No.: PCT/EP2016/071420
§ 371 (c)(1),
(2) Date: Mar. 8, 2018

(87) PCT Pub. No.: WO2017/042382
PCT Pub. Date: Mar. 16, 2017

(65) Prior Publication Data
US 2018/0305724 A1 Oct. 25, 2018

(30) Foreign Application Priority Data
Sep. 12, 2015 (EP) .................. 15184968

(51) Int. Cl.
C12P 19/18 (2006.01)
C07H 3/06 (2006.01)
C12N 15/70 (2006.01)
C12N 9/10 (2006.01)

(52) U.S. Cl.
CPC ............ C12P 19/18 (2013.01); C12N 9/1051 (2013.01); C12N 15/70 (2013.01); *C12Y 204/01146* (2013.01)

(58) Field of Classification Search
CPC .......... C12P 19/18; C12P 19/26; C12P 19/00; C12N 9/00; C12N 9/10; C12N 9/38; C07H 3/06; C07H 13/04; C07H 15/70; C07H 9/14
See application file for complete search history.

(56) References Cited

U.S. PATENT DOCUMENTS

| | | | |
|---|---|---|---|
| 8,652,808 B2 | 2/2014 | Jennewein et al. | |
| 9,512,433 B2 | 12/2016 | Jennewein et al. | |
| 2011/0236934 A1* | 9/2011 | Samain | C12N 9/1048 435/97 |
| 2012/0135467 A1 | 5/2012 | Jennewein et al. | |
| 2014/0120611 A1 | 5/2014 | Jennewein et al. | |

FOREIGN PATENT DOCUMENTS

| | | |
|---|---|---|
| EP | 2722394 A1 | 4/2014 |
| JP | 2003504072 A | 2/2003 |
| JP | 2007525186 A | 9/2007 |
| JP | 2012529274 A | 11/2012 |
| WO | 2010142305 A1 | 6/2010 |
| WO | 2014122328 A1 | 8/2014 |
| WO | 2015032413 A1 | 3/2015 |
| WO | 2015117812 A1 | 8/2015 |
| WO | 2015150328 A1 | 10/2015 |

OTHER PUBLICATIONS

PCT International Search Report for PCT/EP2016/071420, dated Oct. 28, 2016.
Weichert, et al., "Bioengineered 2'-fucosyllactose and 3-fucosyllactose inhibit the adhesion of Pseudomonas aeruginosa and enteric pathogens to human intestinal and respiratory cell lines," Nutrition Research, (2013), vol. 33: 831-838.
Jennewein: "Abschlussbericht zum Forderprojekt Entwicklung eines innovativen Produktionsverfahrens fur Fucosyllctosen Mit dem," Jennewein Biotechnologie GmbH, Project Report, 2012, pp. 1-31.
Koita, Khushnuma, "Optimizing Pentose Sugar Utilization in *Escherichia coli* for the Production of Biofuels," University of Illinois at Urbana-Champaign Dissertation, 2012.
Koita, et al., "Identification and Analysis of the Putative Pentose Sugar Efflux Transporters in *Escherichia coli*," PLOS ONE, (2012), vol. 7, No. 8: pp. 1-10.
Baumgärtner, et al., "Construction of *Escherichia coli* strains with chromosomally integrated expression cassettes for the synthesis of 2'-fucosyllactose," Microbial Cell Factories, (2013), vol. 12: 1-13.
Petschacher, et al., "Biotechnological production of fucosylated human milk oligosaccharides: Prokaryotic fucosyltransferases and their use in biocatalytic cascades or whole cell conversion systems," Journal of Biotechnology, (2016), vol. 235: 61-83.
Baumgärtner et al, "Synthesis of fucosylated lacto-N-tetraose using whole-cell biotransformation," Bioorganic & Medicinal Chemistry, (2015), vol. 23: 6799-6806.
Saumonneau et al: "Design of an alpha-L-transfucosidase for the synthesis of fucosylated HMOs," Glycobiology, (2016), vol. 26, No. 3: 261-269.
Priem, Bernard, et al.. "A new fermentation process allows large-scale production of human milk oligosaccharides by metabolically engineered bacteria," Glycobiology, (2002), vol. 12, No. 4: 235-240.

(Continued)

*Primary Examiner* — Maryam Monshipouri
(74) *Attorney, Agent, or Firm* — McBee Moore & Vanik IP, LLC

(57) ABSTRACT

The present invention relates to methods for the production of oligosaccharides in genetically modified bacterial host cells, as well as to the genetically modified host cells used in the methods. The genetically modified host cell comprises at least one recombinant glycosyltransferase, and at least one nucleic acid sequence coding for a protein enabling the export of the oligosaccharide.

12 Claims, 6 Drawing Sheets

Specification includes a Sequence Listing.

(56) References Cited

OTHER PUBLICATIONS

Florian Baumgartner, "Synthesis of the Human Milk Oligosaccharide Lacto-N-Tetraose in Metabolically Engineered, Plasmid-Free *E. coli*," ChemBioChem Communications, (201), vol. 15, 1896-1900.

* cited by examiner

SEQUENCE LISTING

<160> NUMBER OF SEQ ID NOS: 102

<210> SEQ ID NO 1
<211> LENGTH: 2851
<212> TYPE: DNA
<213> ORGANISM: Artificial Sequence
<220> FEATURE:
<223> OTHER INFORMATION: construct Ptet-lacY-FRT-add1-FRT

<400> SEQUENCE: 1

```
tggccagatg attaattcct aattttttgtt gacactctat cattgataga gttatttttac      60
cactccctat cagtgataga gaaaagtgaa atgaatagtt cgacaaaaat ctagaaataa     120
ttttgtttaa ctttaagaag gagatataca aatgtactat ttaaaaaaca caaacttttg     180
gatgttcggt ttattctttt tcttttactt ttttatcatg ggagcctact tcccgttttt     240
cccgatttgg ctacatgaca tcaaccatat cagcaaaagt gatacgggta ttattttttgc     300
cgctatttct ctgttctcgc tattattcca accgctgttt ggtctgcttt ctgacaaact     360
cgggctgcgc aaatacctgc tgtggattat taccggcatg ttagtgatgt ttgcgccgtt     420
ctttattttt atcttcgggc cactgttaca atacaacatt ttagtaggat cgattgttgg     480
tggtatttat ctaggctttt gttttaacgc cggtgcgcca gcagtagagg catttattga     540
gaaagtcagc cgtcgcagta atttcgaatt tggtcgcgcg cggatgtttg gctgtgttgg     600
ctgggcgctg tgtgcctcga ttgtcggcat catgttcacc atcaataatc agtttgtttt     660
ctggctgggc tctggctgtg cactcatcct cgccgtttta ctcttttttcg ccaaaacgga     720
tgcgccctct tctgccacgg ttgccaatgc ggtaggtgcc aaccattcgg catttagcct     780
taagctggca ctggaactgt tcagacagcc aaaactgtgg tttttgtcac tgtatgttat     840
tggcgtttcc tgcacctacg atgttttttga ccaacagttt gctaatttct ttacttcgtt     900
ctttgctacc ggtgaacagg gtacgcgggt atttggctac gtaacgacaa tgggcgaatt     960
acttaacgcc tcgattatgt tctttgcgcc actgatcatt aatcgcatcg gtgggaaaaa    1020
cgccctgctg ctggctggca ctattatgtc tgtacgtatt attggctcat cgttcgccac    1080
ctcagcgctg gaagtggtta ttctgaaaac gctgcatatg tttgaagtac cgttcctgct    1140
ggtgggctgc tttaaatata ttaccagcca gtttgaagtg cgttttttcag cgacgattta    1200
```

```
tctggtctgt ttctgcttct ttaagcaact ggcgatgatt tttatgtctg tactggcggg    1260
caatatgtat gaaagcatcg gtttccaggg cgcttatctg gtgctgggtc tggtggcgct    1320
gggcttcacc ttaatttccg tgttcacgct tagcggcccc ggcccgcttt ccctgctgcg    1380
tcgtcaggtg aatgaagtcg ctgggagcta agcggccgcg tcgacacgca aaaaggccat    1440
ccgtcaggat ggccttctgc ttaatttgat gcctggcagt ttatggcggg cgtcctgccc    1500
gccaccctcc gggccgttgc ttcgcaacgt tcaaatccgc tcccggcgga tttgtcctac    1560
tcaggagagc gttcaccgac aaacaacaga taaaacgaaa ggcccagtct ttcgactgag    1620
cctttcgttt tatttgatgc ctggcagttc cctactctcg catggggaga ccccacacta    1680
ccatcatgta tgaatatcct ccttagttcc tattccgaag ttcctattct ctagaaagta    1740
taggaacttc ggcgcgtcct acctgtgaca cgcgtgccgc agtctcacgc ccggagcgta    1800
gcgaccgagt gagctagcta tttgtttatt tttctaaata cattcaaata tgtatccgct    1860
catgagacaa taaccctgat aaatgcttca ataatattga aaaaggaaga gtatgaggga    1920
agcggtgatc gccgaagtat cgactcaact atcagaggta gttggcgtca tcgagcgcca    1980
tctcgaaccg acgttgctgg ccgtacattt gtacggctcc gcagtggatg gcggcctgaa    2040
gccacacagt gatattgatt tgctggttac ggtgaccgta aggcttgatg aaacaacgcg    2100
gcgagctttg atcaacgacc ttttggaaac ttcggcttcc cctggagaga gcgagattct    2160
ccgcgctgta gaagtcacca ttgttgtgca cgacgacatc attccgtggc gttatccagc    2220
taagcgcgaa ctgcaatttg gagaatggca gcgcaatgac attcttgcag gtatcttcga    2280
gccagccacg atcgacattg atctggctat cttgctgaca aaagcaagag aacatagcgt    2340
tgccttggta ggtccagcgg cggaggaact ctttgatccg gttcctgaac aggatctatt    2400
tgaggcgcta aatgaaacct aacgctatg gaactcgccg cccgactggg ctggcgatga    2460
gcgaaatgta gtgcttacgt tgtcccgcat ttggtacagc gcagtaaccg gcaaaatcgc    2520
gccgaaggat gtcgctgccg actgggcaat ggagcgcctg ccggcccagt atcagcccgt    2580
catacttgaa gctagacagg cttatcttgg acaagaagaa gatcgcttgg cctcgcgcgc    2640
agatcagttg gaagaatttg tccactacgt gaaaggcgag atcaccaagg tagtcggcaa    2700
ataatgtcta acaattcgtt caagccgagg ggccgcaaga tccggccacg atgacccggt    2760
cgtcgggtac cggcagggcg gggcgtaagg cgcgccattt aaatgaagtt cctattccga    2820
agttcctatt ctctagaaag tataggaact t                                   2851
```

<210> SEQ ID NO 2
<211> LENGTH: 4568
<212> TYPE: DNA
<213> ORGANISM: Artificial Sequence
<220> FEATURE:
<223> OTHER INFORMATION: construct Ptet-lgtA-PT5-galT-FRT-kanR-FRT

<400> SEQUENCE: 2

```
acaggttggc tgataagtcc ccggtctagc ttgcatgcag attgcagcat tacacgtctt      60
gagcgattgt gtaggctgga gctgcttcga agttcctata ctttctagag aataggaact    120
tcggaatagg aacttcattt aaatggcgcg ccttacgccc cgccctgccg gtaccgagag    180
cgcttttgaa gctggggtgg gcgaagaact ccagcatgag atccccgcgc tggaggatca    240
tccagccggc gtcccggaaa acgattccga agcccaacct ttcatagaag gcggcggtgg    300
aatcgaaatc tcgtgatggc aggttgggcg tcgcttggtc ggtcatttcg aaccccagag    360
```

```
tcccgctcag aagaactcgt caagaaggcg atagaaggcg atgcgctgcg aatcgggagc    420
ggcgataccg taaagcacga ggaagcggtc agcccattcg ccgccaagct cttcagcaat    480
atcacgggta gccaacgcta tgtcctgata gcggtccgcc acacccagcc ggccacagtc    540
gatgaatcca gaaaagcggc catttccac catgatattc ggcaagcagg catcgccatg     600
ggtcacgacg agatcctcgc cgtcgggcat gcgcgccttg agcctggcga acagttcggc    660
tggcgcgagc ccctgatgct cttcgtccag atcatcctga tcgacaagac cggcttccat    720
ccgagtacgt gctcgctcga tgcgatgttt cgcttggtgg tcgaatgggc aggtagccgg    780
atcaagcgta tgcagccgcc gcattgcatc agccatgatg atactttct cggcaggagc     840 aaggtgagat gacaggagat cctgccccgg cacttcgccc aatagcagcc agtcccttcc    900
cgcttcagtg acaacgtcga gcacagctgc gcaaggaacg cccgtcgtgg ccagccacga    960
tagccgcgct gcctcgtcct gcagttcatt cagggcaccg gacaggtcgg tcttgacaaa   1020
aagaaccggg cgcccctgcg ctgacagccg gaacacggcg gcatcagagc agccgattgt   1080
ctgttgtgcc cagtcatagc cgaatagcct ctccacccaa gcggccggag aacctgcgtg   1140
caatccatct tgttcaatca tgcgaaacga tcctcatcct gtctcttgat cagatcttga   1200 tccccctgcgc catcagatcc ttggcggcaa gaaagccatc cagtttactt tgcagggctt   1260 cccaaccta ccagagggcg ccccagctgg caattccggt tcgcttgctg tccataaaac    1320
cgcccagtct agctatcgcc atgtaagccc actgcaagct acctgctttc tctttgcgct   1380
tgcgttttcc cttgtccaga tagcccagta gctgacattc atccggggtc agcaccgttt   1440
ctgcggactg gctttctacg tgttccgctt cctttagcag cccttgcgcc ctgagtgctt   1500
gcggcagcgt gagggatct tgacgcgtgt cacaggtagg acgcgccgaa gttcctatac    1560
tttctagaga ataggaactt cggaatagga actaaggagg atattcatac atgatggtag   1620
tgttcgaaat taatacgact cactataggg gaattgattc tggtaccaaa tgagtcgacc   1680
ggccagatga ttaattccta atttttgttg acactctatc attgatagag ttattttacc   1740
actccctatc agtgatagag aaaagtgaaa tgaatagttc gacaaaaatc tagaataat    1800 tttgtttaac tttaagaagg agatatacaa atgccgtccg aagcattccg tcgtcaccgt   1860
gcttatcgcg aaaacaaact gcagccactg gtctctgtcc tgatctgcgc atacaacgtt   1920
gagaaatact tcgcacagtc tctggcagct gtagttaacc agacctggcg taacctggat   1980
atcctgatcg tagatgacgg ctctacggat ggtacgctgg cgatcgcaca gcgtttccag   2040
gaacaggacg tcgtatccg cattctcgct cagccgcgta actctggtct gatcccgtct    2100
ctgaacatcg gtctggacga actggccaaa tctggtggtg gtggcgaata catcgcccgt   2160
actgacgccg acgacattgc ggccccggat tggatcgaaa aaatcgtagg tgaaatggag   2220
aaagaccgct ctatcatcgc gatgggtgct tggctggaag ttctgtccga agagaaagac   2280
ggtaaccgtc tggcccgtca ccatgaacac ggcaaaatct ggaaaaaacc gacccgtcac   2340
gaagatatcg cggacttctt cccgttcggt aacccgatcc ataacaacac catgatcatg   2400
cgtcgtagcg taatcgacgg tggtctgcgt tacaacaccg aacgtgattg ggcagaagac   2460
taccagtttt ggtatgacgt gtctaaactg ggtcgtctgg cttactaccc agaagcgctg   2520
gttaaatacc gtctgcacgc caaccaggtt agctccaaat actccatccg tcagcacgaa   2580
atcgcacagg gtatccagaa aacggctcgt aacgacttcc tgcagtccat gggtttcaaa   2640
acccgtttcg actctctgga gtaccgtcag atcaaagcgg ttgcgtatga gctgctggag   2700
aaacacctgc cggaagagga ctttgaacgt gcgcgtcgtt tcctgtacca gtgcttcaaa   2760
```

```
cgtaccgaca ctctgccggc gggtgcatgg ctcgactttg cagcggatgg tcgtatgcgt    2820
cgtctgttta ccctgcgtca gtacttcggt atcctgcatc gtctcctgaa aaaccgctaa    2880
tgatttcgtc gacacacagg aaacatatta aaaattaaaa cctgcaggag tttaaacgcg    2940
gccgcgatat cgttgtaaaa cgacggccag tgcaagaatc ataaaaaatt tatttgcttt    3000
caggaaaatt tttctgtata atagattcat aaatttgaga gaggagtttt tgtgagcgga    3060
taacaattcc ccatcttagt atattagtta agtataaata caaggagata taccatga      3120 cgcaatttaa tcccgttgat catccacatc gccgctacaa cccgctcacc gggcaatgga    3180
ttctggtttc accgcaccgc gctaagcgcc cctggcaggg ggcgcaggaa acgccagcca    3240
aacaggtgtt acctgcgcac gatccagatt gcttcctctg cgcaggtaat gtgcgggtga    3300
caggcgataa aaaccccgat tacaccggga cttacgtttt cactaatgac tttgcggctt    3360
tgatgtctga cacgccagat gcgccagaaa gtcacgatcc gctgatgcgt tgccagagcg    3420
cgcgcggcac cagccgggtg atctgctttt caccggatca cagtaaaacg ctgccagagc    3480
tcagcgttgc agcattgacg gaaatcgtca aaacctggca ggagcaaacc gcagaactgg    3540
ggaaaacgta cccatgggtg caggttttg aaaacaaagg cgcggcgatg ggctgctcta    3600
acccgcatcc gcacggtcag atttgggcaa atagcttcct gcctaacgaa gctgagcgcg    3660
aagaccgcct gcaaaagaa tattttgccg aacagaaatc accatgctg gtggattatg     3720 ttcagcgcga gctggcagac ggtagccgta ccgttgtcga aaccgaacac tggttagccg    3780 tcgtgccctta ctgggctgcc tggccgttcg aaacgctact gctgcccaaa gcccacgttt    3840
tacggatcac cgatttgacc gacgcccagc gcagcgatct ggcgctggcg ttgaaaaagc    3900
tgaccagtcg ttatgacaac ctcttccagt gctccttccc ctactctatg ggctggcacg    3960
gcgcgccatt taatggcgaa gagaatcaac actggcagct gcacgcgcac ttttatccgc    4020
ctctgctgcg ctccgccacc gtacgtaaat ttatggttgg ttatgaaatg ctggcagaga    4080
cccagcgaga cctgaccgca gaacaggcag cagagcgttt gcgcgcagtc agcgatatcc    4140
attttcgcga atccggagtg taacgcggag gcgcgccatt taaatcaacc tcagcggtca    4200
tagctgtttc ctgtgactga gcaataacta gcataacccc ttggggcctc taaacgggtc    4260 ttgagggggtt tttgctgaaa ccaatttgc ctggcggcag tagcgcggtg gtcccacctg    4320
accccatgcc gaactcagaa gtgaaacgcc gtagcgccga tggtagtgtg gggtctcccc    4380
atgcgagagt agggaactgc caggcatcaa ataaaacgaa aggctcagtc gaaagactgg    4440
gcctttcggg atccaggccg gcctgttaac gaattaatct tccgcggcaa caaaaattag    4500
gaattaatca tctggccaat ttcaggtggc acttttcggg cagaccgggg acttatcagc    4560
caacctgt                                                            4568
```

<210> SEQ ID NO 3
<211> LENGTH: 6521
<212> TYPE: DNA
<213> ORGANISM: Artificial Sequence
<220> FEATURE:
<223> OTHER INFORMATION: construct Ptet-glmUM-PT5-glmS-FRT-dhfr-FRT

<400> SEQUENCE: 3

```
acaggttggc tgataagtcc ccggtctagc ttgcatgcag attgcagcat tacacgtctt      60
gagcgattgt gtaggctgga gctgcttcga aattaatacg actcactata ggggaattga    120
ttctggtacc aaatgagtcg accggccaga tgattaattc ctaattttg ttgacactct     180
```

```
atcattgata gagttatttt accactccct atcagtgata gagaaaagtg aaatgaatag    240
ttcgacaaaa atctagaaat aattttgttt aactttaaga aggagatata caaatgctga    300
acaacgcgat gtctgttgtt atcctggcgg cgggtaaagg tacccgtatg tactctgacc    360
tgccgaaagt tctgcacacc ctggcgggta aagcgatggt tcagcacgtt atcgacgcgg    420
cgaacgaact gggtgcggcg cacgttcacc tggtttacgg tcacggtggt gacctgctga    480
aacaggcgct gaaagacgac aacctgaact gggttctgca ggcggaacag ctgggtaccg    540
gtcacgcgat gcagcaggcg cgccgttct tcgcggacga cgaagacatc ctgatgctgt    600
acggtgacgt tccgctgatc tctgttgaaa ccctgcagcg tctgcgtgac gcgaaaccgc    660
agggtggtat cggtctgctg accgttaaac tggacgaccc gaccggttac ggtcgtatca    720
cccgtgaaaa cggtaaagta accggtatcg ttgaacacaa agacgcgacc gacgaacagc    780
gtcagatcca ggagatcaac accggtatcc tgatcgcgaa cggtgcagac atgaaacgtt    840
ggctggcgaa actgaccaac aacaacgcgc agggtgaata ctacatcacc gacatcatcg    900
cgctggcgta ccaggaaggt cgtgaaatcg ttgcggttca cccgcagcgt ctgtctgaag    960
ttgaaggtgt taacaaccgt ctgcagctgt ctcgtctgga acgtgtttac cagtctgaac    1020
aggcggaaaa actgctgctg gcgggtgtta tgctgcgtga cccggcgcgt ttcgacctgc    1080
gtggtaccct gacccacggt cgtgacgttg aaatcgacac caacgttatc atcgaaggta    1140
acgttaccct gggtcaccgt gtaaaaatcg gcaccggttg cgttatcaaa aactctgtta    1200
tcggtgacga ctgcgaaatc tctccgtaca ccgttgttga agacgcgaac ctggcggcgg    1260
cgtgcaccat cggtccgttc gcgcgtctgc gtccgggtgc ggaactgctg gaaggtgcgc    1320
acgttggtaa cttcgttgaa atgaaaaaag cgcgtctggg taaaggttct aaagcgggtc    1380
acctgaccta cctgggtgac gcggaaatcg gtgacaacgt taacatcggt gcgggtacca    1440
tcacctgcaa ctacgacggt gcgaacaaat caaaaccat catcggtgac gacgttttcg    1500
ttggttctga cacccagctg gttgcgccgg ttaccgttgg taaaggtgcg accatcgcgg    1560
cgggtaccac cgttacccgt aacgttggtg aaaacgcgct ggcgatctct cgtgttccgc    1620
agacccagaa agaaggttgg cgtcgtccgg ttaaaaaaaa ataacgaagg agatagaacc    1680
atgtccaacc gtaaatactt cggtacggac ggtatccgtg gtcgtgtagg tgatgctccg    1740
attacgccgg atttcgtcct gaaactcggt tgggcagcgg gtaaagttct cgcacgtcac    1800
ggctctcgta aaatcatcat cggtaaagac accgtatct ctggttacat gctcgaatct    1860
gcactggaag cgggtctggc tgcagctggt ctgtctgcac tgttcacggg tccgatgcca    1920
accccagctg tagcgtacct gactcgcact ttccgtgcag aagcaggtat cgtgatctct    1980
gcctctcaca acccgttcta cgacaacggt atcaaattct tcagcatcga tggtaccaaa    2040
ctcccagacg cggttgaaga ggctatcgaa gcggaaatgg agaaagaaat ctcttgtgta    2100
gactctgccg aactcggtaa agcgtctcgt atcgttgatg cagcgggtcg ttacatcgag    2160
ttctgcaaag ccaccttcc gaacgaactg agcctgtctg agctgaaaat cgtcgtagac    2220
tgtgccaacg gtgcgactta ccacattgcc ccaaacgtac tgcgtgagct gggtgctaac    2280
gtcatcgcga tcggttgtga accgaacggt gtcaacatca cgcggaagt aggtgcgacc    2340 gatgttcgtg cactgcaggc tcgtgtactc gcggagaaag cggatctcgg tatcgccttt    2400
gacggtgatg gtgaccgtgt tatcatggtt gaccacgaag gtaacaaagt ggatggtgac    2460
cagatcatgt acatcattgc ccgtgaaggt ctgcgtcagg gtcagctgcg tggtggtgca    2520
gtaggtaccc tcatgagcaa catgggtctg gaactggccc tgaaacagct gggtatccca    2580
```

```
ttcgctcgtg ctaaagtagg cgaccgttac gttctggaga aaatgcagga gaaaggttgg    2640
cgtatcggtg ccgaaaactc tggtcacgtc atcctgctgg acaaaaccac taccggtgac    2700
ggtatcgtag caggtctgca ggtactcgcc gctatggccc gtaaccacat gtccctccat    2760
gacctctgct ctggtatgaa aatgttcccg cagatcctgg ttaacgttcg ttacaccgca    2820
ggttctggtg atccgctgga acacgagtct gtgaaagccg ttaccgcaga agtggaagcg    2880
gccctgggta accgtggtcg tgtactgctg cgtaaatccg gtactgagcc actgatccgt    2940
gttatggttg agggcgaaga tgaagcccag gtcaccgaat tgcgcaccg tattgccgac    3000 gcagtcaaag cggtttaatt tcgtcgacac acaggaaaca tattaaaaat taaaacctgc    3060
aggagtttaa acgcggccgc gatatcgttg taaaacgacg gccagtgcaa gaatcataaa    3120
aaatttattt gctttcagga aaattttct gtataataga ttcataaatt tgagagagga    3180 gttttgtga gcggataaca attccccatc ttagtatatt agttaagtat aaatacacaa    3240
ggagatatac atatgtgcgg tatcgttggt gctatcgcac agcgtgatgt agcggagatc    3300
ctcctggaag gtctgcgtcg tctcgaatac cgtggttacg actctgccgg tctggcagta    3360
gtggatgcag aaggtcacat gactcgtctg cgtcgtctgg gtaaagtgca gatgctcgcg    3420
caggcggcgg aagaacaccc actccacggt ggtacgggta tcgcacacac tcgttgggca    3480
acccacggtg aaccgtctga ggtcaacgca caccgcatg ttagcgagca catcgtagtc    3540
gttcacaacg gtatcatcga gaaccacgaa ccactccgtg aggaactcaa agcccgtggt    3600
tacaccttcg taagcgaaac cgacacgaa gttatcgccc acctcgttaa ctgggaactc    3660
aaacagggtg gtactctgcg tgaagcagtt ctgcgtgcca ttccacagct gcgtggtgca    3720
tacggtaccg tgatcatgga ctctcgtcat ccggataccc tgctcgccgc acgttctggt    3780
tctccactcg ttatcggtct gggtatgggt gagaacttca tcgcctctga tcagctggcc    3840
ctgctcccag ttacccgtcg cttcatcttc ctggaagagg gtgacatcgc cgaaatcacc    3900
cgtcgttccg ttaacatctt cgacaaaacg ggtgcggaag ttaaacgtca ggacatcgag    3960
tctaacctgc agtatgacgc tggtgacaaa ggcatctacc gtcactacat gcagaaagag    4020
atctacgaac agccgaacgc gatcaaaaac accctgaccg tcgtatctc tcacggtcag    4080 gttgacctgt ctgagctggg tccaaacgcg gacgaactcc tgtccaaagt cgagcacatc    4140
cagatcctgg cttgtggtac ctcttacaac tccggtatgg tttctcgtta ctggttcgaa    4200
tctctggcag gtatcccatg cgacgttgaa atcgcctccg aattccgtta tcgtaaatct    4260
gcggtacgtc gtaactccct catgatcacc ctgtctcagt ctggtgaaac cgctgatact    4320
ctggcaggtc tgcgtctcag caaagaactg ggttacctgg ttctctggc catctgcaac    4380 gttccgggtt ctagcctggt tcgtgagtct gacctggctc tgatgaccaa cgcgggtacg    4440
gagatcggtg ttgcctctac caaagcgttc actacccagc tcactgtcct gctgatgctg    4500
gttgccaaac tgtctcgtct caaaggcctc gacgctagca tcgaacacga catcgtacac    4560
ggtctgcagg ccctcccatc tcgtatcgag cagatgctgt ctcaggacaa acgtatcgaa    4620
gcactggcag aagacttcag cgacaaacac cacgcgctgt ttctgggtcg tggtgaccag    4680
tacccaattg cgctggaagg tgccctgaaa ctgaaagaga tcagctacat ccatgcagag    4740
gcatacgcag cgggtgagct gaaacatggt ccactggccc tgatcgacgc agatatgccg    4800
gttattgtgg ttgctccgaa caacgaactg ctggagaaac tgaaatccaa catcgaggaa    4860
gtacgtgcgc gtggtggtca gctgtacgtg tttgctgacc aggacgcggg tttcgtttcc    4920
```

-continued

| | |
|---|---|
| agcgacaaca tgcacatcat cgaaatgccg catgttgaag aggtaatcgc gccaatcttc | 4980 |
| tacaccgtac cgctgcagct gctggcgtac catgtagccc tgatcaaagg tacggacgtt | 5040 |
| gaccagccgc gtaacctggc gaaatccgtg accgtggaat aacgcggagg cgcgccattt | 5100 |
| aaatcaacct cagcggtcat agctgttccc tgtgactgag caataactag cataaccccct | 5160 |
| tggggcctct aaacgggtct tgaggggttt tttgctgaaa ccaatttgcc tggcggcagt | 5220 |
| agcgcggtgg tcccacctga ccccatgccg aactcagaag tgaaacgccg tagcgccgat | 5280 |
| ggtagtgtgg ggtctcccca tgcgagagta gggaactgcc aggcatcaaa taaaacgaaa | 5340 |
| ggctcagtcg aaagactggg cctttcggga tccaggccgg cctgttaacg aattaatctt | 5400 |
| ccgcggcggt atcgataagc ttgatatcga attccgaagt tcctattctc tagaaagtat | 5460 |
| aggaacttca ggtctgaaga ggagtttacg tccagccaag ctagcttggc tgcaggtcgt | 5520 |
| cgaaattcta ccgggtaggg gaggcgcttt tcccaaggca gtctggagca tgcgctttag | 5580 |
| cagccccgct gggcacttgg cgctacacaa gtggcctctg gcctcgcaca cattccacat | 5640 |
| ccaccggtag gcgccaaccg gctccgttct ttggtggccc cttcgcgcca ccttctactc | 5700 |
| ctcccctagt caggaagttc ccccccgccc cgcagctcgc gtcgtgcagg acgtgacaaa | 5760 |
| tggaagtagc acgtctcact agtctcgtgc agatggacag caccgctgag caatggaagc | 5820 |
| gggtaggcct tggggcagc ggccaatagc agctttgctc cttcgctttc tgggctcaga | 5880 |
| ggctgggaag gggtgggtcc ggggcgggc tcaggggcgg gctcagggc ggggcgggcg | 5940 |
| cccgaaggtc ctccggaggc ccggcattct gcacgcttca aaagcgcacg tctgccgcgc | 6000 |
| tgttctcctc ttcctcatct ccgggccttt cgacctgcag cctgttgaca attaatcatc | 6060 |
| ggcatagtat atcggcatag tataatacga caaggtgagg aactaaacca tgggtcaaag | 6120 |
| tagcgatgaa gccaacgctc ccgttgcagg cagtttgcg cttcccctga gtgccacctt | 6180 |
| tggcttaggg gatcgcgtac gcaagaaatc tggtgccgct tggcagggtc aagtcgtcgg | 6240 |
| ttggtattgc acaaaactca ctcctgaagg ctatgcggtc gagtccgaat cccacccagg | 6300 |
| ctcagtgcaa atttatcctg tggctgcact tgaacgtgtg gcctaatgag gggatcaatt | 6360 |
| ctctagagct cgctgatcag aagttcctat tctctagaaa gtataggaac ttcgatggcg | 6420 |
| cctcatccct gaagccaata caacaaaaat taggaattaa tcatctggcc aatttcaggt | 6480 |
| ggcacttttc gggcagaccg gggacttatc agccaacctg t | 6521 |

<210> SEQ ID NO 4
<211> LENGTH: 2937
<212> TYPE: DNA
<213> ORGANISM: Artificial Sequence
<220> FEATURE:
<223> OTHER INFORMATION: construct <Ptet-lacY(6HIS)-FRT-aadA-FRT>

<400> SEQUENCE: 4

| | |
|---|---|
| ggccagatga ttaattccta atttttgttg acactctatc attgatagag ttattttacc | 60 |
| actccctatc agtgatagag aaaagtgaaa tgaatagttc gacaaaaatc tagaaataat | 120 |
| tttgtttaac tttaagaagg agatatacaa atgggctact atttaaaaaa cacaaacttt | 180 |
| tgatgttcg gttattctt tttcttttac ttttttatca tgggagccta cttcccgttt | 240 |
| ttcccgattt ggctacatga catcaaccat atcagcaaaa gtgatacggg tattattttt | 300 |
| gccgctattt ctctgttctc gctattattc caaccgctgt ttggtctgct ttctgacaaa | 360 |
| ctcgggctgc gcaaatacct gctgtggatt attaccggca tgttagtgat gtttgcgccg | 420 |
| ttctttattt ttatcttcgg gccactgtta caatacaaca ttttagtagg atcgattgtt | 480 |

```
ggtggtattt atctaggctt ttgttttaac gccggtgcgc cagcagtaga ggcatttatt    540
gagaaagtca gccgtcgcag taatttcgaa tttggtcgcg cgcggatgtt tggctgtgtt    600
ggctgggcgc tgtgtgcctc gattgtcggc atcatgttca ccatcaataa tcagtttgtt    660
ttctggctgg gctctggctg tgcactcatc ctcgccgttt tactcttttt cgccaaaacg    720
gatgcgccct cttctcatca ccatcaccat cacgccacgg ttgccaatgc ggtaggtgcc    780
aaccattcgg catttagcct taagctggca ctggaactgt tcagacagcc aaaactgtgg    840
tttttgtcac tgtatgttat tggcgtttcc tgcacctacg atgttttga ccaacagttt     900 gctaatttct ttacttcgtt ctttgctacc ggtgaacagg gtacgcgggt atttggctac    960
gtaacgacaa tgggcgaatt acttaacgcc tcgattatgt tctttgcgcc actgatcatt   1020
aatcgcatcg gtgggaaaaa cgccctgctg ctggctggca ctattatgtc tgtacgtatt   1080
attggctcat cgttcgccac ctcagcgctg gaagtggtta ttctgaaaac gctgcatatg   1140
tttgaagtac cgttcctgct ggtgggctgc tttaaatata ttaccagcca gtttgaagtg   1200 cgttttcag cgacgattta tctggtctgt ttctgcttct ttaagcaact ggcgatgatt    1260
tttatgtctg tactgcgggg caatatgtat gaaagcatcg gtttccaggg cgcttatctg   1320
gtgctgggtc tggtggcgct gggcttcacc ttaatttccg tgttcacgct tagcggcccc   1380
ggcccgcttt ccctgctgcg tcgtcaggtg aatgaagtcg cttaagcggc cgcgtcgaca   1440
cgcaaaaagg ccatccgtca ggatggcctt ctgcttaatt tgatgcctgg cagtttatgg   1500
cgggcgtcct gcccgccacc ctccgggccg ttgcttcgca acgttcaaat ccgctcccgg   1560
cggatttgtc ctactcagga gagcgttcac cgacaaacaa cagataaaac gaaaggccca   1620
gtctttcgac tgagcctttc gttttatttg atgcctggca gttccctact ctcgcatggg   1680 gagacccac actaccatca tgtatgaata tcctccttag ttcctattcc gaagttccta    1740
ttctctagaa agtataggaa cttcggcgcg tcctacctgt gacacgcgtg ccgcagtctc   1800
acgcccggag cgtagcgacc gagtgagcta gctatttgtt tattttttcta aatacattca   1860 aatatgtatc cgctcatgag acaataaccc tgataaatgc ttcaataata ttgaaaaagg   1920
aagagtatga gggaagcggt gatcgccgaa gtatcgactc aactatcaga ggtagttggc   1980
gtcatcgagc gccatctcga accgacgttg ctggccgtac atttgtacgg ctccgcagtg   2040
gatggcggcc tgaagccaca cagtgatatt gatttgctgg ttacggtgac cgtaaggctt   2100
gatgaaacaa cgcggcgagc tttgatcaac gaccttttgg aaacttcggc ttcccctgga   2160
gagagcgaga ttctccgcgc tgtagaagtc accattgttg tgcacgacga catcattccg   2220
tggcgttatc cagctaagcg cgaactgcaa tttggagaat ggcagcgcaa tgacattctt   2280
gcaggtatct tcgagccagc cacgatcgac attgatctgg ctatcttgct gacaaaagca   2340
agagaacata gcgttgcctt ggtaggtcca gcggcggagg aactctttga tccggttcct   2400
gaacaggatc tatttgaggc gctaaatgaa accttaacgc tatggaactc gccgcccgac   2460
tgggctggcg atgagcgaaa tgtagtgctt acgttgtccc gcatttggta cagcgcagta   2520
accggcaaaa tcgcgccgaa ggatgtcgct gccgactggg caatggagcg cctgccggcc   2580
cagtatcagc ccgtcatact tgaagctaga caggcttatc ttggacaaga agaagatcgc   2640
ttggcctcgc gcgcagatca gttggaagaa tttgtccact acgtgaaagg cgagatcacc   2700
aaggtagtcg gcaaataatg tctaacaatt cgttcaagcc gaggggccgc aagatccggc   2760
cacgatgacc cggtcgtcgg gtaccggcag ggcggggcgt aaggcgcgcc atttaaatga   2820
```

-continued

| agttcctatt | ccgaagttcc | tattctctag | aaagtatagg | aacttcgaag | cagctccagc | 2880 |
| ctacacaatc | gctcaagacg | tgtaatgctg | caatctgcat | gcaagcttgg | cactggc | 2937 |

```
<210> SEQ ID NO 5
<211> LENGTH: 3856
<212> TYPE: DNA
<213> ORGANISM: Artificial Sequence
<220> FEATURE:
<223> OTHER INFORMATION: construct <Ptet-wbdO-PT5-galE-FRT-cat-FRT>

<400> SEQUENCE: 5
```

| acaggttggc | tgataagtcc | ccggtctgcc | cgaaaagtgc | cacctgaaat | tggccagatg | 60 |
| attaattcct | aattttgtt | gattctggta | ccaaatgagt | cgaccggcca | gatgattaat | 120 |
| tcctaattt | tgttgacact | ctatcattga | tagagttatt | ttaccactcc | ctatcagtga | 180 |
| tagagaaaag | tgaaatgaat | agttcgacaa | aaatctagaa | ataattttgt | ttaactttaa | 240 |
| gaaggagata | tacaaatgct | gacggaagtg | cgcccggtct | ctacgacgaa | accgctggtg | 300 |
| tctgtgattc | tgccggtgaa | caaattcaac | ccgtatctgg | atcgtgcaat | tcattcaatc | 360 |
| ctgagtcagt | cctatccgtc | gattgaactg | attatcattg | caaacaattg | caccaatgac | 420 |
| tttttcgatg | ctctgaaaaa | acgtgaatgt | gaaaccatta | agtgctgcg | cacgaacatc | 480 |
| gcgtatctgc | cgtactgcct | gaataaaggc | ctggatctgt | gtaacggtga | ctttgttgcc | 540 |
| cgcatggatt | cagatgacat | ttcgcacccg | gaacgtatcg | atcgccaggt | cgacttcctg | 600 |
| attaacaatc | cggacatcga | tgtggttggc | accaatgcag | tctatattga | tgaagatgac | 660 |
| atcgaactgg | aaaaaagcaa | cctgccggtg | aacaataacg | ctattcgtaa | aatgctgccg | 720 |
| tataaatgct | gtctggtgca | tccgtctgtt | atgtttcgca | aaaatgtcgt | gatcaccagc | 780 |
| ggcggttaca | tgttcgcgaa | ttattctgaa | gattacgaac | tgtggaaccg | tctggccgtt | 840 |
| gaaggccgca | attttatta | cctgagcgaa | tacctgctgt | attaccgtct | gcacaataac | 900 |
| caatcaacgt | cgaaaaataa | cctgtttatg | gtgatggcga | acgatgtcgc | cattaaagtg | 960 |
| aaatatttcc | tgctgaccaa | gaaaattagc | tacctgctgg | gtatcattcg | cacggtcttt | 1020 |
| tctgtgttct | attgcaaata | catcaaatga | tttcgtcgac | acacaggaaa | catattaaaa | 1080 |
| attaaaacct | gcaggagttt | aaacgcggcc | gcgatatcgt | tgtaaaacga | cggccagtgc | 1140 |
| aagaatcata | aaaatttat | ttgctttcag | gaaaattttt | ctgtataata | gattcataaa | 1200 |
| tttgagagag | gagttttgt | gagcggataa | caattcccca | tcttagtata | ttagttaagt | 1260 |
| ataaatacac | cgcggaggcg | tcgaaggaga | tacaaccatg | agagttctgg | ttaccggtgg | 1320 |
| tagcggttac | attggaagtc | atacctgtgt | gcaattactg | caaaacggtc | atgatgtcat | 1380 |
| cattcttgat | aacctctgta | acagtaagcg | cagcgtactg | cctgttatcg | agcgtttagg | 1440 |
| cggcaaacat | ccaacgtttg | ttgaaggcga | tattcgtaac | gaagcgttga | tgaccgagat | 1500 |
| cctgcacgat | cacgctatcg | acaccgtgat | ccacttcgcc | gggctgaaag | ccgtgggcga | 1560 |
| atcggtacaa | aaaccgctgg | aatattacga | caacaatgtc | aacggcactc | tgcgcctgat | 1620 |
| tagcgccatg | cgcgccgcta | acgtcaaaaa | ctttatttt | agctcctccg | ccaccgttta | 1680 |
| tggcgatcag | cccaaaattc | catacgttga | aagcttcccg | accggcacac | cgcaaagccc | 1740 |
| ttacggcaaa | agcaagctga | tggtggaaca | gatcctcacc | gatctgcaaa | aagcccagcc | 1800 |
| ggactggagc | attgccctgc | tgcgctactt | caacccggtt | ggcgcgcatc | cgtcgggcga | 1860 |
| tatgggcgaa | gatccgcaag | gcattccgaa | taacctgatg | ccatacatcg | cccaggttgc | 1920 |
| tgtaggccgt | cgcgactcgc | tggcgatttt | tggtaacgat | tatccgaccg | aagatggtac | 1980 |

```
tggcgtacgc gattacatcc acgtaatgga tctggcggac ggtcacgtcg tggcgatgga    2040
aaaactggcg aacaagccag gcgtacacat ctacaacctc ggcgctggcg taggcaacag    2100
cgtgctggac gtggttaatg ccttcagcaa agcctgcggc aaaccggtta attatcattt    2160
tgcaccgcgt cgcgagggcg accttccggc ctactgggcg gacgccagca aagccgaccg    2220
tgaactgaac tggcgcgtaa cgcgcacact cgatgaaatg gcgcaggaca cctggcactg    2280
gcagtcacgc catccacagg gatatcccga ttaacgccat ttaaatcaac ctcagcggtc    2340
atagctgttt cctgtgactg agcaataact agcataaccc cttggggcct ctaaacgggt    2400
cttgaggggt ttttgctga aaccaatttg cctggcggca gtagcgcggt ggtcccacct    2460
gaccccatgc cgaactcaga agtgaaacgc cgtagcgccg atggtagtgt ggggtctccc    2520
catgcgagag tagggaactg ccaggcatca aataaaacga aggctcagt cgaaagactg    2580 ggcctttcgg gatccaggcc ggcctgttaa cgaattaatc ttccgcggcg gtatcgataa    2640
gcttgatatc gaggctgaca tgggaattag ccatggtcca tatgaatatc ctccttagtt    2700
cctattccga agttcctatt ctctagaaag tataggaact tcggcgcgcc tacctgtgac    2760
ggaagatcac ttcgcagaat aaataaatcc tggtgtccct gttgataccg ggaagccctg    2820
ggccaacttt tggcgaaaat gagacgttga tcggcacgta agaggttcca actttcacca    2880
taatgaaata agatcactac cgggcgtatt ttttgagttg tcgagatttt caggagctaa    2940
ggaagctaaa atggagaaaa aaatcactgg ataccacc gttgatatat cccaatggca    3000
tcgtaaagaa cattttgagg catttcagtc agttgctcaa tgtacctata accagaccgt    3060
tcagctggat attacggcct ttttaaagac cgtaaagaaa aataagcaca gtttatcc    3120 ggccttatt cacattcttg cccgcctgat gaatgctcat ccggaattac gtatggcaat    3180
gaaagacggt gagctggtga tatgggatag tgttcaccct tgttacaccg ttttccatga    3240
gcaaactgaa acgttttcat cgctctggag tgaataccac gacgatttcc ggcagtttct    3300
acacatatat tcgcaagatg tggcgtgtta cggtgaaaac ctggcctatt tccctaaagg    3360
gtttattgag aatatgtttt tcgtctcagc caatccctgg gtgagtttca ccagttttga    3420
tttaaacgtg gccaatatgg acaacttctt cgccccgtt ttcaccatgg gcaaatatta    3480
tacgcaaggc gacaaggtgc tgatgccgct ggcgattcag gttcatcatg ccgtttgtga    3540
tggcttccat gtcggcagat gcttaatgaa tacaacagta ctgcgatgag tggcagggcg    3600
gggcgtaagg cgcgccattt aaatgaagtt cctattccga agttcctatt ctctagaaag    3660
tataggaact tcgaagcagc tccagcctac acaatcgctc aagacgtgta atgctgcaat    3720
ctgcatgcaa gcttggcact ggcgatggcg cctcatccct gaagccaata agcagctcca    3780
gcctacacaa tcgctcaaga cgtgtaatgc tgcaatctgc atgcaagcta gaccggggac    3840
ttatcagcca acctgt                                                   3856

<210> SEQ ID NO 6
<211> LENGTH: 4259
<212> TYPE: DNA
<213> ORGANISM: Artificial Sequence
<220> FEATURE:
<223> OTHER INFORMATION: construct galMKTE

<400> SEQUENCE: 6
ttactcagca ataaactgat attccgtcag gctggaatac tcttcgccag gacgcaggaa      60
gcagtccggt tgcggccatt cagggtggtt cgggctgtcc ggtagaaact cgcttttccag    120
```

```
agccagccct tgccagtcgg cgtaaggttc ggttccccgc gacggtgtgc cgccgaggaa      180
gttgccggag tagaattgca gagccggagc ggtggtgtag accttcagct gcaattttc       240 atctgctgac cagacatgcg ccgccacttt cttgccatcg cctttggcct gtaacaagaa      300
tgcgtgatcg taacctttca ctttgcgctg atcgtcgtcg gcaagaaact cactggcgat      360
gattttggcg ctgcggaaat caaaagacgt tccggcgaca gatttcaggc cgtcgtgcgg      420
aatgccgcct tcatcaaccg gcagatattc gtccgccaga atctgcaact tgtgattgcg      480
cacgtcagac tgctcgccgt caagattgaa atagacgtga ttagtcatat tcaccgggca     540
aggtttatca actgtggcgc gataagtaat ggagatacgg ttatcgtcgg tcagacgata     600
ttgcaccgtc gcgccgagat tacccgggaa gccctgatca ccatcatctg aactcagggc     660
aaacagcacc tgacgatcgt tctggttcac aatctgccag cgacgtttgt cgaacccttc     720
cggcccgccg tgcagctggt taacgccctg acttggcgaa agcgtcacgg tttcaccgtc     780
aaaggtataa cggctattgg cgataccggt ggcataacga ccaatagagg ccccagaaa      840 cgcggcctga tcctgatagc attccgggct ggcacagccg agcagcgcct cgcggacgct     900
gccatcggaa agcggaatac gggcggaaag taaagtcgca ccccagtcca tcagcgtgac     960
taccatccct gcgttgttac gcaaagttaa cagtcggtac ggctgaccat cgggtgccag   1020
tgcgggagtt tcgttcagca ctgtcctgct ccttgtgatg gtttacaaac gtaaaaagtc   1080
tctttaatac ctgtttttgc ttcatattgt tcagcgacac cttgctgtac ggcaggcacc   1140
agctcttccg ggatcagcgc gacgatacag ccgccaaatc cgccgccggt catgcgtacg   1200
ccacctttgt cgccaatcac agctttgacg atttctacca gagtgtcaat ttgcggcacg   1260
gtgatttcga aatcatcgcg catagaggca tgagactccg ccatcaactc gcccatacgt   1320
ttcaggtcgc cttgctccag cgcgctggca gcttcaacgg tgcgggcgtt ttcagtcagt   1380
atatgacgca cgcgttttgc cacgatcggg tccagttcat gcgcaacagc gttgaactct   1440
tcaatggtga catcacgcag ggctggctgc tggaagaaac gcgcaccggt ttcgcactgt   1500
tcacgacggg tgttgtattc gctgccaacc agggtacgtt tgaagttact gttgatgatg   1560
acgacagcca cacctttggg catggaaact gctttggtcc ccagtgagcg caatcgatc    1620 agcaaggcat gatctttctt gccgagcgcg gaaattagct gatccatgat cccgcagtta   1680
cagcctacaa actggttttc tgcttcctga ccgttaagcg cgatttgtgc gccgtccagc   1740
ggcagatgat aaagctgctg caatacggtt ccgaccgcga cttccagtga agcggaagaa   1800
cttaacccgg caccctgcgg cacattgccg ctgatcacca tgtccacgcc gccgaagctg   1860
ttgttacgca gttgcagatg tttcaccacg ccacgaacgt agttagccca ttgatagttt   1920
tcatgtgcga caatgggcgc atcgagggaa aactcgtcga gctgattttc ataatcggct   1980
gccatcacgc gaactttacg gtcatcgcgt ggtgcacaac tgatcacggt ttgataatca   2040
atcgcgcagg gcagaacgaa accgtcgttg tagtcggtgt gttcaccaat caaattcacg   2100
cggccaggcg cctgaatggt gtgagtggca gggtagccaa atgcgttggc aaacagagat   2160
tgtgtttttt ctttcagact catttcttac actccggatt cgcgaaaatg gatatcgctg   2220
actgcgcgca aacgctctgc tgcctgttct gcggtcaggt ctcgctgggt ctctgccagc   2280
atttcataac caaccataaa tttacgtacg gtggcggagc gcagcagagg cggataaaag   2340
tgcgcgtgca gctgccagtg ttgattctct tcgccattaa atggcgcgcc gtgccagccc   2400
atagagtagg ggaaggagca ctggaagagg ttgtcataac gactggtcag cttttttcaac   2460 gccagcgcca gatcgctgcg ctgggcgtcg gtcaaatcgg tgatccgtaa aacgtgggct   2520
```

```
ttgggcagca gtagcgtttc gaacggccag gcagcccagt aaggcacgac ggctaaccag    2580
tgttcggttt cgacaacggt acggctaccg tctgccagct cgcgctgaac ataatccacc    2640
agcattggtg atttctgttc ggcaaaatat tcttttttgca ggcggtcttc gcgctcagct   2700
tcgttaggca ggaagctatt tgcccaaatc tgaccgtgcg gatgcgggtt agagcagccc    2760
atcgccgcgc ctttgttttc aaaaacctgc acccatgggt acgttttccc cagttctgcg    2820
gtttgctcct gccaggtttt gacgatttcc gtcaatgctg caacgctgag ctctggcagc    2880
gttttactgt gatccggtga aaagcagatc acccggctgg tgccgcgcgc gctctggcaa    2940
cgcatcagcg gatcgtgact ttctggcgca tctggcgtgt cagacatcaa agccgcaaag    3000
tcattagtga aaacgtaagt cccggtgtaa tcggggtttt tatcgcctgt cacccgcaca    3060
ttacctgcgc agaggaagca atctggatcg tgcgcaggta acacctgttt ggctggcgtt    3120
tcctgcgccc cctgccaggg gcgcttagcg cggtgcggtg aaaccagaat ccattgcccg    3180
gtgagcgggt tgtagcggcg atgtggatga tcaacgggat taaattgcgt catggtcgtt    3240
ccttaatcgg gatatccctg tggatggcgt gactgccagt gccaggtgtc ctgcgccatt    3300
tcatcgagtg tgcgcgttac gcgccagttc agttcacggt cggctttgct ggcgtccgcc    3360
cagtaggccg gaaggtcgcc ctcgcgacgc ggtgcaaaat gataattaac cggtttgccg    3420
caggctttgc tgaaggcatt aaccacgtcc agcacgctgt tgcctacgcc agcgccgagg    3480
ttgtagatgt gtacgcctgg cttgttcgcc agttttttcca tcgccacgac gtgaccgtcc    3540
gccagatcca ttacgtggat gtaatcgcgt acgccagtac catcttcggt cggataatcg    3600
ttaccaaaaa tcgccagcga gtcgcgacgg cctacagcaa cctgggcgat gtatggcatc    3660
aggttattcg gaatgccttg cggatcttcg cccatatcgc ccgacggatg cgcgccaacc    3720
gggttgaagt agcgcagcag gcaatgctcc agtccggct gggcttttg cagatcggtg      3780 aggatctgtt ccaccatcag cttgcttttg ccgtaagggc tttgcggtgt gccggtcggg    3840
aagctttcaa cgtatggaat tttgggctga tcgccataaa cggtggcgga ggagctaaaa    3900
ataaagtttt tgacgttagc ggcgcgcatg gcgctaatca ggcgcagagt gccgttgaca    3960
ttgttgtcgt aatattccag cggttttttgt accgattcgc ccacggcttt cagcccggcg    4020
aagtggatca cggtgtcgat agcgtgatcg tgcaggatct cggtcatcaa cgcttcgtta    4080
cgaatatcgc cttcaacaaa cgttggatgt ttgccgccta aacgctcgat aacaggcagt    4140
acgctgcgct tactgttaca gaggttatca agaatgatga catcatgacc gttttgcagt    4200
aattgcacac aggtatgact tccaatgtaa ccgctaccac cggtaaccag aactctcat     4259
```

<210> SEQ ID NO 7
<211> LENGTH: 6431
<212> TYPE: DNA
<213> ORGANISM: Artificial Sequence
<220> FEATURE:
<223> OTHER INFORMATION: construct pET-lgtA

<400> SEQUENCE: 7

```
ggggaattgt gagcggataa caattcccct ctagaaataa ttttgtttaa ctttaagaag      60
gagatatacc atgggcagca gccatcacca tcatcaccac agccaggatc cgaattcgag     120
ctcggcgcgc ctgcaggtcg acaagcttgc ggccgcataa tgcttaagtc gaacagaaag    180
taatcgtatt gtacacggcc gcataatcga aattaatacg actcactata ggggaattgt    240
gagcggataa caattcccca tcttagtata ttagttaagt ataagaagga gatatacata    300
```

```
tgccgtccga agcattccgt cgtcaccgtg cttatcgcga aaacaaactg cagccactgg      360
tctctgtcct gatctgcgca tacaacgttg agaaatactt cgcacagtct ctggcagctg      420
tagttaacca gacctggcgt aacctggata tcctgatcgt agatgacggc tctacggatg      480
gtacgctggc gatcgcacag cgtttccagg aacaggacgg tcgtatccgc attctcgctc      540
agccgcgtaa ctctggtctg atcccgtctc tgaacatcgg tctggacgaa ctggccaaat      600
ctggtggtgg tggcgaatac atcgcccgta ctgacgccga cgacattgcg gccccggatt      660
ggatcgaaaa aatcgtaggt gaaatggaga agaccgctc tatcatcgcg atgggtgctt      720
ggctggaagt tctgtccgaa gagaaagacg gtaaccgtct ggcccgtcac catgaacacg      780
gcaaaatctg gaaaaaaccg acccgtcacg aagatatcgc ggacttcttc ccgttcggta      840
acccgatcca taacaacacc atgatcatgc gtcgtagcgt aatcgacggt ggtctgcgtt      900
acaacaccga acgtgattgg gcagaagact accagttttg gtatgacgtg tctaaactgg      960
gtcgtctggc ttactaccca gaagcgctgg ttaaataccg tctgcacgcc aaccaggtta     1020
gctccaaata ctccatccgt cagcacgaaa tcgcacaggg tatccagaaa acggctcgta     1080
acgacttcct gcagtccatg ggtttcaaaa cccgtttcga ctctctggag taccgtcaga     1140
tcaaagcggt tgcgtatgag ctgctggaga acacctgcc ggaagaggac tttgaacgtg     1200
cgcgtcgttt cctgtaccag tgcttcaaac gtaccgacac tctgccggcg ggtgcatggc     1260
tcgactttgc agcggatggt cgtatgcgtc gtctgtttac cctgcgtcag tacttcggta     1320
tcctgcatcg tctcctgaaa aaccgctaat gagacgtcgg taccctcgag tctggtaaag     1380
aaaccgctgc tgcgaaattt gaacgccagc acatggactc gtctactagc gcagcttaat     1440
taacctaggc tgctgccacc gctgagcaat aactagcata acccttggg gcctctaaac     1500 gggtcttgag gggttttttg ctgaaaggag gaactatatc cggattggcg aatgggacgc     1560
gccctgtagc ggcgcattaa gcgcggcggg tgtggtggtt acgcgcagcg tgaccgctac     1620
acttgccagc gccctagcgc ccgctccttt cgctttcttc ccttcctttc tcgccacgtt     1680
cgccggcttt ccccgtcaag ctctaaatcg gggctccct ttagggttcc gatttagtgc     1740
tttacggcac ctcgacccca aaaaacttga ttagggtgat ggttcacgta gtgggccatc     1800
gccctgatag acggtttttc gccctttgac gttggagtcc acgttcttta atagtggact     1860
cttgttccaa actggaacaa cactcaaccc tatctcggtc tattcttttg atttataagg     1920
gattttgccg atttcggcct attggttaaa aaatgagctg atttaacaaa aatttaacgc     1980
gaattttaac aaaatattaa cgtttacaat ttctggcggc acgatggcat gagattatca     2040
aaaaggatct tcacctagat ccttttaaat taaaaatgaa gttttaaatc aatctaaagt     2100
atatatgagt aaacttggtc tgacagttac caatgcttaa tcagtgaggc acctatctca     2160
gcgatctgtc tatttcgttc atccatagtt gcctgactcc ccgtcgtgta gataactacg     2220
atacgggagg gcttaccatc tggccccagt gctgcaatga taccgcgaga cccacgctca     2280
ccggctccag atttatcagc aataaaccag ccagccggaa gggccgagcg cagaagtggt     2340
cctgcaactt tatccgcctc catccagtct attaattgtt gccgggaagc tagagtaagt     2400
agttcgccag ttaatagttt cgcaacgtt gttgccattg ctacaggcat cgtggtgtca     2460
cgctcgtcgt ttggtatggc ttcattcagc tccggttccc aacgatcaag gcgagttaca     2520
tgatccccca tgttgtgcaa aaaagcggtt agctccttcg gtcctccgat cgttgtcaga     2580
agtaagttgg ccgcagtgtt atcactcatg gttatggcag cactgcataa ttctcttact     2640
gtcatgccat ccgtaagatg cttttctgtg actggtgagt actcaaccaa gtcattctga     2700
```

```
gaatagtgta tgcggcgacc gagttgctct tgcccggcgt caatacggga taataccgcg    2760
ccacatagca gaactttaaa agtgctcatc attggaaaac gttcttcggg gcgaaaactc    2820
tcaaggatct taccgctgtt gagatccagt tcgatgtaac ccactcgtgc acccaactga    2880
tcttcagcat cttttacttt caccagcgtt tctgggtgag caaaaacagg aaggcaaaat    2940
gccgcaaaaa agggaataag ggcgacacgg aaatgttgaa tactcatact cttccttttt    3000
caatcatgat tgaagcattt atcagggtta ttgtctcatg agcggataca tatttgaatg    3060
tatttagaaa aataaacaaa taggtcatga ccaaaatccc ttaacgtgag ttttcgttcc    3120
actgagcgtc agacccgta gaaaagatca aaggatcttc ttgagatcct ttttttctgc    3180
gcgtaatctg ctgcttgcaa acaaaaaaac caccgctacc agcggtggtt tgtttgccgg    3240
atcaagagct accaactctt tttccgaagg taactggctt cagcagagcg cagataccaa    3300
atactgtcct tctagtgtag ccgtagttag gccaccactt caagaactct gtagcaccgc    3360
ctacatacct cgctctgcta atcctgttac cagtggctgc tgccagtggc gataagtcgt    3420
gtcttaccgg gttggactca agacgatagt taccggataa ggcgcagcgg tcgggctgaa    3480
cggggggttc gtgcacacag cccagcttgg agcgaacgac ctacaccgaa ctgagatacc    3540
tacagcgtga gctatgagaa agcgccacgc ttcccgaagg gagaaaggcg gacaggtatc    3600
cggtaagcgg cagggtcgga acaggagagc gcacgaggga gcttccaggg ggaaacgcct    3660
ggtatcttta tagtcctgtc gggtttcgcc acctctgact tgagcgtcga tttttgtgat    3720
gctcgtcagg gggcggagc ctatggaaaa acgccagcaa cgcggccttt ttacggttcc    3780
tggccttttg ctggcctttt gctcacatgt tctttcctgc gttatcccct gattctgtgg    3840
ataaccgtat taccgccttt gagtgagctg ataccgctcg ccgcagccga acgaccgagc    3900
gcagcgagtc agtgagcgag gaagcggaag agcgcctgat gcggtatttt ctccttacgc    3960
atctgtgcgg tatttcacac cgcatatatg gtgcactctc agtacaatct gctctgatgc    4020
cgcatagtta agccagtata cactccgcta tcgctacgtg actgggtcat ggctgcgccc    4080
cgacacccgc caacacccgc tgacgcgccc tgacgggctt gtctgctccc ggcatccgct    4140
tacagacaag ctgtgaccgt ctccgggagc tgcatgtgtc agaggttttc accgtcatca    4200
ccgaaacgcg cgaggcagct gcggtaaagc tcatcagcgt ggtcgtgaag cgattcacag    4260
atgtctgcct gttcatccgc gtccagctcg ttgagtttct ccagaagcgt taatgtctgg    4320
cttctgataa agcgggccat gttaagggcg gttttttcct gtttggtcac tgatgcctcc    4380
gtgtaagggg gatttctgtt catggggta atgataccga tgaaacgaga gaggatgctc    4440
acgatacggg ttactgatga tgaacatgcc cggttactgg aacgttgtga gggtaaacaa    4500
ctggcggtat ggatgcggcg ggaccagaga aaaatcactc agggtcaatg ccagcgcttc    4560
gttaatacag atgtaggtgt tccacagggt agccagcagc atcctgcgat gcagatccgg    4620
aacataatgt gcagggcgc tgacttccgc gtttccagac tttacgaaac acggaaaccg    4680
aagaccattc atgttgttgc tcaggtcgca gacgttttgc agcagcagtc gcttcacgtt    4740
cgctcgcgta tcggtgattc attctgctaa ccagtaaggc aaccccgcca gcctagccgg    4800
gtcctcaacg acaggagcac gatcatgcta gtcatgcccc gcgcccaccg gaaggagctg    4860
actgggttga aggctctcaa gggcatcggt cgagatcccg gtgcctaatg agtgagctaa    4920
cttacattaa ttgcgttgcg ctcactgccc gctttccagt cgggaaacct gtcgtgccag    4980
ctgcattaat gaatcggcca acgcgcgggg agaggcggtt tgcgtattgg gcgccagggt    5040
```

```
ggttttctt ttcaccagtg agacgggcaa cagctgattg cccttcaccg cctggccctg      5100
agagagttgc agcaagcggt ccacgctggt ttgccccagc aggcgaaaat cctgtttgat      5160
ggtggttaac ggcgggatat aacatgagct gtcttcggta tcgtcgtatc ccactaccga      5220
gatgtccgca ccaacgcgca gcccggactc ggtaatggcg cgcattgcgc ccagcgccat      5280
ctgatcgttg caaccagca tcgcagtggg aacgatgccc tcattcagca tttgcatggt      5340
ttgttgaaaa ccggacatgg cactccagtc gccttcccgt tccgctatcg gctgaatttg      5400
attgcgagtg agatatttat gccagccagc cagacgcaga cgcgccgaga cagaacttaa      5460
tgggcccgct aacagcgcga tttgctggtg acccaatgcg accagatgct ccacgcccag      5520
tcgcgtaccg tcttcatggg agaaaataat actgttgatg ggtgtctggt cagagacatc      5580
aagaaataac gccggaacat tagtgcaggc agcttccaca gcaatggcat cctggtcatc      5640
cagcggatag ttaatgatca gcccactgac gcgttgcgcg agaagattgt gcaccgccgc      5700
tttacaggct tcgacgccgc ttcgttctac catcgacacc accacgctgg cacccagttg      5760
atcggcgcga gatttaatcg ccgcgacaat ttgcgacggc gcgtgcaggg ccagactgga      5820
ggtggcaacg ccaatcagca acgactgttt gcccgccagt tgttgtgcca cgcggttggg      5880
aatgtaattc agctccgcca tcgccgcttc cacttttttcc cgcgttttcg cagaaacgtg      5940
gctggcctgg ttcaccacgc gggaaacggt ctgataagag acaccggcat actctgcgac      6000
atcgtataac gttactggtt tcacattcac caccctgaat tgactctctt ccgggcgcta      6060
tcatgccata ccgcgaaagg ttttgcgcca ttcgatggtg ccgggatct cgacgctctc      6120 ccttatgcga ctcctgcatt aggaagcagc ccagtagtag gttgaggccg ttgagcaccg      6180
ccgccgcaag gaatggtgca tgcaaggaga tggcgcccaa cagtccccg gccacggggc      6240 ctgccaccat acccacgccg aaacaagcgc tcatgagccc gaagtggcga gcccgatctt      6300
ccccatcggt gatgtcggcg atataggcgc cagcaaccgc acctgtggcg ccggtgatgc      6360
cggccacgat gcgtccggcg tagaggatcg agatcgatct cgatcccgcg aaattaatac      6420
gactcactat a                                                          6431
```

<210> SEQ ID NO 8
<211> LENGTH: 5739
<212> TYPE: DNA
<213> ORGANISM: Artificial Sequence
<220> FEATURE:
<223> OTHER INFORMATION: construct pCDF-galT-galE

<400> SEQUENCE: 8

```
ggggaattgt gagcggataa caattcccct gtagaaataa ttttgtttaa ctttaataag       60
gagatatacc atgacgcaat ttaatcccgt tgatcatcca catcgccgct acaacccgct      120
caccgggcaa tggattctgg tttcaccgca ccgcgctaag cgccctggc aggggcgca      180 ggaaacgcca gccaaacagg tgttacctgc gcacgatcca gattgcttcc tctgcgcagg      240
taatgtgcgg gtgacaggcg ataaaaaccc cgattacacc gggacttacg ttttcactaa      300
tgactttgcg gctttgatgt ctgacacgcc agatgcgcca gaaagtcacg atccgctgat      360
gcgttgccag agcgcgcgcg gcaccagccg ggtgatctgc ttttcaccgg atcacagtaa      420
aacgctgcca gagctcagcg ttgcagcatt gacggaaatc gtcaaaacct ggcaggagca      480
aaccgcagaa ctggggaaaa cgtacccatg ggtgcaggtt tttgaaaaca aaggcgcggc      540
gatgggctgc tctaacccgc atccgcacgg tcagatttgg gcaaatagct tcctgcctaa      600
cgaagctgag cgcgaagacc gcctgcaaaa agaatatttt gccgaacaga atcaccaat      660
```

| | |
|---|---|
| gctggtggat tatgttcagc gcgagctggc agacggtagc cgtaccgttg tcgaaaccga | 720 |
| acactggtta gccgtcgtgc cttactgggc tgcctggccg ttcgaaacgc tactgctgcc | 780 |
| caaagcccac gttttacgga tcaccgattt gaccgacgcc cagcgcagcg atctggcgct | 840 |
| ggcgttgaaa aagctgacca gtcgttatga caacctcttc cagtgctcct tcccctactc | 900 |
| tatgggctgg cacggcgcgc catttaatgg cgaagagaat caacactggc agctgcacgc | 960 |
| gcacttttat ccgcctctgc tgcgctccgc caccgtacgt aaatttatgg ttggttatga | 1020 |
| aatgctggca gagacccagc gagacctgac cgcagaacag gcagcagagc gtttgcgcgc | 1080 |
| agtcagcgat atccattttc gcgaatccgg agtgtaaaag cttgcggccg cataatgctt | 1140 |
| aagtcgaaca gaaagtaatc gtattgtaca cggccgcata tcgaaatta atacgactca | 1200 |
| ctataggga attgtgagcg gataacaatt ccccatctta gtatattagt taagtataag | 1260 |
| aaggagatat acagatcaca tatgagagtt ctggttaccg gtggtagcgg ttacattgga | 1320 |
| agtcatacct gtgtgcaatt actgcaaaac ggtcatgatg tcatcattct tgataacctc | 1380 |
| tgtaacagta agcgcagcgt actgcctgtt atcgagcgtt taggcggcaa acatccaacg | 1440 |
| tttgttgaag gcgatattcg taacgaagcg ttgatgaccg agatcctgca cgatcacgct | 1500 |
| atcgacaccg tgatccactt cgccgggctg aaagccgtgg gcgaatcggt acaaaaaccg | 1560 |
| ctggaatatt acgacaacaa tgtcaacggc actctgcgcc tgattagcgc catgcgcgcc | 1620 |
| gctaacgtca aaaactttat ttttagctcc tccgccaccg tttatggcga tcagcccaaa | 1680 |
| attccatacg ttgaaagctt cccgaccggc acaccgcaaa gcccttacgg caaaagcaag | 1740 |
| ctgatggtgg aacagatcct caccgatctg caaaaagccc agccggactg gagcattgcc | 1800 |
| ctgctgcgct acttcaaccc ggttggcgcg catccgtcgg gcgatatggg cgaagatccg | 1860 |
| caaggcattc cgaataacct gatgccatac atcgcccagg ttgctgtagg ccgtcgcgac | 1920 |
| tcgctggcga ttttttggtaa cgattatccg accgaagatg gtactggcgt acgcgattac | 1980 |
| atccacgtaa tggatctggc ggacggtcac gtcgtggcga tggaaaaact ggcgaacaag | 2040 |
| ccaggcgtac acatctacaa cctcggcgct ggcgtaggca acagcgtgct ggacgtggtt | 2100 |
| aatgccttca gcaaagcctg cggcaaaccg gttaattatc attttgcacc gcgtcgcgag | 2160 |
| ggcgaccttc cggcctactg ggcggacgcc agcaaagccg accgtgaact gaactggcgc | 2220 |
| gtaacgcgca cactcgatga aatggcgcag gacacctggc actggcagtc acgccatcca | 2280 |
| cagggatatc ccgattaatg actcgagtga tctcgagtct ggtaaagaaa ccgctgctgc | 2340 |
| gaaatttgaa cgccagcaca tggactcgtc tactagcgca gcttaattaa cctaggctgc | 2400 |
| tgccaccgct gagcaataac tagcataacc ccttggggcc tctaaacggg tcttgagggg | 2460 |
| ttttttgctg aaacctcagg catttgagaa gcacacggtc acactgcttc cggtagtcaa | 2520 |
| taaaccggta aaccagcaat agacataagc ggctatttaa cgaccctgcc ctgaaccgac | 2580 |
| gaccgggtca tcgtggccgg atcttgcggc ccctcggctt gaacgaattg ttagacatta | 2640 |
| tttgccgact accttggtga tctcgccttt cacgtagtgg acaaattctt ccaactgatc | 2700 |
| tgcgcgcgag gccaagcgat cttcttcttg tccaagataa gcctgtctag cttcaagtat | 2760 |
| gacgggctga tactgggccg gcaggcgctc cattgcccag tcggcagcga catccttcgg | 2820 |
| cgcgattttg ccggttactg cgctgtacca aatgcgggac aacgtaagca ctacatttcg | 2880 |
| ctcatcgcca gcccagtcgg gcggcgagtt ccatagcgtt aaggtttcat ttagcgcctc | 2940 |
| aaatagatcc tgttcaggaa ccggatcaaa gagttcctcc gccgctggac ctaccaaggc | 3000 |

```
aacgctatgt tctcttgctt ttgtcagcaa gatagccaga tcaatgtcga tcgtggctgg    3060
ctcgaagata cctgcaagaa tgtcattgcg ctgccattct ccaaattgca gttcgcgctt    3120
agctggataa cgccacggaa tgatgtcgtc gtgcacaaca atggtgactt ctacagcgcg    3180
gagaatctcg ctctctccag gggaagccga agtttccaaa aggtcgttga tcaaagctcg    3240
ccgcgttgtt tcatcaagcc ttacggtcac cgtaaccagc aaatcaatat cactgtgtgg    3300
cttcaggccg ccatccactg cggagccgta caaatgtacg gccagcaacg tcggttcgag    3360
atggcgctcg atgacgccaa ctacctctga tagttgagtc gatacttcgg cgatcaccgc    3420
ttccctcata ctcttccttt ttcaatatta ttgaagcatt tatcagggtt attgtctcat    3480
gagcggatac atatttgaat gtatttagaa aaataaacaa atagctagct cactcggtcg    3540
ctacgctccg ggcgtgagac tgcggcgggc gctgcggaca catacaaagt tacccacaga    3600
ttccgtggat aagcagggga ctaacatgtg aggcaaaaca gcagggccgc gccggtggcg    3660
tttttccata ggctccgccc tcctgccaga gttcacataa acagacgctt ttccggtgca    3720
tctgtgggag ccgtgaggct caaccatgaa tctgacagta cgggcgaaac ccgacaggac    3780
ttaaagatcc ccaccgtttc cggcgggtcg ctccctcttg cgctctcctg ttccgaccct    3840
gccgtttacc ggatacctgt tccgcctttc tcccttacgg gaagtgtggc gctttctcat    3900
agctcacaca ctggtatctc ggctcggtgt aggtcgttcg ctccaagctg ggctgtaagc    3960
aagaactccc cgttcagccc gactgctgcg ccttatccgg taactgttca cttgagtcca    4020
acccggaaaa gcacggtaaa acgccactgg cagcagccat ggtaactgg gagttcgcag    4080 aggatttgtt tagctaaaca cgcggttgct cttgaagtgt gcgccaaagt ccggctacac    4140
tggaaggaca gatttggttg ctgtgctctg cgaaagccag ttaccacggt taagcagttc    4200
cccaactgac ttaaccttcg atcaaaccac ctccccaggt ggttttttcg tttacagggc    4260
aaaagattac gcgcagaaaa aaaggatctc aagaagatcc tttgatcttt tctactgaac    4320
cgctctagat ttcagtgcaa tttatctctt caaatgtagc acctgaagtc agccccatac    4380
gatataagtt gtaattctca tgttagtcat gccccgcgcc caccggaagg agctgactgg    4440
gttgaaggct ctcaagggca tcggtcgaga tccggtgcc taatgagtga gctaacttac    4500
attaattgcg ttgcgctcac tgcccgcttt ccagtcggga aacctgtcgt gccagctgca    4560
ttaatgaatc ggccaacgcg cggggagagg cggtttgcgt attgggcgcc agggtggttt    4620
ttcttttcac cagtgagacg ggcaacagct gattgcccct caccgcctgg ccctgagaga    4680
gttgcagcaa gcggtccacg ctggtttgcc ccagcaggcg aaaatcctgt ttgatggtgg    4740
ttaacggcgg gatataacat gagctgtctt cggtatcgtc gtatcccact accgagatgt    4800
ccgcaccaac gcgcagcccg gactcggtaa tggcgcgcat gcgcccagc gccatctgat    4860 cgttggcaac cagcatcgca gtgggaacga tgccctcatt cagcatttgc atggtttgtt    4920
gaaaaccgga catggcactc cagtcgcctt cccgttccgc tatcggctga atttgattgc    4980
gagtgagata tttatgccag ccagccagac gcagacgcgc cgagacagaa cttaatgggc    5040
ccgctaacag cgcgatttgc tggtgaccca atgcgaccag atgctccacg cccagtcgcg    5100
taccgtcttc atgggagaaa ataatactgt tgatgggtgt ctggtcagag acatcaagaa    5160
ataacgccgg aacattagtg caggcagctt ccacagcaat ggcatcctgg tcatccagcg    5220
gatagttaat gatcagccca ctgacgcgtt gcgcgagaag attgtgcacc gccgctttac    5280
aggcttcgac gccgcttcgt tctaccatcg acaccaccac gctggcaccc agttgatcgg    5340
cgcgagattt aatcgccgcg acaatttgcg acggcgcgtg cagggccaga ctggaggtgg    5400
```

```
caacgccaat cagcaacgac tgtttgcccg ccagttgttg tgccacgcgg ttgggaatgt      5460
aattcagctc cgccatcgcc gcttccactt tttcccgcgt tttcgcagaa acgtggctgg      5520
cctggttcac cacgcgggaa acggtctgat aagagacacc ggcatactct gcgacatcgt      5580
ataacgttac tggtttcaca ttcaccaccc tgaattgact ctcttccggg cgctatcatg      5640
ccataccgcg aaaggttttg cgccattcga tggtgtccgg gatctcgacg ctctccctta      5700
tgcgactcct gcattaggaa attaatacga ctcactata                              5739

<210> SEQ ID NO 9
<211> LENGTH: 8232
<212> TYPE: DNA
<213> ORGANISM: Artificial Sequence
<220> FEATURE:
<223> OTHER INFORMATION: construct pCOLA-glmUM-glmS

<400> SEQUENCE: 9
cagcccactg acgcgttgcg cgagaagatt gtgcaccgcc gctttacagg cttcgacgcc        60
gcttcgttct accatcgaca ccaccacgct ggcacccagt tgatcggcgc gagatttaat       120
cgccgcgaca atttgcgacg gcgcgtgcag ggccagactg gaggtggcaa cgccaatcag       180
caacgactgt ttgcccgcca gttgttgtgc cacgcggttg gaatgtaat tcagctccgc       240 catcgccgct ccactttttt cccgcgtttt cgcagaaacg tggctggcct ggttcaccac       300
gcgggaaacg gtctgataag agacaccggc atactctgcg acatcgtata acgttactgg       360
tttcacattc accacctga attgactctc ttccgggcgc tatcatgcca taccgcgaaa       420
ggttttgcgc cattcgatgg tgtccgggat ctcgacgctc tcccttatgc gactcctgca       480
ttaggaaatt aatacgactc actataggg aattgtgagc ggataacaat tcccctgtag       540
aaataatttt gtttaacttt aataaggaga tataccatgc tgaacaacgc gatgtctgtt       600
gttatcctgg cggcgggtaa aggtacccgt atgtactctg acctgccgaa agttctgcac       660
accctggcgg gtaaagcgat ggttcagcac gttatcgacg cggcgaacga actgggtgcg       720
gcgcacgttc acctggttta cggtcacggt ggtgacctgc tgaaacaggc gctgaaagac       780
gacaacctga actgggttct gcaggcggaa cagctgggta ccggtcacgc gatgcagcag       840
gcggcgccgt tcttcgcgga cgacgaagac atcctgatgc tgtacggtga cgttccgctg       900
atctctgttg aaaccctgca gcgtctgcgt gacgcgaaac gcagggtgg tatcggtctg       960 ctgaccgtta aactggacga cccgaccggt tacggtcgta tcacccgtga aaacggtaaa      1020
gtaaccggta tcgttgaaca caagacgcg accgacgaac agcgtcagat ccaggagatc      1080
aacaccggta tcctgatcgc gaacggtgca gacatgaaac gttggctggc gaaactgacc      1140
aacaacaacg cgcagggtga atactacatc accgacatca tcgcgctggc gtaccaggaa      1200
ggtcgtgaaa tcgttgcggt tcacccgcag cgtctgtctg aagttgaagg tgttaacaac      1260
cgtctgcagc tgtctcgtct ggaacgtgtt taccagtctg aacaggcgga aaaactgctg      1320
ctggcgggtg ttatgctgcg tgacccggcg cgtttcgacc tgcgtggtac cctgacccac      1380
ggtcgtgacg ttgaaatcga caccaacgtt atcatcgaag gtaacgttac cctgggtcac      1440
cgtgtaaaaa tcggcaccgg ttgcgttatc aaaaactctg ttatcggtga cgactgcgaa      1500
atctctccgt acaccgttgt tgaagacgcg aacctggcgg cggcgtgcac catcggtccg      1560
ttcgcgcgtc tgcgtccggg tgcggaactg ctggaaggtg cgcacgttgg taacttcgtt      1620
gaaatgaaaa aagcgcgtct gggtaaaggt tctaaagcgg gtcacctgac ctacctgggt      1680
```

```
gacgcggaaa tcggtgacaa cgttaacatc ggtgcgggta ccatcacctg caactacgac    1740
ggtgcgaaca aattcaaaac catcatcggt gacgacgttt tcgttggttc tgacacccag    1800
ctggttgcgc cggttaccgt tggtaaaggt gcgaccatcg cggcgggtac caccgttacc    1860
cgtaacgttg gtgaaaacgc gctggcgatc tctcgtgttc cgcagaccca gaaagaaggt    1920
tggcgtcgtc cggttaaaaa aaaataacga aggagataga accatgtcca accgtaaata    1980
cttcggtacg gacggtatcc gtggtcgtgt aggtgatgct ccgattacgc cggatttcgt    2040
cctgaaactc ggttgggcag cgggtaaagt tctcgcacgt cacggctctc gtaaaatcat    2100
catcggtaaa gacacccgta tctctggtta catgctcgaa tctgcactgg aagcgggtct    2160
ggctgcagct ggtctgtctg cactgttcac gggtccgatg ccaaccccag ctgtagcgta    2220
cctgactcgc actttccgtg cagaagcagg tatcgtgatc tctgcctctc acaacccgtt    2280
ctacgacaac ggtatcaaat tcttcagcat cgatggtacc aaactcccag acgcggttga    2340
agaggctatc gaagcggaaa tggagaaaga atctcttgt gtagactctg ccgaactcgg    2400
taaagcgtct cgtatcgttg atgcagcggg tcgttacatc gagttctgca aagccacctt    2460
tccgaacgaa ctgagcctgt ctgagctgaa aatcgtcgta gactgtgcca acggtgcgac    2520
ttaccacatt gccccaaacg tactgcgtga gctgggtgct aacgtcatcg cgatcggttg    2580
tgaaccgaac ggtgtcaaca tcaacgcgga agtaggtgcg accgatgttc gtgcactgca    2640
ggctcgtgta ctcgcggaga aagcggatct cggtatcgcc tttgacggtg atggtgaccg    2700
tgttatcatg gttgaccacg aaggtaacaa agtggatggt gaccagatca tgtacatcat    2760
tgcccgtgaa ggtctgcgtc agggtcagct gcgtggtggt gcagtaggta ccctcatgag    2820
caacatgggt ctggaactgg ccctgaaaca gctgggtatc ccattcgctc gtgctaaagt    2880
aggcgaccgt tacgttctgg agaaaatgca ggagaaaggt tggcgtatcg gtgccgaaaa    2940
ctctggtcac gtcatcctgc tggacaaaac cactaccggt gacggtatcg tagcaggtct    3000
gcaggtactc gccgctatgg cccgtaacca catgtccctc catgacctct gctctggtat    3060
gaaaatgttc ccgcagatcc tggttaacgt tcgttacacc gcaggttctg gtgatccgct    3120
ggaacacgag tctgtgaaag ccgttaccgc agaagtggaa gcggccctgg gtaaccgtgg    3180
tcgtgtactg ctgcgtaaat ccggtactga gccactgatc cgtgttatgg ttgagggcga    3240
agatgaagcc caggtcaccg aatttgcgca ccgtattgcc gacgcagtca aagcggttta    3300
aatgggcagc agccatcacc atcatcacca cagccaggat ccgaattcga gctcggcgcg    3360
cctgcaggtc gacaagcttg cggccgcata atgcttaagt cgaacagaaa gtaatcgtat    3420
tgtacacggc cgcataatcg aaattaatac gactcactat aggggaattg tgagcggata    3480
acaattcccc atcttagtat attagttaag tataagaagg agatatacat atgtgcggta    3540
tcgttggtgc tatcgcacag cgtgatgtag cggagatcct cctggaaggt ctgcgtcgtc    3600
tcgaataccg tggttacgac tctgccggtc tggcagtagt ggatgcagaa ggtcacatga    3660
ctcgtctgcg tcgtctgggt aaagtgcaga tgctcgcgca ggcggcggaa gaacacccac    3720
tccacggtgg tacgggtatc gcacacactc gttgggcaac ccacggtgaa ccgtctgagg    3780
tcaacgcaca cccgcatgtt agcgagcaca tcgtagtcgt tcacaacggt atcatcgaga    3840
accacgaacc actccgtgag gaactcaaag cccgtggtta caccttcgta agcgaaaccg    3900
acacggaagt tatcgcccac ctcgttaact gggaactcaa acagggtggt actctgcgtg    3960
aagcagttct gcgtgccatt ccacagctgc gtggtgcata cggtaccgtg atcatggact    4020
ctcgtcatcc ggatacccctg ctcgccgcac gttctggttc tccactcgtt atcggtctgg    4080
```

-continued

```
gtatgggtga gaacttcatc gcctctgatc agctggccct gctcccagtt acccgtcgct    4140
tcatcttcct ggaagagggt gacatcgccg aaatcacccg tcgttccgtt aacatcttcg    4200
acaaaacggg tgcggaagtt aaacgtcagg acatcgagtc taacctgcag tatgacgctg    4260
gtgacaaagg catctaccgt cactacatgc agaaagagat ctacgaacag ccgaacgcga    4320
tcaaaaacac cctgaccggt cgtatctctc acggtcaggt tgacctgtct gagctgggtc    4380
caaacgcgga cgaactcctg tccaaagtcg agcacatcca gatcctggct tgtggtacct    4440
cttacaactc cggtatggtt tctcgttact ggttcgaatc tctggcaggt atcccatgcg    4500
acgttgaaat cgcctccgaa ttccgttatc gtaaatctgc ggtacgtcgt aactccctca    4560
tgatcaccct gtctcagtct ggtgaaaccg ctgatactct ggcaggtctg cgtctcagca    4620
aagaactggg ttacctgggt tctctggcca tctgcaacgt tccgggttct agcctggttc    4680
gtgagtctga cctggctctg atgaccaacg cgggtacgga gatcggtgtt gcctctacca    4740
aagcgttcac tacccagctc actgtcctgc tgatgctggt tgccaaactg tctcgtctca    4800
aaggcctcga cgctagcatc gaacacgaca tcgtacacgg tctgcaggcc ctcccatctc    4860
gtatcgagca gatgctgtct caggacaaac gtatcgaagc actggcagaa gacttcagcg    4920
acaaacacca cgcgctgttt ctgggtcgtg gtgaccagta cccaattgcg ctggaaggtg    4980
ccctgaaact gaaagagatc agctacatcc atgcagaggc atacgcagcg ggtgagctga    5040
aacatggtcc actggccctg atcgacgcag atatgccggt tattgtggtt gctccgaaca    5100
acgaactgct ggagaaactg aaatccaaca tcgaggaagt acgtgcgcgt ggtggtcagc    5160
tgtacgtgtt tgctgaccag gacgcgggtt tcgtttccag cgacaacatg cacatcatcg    5220
aaatgccgca tgttgaagag gtaatcgcgc aatcttcta caccgtaccg ctgcagctgc    5280
tggcgtacca tgtagccctg atcaaaggta cggacgttga ccagccgcgt aacctggcga    5340
aatccgtgac cgtggaataa gacgtcggta ccctcgagtc tggtaaagaa accgctgctg    5400
cgaaatttga acgccagcac atggactcgt ctactagcgc agcttaatta acctaggctg    5460
ctgccaccgc tgagcaataa ctagcataac cccttggggc ctctaaacgg gtcttgaggg    5520
gttttttgct gaaacctcag gcatttgaga agcacacggt cacactgctt ccggtagtca    5580
ataaaccggt aaaccagcaa tagacataag cggctattta cgaccctgc cctgaaccga    5640 cgacaagctg acgaccgggt ctccgcaagt ggcacttttc ggggaaatgt gcgcggaacc    5700
cctatttgtt tatttttcta aatacattca aatatgtatc cgctcatgaa ttaattctta    5760
gaaaaactca tcgagcatca aatgaaactg caatttattc atatcaggat tatcaatacc    5820
atatttttga aaaagccgtt tctgtaatga aggagaaaac tcaccgaggc agttccatag    5880
gatggcaaga tcctggtatc ggtctgcgat tccgactcgt ccaacatcaa tacaacctat    5940
taatttcccc tcgtcaaaaa taaggttatc aagtgagaaa tcaccatgag tgacgactga    6000
atccggtgag aatggcaaaa gtttatgcat ttctttccag acttgttcaa caggccagcc    6060
attacgctcg tcatcaaaat cactcgcatc aaccaaaccg ttattcattc gtgattgcgc    6120
ctgagcgaga cgaaatacgc ggtcgctgtt aaaaggacaa ttacaaacag gaatcgaatg    6180
caaccggcgc aggaacactg ccagcgcatc aacaatattt tcacctgaat caggatattc    6240
ttctaatacc tggaatgctg ttttcccggg gatcgcagtg gtgagtaacc atgcatcatc    6300
aggagtacgg ataaaatgct tgatggtcgg aagaggcata aattccgtca gccagtttag    6360
tctgaccatc tcatctgtaa catcattggc aacgctacct ttgccatgtt tcagaaacaa    6420
```

```
ctctggcgca tcgggcttcc catacaatcg atagattgtc gcacctgatt gcccgacatt    6480
atcgcgagcc catttatacc catataaatc agcatccatg ttggaattta atcgcggcct    6540
agagcaagac gtttcccgtt gaatatggct catactcttc cttttcaat attattgaag    6600 catttatcag ggttattgtc tcatgagcgg atacatattt gaatgtattt agaaaaataa    6660
acaaataggc atgctagcgc agaaacgtcc tagaagatgc caggaggata cttagcagag    6720
agacaataag gccggagcga agccgttttt cataggctc cgccccctg acgaacatca    6780 cgaaatctga cgctcaaatc agtggtggcg aaacccgaca ggactataaa gataccaggc    6840
gtttccccct gatggctccc tcttgcgctc tcctgttccc gtcctgcggc gtccgtgttg    6900
tggtggaggc tttacccaaa tcaccacgtc ccgttccgtg tagacagttc gctccaagct    6960
gggctgtgtg caagaacccc ccgttcagcc cgactgctgc gccttatccg gtaactatca    7020
tcttgagtcc aacccggaaa gacacgacaa acgccactg gcagcagcca ttggtaactg    7080
agaattagtg gatttagata tcgagagtct tgaagtggtg gcctaacaga ggctacactg    7140
aaaggacagt atttggtatc tgcgctccac taaagccagt taccaggtta agcagttccc    7200
caactgactt aaccttcgat caaaccgcct ccccaggcgg ttttttcgtt tacagagcag    7260
gagattacga cgatcgtaaa aggatctcaa gaagatcctt tacggattcc cgacaccatc    7320
actctagatt tcagtgcaat ttatctcttc aaatgtagca cctgaagtca gccccatacg    7380
atataagttg taattctcat gttagtcatg ccccgcgccc accggaagga gctgactggg    7440
ttgaaggctc tcaagggcat cggtcgagat cccggtgcct aatgagtgag ctaacttaca    7500
ttaattgcgt tgcgctcact gcccgctttc cagtcgggaa acctgtcgtg ccagctgcat    7560
taatgaatcg gccaacgcgc ggggagaggc ggtttgcgta ttgggcgcca gggtggtttt    7620
tcttttcacc agtgagacgg gcaacagctg attgcccttc accgcctggc cctgagagag    7680
ttgcagcaag cggtccacgc tggtttgccc cagcaggcga aaatcctgtt tgatggtggt    7740
taacggcggg atataacatg agctgtcttc ggtatcgtcg tatcccacta ccagatgtc    7800 cgcaccaacg cgcagcccgg actcggtaat ggcgcgcatt cgcccagcg ccatctgatc    7860 gttggcaacc agcatcgcag tgggaacgat gccctcattc agcatttgca tggtttgttg    7920
aaaaccggac atggcactcc agtcgccttc ccgttccgct atcggctgaa tttgattgcg    7980
agtgagatat ttatgccagc cagccagacg cagacgcgcc gagacagaac ttaatgggcc    8040
cgctaacagc gcgatttgct ggtgacccaa tgcgaccaga tgctccacgc ccagtcgcgt    8100
accgtcttca tgggagaaaa taatactgtt gatgggtgtc tggtcagaga catcaagaaa    8160
taacgccgga acattagtgc aggcagcttc cacagcaatg gcatcctggt catccagcgg    8220
atagttaatg at                                                        8232
```

<210> SEQ ID NO 10
<211> LENGTH: 6792
<212> TYPE: DNA
<213> ORGANISM: Artificial Sequence
<220> FEATURE:
<223> OTHER INFORMATION: construct pINT-malE-PmgalT7

<400> SEQUENCE: 10

```
tcgcgcgttt cggtgatgac ggtgaaaacc tctgacacat gcagctcccg gagacggtca     60
cagcttgtct gtaagcggat gccgggagca gacaagcccg tcaggcgcg tcagcgggtg    120 ttggcgggtg tcgggctgg cttaactatg cggcatcaga gcagattgta ctgagagtgc    180
accatatgcg gtgtgaaata ccgcacagat gcgtaaggag aaaataccgc atcaggcgcc    240
```

```
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgaagatcct ttgatctttt    420
ctacggggtc tgacgctcag tggaacgaaa actcacgtta agggattttg gtcatgagat    480
tatcaaaaag gatcttcacc tagatccttt aaactagtg aagttaccat cacggaaaaa     540
ggttatgctg cttttaagac ccactttcac atttaagttg ttttctaat ccgcatatga     600 tcaattcaag gccgaataag aaggctggct ctgcaccttg gtgatcaaat aattcgatag    660
cttgtcgtaa taatggcggc atactatcag tagtaggtgt ttccctttct tctttagcga    720
cttgatgctc ttgatcttcc aatacgcaac ctaaagtaaa atgccccact gcgctgagtg    780
catataatgc attctctagt gaaaaacctt gttggcataa aaaggctaat tgattttcga    840
gagtttcata ctgttttct gtaggccgtg tacctaaatg tacttttgct ccatcgcgat     900
gacttagtaa agcacatcta aaacttttag cgttattacg taaaaaatct tgccagcttt    960
ccccttctaa agggcaaaag tgagtatggt gcctatctaa catctcaatg gctaaggcgt    1020
cgagcaaagc ccgcttattt tttacatgcc aatacaatgt aggctgctct acacctagct    1080
tctgggcgag tttacggggt gttaaaccct cgattccgac ctcattaagc agctctaatg    1140
cgctgttaat cactttactt ttatctaaac gagacatact cttcctttt caatattatt     1200 gaagcattta tcagggttat tgtctcatga gcggatacat atttgaatgt atttagaaaa    1260
ataaacaaat aggggttccg cgcacatttc cccgaaaagt gccacctgaa attggccaga    1320
tgattaattc ctaattttg ttgacactct atcattgata gagttatttt accactccct     1380
atcagtgata gagaaaagtg aaatgaatag ttcgacaaaa atctagaaat aattttgttt    1440
aactttaaga aggagatata caaatgaaaa tcgaagaagg taaactggta atctggatta    1500
acggcgataa aggctataac ggtctcgctg aagtcggtaa gaaattcgag aaagataccg    1560
gaattaaagt caccgttgag catccggata aactggaaga gaaattccca caggttgcgg    1620
caactggcga tggccctgac attatcttct gggcacacga ccgctttggt ggctacgctc    1680
aatctggcct gttggctgaa atcaccccgg acaaagcgtt ccaggacaag ctgtatccgt    1740
ttacctggga tgccgtacgt tacaacggca agctgattgc ttacccgatc gctgttgaag    1800
cgttatcgct gatttataac aaagatctgc tgccgaaccc gccaaaaacc tgggaagaga    1860
tcccggcgct ggataaagaa ctgaaagcga aaggtaagag cgcgctgatg ttcaacctgc    1920
aagaaccgta cttcacctgg ccgctgattg ctgctgacgg gggttatgcg ttcaagtatg    1980
aaaacggcaa gtacgacatt aaagacgtgg gcgtggataa cgctggcgcg aaagcgggtc    2040
tgaccttcct ggttgacctg attaaaaaca acacatgaa tgcagacacc gattactcca     2100
tcgcagaagc tgcctttaat aaaggcgaaa cagcgatgac catcaacggc ccgtgggcat    2160
ggtccaacat cgacaccagc aaagtgaatt atggtgtaac ggtactgccg accttcaagg    2220
gtcaaccatc caaaccgttc gttggcgtgc tgagcgcagg tattaacgcc gccagtccga    2280
acaaagagct ggcaaagag ttcctcgaaa actatctgct gactgatgaa ggtctggaag     2340
cggttaataa agacaaaccg ctgggtgccg tagcgctgaa gtcttacgag gaagagttgg    2400
cgaaagatcc acgtattgcc gccaccatgg aaaacgccca gaaggtgaa atcatgccga     2460 acatcccgca gatgtccgct ttctggtatg ccgtgcgtac tgcggtgatc aacgccgcca    2520
gcggtcgtca gactgtcgat gaagccctga aagacgcgca gactatgagc ggtgaacact    2580
```

```
atgtcattag cctgtcgtcg gcagttgaac gtcgccagca cattcgtaac cagttttcgc    2640
agaagaacat cccgtttcag tttttcgatg caatttcacc gtcgccgctg ctggaccagc    2700
tggtgctgca attttteeeg cgtctggcgg atagctctct gaccggcggt gaaaaagcct    2760
gctttatgag ccatctgtct ctgtggcaca aatgtgtgga agaaaacctg ccgtatattg    2820 tggttttttga agatgacatc gttctgggca agatgcggca caagttcctg attggtgatg    2880
aatggctgtt ttctcgtttc gacccggaag aaatctttat tatccgcctg gaaaccttcc    2940
tgcagaaagt cgtgtgcgaa agcacccata ttgccccgta tacgcaccgc gattttctga    3000
gtctgaaatc cgcacatttc ggcacggctg gttacgtcat cagtcagggc gcggccaaat    3060
ttctgctgga tattttcaag aacatctcca atgaacacat gcgccgatc gacgaactga     3120 tttttaacca gttcctggtt aagaactcat tcaacgtcta ccaactgtcg ccggcaatct    3180
gtgttcagga actgcaactg aacaatgaaa gttccgctct gcagagccaa ctggaactgg    3240
aacgtaacaa attccgcaat aaaaagtctg aagaactgaa gcgtaaccgc aagaacttca    3300
tcgaaaagtt catctacatc ctgaaaaagc cgaagcgtat gctggataac aataagcgta    3360
agcgcgaaga gagtaagatc gaaaacgaca agatgatcat cgaatttaaa tgagcggccg    3420
cgtcgacacg caaaaaggcc atccgtcagg atggccttct gcttaattat ctagatgcct    3480
ggcagtttat ggcgggcgtc ctgcccgcca ccctccgggc cgttgcttcg caacgttcaa    3540
atccgctccc ggcggatttg tcctactcag gagagcgttc accgacaaac aacagataaa    3600
acgaaaggcc cagtctttcg actgagcctt tcgttttatt tgatgcctgg cagttccct     3660 ctctcgcatg gggagacccc cactaccat catgtatgaa tatcctcctt agttcctatt    3720
ccgaagggta atggcatcag ggaatggcga acgcgctccc cacactacca tcatgtatga    3780
atatcctcct tagttcctat tccgaagttc ctattctcta gaaagtatag gaacttcggt    3840
ggaacgacgc gtaactcacg ttaagggatt ttggtcatga tcagcacgtg ttgacaatta    3900
atcatcggca tagtatatcg gcatagtata atacgacaag gtgaggaact aaaccatggc    3960
caagttgacc agtgccgttc cggtgctcac cgcgcgcgac gtcgccggag cggtcgagtt    4020
ctggaccgac cggctcgggt tctccccggga cttcgtggag gacgacttcg ccggtgtggt    4080
ccgggacgac gtgaccctgt tcatcagcgc ggtccaggac caggtggtgc cggacaacac    4140
cctggcctgg gtgtgggtgc gcggcctgga cgagctgtac gccgagtggt cggaggtcgt    4200
gtccacgaac ttccgggacg cctccgggcc ggccatgacc gagatcggcg agcagccgtg    4260
ggggcgggag ttcgccctgc gcgacccggc cggcaactgc gtgcacttcg tggccgagga    4320
gcaggactga gtggcagggc ggggcgtaag gcgcgccatt taaatgaagt tcctattccg    4380
aagttcctat tctctagaaa gtataggaac ttcgaagcag ctccagccta cacaatcgct    4440
caagacggaa cccgcgcttg gcaggaaagt aatagggata gcagctccag cctacacaat    4500
cgctcaagac gtgtaatgct gcacaataac cctgctgcag aggcctgcat gcaagcttgg    4560
cgtaatcatg gtcatagctg tttcctgtgt gaaattgtta tccgctcaca attccacaca    4620
acatacgagc cggaagcata aagtgtaaag cctggggtgc ctaatgagtg agctaactca    4680
cattaattgc gttgcgctca ctgcccgctt tccagtcggg aaacctgtcg tgccagctgc    4740
attaatgaat cggccaacgc gcggggagag gcggtttgcg tattgggcgc tcttccgctt    4800
cctcgctcac tgactcgctg cgctcggtcg ttcggctgcg gcgagcggta tcagctcact    4860
caaaggcggt aatacggtta tccacagaat caggggataa cgcaggaaag aacatgtgag    4920
caaaaggcca gcaaaaggcc aggaaccgta aaaaggccgc gttgctggcg tttttccata    4980
```

```
ggctccgccc ccctgacgag catcacaaaa atcgacgctc aagtcagagg tggcgaaacc    5040
cgacaggact ataaagatac caggcgtttc ccctggaag ctccctcgtg cgctctcctg    5100
ttccgaccct gccgcttacc ggatacctgt ccgcctttct cccttcggga agcgtggcgc    5160
tttctcatag ctcacgctgt aggtatctca gttcggtgta ggtcgttcgc tccaagctgg    5220
gctgtgtgca cgaaccccc gttcagcccg accgctgcgc cttatccggt aactatcgtc    5280
ttgagtccaa cccggtaaga cacgacttat cgccactggc agcagccact ggtaacagga    5340
ttagcagagc gaggtatgta ggcggtgcta cagagttctt gaagtggtgg cctaactacg    5400
gctacactag aagaacagta tttggtatct gcgctctgct gaagccagtt accttcggaa    5460
aaagagttgg tagctcttga tccggcaaac aaaccaccgc tggtagcggt ggtttttttg    5520
tttgcaagca gcagattacg cgcagaaaaa aaggatctca agaagatcct ttgatctttt    5580
ctacggggtc tgacgctcag tggaacgaaa actcacgtta agggattttg gtcatgagat    5640
tatcaaaaag gatcttcacc tagatccttt taaattaaaa atgaagtttt aaatcaatct    5700
aaagtatata tgagtaaact tggtctgaca gttaccaatg cttaatcagt gaggcaccta    5760
tctcagcgat ctgtctattt cgttcatcca tagttgcctg actccccgtc gtgtagataa    5820
ctacgatacg ggagggctta ccatctggcc ccagtgctgc aatgataccg cgagacccac    5880
gctcaccggc tccagattta tcagcaataa accagccagc cggaagggcc gagcgcagaa    5940
gtggtcctgc aactttatcc gcctccatcc agtctattaa ttgttgccgg gaagctagag    6000
taagtagttc gccagttaat agtttgcgca acgttgttgc cattgctaca ggcatcgtgg    6060
tgtcacgctc gtcgtttggt atggcttcat tcagctccgg ttcccaacga tcaaggcgag    6120
ttacatgatc ccccatgttg tgcaaaaaag cggttagctc cttcggtcct ccgatcgttg    6180
tcagaagtaa gttggccgca gtgttatcac tcatggttat ggcagcactg cataattctc    6240
ttactgtcat gccatccgta agatgctttt ctgtgactgg tgagtactca accaagtcat    6300
tctgagaata gtgtatgcgg cgaccgagtt gctcttgccc ggcgtcaata cgggataata    6360
ccgcgccaca tagcagaact ttaaaagtgc tcatcattgg aaaacgttct cggggcgaa    6420 aactctcaag gatcttaccg ctgttgagat ccagttcgat gtaacccact cgtgcaccca    6480
actgatcttc agcatctttt actttcacca gcgtttctgg gtgagcaaaa acaggaaggc    6540
aaaatgccgc aaaaagggg ataagggcga cacggaaatg ttgaatactc atactcttcc    6600
tttttcaata ttattgaagc atttatcagg gttattgtct catgagcgga tacatatttg    6660
aatgtattta gaaaaataaa caataggggg ttccgcgcac atttccccga aaagtgccac    6720
ctgacgtcta agaaaccatt attatcatga cattaaccta taaaaatagg cgtatcacga    6780
ggccctttcg tc                                                       6792
```

<210> SEQ ID NO 11
<211> LENGTH: 6702
<212> TYPE: DNA
<213> ORGANISM: Artificial Sequence
<220> FEATURE:
<223> OTHER INFORMATION: construct pINT-malE-MsgalT8

<400> SEQUENCE: 11

```
tcgcgcgttt cggtgatgac ggtgaaaacc tctgacacat gcagctcccg gagacggtca     60
cagcttgtct gtaagcggat gccgggagca gacaagcccg tcaggcgcg tcagcgggtg    120 ttggcgggtg tcgggctgg cttaactatg cggcatcaga gcagattgta ctgagagtgc    180
```

```
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgaagatcct ttgatctttt    420
ctacggggtc tgacgctcag tggaacgaaa actcacgtta agggattttg gtcatgagat    480
tatcaaaaag gatcttcacc tagatccttt taaactagtg aagttaccat cacggaaaaa    540
ggttatgctg cttttaagac ccactttcac atttaagttg ttttttctaat ccgcatatga    600 tcaattcaag gccgaataag aaggctggct ctgcaccttg gtgatcaaat aattcgatag    660
cttgtcgtaa taatggcggc atactatcag tagtaggtgt ttcccttttct tctttagcga    720 cttgatgctc ttgatcttcc aatacgcaac ctaaagtaaa atgccccact gcgctgagtg    780
catataatgc attctctagt gaaaaacctt gttggcataa aaaggctaat tgattttcga    840
gagtttcata ctgtttttct gtaggccgtg tacctaaatg tacttttgct ccatcgcgat    900
gacttagtaa agcacatcta aaacttttag cgttattacg taaaaaatct tgccagcttt    960
ccccttctaa agggcaaaag tgagtatggt gcctatctaa catctcaatg ctaaggcgt   1020 cgagcaaagc ccgcttattt tttacatgcc aatacaatgt aggctgctct acacctagct   1080
tctgggcgag tttacggggt tgttaaacctt cgattccgac ctcattaagc agctctaatg   1140
cgctgttaat cactttactt ttatctaaac gagacatact cttccttttt caatattatt   1200
gaagcattta tcagggttat tgtctcatga gcggatacat atttgaatgt atttagaaaa   1260
ataaacaaat gggggttccg cgcacatttc cccgaaaagt gccacctgaa attggcaga   1320 tgattaattc ctaattttg ttgacactct atcattgata gagttatttt accactccct   1380
atcagtgata gagaaaagtg aaatgaatag ttcgacaaaa atctagaaat aatttttgttt   1440 aactttaaga aggagatata caaatgaaaa tcgaagaagg taaactggta atctggatta   1500
acggcgataa aggctataac ggtctcgctg aagtcggtaa gaaattcgag aaagataccg   1560
gaattaaagt caccgttgag catccggata aactggaaga gaaattccca caggttgcgg   1620
caactggcga tggcccctgac attatcttct gggcacacga ccgctttggt ggctacgctc   1680
aatctggcct gttggctgaa atcaccccgg acaaagcgtt ccaggacaag ctgtatccgt   1740
ttacctggga tgccgtacgt tacaacggca agctgattgc ttacccgatc gctgttgaag   1800
cgttatcgct gatttataac aaagatctgc tgccgaaccc gccaaaaacc tgggaagaga   1860
tcccggcgcg ggataaagaa ctgaaagcga aggtaagag cgcgctgatg ttcaacctgc   1920
aagaaccgta cttcacctgg ccgctgattg ctgctgacgg gggttatgcg ttcaagtatg   1980
aaaacggcaa gtacgacatt aaagacgtgg gcgtggataa cgctggcgcg aaagcgggtc   2040
tgaccttcct ggttgacctg attaaaaaca aacacatgaa tgcagacacc gattactcca   2100
tcgcagaagc tgcctttaat aaaggcgaaa cagcgatgac catcaacggc ccgtgggcat   2160
ggtccaacat cgacaccagc aaagtgaatt atggtgtaac ggtactgccg accttcaagg   2220
gtcaaccatc caaaccgttc gttggcgtgc tgagcgcagg tattaacgcc gccagtccga   2280
acaaagagct ggcaaagag ttcctcgaaa actatctgct gactgatgaa ggtctggaag   2340
cggttaataa agacaaaccg ctgggtgccg tagcgctgaa gtcttacgag gaagagttgg   2400
cgaaagatcc acgtattgcc gccaccatgg aaaacgccca gaaaggtgaa atcatgccga   2460
acatcccgca gatgtccgct ttctggtatg ccgtgcgtac tgcggtgatc aacgccgcca   2520
gcggtcgtca gactgtcgat gaagcccctga agacgcgca gactatggat gaaatcaaac   2580
```

```
tgtcggtggt tatgccgtat tacaaacgtc tgcgtgaatt tatgcgtgtc ctgccgctga   2640
atgcccgctt ctttagccgt catgaatatg aagtggttct gagtctggac gaaccgtccg   2700
aagaagccga tctgctgcgt gtcctgcgcg acttcccgtc tattcgttgg cgcgttctgg   2760
tcaatgacct ggatcacccg tggcgtccgc cgtgccgtgc actgaacgtt ggcatccgta   2820
atgctctggg tgaaaacgtc ctggtcgtga gcccggaatc tgcgtttgtg accgatgttc   2880
cggcacgcgc tctggatcat attgcagcaa acccgggtac cgcagctctg ggtcacgttt   2940
gttttgcaac gttcgatgcg ctggaagccc gtcagggcag cctggaaaaa acgtgcgctc   3000
cgccgtggaa tctgtatggt tctatctgtg tcccgcgtga acgtctggca cgtgtgcatg   3060
gctacgacga aagcttcgat cgctggggcg gtgatgacga taacctgcgt attcgcctga   3120
tgcagaccga aacgtatctg catccgctgg acgatatgcg catcctgcac ctgagttttg   3180
aagcccgtaa agtgcgtcaa gcagcagaac cgccgtcccc ggaatacgca gaacgtattt   3240
tccagccggt gtcaccgcaa gcaaatccgg cggttgggg tgaatcgttt cagcgcgttg   3300
cgttcgattg gcgtcgccaa tgagcggccg cgtcgacacg caaaaaggcc atccgtcagg   3360
atggccttct gcttaattat ctagatgcct ggcagtttat ggcgggcgtc ctgcccgcca   3420
ccctccgggc cgttgcttcg caacgttcaa atccgctccc ggcggatttg tcctactcag   3480
gagagcgttc accgacaaac aacagataaa acgaaaggcc cagtctttcg actgagcctt   3540
tcgttttatt tgatgcctgg cagttcccta ctctcgcatg gggagacccc acactaccat   3600
catgtatgaa tatcctcctt agttcctatt ccgaagggta atggcatcag gaatggcga   3660 acgcgctccc cacactacca tcatgtatga atatcctcct tagttcctat tccgaagttc   3720
ctattctcta gaaagtatag gaacttcggt ggaacgacgc gtaactcacg ttaagggatt   3780
ttggtcatga tcagcacgtg ttgacaatta atcatcggca tagtatatcg gcatagtata   3840
atacgacaag gtgaggaact aaaccatggc caagttgacc agtgccgttc cggtgctcac   3900
cgcgcgcgac gtcgccggag cggtcgagtt ctggaccgac cggctcgggt ctcccggga   3960 cttcgtggag gacgacttcg ccggtgtggt ccgggacgac gtgaccctgt tcatcagcgc   4020
ggtccaggac caggtggtgc cggacaacac cctggcctgg gtgtgggtgc gcggcctgga   4080
cgagctgtac gccgagtggt cggaggtcgt gtccacgaac ttccgggacg cctccgggcc   4140
ggccatgacc gagatcggcg agcagccgtg ggggcggag ttcgccctgc gcgacccggc   4200
cggcaactgc gtgcacttcg tggccgagga gcaggactga gtggcagggc ggggcgtaag   4260
gcgcgccatt taaatgaagt tcctattccg aagttcctat tctctagaaa gtataggaac   4320
ttcgaagcag ctccagccta cacaatcgct caagacggaa cccgcgcttg caggaaagt   4380 aataggata gcagctccag cctacacaat cgctcaagac gtgtaatgct gcacaataac   4440
cctgctgcag aggcctgcat gcaagcttgg cgtaatcatg gtcatagctg tttcctgtgt   4500
gaaattgtta tccgctcaca attccacaca acatacgagc cggaagcata agtgtaaag   4560 cctggggtgc ctaatgagtg agctaactca cattaattgc gttgcgctca ctgcccgctt   4620
tccagtcggg aaacctgtcg tgccagctgc attaatgaat cggccaacgc gcggggagag   4680
gcggtttgcg tattgggcgc tcttccgctt cctcgctcac tgactcgctg cgctcggtcg   4740
ttcggctgcg gcgagcggta tcagctcact caaaggcggt aatacggtta ccacagaat   4800 caggggataa cgcaggaaag aacatgtgag caaaaggcca gcaaaggcc aggaaccgta   4860 aaaaggccgc gttgctggcg tttttccata ggctccgccc cctgacgag catcacaaaa   4920
```

```
atcgacgctc aagtcagagg tggcgaaacc cgacaggact ataaagatac caggcgtttc    4980
cccctggaag ctccctcgtg cgctctcctg ttccgaccct gccgcttacc ggatacctgt    5040
ccgcctttct cccttcggga agcgtggcgc tttctcatag ctcacgctgt aggtatctca    5100
gttcggtgta ggtcgttcgc tccaagctgg gctgtgtgca cgaaccccccc gttcagcccg   5160 accgctgcgc cttatccggt aactatcgtc ttgagtccaa cccggtaaga cacgacttat    5220
cgccactggc agcagccact ggtaacagga ttagcagagc gaggtatgta ggcggtgcta    5280
cagagttctt gaagtggtgg cctaactacg gctacactag aagaacagta tttggtatct    5340
gcgctctgct gaagccagtt accttcggaa aaagagttgg tagctcttga tccggcaaac    5400
aaaccaccgc tggtagcggt ggtttttttg tttgcaagca gcagattacg cgcagaaaaa    5460
aaggatctca agaagatcct ttgatctttt ctacggggtc tgacgctcag tggaacgaaa    5520
actcacgtta agggattttg gtcatgagat tatcaaaaag gatcttcacc tagatccttt    5580
taaattaaaa atgaagtttt aaatcaatct aaagtatata tgagtaaact tggtctgaca    5640
gttaccaatg cttaatcagt gaggcaccta tctcagcgat ctgtctattt cgttcatcca    5700
tagttgcctg actccccgtc gtgtagataa ctacgatacg ggagggctta ccatctggcc    5760
ccagtgctgc aatgataccg cgagacccac gctcaccggc tccagattta tcagcaataa    5820
accagccagc cggaagggcc gagcgcagaa gtggtcctgc aactttatcc gcctccatcc    5880
agtctattaa ttgttgccgg gaagctagag taagtagttc gccagttaat agtttgcgca    5940
acgttgttgc cattgctaca ggcatcgtgg tgtcacgctc gtcgtttggt atggcttcat    6000
tcagctccgg ttcccaacga tcaaggcgag ttacatgatc ccccatgttg tgcaaaaaag    6060
cggttagctc cttcggtcct ccgatcgttg tcagaagtaa gttggccgca gtgttatcac    6120
tcatggttat ggcagcactg cataattctc ttactgtcat gccatccgta agatgctttt    6180
ctgtgactgg tgagtactca accaagtcat tctgagaata gtgtatgcgg cgaccgagtt    6240
gctcttgccc ggcgtcaata cgggataata ccgcgccaca tagcagaact ttaaaagtgc    6300
tcatcattgg aaaacgttct cggggcgaaa actctcaag gatcttaccg ctgttgagat    6360
ccagttcgat gtaacccact cgtgcaccca actgatcttc agcatctttt actttcacca    6420
gcgtttctgg gtgagcaaaa acaggaaggc aaaatgccgc aaaaaaggga taagggcga    6480 cacgaaaatg ttgaatactc atactcttcc ttttttcaata ttattgaagc atttatcagg    6540
gttattgtct catgagcgga tacatatttg aatgtattta gaaaaataaa caaataggggg   6600 ttccgcgcac atttccccga aaagtgccac ctgacgtcta agaaaccatt attatcatga    6660
cattaaccta taaaaatagg cgtatcacga ggccctttcg tc                       6702

<210> SEQ ID NO 12
<211> LENGTH: 6777
<212> TYPE: DNA
<213> ORGANISM: Artificial Sequence
<220> FEATURE:
<223> OTHER INFORMATION: construct pINT-malE-KdgalT10

<400> SEQUENCE: 12
tcgcgcgttt cggtgatgac ggtgaaaacc tctgacacat gcagctcccg gagacggtca      60
cagcttgtct gtaagcggat gccggagca gacaagcccg tcagggcgcg tcagcgggtg     120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aaggggcgatc ggtgcgggcc tcttcgctat    300
```

```
tacgccagct ggcgaaaggg ggatgtgctg caaggcgatt aagttgggta acgccagggt    360
tttcccagtc acgacgttgt aaaacgacgg ccagtgaatt cgaagatcct ttgatctttt    420
ctacggggtc tgacgctcag tggaacgaaa actcacgtta agggattttg gtcatgagat    480
tatcaaaaag gatcttcacc tagatccttt taaactagtg aagttaccat cacggaaaaa    540
ggttatgctg cttttaagac ccactttcac atttaagttg tttttctaat ccgcatatga    600
tcaattcaag gccgaataag aaggctggct ctgcaccttg gtgatcaaat aattcgatag    660
cttgtcgtaa taatggcggc atactatcag tagtaggtgt ttcccttttct tctttagcga    720 cttgatgctc ttgatcttcc aatacgcaac ctaaagtaaa atgccccact cgcctgagtg    780
catataatgc attctctagt gaaaaacctt gttggcataa aaaggctaat tgattttcga    840
gagtttcata ctgtttttct gtaggccgtg tacctaaatg tacttttgct ccatcgcgat    900
gacttagtaa agcacatcta aaacttttag cgttattacg taaaaaatct tgccagcttt    960
ccccttctaa agggcaaaag tgagtatggt gcctatctaa catctcaatg gctaaggcgt   1020
cgagcaaagc ccgcttattt tttacatgcc aatacaatgt aggctgctct acacctagct   1080
tctgggcgag tttacgggtt gttaaacctt cgattccgac ctcattaagc agctctaatg   1140
cgctgttaat cactttactt ttatctaaac gagacatact cttcctttttt caatattatt   1200 gaagcattta tcagggttat tgtctcatga gcggatacat atttgaatgt atttagaaaa   1260
ataaacaaat aggggttccg cgcacatttc cccgaaaagt gccacctgaa attggccaga   1320
tgattaattc ctaattttttg ttgacactct atcattgata gagttatttt accactccct   1380
atcagtgata gagaaaagtg aaatgaatag ttcgacaaaa atctagaaat aattttgttt   1440
aactttaaga aggagatata caatgaaaa tcgaagaagg taaactggta atctggatta   1500
acggcgataa aggctataac ggtctcgctg aagtcggtaa gaaattcgag aaagataccg   1560
gaattaaagt caccgttgag catccggata aactggaaga gaaattccca caggttgcgg   1620
caactggcga tggccctgac attatcttct gggcacacga ccgctttggt ggctacgctc   1680
aatctggcct gttggctgaa atcacccccgg acaaagcgtt ccaggacaag ctgtatccgt   1740
ttacctggga tgccgtacgt tacaacggca agctgattgc ttacccgatc gctgttgaag   1800
cgttatcgct gatttataac aaagatctgc tgccgaaccc gccaaaaacc tgggaagaga   1860 tccccggcgct ggataaagaa ctgaaagcga aggtaagag cgcgctgatg ttcaacctgc   1920
aagaaccgta cttcacctgg ccgctgattg ctgctgacgg gggttatgcg ttcaagtatg   1980
aaaacggcaa gtacgacatt aaagacgtgg gcgtggataa cgctggcgcg aaagcgggtc   2040
tgaccttcct ggttgaccta ttaaaaaca acacatgaa tgcagacacc gattactcca   2100
tcgcagaagc tgccttttaat aaaggcgaaa cagcgatgac catcaacggc ccgtgggcat   2160
ggtccaacat cgacaccagc aaagtgaatt atggtgtaac ggtactgccg accttcaagg   2220
gtcaaccatc caaaccgttc gttggcgtgc tgagcgcagg tattaacgcc gccagtccga   2280
acaaagagct ggcaaaagag ttcctcgaaa actatctgct gactgatgaa ggtctggaag   2340
cggttaataa agacaaaccg ctgggtgccg tagcgctgaa gtcttacgag gaagagttgg   2400
cgaaagatcc acgtattgcc gccaccatgg aaaacgccca gaaaggtgaa atcatgccga   2460
acatcccgca gatgtccgct ttctggtatg ccgtgcgtac tgcggtgatc aacgccgcca   2520
gcggtcgtca gactgtcgat gaagcccctga aagacgcgca gactatggaa aactatgtcg   2580
tctctatccg caccgcagcc caacgccgcc agcatgtcgc cgccgaattc aataagcacc   2640
```

```
aaatcgcctt tcatttcttt gatgcggtga ccccggaaac gctggcggaa agcatcgcag   2700
aacactgccc gaacctggca gacgcctttc tgaccggcgg tgaaaagggc tgtttcatgt   2760
ctcatgtctg cctgtgggca aaatgtgtgg ctgatgacct gccgtatatt ggcatctttg   2820
aagatgacgt tattttcggt cagaacagct ctcgttttct gaatgatacc aaatggctgg   2880
acgaacgttt tcagaaccaa tcattcatta ccgcatggaa acgtttctg aaggcgaacc    2940 cggttgccct gagcaaatct ggcgtccgtc cgttcaatgg tcgtaagatc ctgcgcctgc   3000
agagttttgg cttcggtacc gcggcctatc tgatttccca gcaaaccgca atcacgctgc   3060
tgaattggat tcgcgaagtc gctccggaaa aactggaacc gattgataac atgctgttta   3120
atgcagcttc agaaattccg gaaatccaga tgtaccaaat ctcgccggcc ctgtgcattc   3180
aggaactgca actgaaccgc gcagatagtt ccctgtcatc gaccctggaa gacggtcgtc   3240
tggcacgtca ccagcaactg gatggcggta aacccagcc ggaacagacg caagaaaacc    3300
gtaacatctt cgcatgggct aagaacaaga tcgtgaagga atacaagcgc gttaaacgtc   3360
gctggacgga tgacaaaaag attgttccgt tcaaatgagc ggccgcgtcg acacgcaaaa   3420
aggccatccg tcaggatggc cttctgctta attatctaga tgcctggcag tttatggcgg   3480
gcgtcctgcc cgccaccctc cgggccgttg cttcgcaacg ttcaaatccg ctcccggcgg   3540
atttgtccta ctcaggagag cgttcaccga caaacaacag ataaaacgaa aggcccagtc   3600
tttcgactga gcctttcgtt ttatttgatg cctggcagtt ccctactctc gcatggggag   3660
accccacact accatcatgt atgaatatcc tccttagttc ctattccgaa gggtaatggc   3720
atcagggaat ggcgaacgcg ctccccacac taccatcatg tatgaatatc ctccttagtt   3780
cctattccga agttcctatt ctctagaaag tataggaact tcggtggaac gacgcgtaac   3840
tcacgttaag ggattttggt catgatcagc acgtgttgac aattaatcat cggcatagta   3900
tatcggcata gtataatacg acaaggtgag gaactaaacc atggccaagt tgaccagtgc   3960
cgttccggtg ctcaccgcgc gcgacgtcgc cggagcggtc gagttctgga ccgaccggct   4020
cgggttctcc cggacttcg tggaggacga cttcgccggt gtggtccggg acgacgtgac    4080
cctgttcatc agcgcggtcc aggaccaggt ggtgccggac aacacctg cctgggtgtg     4140 ggtgcgcggc ctggacgagc tgtacgccga gtggtcggag gtcgtgtcca cgaacttccg   4200
ggacgcctcc gggccggcca tgaccgagat cggcgagcag ccgtggggc gggagttcgc    4260 cctgcgcgac ccggccggca actgcgtgca cttcgtggcc gaggagcagg actgagtggc   4320
agggcggggc gtaaggcgcg ccatttaaat gaagttccta ttccgaagtt cctattctct   4380
agaaagtata ggaacttcga agcagctcca gcctacacaa tcgctcaaga cggaacccgc   4440
gcttggcagg aaagtaatag ggatagcagc tccagcctac acaatcgctc aagacgtgta   4500
atgctgcaca ataaccctgc tgcagaggcc tgcatgcaag cttggcgtaa tcatggtcat   4560
agctgtttcc tgtgtgaaat tgttatccgc tcacaattcc acacaacata cgagccggaa   4620
gcataaagtg taaagcctgg ggtgcctaat gagtgagcta actcacatta attgcgttgc   4680
gctcactgcc cgctttccag tcgggaaacc tgtcgtgcca gctgcattaa tgaatcggcc   4740
aacgcgcggg gagaggcggt ttgcgtattg gcgctcttc cgcttcctcg ctcactgact    4800
cgctgcgctc ggtcgttcgg ctgcggcgag cggtatcagc tcactcaaag gcggtaatac   4860
ggttatccac agaatcaggg gataacgcag gaaagaacat gtgagcaaaa ggccagcaaa   4920
aggccaggaa ccgtaaaaag gccgcgttgc tggcgttttt ccataggctc cgcccccctg   4980
acgagcatca caaaaatcga cgctcaagtc agaggtggcg aaacccgaca ggactataaa   5040
```

```
gataccaggc gtttcccct  ggaagctccc tcgtgcgctc tcctgttccg accctgccgc    5100
ttaccggata cctgtccgcc tttctccctt cgggaagcgt ggcgctttct catagctcac    5160
gctgtaggta tctcagttcg gtgtaggtcg ttcgctccaa gctgggctgt gtgcacgaac    5220
cccccgttca gcccgaccgc tgcgccttat ccggtaacta tcgtcttgag tccaacccgg    5280
taagacacga cttatcgcca ctggcagcag ccactggtaa caggattagc agagcgaggt    5340
atgtaggcgg tgctacagag ttcttgaagt ggtggcctaa ctacggctac actagaagaa    5400
cagtatttgg tatctgcgct ctgctgaagc cagttacctt cggaaaaaga gttggtagct    5460
cttgatccgg caaacaaacc accgctggta gcggtggttt ttttgtttgc aagcagcaga    5520
ttacgcgcag aaaaaaagga tctcaagaag atcctttgat cttttctacg ggtctgacg    5580 ctcagtggaa cgaaaactca cgttaaggga ttttggtcat gagattatca aaaggatct    5640 tcacctagat ccttttaaat taaaaatgaa gttttaaatc aatctaaagt atatatgagt    5700
aaacttggtc tgacagttac caatgctta  tcagtgaggc acctatctca gcgatctgtc    5760
tatttcgttc atccatagtt gcctgactcc ccgtcgtgta gataactacg atacgggagg    5820
gcttaccatc tggccccagt gctgcaatga taccgcgaga cccacgctca ccggctccag    5880
atttatcagc aataaaccag ccagccggaa gggccgagcg cagaagtggt cctgcaactt    5940
tatccgcctc catccagtct attaattgtt gccgggaagc tagagtaagt agttcgccag    6000
ttaatagttt gcgcaacgtt gttgccattg ctacaggcat cgtggtgtca cgctcgtcgt    6060
ttggtatggc ttcattcagc tccggttccc aacgatcaag gcgagttaca tgatccccca    6120
tgttgtgcaa aaaagcggtt agctccttcg gtcctccgat cgttgtcaga agtaagttgg    6180
ccgcagtgtt atcactcatg gttatggcag cactgcataa ttctcttact gtcatgccat    6240
ccgtaagatg cttttctgtg actggtgagt actcaaccaa gtcattctga aatagtgta    6300 tgcggcgacc gagttgctct tgcccggcgt caatacggga taataccgcg ccacatagca    6360
gaactttaaa agtgctcatc attggaaaac gttcttcggg gcgaaaactc tcaaggatct    6420
taccgctgtt gagatccagt tcgatgtaac ccactcgtgc acccaactga tcttcagcat    6480
cttttacttt caccagcgtt tctgggtgag caaaaacagg aaggcaaaat gccgcaaaaa    6540
agggaataag ggcgacacgg aaatgttgaa tactcatact cttcctttt  caatattatt    6600 gaagcattta tcagggttat tgtctcatga gcggatacat atttgaatgt atttagaaaa    6660
ataaacaaat aggggttccg cgcacatttc cccgaaaagt gccacctgac gtctaagaaa    6720
ccattattat catgacatta acctataaaa ataggcgtat cacgaggccc tttcgtc       6777
```

<210> SEQ ID NO 13
<211> LENGTH: 6786
<212> TYPE: DNA
<213> ORGANISM: Artificial Sequence
<220> FEATURE:
<223> OTHER INFORMATION: construct pINT-malE-gatD

<400> SEQUENCE: 13

```
tcgcgcgttt cggtgatgac ggtgaaaacc tctgacacat gcagctcccg gagacggtca     60
cagcttgtct gtaagcggat gccggagca  gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
```

```
tacgccagct ggcgaaaggg ggatgtgctg caaggcgatt aagttgggta acgccagggt      360
tttcccagtc acgacgttgt aaaacgacgg ccagtgaatt cgaagatcct ttgatctttt      420
ctacggggtc tgacgctcag tggaacgaaa actcacgtta agggattttg gtcatgagat      480
tatcaaaaag gatcttcacc tagatccttt taaactagtg aagttaccat cacggaaaaa      540
ggttatgctg cttttaagac ccactttcac atttaagttg tttttctaat ccgcatatga      600
tcaattcaag gccgaataag aaggctggct ctgcaccttg gtgatcaaat aattcgatag      660
cttgtcgtaa taatggcggc atactatcag tagtaggtgt ttcccttttct tctttagcga      720 cttgatgctc ttgatcttcc aatacgcaac ctaaagtaaa atgccccact cgcctgagtg      780
catataatgc attctctagt gaaaaacctt gttggcataa aaaggctaat tgattttcga      840
gagtttcata ctgttttttct gtaggccgtg tacctaaatg tacttttgct ccatcgcgat      900
gacttagtaa agcacatcta aaacttttag cgttattacg taaaaaatct tgccagcttt      960 cccttctaa agggcaaaag tgagtatggt gcctatctaa catctcaatg gctaaggcgt     1020
cgagcaaagc ccgcttattt tttacatgcc aatacaatgt aggctgctct acacctagct     1080
tctgggcgag tttacggggtt gttaaacctt cgattccgac ctcattaagc agctctaatg     1140
cgctgttaat cactttactt ttatctaaac gagacatact cttcctttttt caatattatt     1200 gaagcattta tcagggttat tgtctcatga gcggatacat atttgaatgt atttagaaaa     1260
ataaacaaat aggggttccg cgcacatttc cccgaaaagt gccacctgaa attggccaga     1320
tgattaattc ctaattttgg ttgacactct atcattgata gagttatttt accactccct     1380
atcagtgata gagaaaagtg aaatgaatag ttcgacaaaa atctagaaat aattttgttt     1440
aactttaaga aggagatata caaatgaaaa tcgaagaagg taaactggta atctggatta     1500
acggcgataa aggctataac ggtctcgctg aagtcggtaa gaaattcgag aaagataccg     1560
gaattaaagt caccgttgag catccggata aactggaaga gaaattccca caggttgcgg     1620
caactggcga tggccctgac attatcttct gggcacacga ccgctttggt ggctacgctc     1680
aatctggcct gttggctgaa atcaccccgg acaaagcgtt ccaggacaag ctgtatccgt     1740
ttacctggga tgccgtacgt tacaacggca agctgattgc ttacccgatc gctgttgaag     1800
cgttatcgct gatttataac aaagatctgc tgccgaaccc gccaaaaacc tgggaagaga     1860
tcccggcgct ggataaagaa ctgaaagcga aggtaagag cgcgctgatg ttcaacctgc     1920
aagaaccgta cttcacctgg ccgctgattg ctgctgacgg gggttatgcg ttcaagtatg     1980
aaaacggcaa gtacgacatt aaagacgtgg gcgtggataa cgctggcgcg aaagcgggtc     2040
tgaccttcct ggttgacctg attaaaaaca acacatgaa tgcagacacc gattactcca     2100
tcgcagaagc tgccttttaat aaaggcgaaa cagcgatgac catcaacggc ccgtgggcat     2160
ggtccaacat cgacaccagc aaagtgaatt atggtgtaac ggtactgccg accttcaagg     2220
gtcaaccatc caaaccgttc gttggcgtgc tgagcgcagg tattaacgcc gccagtccga     2280
acaaagagct ggcaaaagag ttcctcgaaa actatctgct gactgatgaa ggtctggaag     2340
cggttaataa agacaaaccg ctgggtgccg tagcgctgaa gtcttacgag gaagagttgg     2400
cgaaagatcc acgtattgcc gccaccatgg aaaacgccca gaaaggtgaa atcatgccga     2460
acatcccgca gatgtccgct ttctggtatg ccgtgcgtac tgccggtgatc aacgccgcca     2520 gcggtcgtca gactgtcgat gaagccctga aagacgcgca gactatgtcc tcagcttttcc     2580 attacgtcat tagcctggca tcggcagttg aacgccgtca gcacattagc gaacagtttt     2640
cccaatacga cattccgttt cagttttttcg atgcgatcag tccgtccccg ctgctgaacc     2700
```

```
agctggtgtc tcaattttc ccgtccctgg ccgatagctc tctgaccgac ggcgaaaaag    2760
gttgctttat ttcacatctg tcgctgtggc acaagtgtgt tgaaaagaac ctgccgtata    2820
ttgtggtttt tgaagatgac atcctgctgg gcaagaatgc agataaattc ctgattgaag    2880
acgaatggtt tttctctcgt tttaacacga atgatgtctt catcgtgcgc ctggaaacct    2940
ttctgcagaa agtgtattgc caaccgagct acatcaagtc ttactacaac cgtgaactgc    3000
tgaccctgaa aagcacgcat ttcggcaccg caggttatat tatcagtctg ggtgcggcca    3060
agtttctgct gtccctgttc aacaaaatgc acattgaaga agttgctccg atcgatgaac    3120
tgctgtttaa taagttcctg gaacgcaaag acttttacggt ctaccagttc agtccggcac    3180
tgtgcattca ggaactgcaa ctgaacaaat cagatgctgt cctgctgtcg caactggaac    3240
tggaacgtag caaatgtcgc attatgaccg aatctcgtat cggccgcgaa aagaaaaaac    3300
tgaaggataa gatcatccat gttctgacga agccgaaacg tatgctggaa aagaaacgtc    3360
agcgcaatga agacaagaaa atcaccatga ttatcgaatt tgaatgagcg gccgcgtcga    3420
cacgcaaaaa ggccatccgt caggatggcc ttctgcttaa ttatctagat gcctggcagt    3480
ttatggcggg cgtcctgccc gccaccctcc gggccgttgc ttcgcaacgt tcaaatccgc    3540
tcccggcgga tttgtcctac tcaggagagc gttcaccgac aaacaacaga taaaacgaaa    3600
ggcccagtct ttcgactgag cctttcgttt tatttgatgc ctggcagttc cctactctcg    3660
catggggaga ccccacacta ccatcatgta tgaatatcct ccttagttcc tattccgaag    3720
ggtaatggca tcagggaatg cgaacgcgc tccccacact accatcatgt atgaatatcc    3780
tccttagttc ctattccgaa gttcctattc tctagaaagt ataggaactt cggtggaacg    3840
acgcgtaact cacgttaagg gattttggtc atgatcagca cgtgttgaca attaatcatc    3900
ggcatagtat atcggcatag tataatacga caaggtgagg aactaaacca tggccaagtt    3960
gaccagtgcc gttccggtgc tcaccgcgcg cgacgtcgcc ggagcggtcg agttctggac    4020
cgaccggctc gggttctccc gggacttcgt ggaggacgac ttcgccggtg tggtccggga    4080
cgacgtgacc ctgttcatca gcgcggtcca ggaccaggtg gtgccggaca cacccctggc    4140
ctgggtgtgg gtgcgcggcc tggacgagct gtacgccgag tggtcggagg tcgtgtccac    4200
gaacttccgg gacgcctccg ggccggccat gaccgagatc ggcgagcagc gtgggggcg    4260 ggagttcgcc ctgcgcgacc cggccggcaa ctgcgtgcac ttcgtggccg aggagcagga    4320
ctgagtggca gggcggggcg taaggcgcgc catttaaatg aagttcctat tccgaagttc    4380
ctattctcta gaaagtatag gaacttcgaa gcagctccag cctacacaat cgctcaagac    4440
ggaacccgcg cttggcagga aagtaatagg gatagcagct ccagcctaca caatcgctca    4500
agacgtgtaa tgctgcacaa taaccctgct gcagaggcct gcatgcaagc ttggcgtaat    4560
catggtcata gctgtttcct gtgtgaaatt gttatccgct cacaattcca cacaacatac    4620
gagccggaag cataaagtgt aaagcctggg gtgcctaatg agtgagctaa ctcacattaa    4680
ttgcgttgcg ctcactgccc gctttccagt cgggaaacct gtcgtgccag ctgcattaat    4740
gaatcggcca acgcgcgggg agaggcggtt tgcgtattgg gcgctcttcc gcttcctcgc    4800
tcactgactc gctgcgctcg tcgttcggc tgcggcgagc ggtatcagct cactcaaagg    4860
cggtaatacg gttatccaca gaatcagggg ataacgcagg aaagaacatg tgagcaaaag    4920
gccagcaaaa ggccaggaac cgtaaaaagg ccgcgttgct ggcgtttttc cataggctcc    4980
gcccccctga cgagcatcac aaaaatcgac gctcaagtca gaggtggcga aacccgacag    5040
```

| | |
|---|---:|
| gactataaag ataccaggcg tttcccctg gaagctccct cgtgcgctct cctgttccga | 5100 |
| ccctgccgct taccggatac ctgtccgcct ttctcccttc gggaagcgtg gcgctttctc | 5160 |
| atagctcacg ctgtaggtat ctcagttcgg tgtaggtcgt tcgctccaag ctgggctgtg | 5220 |
| tgcacgaacc ccccgttcag cccgaccgct gcgccttatc cggtaactat cgtcttgagt | 5280 |
| ccaacccggt aagacacgac ttatcgccac tggcagcagc cactggtaac aggattagca | 5340 |
| gagcgaggta tgtaggcggt gctacagagt tcttgaagtg gtggcctaac tacggctaca | 5400 |
| ctagaagaac agtatttggt atctgcgctc tgctgaagcc agttaccttc ggaaaaagag | 5460 |
| ttggtagctc ttgatccggc aaacaaacca ccgctggtag cggtggtttt tttgtttgca | 5520 |
| agcagcagat tacgcgcaga aaaaaggat ctcaagaaga tcctttgatc ttttctacgg | 5580 |
| ggtctgacgc tcagtggaac gaaaactcac gttaagggat tttggtcatg agattatcaa | 5640 |
| aaaggatctt cacctagatc cttttaaatt aaaaatgaag ttttaaatca atctaaagta | 5700 |
| tatatgagta aacttggtct gacagttacc aatgcttaat cagtgaggca cctatctcag | 5760 |
| cgatctgtct atttcgttca tccatagttg cctgactccc cgtcgtgtag ataactacga | 5820 |
| tacgggaggg cttaccatct ggccccagtg ctgcaatgat accgcgagac ccacgctcac | 5880 |
| cggctccaga tttatcagca ataaaccagc cagccggaag ggccgagcgc agaagtggtc | 5940 |
| ctgcaacttt atccgcctcc atccagtcta ttaattgttg ccgggaagct agagtaagta | 6000 |
| gttcgccagt taatagtttg cgcaacgttg ttgccattgc tacaggcatc gtggtgtcac | 6060 |
| gctcgtcgtt tggtatggct tcattcagct ccggttccca acgatcaagg cgagttacat | 6120 |
| gatccccat gttgtgcaaa aaagcggtta gctccttcgg tcctccgatc gttgtcagaa | 6180 |
| gtaagttggc cgcagtgtta tcactcatgg ttatggcagc actgcataat tctcttactg | 6240 |
| tcatgccatc cgtaagatgc ttttctgtga ctggtgagta ctcaaccaag tcattctgag | 6300 |
| aatagtgtat gcggcgaccg agttgctctt gcccggcgtc aatacgggat aataccgcgc | 6360 |
| cacatagcag aactttaaaa gtgctcatca ttggaaaacg ttcttcgggg cgaaaactct | 6420 |
| caaggatctt accgctgttg agatccagtt cgatgtaacc cactcgtgca cccaactgat | 6480 |
| cttcagcatc ttttactttc accagcgttt ctgggtgagc aaaaacagga aggcaaaatg | 6540 |
| ccgcaaaaaa gggaataagg gcgacacgga aatgttgaat actcatactc ttcctttttc | 6600 |
| aatattattg aagcatttat cagggttatt gtctcatgag cggatacata tttgaatgta | 6660 |
| tttagaaaaa taaacaaata ggggttccgc gcacatttcc ccgaaaagtg ccacctgacg | 6720 |
| tctaagaaac cattattatc atgacattaa cctataaaaa taggcgtatc acgaggccct | 6780 |
| ttcgtc | 6786 |

<210> SEQ ID NO 14
<211> LENGTH: 7506
<212> TYPE: DNA
<213> ORGANISM: Artificial Sequence
<220> FEATURE:
<223> OTHER INFORMATION: construct pINT-malE-BFgalT2

<400> SEQUENCE: 14

| | |
|---|---:|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |

```
tacgccagct ggcgaaaggg ggatgtgctg caaggcgatt aagttgggta acgccagggt    360
tttcccagtc acgacgttgt aaaacgacgg ccagtgaatt cgaagatcct ttgatctttt    420
ctacggggtc tgacgctcag tggaacgaaa actcacgtta agggattttg gtcatgagat    480
tatcaaaaag gatcttcacc tagatccttt taaactagtg aagttaccat cacggaaaaa    540
ggttatgctg cttttaagac ccactttcac atttaagttg tttttctaat ccgcatatga    600
tcaattcaag gccgaataag aaggctggct ctgcaccttg gtgatcaaat aattcgatag    660
cttgtcgtaa taatggcggc atactatcag tagtaggtgt ttcccttttct tctttagcga    720 cttgatgctc ttgatcttcc aatacgcaac ctaaagtaaa atgccccact cgctgagtg    780 catataatgc attctctagt gaaaaacctt gttggcataa aaaggctaat tgattttcga    840
gagtttcata ctgttttttct gtaggccgtg tacctaaatg tacttttgct ccatcgcgat    900
gacttagtaa agcacatcta aaactttta g cgttattacg taaaaaatct tgccagcttt    960 cccttctaa agggcaaaag tgagtatggt gcctatctaa catctcaatg gctaaggcgt   1020
cgagcaaagc ccgcttattt tttacatgcc aatacaatgt aggctgctct acacctagct   1080
tctgggcgag tttacgggtt gttaaacctt cgattccgac ctcattaagc agctctaatg   1140
cgctgttaat cactttactt ttatctaaac gagacatact cttcctttt t caatattatt   1200 gaagcattta tcagggttat tgtctcatga gcggatacat atttgaatgt atttagaaaa   1260
ataaacaaat aggggttccg cgcacatttc cccgaaaagt gccacctgaa attggccaga   1320
tgattaattc ctaattttg ttgacactct atcattgata gagttatttt accactccct   1380
atcagtgata gagaaaagtg aaatgaatag ttcgacaaaa atctagaaat aattttgttt   1440
aactttaaga aggagatata caaatgaaaa tcgaagaagg taaactggta atctggatta   1500
acggcgataa aggctataac ggtctcgctg aagtcggtaa gaaattcgag aaagataccg   1560
gaattaaagt caccgttgag catccggata aactggaaga gaaattccca caggttgcgg   1620
caactggcga tggccctgac attatcttct gggcacacga ccgctttggt ggctacgctc   1680
aatctggcct gttggctgaa atcacccccgg acaaagcgtt ccaggacaag ctgtatccgt   1740
ttacctggga tgccgtacgt tacaacggca agctgattgc ttacccgatc gctgttgaag   1800
cgttatcgct gatttataac aaagatctgc tgccgaaccc gccaaaaacc tgggaagaga   1860 tccccggcgct ggataaagaa ctgaaagcga aggtaagag cgcgctgatg ttcaacctgc   1920
aagaaccgta cttcacctgg ccgctgattg ctgctgacgg gggttatgcg ttcaagtatg   1980
aaaacggcaa gtacgacatt aaagacgtgg gcgtggataa cgctggcgcg aaagcgggtc   2040
tgaccttcct ggttgacctg attaaaaaca acacatgaa tgcagacacc gattactcca   2100
tcgcagaagc tgccttttaat aaaggcgaaa cagcgatgac catcaacggc ccgtgggcat   2160
ggtccaacat cgacaccagc aaagtgaatt atggtgtaac ggtactgccg accttcaagg   2220
gtcaaccatc caaaccgttc gttggcgtgc tgagcgcagg tattaacgcc gccagtccga   2280
acaaagagct ggcaaaagag ttcctcgaaa actatctgct gactgatgaa ggtctggaag   2340
cggttaataa agacaaaccg ctgggtgccg tagcgctgaa gtcttacgag gaagagttgg   2400
cgaaagatcc acgtattgcc gccaccatgg aaaacgccca gaaaggtgaa atcatgccga   2460
acatcccgca gatgtccgct ttctggtatg ccgtgcgtac tgcggtgatc aacgccgcca   2520
gcggtcgtca gactgtcgat gaagcccctga aagacgcgca gactatgaac gtgaataagc   2580
cgaccaccga aaagaaactg attgacctga acaacgacat tatccataac tttgatgtga   2640
```

```
gcattgtgat gagcttctat aagcgttaca ccgaatttcg caaagtgctg ccgcataacg      2700
cgccgtatct gcagcgtaat ggcattgaag tcattatcgt gctggatgac ccggatgaaa      2760
aaagcgaact gctgatgctg ctgcaaaact atccgttcat caattggaag ctgattatca      2820
acgaacgtaa acatgcaccg cgcaaccacg cttctgttct gaatgtcggt ctgaaacatg      2880
cgaccaaaaa gtatattctg cagatcgatc cggaagttga atttctgacg gatattatct      2940
ggcaaatgcg tgacgccatt gaaaaatatc cgatgcacta catcctggcg atgatggcct      3000
atgtcccgta cgaacaggaa ctgaccgaaa acaacatcaa ggaactggat ttcatcccgt      3060
ggggcaacct gatggtggaa cgcaatcatc tgtataaact gcacggttac gatgaaacct      3120
tcattacgtg gggcggtgaa gataacaata tgcgtgcgcg cctggacatg tcaggcatta      3180
aaaagtttat cctgccggaa gccaagacca tccatcgtga aaagaactat gatccgaatg      3240
aacgttcgaa gcgcattaat aaacacagta tctccgactg gcgcaaaatg aactacccgt      3300
cagaagcaat tgctaataag gatatctggg gctcggaatt caacaaagtt atttatgatt      3360
ggcaggacaa tcaatacgcc aaagatctgt gctataccta cctgcagcaa tttattggtt      3420
tcgaaatccg tcatccggcg gccttcgta aacgccacaa aaagattgtc ctgtgtcagg      3480
catataacga agaaaaactg atcgaaggct tcctgacgaa catggctaat tactttgatg      3540
gtattatcct gctggatgac gaaagtaccg atcgcacgtg ggacctggca atccatgata      3600
agatcatcct gaaggtgaaa aagaaacgtt ccggttttaa tgatctggaa accgcaata      3660 ttctgctgga cctgtcagcg ttttccagt cggaatggtt ttgcttcatg gatatcgacg      3720
aacgtttcga tgaacgcttt accaacttca gcgaattcga aaacaacaag gaaatccacg      3780
tggtttcttt tcgtggcgtg tatctgtgga atgatgaaca gagctacaag ggcgacattc      3840
cgaactctaa taaggtatc ctgaccgttt atcgtatgtt ccgcccgatt ggtcataccc      3900
acatcaacac gcataagaaa ctgcacttca ttgcgacgcc gtattttacc aacacgtggc      3960
agagtaatat cctgtttaag gattacggct ccatgaaaga aaatgaccgt attcgcaagt      4020
atgaacgcta catccaggaa gatcagcaaa aagacatgag ctctggttat gattacctgc      4080
tgaacagcga aaatctgtat caactggaca aaattgaaga atactgagcg gccgcgtcga      4140
cacgcaaaaa ggccatccgt caggatggcc ttctgcttaa ttatctagat gcctggcagt      4200
ttatggcggg cgtcctgccc gccaccctcc gggccgttgc ttcgcaacgt tcaaatccgc      4260
tcccggcgga tttgtcctac tcaggagagc gttcaccgac aaacaacaga taaaacgaaa      4320
ggcccagtct ttcgactgag cctttcgttt tatttgatgc ctggcagttc cctactctcg      4380
catggggaga ccccacacta ccatcatgta tgaatatcct ccttagttcc tattccgaag      4440
ggtaatggca tcagggaatg gcgaacgcgc tccccacact accatcatgt atgaatatcc      4500
tccttagttc ctattccgaa gttcctattc tctagaaagt ataggaactt cggtggaacg      4560
acgcgtaact cacgttaagg gattttggtc atgatcagca cgtgttgaca attaatcatc      4620
ggcatagtat atcggcatag tataatacga caaggtgagg aactaaacca tggccaagtt      4680
gaccagtgcc gttccggtgc tcaccgcgcg cgacgtcgcc ggagcggtcg agttctggac      4740
cgaccggctc gggttctccc gggacttcgt ggaggacgac ttcgccggtg tggtccggga      4800
cgacgtgacc ctgttcatca gcgcggtcca ggaccaggtg gtgccggaca cacccctggc      4860
ctgggtgtgg gtgcgcggcc tggacgagct gtacgccgag tggtcggagg tcgtgtccac      4920
gaacttccgg gacgcctccg ggccggccat gaccgagatc ggcgagcagc gtggggggcg      4980
ggagttcgcc ctgcgcgacc cggccggcaa ctgcgtgcac ttcgtggccg aggagcagga      5040
```

```
ctgagtggca gggcggggcg taaggcgcgc catttaaatg aagttcctat tccgaagttc   5100
ctattctcta gaaagtatag gaacttcgaa gcagctccag cctacacaat cgctcaagac   5160
ggaacccgcg cttggcagga aagtaatagg gatagcagct ccagcctaca caatcgctca   5220
agacgtgtaa tgctgcacaa taaccctgct gcagaggcct gcatgcaagc ttggcgtaat   5280
catggtcata gctgtttcct gtgtgaaatt gttatccgct cacaattcca cacaacatac   5340
gagccggaag cataaagtgt aaagcctggg gtgcctaatg agtgagctaa ctcacattaa   5400
ttgcgttgcg ctcactgccc gctttccagt cgggaaacct gtcgtgccag ctgcattaat   5460
gaatcggcca acgcgcgggg agaggcggtt tgcgtattgg gcgctcttcc gcttcctcgc   5520
tcactgactc gctgcgctcg gtcgttcggc tgcggcgagc ggtatcagct cactcaaagg   5580
cggtaatacg gttatccaca gaatcagggg ataacgcagg aaagaacatg tgagcaaaag   5640
gccagcaaaa ggccaggaac cgtaaaaagg ccgcgttgct ggcgtttttc cataggctcc   5700
gcccccctga cgagcatcac aaaaatcgac gctcaagtca gaggtggcga acccgacag   5760 gactataaag ataccaggcg tttccccctg gaagctccct cgtgcgctct cctgttccga   5820
ccctgccgct taccggatac ctgtccgcct ttctcccttc gggaagcgtg gcgctttctc   5880
atagctcacg ctgtaggtat ctcagttcgg tgtaggtcgt tcgctccaag ctgggctgtg   5940
tgcacgaacc ccccgttcag cccgaccgct gcgccttatc cggtaactat cgtcttgagt   6000
ccaacccggt aagacacgac ttatcgccac tggcagcagc cactggtaac aggattagca   6060
gagcgaggta tgtaggcggt gctacagagt tcttgaagtg gtggcctaac tacggctaca   6120
ctagaagaac agtatttggt atctgcgctc tgctgaagcc agttaccttc ggaaaaagag   6180
ttggtagctc ttgatccggc aaacaaacca ccgctggtag cggtggtttt tttgtttgca   6240
agcagcagat tacgcgcaga aaaaaggat ctcaagaaga tcctttgatc ttttctacgg   6300
ggtctgacgc tcagtggaac gaaaactcac gttaagggat tttggtcatg agattatcaa   6360
aaaggatctt cacctagatc cttttaaatt aaaaatgaag ttttaaatca atctaaagta   6420
tatatgagta aacttggtct gacagttacc aatgcttaat cagtgaggca cctatctcag   6480
cgatctgtct atttcgttca tccatagttg cctgactccc cgtcgtgtag ataactacga   6540
tacgggaggg cttaccatct ggccccagtg ctgcaatgat accgcgagac ccacgctcac   6600
cggctccaga tttatcagca ataaaccagc cagccggaag ggccgagcgc agaagtggtc   6660
ctgcaacttt atccgcctcc atccagtcta ttaattgttg ccgggaagct agagtaagta   6720
gttcgccagt taatagtttg cgcaacgttg ttgccattgc tacaggcatc gtggtgtcac   6780
gctcgtcgtt tggtatggct tcattcagct ccggttccca acgatcaagg cgagttacat   6840
gatcccccat gttgtgcaaa aaagcggtta gctccttcgg tcctccgatc gttgtcagaa   6900
gtaagttggc cgcagtgtta tcactcatgg ttatggcagc actgcataat tctcttactg   6960
tcatgccatc cgtaagatgc ttttctgtga ctggtgagta ctcaaccaag tcattctgag   7020
aatagtgtat gcggcgaccg agttgctctt gcccggcgtc aatacgggat aataccgcgc   7080
cacatagcag aactttaaaa gtgctcatca ttggaaaacg ttcttcgggg cgaaaactct   7140
caaggatctt accgctgttg agatccagtt cgatgtaacc cactcgtgca cccaactgat   7200
cttcagcatc ttttactttc accagcgttt ctgggtgagc aaaaacagga aggcaaaatg   7260
ccgcaaaaaa gggaataagg gcgacacgga aatgttgaat actcatactc ttcctttttc   7320
aatattattg aagcatttat cagggttatt gtctcatgag cggatacata tttgaatgta   7380
```

```
tttagaaaaa taaacaaata ggggttccgc gcacatttcc ccgaaaagtg ccacctgacg     7440
tctaagaaac cattattatc atgacattaa cctataaaaa taggcgtatc acgaggccct     7500
ttcgtc                                                                7506

<210> SEQ ID NO 15
<211> LENGTH: 6717
<212> TYPE: DNA
<213> ORGANISM: Artificial Sequence
<220> FEATURE:
<223> OTHER INFORMATION: construct pINT-malE-lsgD

<400> SEQUENCE: 15
tcgcgcgttt cggtgatgac ggtgaaaacc tctgacacat gcagctcccg gagacggtca       60
cagcttgtct gtaagcggat gccgggagca gacaagcccg tcaggcgcg tcagcgggtg      120 ttggcgggtg tcgggctgg cttaactatg cggcatcaga gcagattgta ctgagagtgc      180
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct ggcgaaaggg ggatgtgctg caaggcgatt aagttgggta acgccagggt      360
tttcccagtc acgacgttgt aaaacgacgg ccagtgaatt cgaagatcct ttgatctttt      420
ctacggggtc tgacgctcag tggaacgaaa actcacgtta agggattttg gtcatgagat      480
tatcaaaaag gatcttcacc tagatccttt taaactagtg aagttaccat cacggaaaaa      540
ggttatgctg cttttaagac ccactttcac atttaagttg ttttttctaat ccgcatatga      600 tcaattcaag gccgaataag aaggctggct ctgcaccttg gtgatcaaat aattcgatag      660
cttgtcgtaa taatggcggc atactatcag tagtaggtgt ttcccttttct tctttagcga      720 cttgatgctc ttgatcttcc aatacgcaac ctaaagtaaa atgccccact gcgctgagtg      780
catataatgc attctctagt gaaaaacctt gttggcataa aaaggctaat tgatttttcga      840 gagtttcata ctgttttttct gtaggccgtg tacctaaatg tacttttgct ccatcgcgat      900
gacttagtaa agcacatcta aaacttttag cgttattacg taaaaaatct tgccagcttt      960 cccccttctaa agggcaaaag tgagtatggt gcctatctaa catctcaatg gctaaggcgt     1020
cgagcaaagc ccgcttatt tttacatgcc aatacaatgt aggctgctct acacctagct     1080
tctgggcgag tttacgggtt gttaaaccctt cgattccgac ctcattaagc agctctaatg     1140
cgctgttaat cactttactt ttatctaaac gagacatact cttccttttt caatattatt     1200
gaagcattta tcagggttat tgtctcatga gcggatacat atttgaatgt atttagaaaa     1260
ataaacaaat aggggttccg cgcacatttc ccgaaaagt gccacctgaa attggccaga     1320
tgattaattc ctaattttg ttgacactct atcattgata gagttatttt accactccct     1380
atcagtgata gagaaaagtg aaatgaatag ttcgacaaaa atctagaaat aatttttgttt     1440 aactttaaga aggagatata caaatgaaaa tcgaagaagg taaactggta atctggatta     1500
acggcgataa aggctataac ggtctcgctg aagtcggtaa gaaattcgag aaagataccg     1560
gaattaaagt caccgttgag catccggata aactggaaga gaaattccca caggttgcgg     1620
caactggcga tggccctgac attatcttct gggcacacga ccgctttggt ggctacgctc     1680
aatctggcct gttggctgaa atcacccggg acaaagcgtt ccaggacaag ctgtatccgt     1740
ttacctggga tgccgtacgt tacaacggca agctgattgc ttacccgatc gctgttgaag     1800
cgttatcgct gatttataac aaagatctgc tgccgaaccc gccaaaaacc tgggaagaga     1860
tcccggcgct ggataaagaa ctgaaagcga aaggtaagag cgcgctgatg ttcaacctgc     1920
```

```
aagaaccgta cttcacctgg ccgctgattg ctgctgacgg gggttatgcg ttcaagtatg    1980
aaaacggcaa gtacgacatt aaagacgtgg gcgtggataa cgctggcgcg aaagcgggtc    2040
tgaccttcct ggttgacctg attaaaaaca acacatgaa tgcagacacc gattactcca     2100
tcgcagaagc tgcctttaat aaaggcgaaa cagcgatgac catcaacggc ccgtgggcat    2160
ggtccaacat cgacaccagc aaagtgaatt atggtgtaac ggtactgccg accttcaagg    2220
gtcaaccatc caaaccgttc gttggcgtgc tgagcgcagg tattaacgcc gccagtccga    2280
acaaagagct ggcaaaagag ttcctcgaaa actatctgct gactgatgaa ggtctggaag    2340
cggttaataa agacaaaccg ctgggtgccg tagcgctgaa gtcttacgag aagagttgg    2400 cgaaagatcc acgtattgcc gccaccatgg aaaacgccca gaaaggtgaa atcatgccga    2460
acatcccgca gatgtccgct ttctggtatg ccgtgcgtac tgcggtgatc aacgccgcca    2520
gcggtcgtca gactgtcgat gaagccctga agacgcgca gactatgctg aagaagtacc    2580
tgattagcct ggataaggac attcaacgcc gcaagctgtt tttctcgcag aagaacacgg    2640
aagattttca aattttctca gcgatcaaca ccatgcagaa agattgggac gaactggcat    2700
cgatcttcaa catcgaacaa ttcaaggctc attacttccg taacgtcacc aagggcgaaa    2760
ttggttgcac gctgagtcac ctgtccgtct atcagaaaat tgtggaagat aacgacatcg    2820
cagaagattc atacgctctg gtttgtgaag atgacgccct gtttcatctg gatttccagc    2880
aaaatctgac cgcactgctg agtgaaaaac tggaagctga aattatcctg ctgggccagt    2940
ccaacattaa caattttaat gatacggacc tggaaatcaa ttacccgacc acgtttagct    3000
tcctgtgcaa aaagaccggt aacgtgaatt atgcgttccc gtataaatct tactttgccg    3060
gcacggttgg ttacctgatt aaaaagagcg cggcccgtcg cttcattcag caaatctctc    3120
agaacaaacc gttttggctg gcggatgact ttctgctgtt cgaacaaaac ttcaatatcc    3180
gtaataaggt ggttcgcccg ctgatggtta ttgaaaaccc ggtcctgatc tcaaatctgg    3240
aatcggtgcg cggcagcctg tctaacaatc tgctgaaaaa gctgatgaaa tatccgctga    3300
aaaagatttt tgcgatcaaa aagaacctgg ccaattaagc ggccgcgtcg acacgcaaaa    3360
aggccatccg tcaggatggc cttctgctta attatctaga tgcctggcag tttatggcgg    3420
gcgtcctgcc cgccaccctc cgggccgttg cttcgcaacg ttcaaatccg ctcccggcgg    3480
atttgtccta ctcaggagag cgttcaccga caaacaacag ataaaacgaa aggcccagtc    3540
tttcgactga gcctttcgtt ttatttgatg cctggcagtt ccctactctc gcatggggag    3600
accccacact accatcatgt atgaatatcc tccttagttc ctattccgaa gggtaatggc    3660
atcagggaat ggcgaacgcg ctccccacac taccatcatg tatgaatatc ctccttagtt    3720
cctattccga agttcctatt ctctagaaag tataggaact tcggtggaac gacgcgtaac    3780
tcacgttaag ggattttggt catgatcagc acgtgttgac aattaatcat cggcatagta    3840
tatcggcata gtataatacg acaaggtgag gaactaaacc atggccaagt tgaccagtgc    3900
cgttccggtg ctcaccgcgc gcgacgtcgc cggagcggtc gagttctgga ccgaccggct    3960
cgggttctcc cggacttcg tggaggacga cttcgccggt gtggtccggg acgacgtgac     4020
cctgttcatc agcgcggtcc aggaccaggt ggtgccggac aacaccctgg cctgggtgtg    4080
ggtgcgcggc ctggacgagc tgtacgccga gtggtcggag gtcgtgtcca cgaacttccg    4140
ggacgcctcc gggccggcca tgaccgagat cggcgagcag ccgtggggc gggagttcgc    4200 cctgcgcgac ccggccggca actgcgtgca cttcgtggcc gaggagcagg actgagtggc    4260
```

```
agggcggggc gtaaggcgcg ccatttaaat gaagttccta ttccgaagtt cctattctct    4320
agaaagtata ggaacttcga agcagctcca gcctacacaa tcgctcaaga cggaacccgc    4380
gcttggcagg aaagtaatag ggatagcagc tccagcctac acaatcgctc aagacgtgta    4440
atgctgcaca ataaccctgc tgcagaggcc tgcatgcaag cttggcgtaa tcatggtcat    4500
agctgtttcc tgtgtgaaat tgttatccgc tcacaattcc acacaacata cgagccggaa    4560
gcataaagtg taaagcctgg ggtgcctaat gagtgagcta actcacatta attgcgttgc    4620
gctcactgcc cgctttccag tcgggaaacc tgtcgtgcca gctgcattaa tgaatcggcc    4680
aacgcgcggg gagaggcggt ttgcgtattg ggcgctcttc cgcttcctcg ctcactgact    4740
cgctgcgctc ggtcgttcgg ctgcggcgag cggtatcagc tcactcaaag gcggtaatac    4800
ggttatccac agaatcaggg gataacgcag gaaagaacat gtgagcaaaa ggccagcaaa    4860
aggccaggaa ccgtaaaaag gccgcgttgc tggcgttttt ccataggctc cgcccccctg    4920
acgagcatca caaaaatcga cgctcaagtc agaggtggcg aaacccgaca ggactataaa    4980
gataccaggc gtttccccct ggaagctccc tcgtgcgctc tcctgttccg accctgccgc    5040
ttaccggata cctgtccgcc tttctccctt cgggaagcgt ggcgctttct catagctcac    5100
gctgtaggta tctcagttcg gtgtaggtcg ttcgctccaa gctgggctgt gtgcacgaac    5160
cccccgttca gcccgaccgc tgcgccttat ccggtaacta tcgtcttgag tccaacccgg    5220
taagacacga cttatcgcca ctggcagcag ccactggtaa caggattagc agagcgaggt    5280
atgtaggcgg tgctacagag ttcttgaagt ggtggcctaa ctacggctac actagaagaa    5340
cagtatttgg tatctgcgct ctgctgaagc cagttacctt cggaaaaaga gttggtagct    5400
cttgatccgg caaacaaacc accgctggta gcggtggttt ttttgtttgc aagcagcaga    5460
ttacgcgcag aaaaaaagga tctcaagaag atcctttgat cttttctacg gggtctgacg    5520
ctcagtggaa cgaaaactca cgttaaggga ttttggtcat gagattatca aaaaggatct    5580
tcacctagat ccttttaaat taaaaatgaa gttttaaatc aatctaaagt atatatgagt    5640
aaacttggtc tgacagttac caatgcttaa tcagtgaggc acctatctca gcgatctgtc    5700
tatttcgttc atccatagtt gcctgactcc ccgtcgtgta gataactacg atacgggagg    5760
gcttaccatc tggccccagt gctgcaatga taccgcgaga cccacgctca ccggctccag    5820
atttatcagc aataaaccag ccagccggaa gggccgagcg cagaagtggt cctgcaactt    5880
tatccgcctc catccagtct attaattgtt gccgggaagc tagagtaagt agttcgccag    5940
ttaatagttt cgcaacgtt gttgccattg ctacaggcat cgtggtgtca cgctcgtcgt    6000
ttggtatggc ttcattcagc tccggttccc aacgatcaag cgagttaca tgatccccca    6060
tgttgtgcaa aaaagcggtt agctccttcg gtcctccgat cgttgtcaga agtaagttgg    6120
ccgcagtgtt atcactcatg gttatggcag cactgcataa ttctcttact gtcatgccat    6180
ccgtaagatg cttttctgtg actggtgagt actcaaccaa gtcattctga aatagtgta    6240
tgcggcgacc gagttgctct tgcccggcgt caatacggga taataccgcg ccacatagca    6300
gaactttaaa agtgctcatc attggaaaac gttcttcggg gcgaaaactc tcaaggatct    6360
taccgctgtt gagatccagt tcgatgtaac ccactcgtgc acccaactga tcttcagcat    6420
cttttacttt caccagcgtt tctgggtgag caaaaacagg aaggcaaaat gccgcaaaaa    6480
agggaataag ggcgacacgg aaatgttgaa tactcatact cttcctttt caatattatt    6540
gaagcattta tcagggttat tgtctcatga gcggatacat atttgaatgt atttagaaaa    6600
```

-continued

```
ataaacaaat aggggttccg cgcacatttc cccgaaaagt gccacctgac gtctaagaaa      6660
ccattattat catgacatta acctataaaa ataggcgtat cacgaggccc tttcgtc         6717

<210> SEQ ID NO 16
<211> LENGTH: 6769
<212> TYPE: DNA
<213> ORGANISM: Artificial Sequence
<220> FEATURE:
<223> OTHER INFORMATION: construct pINT-malE-HPgalT

<400> SEQUENCE: 16
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcggggctgg cttaactatg cggcatcaga gcagattgta ctgagagtgc      180
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct ggcgaaaggg ggatgtgctg caaggcgatt aagttgggta acgccagggt      360
tttcccagtc acgacgttgt aaaacgacgg ccagtgaatt cgaagatcct ttgatctttt      420
ctacggggtc tgacgctcag tggaacgaaa actcacgtta agggattttg gtcatgagat      480
tatcaaaaag gatcttcacc tagatccttt taaactagtg aagttaccat cacgaaaaaa      540
ggttatgctg cttttaagac ccactttcac atttaagttg ttttttctaat ccgcatatga      600 tcaattcaag gccgaataag aaggctggct ctgcaccttg gtgatcaaat aattcgatag      660
cttgtcgtaa taatggcggc atactatcag tagtaggtgt ttccctttct tctttagcga      720
cttgatgctc ttgatcttcc aatacgcaac ctaaagtaaa atgccccact gcgctgagtg      780
catataatgc attctctagt gaaaaacctt gttggcataa aaaggctaat tgattttcga      840
gagtttcata ctgttttttct gtaggccgtg tacctaaatg tacttttgct ccatcgcgat      900
gacttagtaa agcacatcta aaactttttag cgttattacg taaaaaatct tgccagcttt      960 cccccttctaa agggcaaaag tgagtatggt gcctatctaa catctcaatg gctaaggcgt     1020
cgagcaaagc ccgcttattt tttacatgcc aatacaatgt aggctgctct acacctagct     1080
tctgggcgag tttacgggtt gttaaaccttt cgattccgac ctcattaagc agctctaatg     1140
cgctgttaat cactttactt ttatctaaac gagacatact cttccttttt caatattatt     1200
gaagcattta tcagggttat tgtctcatga gcggatacat atttgaatgt atttagaaaa     1260
ataaacaaat aggggttccg cgcacatttc cccgaaaagt gccacctgaa attggccaga     1320
tgattaattc ctaatttttg ttgacactct atcattgata gagttatttt accactccct     1380
atcagtgata gagaaaagtg aaatgaatag ttcgacaaaa atctagaaat aattttgttt     1440
aactttaaga aggagatata caaatgaaaa tcgaagaagg taaactggta atctggatta     1500
acggcgataa aggctataac ggtctcgctg aagtcggtaa gaaattcgag aaagataccg     1560
gaattaaagt caccgttgag catccggata aactggaaga gaaattccca caggttgcgg     1620
caactggcgc atggccctga cattatcttct gggcacacga ccgctttggt ggctacgctc     1680
aatctggcct gttggctgaa atcaccccgg acaaagcgtt ccaggacaag ctgtatccgt     1740
ttacctggga tgccgtacgt tacaacggca agctgattgc ttacccgatc gctgttgaag     1800
cgttatcgct gatttataac aaagatctgc tgccgaaccc gccaaaaacc tgggaagaga     1860
tcccggcgct ggataaagaa ctgaaagcga aaggtaagag cgcgctgatg ttcaacctgc     1920
```

```
aagaaccgta cttcacctgg ccgctgattg ctgctgacgg gggttatgcg ttcaagtatg   1980
aaaacggcaa gtacgacatt aaagacgtgg gcgtggataa cgctggcgcg aaagcgggtc   2040
tgaccttcct ggttgacctg attaaaaaca aacacatgaa tgcagacacc gattactcca   2100
tcgcagaagc tgcctttaat aaaggcgaaa cagcgatgac catcaacggc ccgtgggcat   2160
ggtccaacat cgacaccagc aaagtgaatt atggtgtaac ggtactgccg accttcaagg   2220
gtcaaccatc caaaccgttc gttggcgtgc tgagcgcagg tattaacgcc gccagtccga   2280
acaaagagct ggcaaaagag ttcctcgaaa actatctgct gactgatgaa ggtctggaag   2340
cggttaataa agacaaaccg ctgggtgccg tagcgctgaa gtcttacgag gaagagttgg   2400
cgaaagatcc acgtattgcc gccaccatgg aaaacgccca gaaggtgaaa atcatgccga   2460
acatcccgca gatgtccgct ttctggtatg ccgtgcgtac tgcggtgatc aacgccgcca   2520
gcggtcgtca gactgtcgat gaagccctga agacgcgca gactatgcgt gtgtttatta   2580
tttccctgaa tcaaaaagtg tgtgatacct tcggtctggt gttccgtgat acgacgaccc   2640
tgctgaacaa cattaacgcg acccatcacc aggcccaaat ttttgatgca atctactcca   2700
aaacgttcga aggcggtctg catccgctgg ttaaaaaaca tctgcacccg tactttatta   2760
cccagaacat caaagacatg ggcattacca cgaatctgat cagcgaagtc tctaaattct   2820
actacgctct gaaataccat gcgaaattca tgagcctggg cgaactgggt tgctatgcta   2880
gtcactactc cctgtgggaa aaatgcattg aactgaacga agcgatttgt atcctggaag   2940
atgacatcac gctgaaagaa gattttaaag aaggcctgga cttcctggaa aaacatattc   3000
aggaactggg ttatgtgcgt ctgatgcacc tgctgtacga tccgaatgtt aaaagcgaac   3060
cgctgaacca taaaaatcac gaaatccagg aacgcgtggg cattatcaaa gcctattctc   3120
atggcgttgg cacccaaggt tacgtcatta cgccgaaaat cgcaaaagtc ttcaaaaaac   3180
atagtcgtaa atgggtggtt ccggtggata ccattatgga cgcgacgttt atccacggtg   3240
tcaaaaatct ggtgctgcaa ccgttcgtta ttgccgatga cgaacaaatt tcaaccatcg   3300
cacgcaaaga agaaccgtat tcgccgaaaa tcgccctgat gcgtgaactg cacttcaaat   3360
acctgaaata ctggcaattc gtctaagcgg ccgcgtcgac acgcaaaaag gccatccatc   3420
cgtcaggatg gccttctgct taattatcta gatgcctggc agtttatggc gggcgtcctg   3480
cccgccaccc tccgggccgt tgcttcgcaa cgttcaaatc cgctcccggc ggatttgtcc   3540
tactcaggag agcgttcacc gacaaacaac agataaaacg aaaggcccag tctttcgact   3600
gagcctttcg ttttatttga tgcctggcag ttccctactc tcgcatgggg agacccccaca   3660 ctaccatcat gtatgaatat cctccttagt tcctattccg aagggtaatg gcatcaggga   3720
atggcgaacg cgctccccac actaccatca tgtatgaata tcctccttag ttcctattcc   3780
gaagttccta ttctctagaa agtataggaa cttcggtgga acgacgcgta actcacgtta   3840
agggattttg gtcatgatca gcacgtgttg acaattaatc atcggcatag tatatcggca   3900
tagtataata cgacaaggtg aggaactaaa ccatggccaa gttgaccagt gccgttccgg   3960
tgctcaccgc gcgcgacgtc gccggagcgg tcgagttctg gaccgaccgg ctcgggttct   4020
cccgggactt cgtggaggac gacttcgccg gtgtggtccg ggacgacgtg accctgttca   4080
tcagcgcggt ccaggaccag gtggtgccgg acaacaccct ggcctgggtg tgggtgcgcg   4140
gcctggacga gctgtacgcc gagtggtcgg aggtcgtgtc cacgaacttc cgggacgcct   4200
ccgggccggc catgaccgag atcggcgagc agccgtgggg gcgggagttc gccctgcgcg   4260
acccggccgg caactgcgtg cacttcgtgg ccgaggagca ggactgagtg gcagggcggg   4320
```

-continued

```
gcgtaaggcg cgccatttaa atgaagttcc tattccgaag ttcctattct ctagaaagta    4380
taggaacttc gaagcagctc cagcctacac aatcgctcaa gacggaaccc gcgcttggca    4440
ggaaagtaat agggatagca gctccagcct acacaatcgc tcaagacgtg taatgctgca    4500
caataaccct gctgcagagg cctgcatgca agcttggcgt aatcatggtc atagctgttt    4560
cctgtgtgaa attgttatcc gctcacaatt ccacacaaca tacgagccgg aagcataaag    4620
tgtaaagcct ggggtgccta atgagtgagc taactcacat taattgcgtt gcgctcactg    4680
cccgctttcc agtcgggaaa cctgtcgtgc cagctgcatt aatgaatcgg ccaacgcgcg    4740
gggagaggcg gtttgcgtat tgggcgctct tccgcttcct cgctcactga ctcgctgcgc    4800
tcggtcgttc ggctgcggcg agcggtatca gctcactcaa aggcggtaat acggttatcc    4860
acagaatcag gggataacgc aggaaagaac atgtgagcaa aaggccagca aaaggccagg    4920
aaccgtaaaa aggccgcgtt gctggcgttt ttccataggc tccgcccccc tgacgagcat    4980
cacaaaaatc gacgctcaag tcagaggtgg cgaaacccga caggactata agataccag    5040 gcgtttcccc ctggaagctc cctcgtgcgc tctcctgttc cgaccctgcc gcttaccgga    5100
tacctgtccg cctttctccc ttcgggaagc gtggcgcttt ctcatagctc acgctgtagg    5160
tatctcagtt cggtgtaggt cgttcgctcc aagctgggct gtgtgcacga acccccgtt    5220 cagcccgacc gctgcgcctt atccggtaac tatcgtcttg agtccaaccc ggtaagacac    5280
gacttatcgc cactggcagc agccactggt aacaggatta gcagagcgag gtatgtaggc    5340
ggtgctacag agttcttgaa gtggtggcct aactacggct acactagaag aacagtattt    5400
ggtatctgcg ctctgctgaa gccagttacc ttcggaaaaa gagttggtag ctcttgatcc    5460
ggcaaacaaa ccaccgctgg tagcggtggt ttttttgttt gcaagcagca gattacgcgc    5520
agaaaaaaag gatctcaaga agatcctttg atcttttcta cggggtctga cgctcagtgg    5580
aacgaaaact cacgttaagg gattttggtc atgagattat caaaaaggat cttcacctag    5640
atccttttaa attaaaaatg aagttttaaa tcaatctaaa gtatatatga gtaaacttgg    5700
tctgacagtt accaatgctt aatcagtgag gcacctatct cagcgatctg tctatttcgt    5760
tcatccatag ttgcctgact ccccgtcgtg tagataacta cgatacggga gggcttacca    5820
tctggcccca gtgctgcaat gataccgcga cccacgct caccggctcc agatttatca    5880
gcaataaacc agccagccgg aagggccgag cgcagaagtg gtcctgcaac tttatccgcc    5940
tccatccagt ctattaattg ttgccgggaa gctagagtaa gtagttcgcc agttaatagt    6000
ttgcgcaacg ttgttgccat tgctacaggc atcgtggtgt cacgctcgtc gtttggtatg    6060
gcttcattca gctccggttc ccaacgatca aggcgagtta catgatcccc catgttgtgc    6120
aaaaaagcgg ttagctcctt cggtcctccg atcgttgtca gaagtaagtt ggccgcagtg    6180
ttatcactca tggttatggc agcactgcat aattctctta ctgtcatgcc atccgtaaga    6240
tgcttttctg tgactggtga gtactcaacc aagtcattct gagaatagtg tatgcggcga    6300
ccgagttgct cttgcccggc gtcaatacgg gataataccg cgccacatag cagaacttta    6360
aaagtgctca tcattggaaa acgttcttcg gggcgaaaac tctcaaggat cttaccgctg    6420
ttgagatcca gttcgatgta acccactcgt gcacccaact gatcttcagc atcttttact    6480
ttcaccagcg tttctgggtg agcaaaaaca ggaaggcaaa atgccgcaaa aagggaata    6540 agggcgacac ggaaatgttg aatactcata ctcttccttt ttcaatatta ttgaagcatt    6600
tatcagggtt attgtctcat gagcggatac atatttgaat gtatttagaa aaataaacaa    6660
```

| | |
|---|---:|
| ataggggttc cgcgcacatt tccccgaaaa gtgccacctg acgtctaaga aaccattatt | 6720 |
| atcatgacat taacctataa aaataggcgt atcacgaggc cctttcgtc | 6769 |

<210> SEQ ID NO 17
<211> LENGTH: 4714
<212> TYPE: DNA
<213> ORGANISM: Artificial Sequence
<220> FEATURE:
<223> OTHER INFORMATION: construct pACYC-waaX

<400> SEQUENCE: 17

| | |
|---|---:|
| ggggaattgt gagcggataa caattcccct gtagaaataa ttttgtttaa ctttaataag | 60 |
| gagatatacc atgaaagtgt tgtggtcaa cctggataag gataaggata aaaagaaaa | 120 |
| aatcaagaat gaatgccgca acgcagaact ggactatgaa attatctcag cagttgatgg | 180 |
| ccgtgaactg agctacaacg aactgaaatc taaggtccat ccggtgtcac tgaattatct | 240 |
| gtcgaaaggc gaaattggtt gcgtcctgtc ccaccagcgt atttacaaac gcatcctgga | 300 |
| tgacgatatt gactatgctc tgatcctgga agacgatgtg gaactgagtc aagatatcaa | 360 |
| ggttttctg aaggaattcc tgtccgtcaa agacaagaac aaaggcgatg tgtttctgct | 420 |
| gtacccgtca ggtctgcgtt tcctgaaccg tcgcatcaac gtgtcgcatg attatttctt | 480 |
| ttatgaagcg tacaacagct cttgtgccca cggttatatt atcagcaaca aagcggccaa | 540 |
| aaagctgatt cgcatcaata ccccgattat cctggttgca gatgcttggc tgtggtttta | 600 |
| ccagatttct ctgctgaaag tgtatgttct gaacaaagaa ctggttcgtg catatgacgt | 660 |
| cgataaaagt ctgtccacca tcgaaacgga acgcagcctg ctgctggacg aaaaggaaaa | 720 |
| gcatcagatg caaatcatca aaaagcaacc gctgtactac ctgatcaagt actaccacaa | 780 |
| gtacatccgt cgcctgttca tcaataagga taaataagaa ttcgagctcg gcgcgcctgc | 840 |
| aggtcgacaa gcttgcggcc gcataatgct taagtcgaac agaaagtaat cgtattgtac | 900 |
| acggccgcat aatcgaaatt aatacgactc actataggg aattgtgagc ggataacaat | 960 |
| tccccatctt agtatattag ttaagtataa gaaggagata tacatatggc agatctcaat | 1020 |
| tggatatcgg ccggccacgc gatcgctgac gtcggtaccc tcgagtctgg taagaaaacc | 1080 |
| gctgctgcga aatttgaacg ccagcacatg gactcgtcta ctagcgcagc ttaattaacc | 1140 |
| taggctgctg ccaccgctga gcaataacta gcataacccc ttggggcctc taaacgggtc | 1200 |
| ttgaggggtt ttttgctgaa acctcaggca tttgagaagc acacggtcac actgcttccg | 1260 |
| gtagtcaata aaccggtaaa ccagcaatag acataagcgg ctatttaacg accctgccct | 1320 |
| gaaccgacga ccgggtcgaa tttgcttccg aatttctgcc attcatccgc ttattatcac | 1380 |
| ttattcaggc gtagcaccag gcgtttaagg gcaccaataa ctgccttaaa aaaattacgc | 1440 |
| cccgccctgc cactcatcgc agtactgttg taattcatta agcattctgc cgacatggaa | 1500 |
| gccatcacag acggcatgat gaacctgaat cgccagcggc atcagcacct tgtcgccttg | 1560 |
| cgtataatat ttgcccatag tgaaaacggg ggcgaagaag ttgtccatat tggccacgtt | 1620 |
| taaatcaaaa ctggtgaaac tcacccaggg attggctgag acgaaaaaca tattctcaat | 1680 |
| aaaccctta gggaaatagg ccaggttttc accgtaacac gccacatctt gcgaatatat | 1740 |
| gtgtagaaac tgccggaaat cgtcgtggta ttcactccag agcgatgaaa acgtttcagt | 1800 |
| ttgctcatgg aaaacggtgt aacaagggtg aacactatcc catatcacca gctcaccgtc | 1860 |
| tttcattgcc atacggaact ccggatgagc attcatcagg cggcaagaa tgtgaataaa | 1920 |
| ggccggataa aacttgtgct tatttttctt tacggtcttt aaaaaggccg taatatccag | 1980 |

```
ctgaacggtc tggttatagg tacattgagc aactgactga aatgcctcaa aatgttcttt    2040
acgatgccat tgggatatat caacggtggt atatccagtg attttttcct ccattttagc    2100
ttccttagct cctgaaaatc tcgataactc aaaaaatacg cccggtagtg atcttatttc    2160
attatggtga aagttggaac ctcttacgtg ccgatcaacg tctcattttc gccaaaagtt    2220
ggcccagggc ttcccggtat caacagggac accaggattt atttattctg cgaagtgatc    2280
ttccgtcaca ggtatttatt cggcgcaaag tgcgtcgggt gatgctgcca acttactgat    2340
ttagtgtatg atggtgtttt tgaggtgctc cagtggcttc tgtttctatc agctgtccct    2400
cctgttcagc tactgacggg gtggtgcgta acggcaaaag caccgccgga catcagcgct    2460
agcggagtgt atactggctt actatgttgg cactgatgag ggtgtcagtg aagtgcttca    2520
tgtggcagga gaaaaaaggc tgcaccggtg cgtcagcaga atatgtgata caggatatat    2580
tccgcttcct cgctcactga ctcgctacgc tcggtcgttc gactgcggcg agcggaaatg    2640
gcttacgaac ggggcggaga tttcctggaa gatgccagga agatacttaa cagggaagtg    2700
agagggccgc ggcaaagccg ttttttccata ggctccgccc ccctgacaag catcacgaaa   2760
tctgacgctc aaatcagtgg tggcgaaacc cgacaggact ataaagatac caggcgtttc    2820
ccctggcggc tccctcgtgc gctctcctgt tcctgccttt cggtttaccg gtgtcattcc    2880
gctgttatgg ccgcgtttgt ctcattccac gcctgacact cagttccggg taggcagttc    2940
gctccaagct ggactgtatg cacgaacccc ccgttcagtc cgaccgctgc gccttatccg    3000
gtaactatcg tcttgagtcc aacccggaaa gacatgcaaa agcaccactg gcagcagcca    3060
ctggtaattg atttagagga gttagtcttg aagtcatgcg ccggttaagg ctaaactgaa    3120
aggacaagtt ttggtgactg cgctcctcca agccagttac ctcggttcaa agagttggta    3180
gctcagagaa ccttcgaaaa accgccctgc aaggcggttt tttcgttttc agagcaagag    3240
attacgcgca gaccaaaacg atctcaagaa gatcatctta ttaatcagat aaaatatttc    3300
tagatttcag tgcaatttat ctcttcaaat gtagcacctg aagtcagccc catacgatat    3360
aagttgtaat tctcatgtta gtcatgcccc gcgcccaccg gaaggagctg actgggttga    3420
aggctctcaa gggcatcggt cgagatcccg gtgcctaatg agtgagctaa cttacattaa    3480
ttgcgttgcg ctcactgccc gctttccagt cgggaaacct gtcgtgccag ctgcattaat    3540
gaatcggcca acgcgcgggg agaggcggtt tgcgtattgg cgccagggt ggttttttctt   3600
ttcaccagtg agacgggcaa cagctgattg cccttcaccg cctggccctg agagagttgc    3660
agcaagcggt ccacgctggt ttgccccagc aggcgaaaat cctgtttgat ggtggttaac    3720
ggcgggatat aacatgagct gtcttcggta tcgtcgtatc ccactaccga tgtccgca    3780
ccaacgcgca gccggactc ggtaatggcg cgcattgcgc ccagcgccat ctgatcgttg    3840
gcaaccagca tcgcagtggg aacgatgccc tcattcagca tttgcatggt ttgttgaaaa    3900
ccggacatgg cactccagtc gccttccgt tccgctatcg gctgaatttg attgcgagtg     3960
agatatttat gccagccagc cagacgcaga cgcgccgaga cagaacttaa tgggcccgct    4020
aacagcgcga tttgctggtg acccaatgcg accagatgct ccacgcccag tcgcgtaccg    4080
tcttcatggg agaaaataat actgttgatg ggtgtctggt cagagacatc aagaaataac    4140
gccggaacat tagtgcaggc agcttccaca gcaatggcat cctggtcatc cagcggatag    4200
ttaatgatca gcccactgac gcgttgcgcg agaagattgt gcaccgccgc tttacaggct    4260
tcgacgccgc ttcgttctac catcgacacc accacgctgg cacccagttg atcggcgcga    4320
```

```
gatttaatcg ccgcgacaat ttgcgacggc gcgtgcaggg ccagactgga ggtggcaacg    4380
ccaatcagca acgactgttt gcccgccagt tgttgtgcca cgcggttggg aatgtaattc    4440
agctccgcca tcgccgcttc cactttttcc cgcgttttcg cagaaacgtg gctggcctgg    4500
ttcaccacgc gggaaacggt ctgataagag acaccggcat actctgcgac atcgtataac    4560
gttactggtt tcacattcac caccctgaat tgactctctt ccgggcgcta tcatgccata    4620
ccgcgaaagg ttttgcgcca ttcgatggtg tccgggatct cgacgctctc ccttatgcga    4680
ctcctgcatt aggaaattaa tacgactcac tata                                4714
```

<210> SEQ ID NO 18
<211> LENGTH: 4760
<212> TYPE: DNA
<213> ORGANISM: Artificial Sequence
<220> FEATURE:
<223> OTHER INFORMATION: construct pACYC-wbdO

<400> SEQUENCE: 18

```
ggggaattgt gagcggataa caattcccct gtagaaataa ttttgtttaa ctttaataag      60
gagatatacc atgctgacgg aagtgcgccc ggtctctacg acgaaaccgc tggtgtctgt     120
gattctgccg gtgaacaaat tcaacccgta tctggatcgt gcaattcatt caatcctgag     180
tcagtcctat ccgtcgattg aactgattat cattgcaaac aattgcacca atgactttt      240 cgatgctctg aaaaaacgtg aatgtgaaac cattaaagtg ctgcgcacga acatcgcgta     300
tctgccgtac tgcctgaata aaggcctgga tctgtgtaac ggtgactttg ttgcccgcat     360
ggattcagat gacatttcgc acccggaacg tatcgatcgc caggtcgact tcctgattaa     420
caatccggac atcgatgtgg ttggcaccaa tgcagtctat attgatgaag atgacatcga     480
actggaaaaa agcaacctgc cggtgaacaa taacgctatt cgtaaaatgc tgccgtataa     540
atgctgtctg gtgcatccgt ctgttatgtt tcgcaaaaat gtcgtgatca ccagcggcgg     600
ttacatgttc gcgaattatt ctgaagatta cgaactgtgg aaccgtctgg ccgttgaagg     660
ccgcaatttt tataacctga gcgaatacct gctgtattac cgtctgcaca ataaccaatc     720
aacgtcgaaa aataacctgt ttatggtgat ggcgaacgat gtcgccatta agtgaaaata     780
tttcctgctg accaagaaaa ttagctacct gctgggtatc attcgcacgg tcttttctgt     840
gttctattgc aaatacatca aatgaattcg agctcggcgc gcctgcaggt cgacaagctt     900
gcggccgcat aatgcttaag tcgaacagaa agtaatcgta ttgtacacgg ccgcataatc     960
gaaattaata cgactcacta tagggaattg tgagcggata acaattccc catcttagta    1020 tattagttaa gtataagaag gagatataca tatggcagat ctcaattgga tatcggccgg    1080
ccacgcgatc gctgacgtcg gtaccctcga gtctggtaaa gaaaccgctg ctgcgaaatt    1140
tgaacgccag cacatggact cgtctactag cgcagcttaa ttaacctagg ctgctgccac    1200
cgctgagcaa taactagcat aaccccttgg ggcctctaaa cgggtcttga gggttttt      1260 gctgaaacct caggcatttg agaagcacac ggtcacactg cttccggtag tcaataaacc    1320
ggtaaaccag caatagacat aagcggctat ttaacgaccc tgccctgaac cgacgaccgg    1380
gtcgaatttg ctttcgaatt tctgccattc atccgcttat tatcacttat tcaggcgtag    1440
caccaggcgt ttaagggcac caataactgc cttaaaaaaa ttacgccccg ccctgccact    1500
catcgcagta ctgttgtaat tcattaagca ttctgccgac atggaagcca tcacagacgg    1560
catgatgaac ctgaatcgcc agcggcatca gcaccttgtc gccttgcgta taatatttgc    1620
ccatagtgaa aacgggggcg aagaagttgt ccatattggc cacgtttaaa tcaaaactgg    1680
```

```
tgaaactcac ccagggattg gctgagacga aaaacatatt ctcaataaac cctttaggga    1740
aataggccag gttttcaccg taacacgcca catcttgcga atatatgtgt agaaactgcc    1800
ggaaatcgtc gtggtattca ctccagagcg atgaaaacgt ttcagtttgc tcatggaaaa    1860
cggtgtaaca agggtgaaca ctatcccata tcaccagctc accgtctttc attgccatac    1920
ggaactccgg atgagcattc atcaggcggg caagaatgtg aataaaggcc ggataaaact    1980
tgtgcttatt tttctttacg gtcttttaaaa aggccgtaat atccagctga acggtctggt    2040
tataggtaca ttgagcaact gactgaaatg cctcaaaatg ttctttacga tgccattggg    2100
atatatcaac ggtggtatat ccagtgattt ttttctccat tttagcttcc ttagctcctg    2160
aaaatctcga taactcaaaa aatacgcccg gtagtgatct tatttcatta tggtgaaagt    2220
tggaacctct tacgtgccga tcaacgtctc attttcgcca aaagttggcc cagggcttcc    2280
cggtatcaac agggacacca ggatttattt attctgcgaa gtgatcttcc gtcacaggta    2340
tttattcggc gcaaagtgcg tcgggtgatg ctgccaactt actgatttag tgtatgatgg    2400 tgttttttgag gtgctccagt ggcttctgtt tctatcagct gtccctcctg ttcagctact    2460
gacggggtgg tgcgtaacgg caaaagcacc gccggacatc agcgctagcg gagtgtatac    2520
tggcttacta tgttggcact gatgagggtg tcagtgaagt gcttcatgtg gcaggagaaa    2580
aaaggctgca ccggtgcgtc agcagaatat gtgatacagg atatattccg cttcctcgct    2640
cactgactcg ctacgctcgg tcgttcgact gcggcgagcg gaaatggctt acgaacgggg    2700
cggagatttc ctggaagatg ccaggaagat acttaacagg gaagtgagag ggccgcggca    2760
aagccgtttt tccataggct ccgcccccct gacaagcatc acgaaatctg acgctcaaat    2820
cagtggtggc gaaacccgac aggactataa agataccagg cgtttcccct ggcggctccc    2880
tcgtgcgctc tcctgttcct gcctttcggt ttaccggtgt cattccgctg ttatggccgc    2940
gtttgtctca ttccacgcct gacactcagt tccgggtagg cagttcgctc caagctggac    3000
tgtatgcacg aaccccccgt tcagtccgac cgctgcgcct tatccggtaa ctatcgtctt    3060
gagtccaacc cggaaagaca tgcaaaagca ccactggcag cagccactgg taattgattt    3120
agaggagtta gtcttgaagt catgcgccgg ttaaggctaa actgaaagga caagttttgg    3180
tgactgcgct cctccaagcc agttacctcg gttcaaagag ttggtagctc agagaacctt    3240
cgaaaaaccg ccctgcaagg cggttttttc gttttcagag caagagatta cgcgcagacc    3300
aaaacgatct caagaagatc atcttattaa tcagataaaa tatttctaga tttcagtgca    3360
atttatctct tcaaatgtag cacctgaagt cagccccata cgatataagt tgtaattctc    3420
atgttagtca tgccccgcgc ccaccggaag gagctgactg ggttgaaggc tctcaagggc    3480
atcggtcgag atcccggtgc ctaatgagtg agctaactta cattaattgc gttgcgctca    3540
ctgcccgctt tccagtcggg aaacctgtcg tgccagctgc attaatgaat cggccaacgc    3600
gcggggagag gcggtttgcg tattgggcgc caggttggtt ttctttttca ccagtgagac    3660
gggcaacagc tgattgccct tcaccgcctg gccctgagag agttgcagca agcggtccac    3720
gctggtttgc cccagcaggc gaaaatcctg tttgatggtg gttaacggcg ggatataaca    3780
tgagctgtct tcggtatcgt cgtatcccac taccgagatg tccgcaccaa cgcgcagccc    3840
ggactcggta atggcgcgca ttgcgcccag cgccatctga tcgttggcaa ccagcatcgc    3900
agtgggaacg atgccctcat tcagcatttg catggtttgt tgaaaaccgg acatggcact    3960
ccagtcgcct tcccgttccg ctatcggctg aatttgattg cgagtgagat atttatgcca    4020
```

-continued

```
gccagccaga cgcagacgcg ccgagacaga acttaatggg cccgctaaca gcgcgatttg    4080
ctggtgaccc aatgcgacca gatgctccac gcccagtcgc gtaccgtctt catgggagaa    4140
aataatactg ttgatgggtg tctggtcaga gacatcaaga aataacgccg gaacattagt    4200
gcaggcagct tccacagcaa tggcatcctg gtcatccagc ggatagttaa tgatcagccc    4260
actgacgcgt tgcgcgagaa gattgtgcac cgccgcttta caggcttcga cgccgcttcg    4320
ttctaccatc gacaccacca cgctggcacc cagttgatcg gcgcgagatt taatcgccgc    4380
gacaatttgc gacggcgcgt gcagggccag actggaggtg gcaacgccaa tcagcaacga    4440
ctgtttgccc gccagttgtt gtgccacgcg gttgggaatg taattcagct ccgccatcgc    4500
cgcttccact ttttcccgcg ttttcgcaga acgtggctg gcctggttca ccacgcggga     4560
aacggtctga taagagacac cggcatactc tgcgacatcg tataacgtta ctggtttcac    4620
attcaccacc ctgaattgac tctcttccgg gcgctatcat gccataccgc gaaaggtttt    4680
gcgccattcg atggtgtccg ggatctcgac gctctccctt atgcgactcc tgcattagga    4740
aattaatacg actcactata                                                4760
```

<210> SEQ ID NO 19
<211> LENGTH: 4795
<212> TYPE: DNA
<213> ORGANISM: Artificial Sequence
<220> FEATURE:
<223> OTHER INFORMATION: construct pACYC-furA

<400> SEQUENCE: 19

```
ggggaattgt gagcggataa caattcccct gtagaaataa ttttgtttaa ctttaataag      60
gagatatacc atggataaaa tcaaacaggg cagcgcctct ctggttgtcg gtgaccagca    120
agaaaaacat ccggtggttt cagtgctgct gccggttaat cgtgtcgatc gcttttcat     180
tccggcagtt gaatcgatcc tgacccaaac gctgcaggat tttgaactga tcattatcgc    240
taatggctgt agcaccgaac atctgaacaa aattcgtctg acgtatggtg atcacaatcg    300
tgttcgcatt ctgaacaccg aaatcaaagg cctgccgttt gcgctgaatc tgggcgtgca    360
caacgcccgt ggtctgtata ttgcacgcat ggatgctgat gacatttcta tcccggaacg    420
cctggaaaaa caactgaata cgctggaaca gaacaagaaa attggcgtcg tgagctctgg    480
tgtggacttt attgatgaaa atgaccaggc gatccgtgag ggtaaattcc cggaactgac    540
cgacaaagat catcgtcgcc tgctgccgct gatttgctgt atcgcccacc cgacggttat    600
ggtccgcaaa gaaattatca acaaactggg cggttatagt tttggtagtt ctccgaagga    660
ctacgatctg tggctgcgta ttatgcgcga actgccggaa gttgaatttt atcgtatccc    720
ggaatccctg ctgaaatacc gtcgccatgg caatcaggcc accagttcca aaaacattaa    780
gaaaattcgc gcgtacaact cagccctgaa aattcgtgaa ctgtttctgt cgcgcaaact    840
gaaattcatt atcggtatta tcctgccggc acgtatggtg accctgtggc gcaaatgaga    900
attcgagctc ggcgcgcctg caggtcgaca agcttgcggc cgcataatgc ttaagtcgaa    960
cagaaagtaa tcgtattgta cacggccgca taatcgaaat taatacgact cactataggg    1020
gaattgtgag cggataacaa ttccccatct tagtatatta gttaagtata agaaggagat    1080
atacatatgg cagatctcaa ttggatatcg gccggccacg cgatcgctga cgtcggtacc    1140
ctcgagtctg gtaaagaaac cgctgctgcg aaatttgaac gccagcacat ggactcgtct    1200
actagcgcag cttaattaac ctaggctgct gccaccgctg agcaataact agcataaccc    1260
cttggggcct ctaaacgggt cttgaggggt tttttgctga aacctcaggc atttgagaag    1320
```

```
cacacggtca cactgcttcc ggtagtcaat aaaccggtaa accagcaata gacataagcg    1380
gctatttaac gaccctgccc tgaaccgacg accgggtcga atttgctttc gaatttctgc    1440
cattcatccg cttattatca cttattcagg cgtagcacca ggcgtttaag ggcaccaata    1500
actgccttaa aaaaattacg ccccgccctg ccactcatcg cagtactgtt gtaattcatt    1560
aagcattctg ccgacatgga agccatcaca gacggcatga tgaacctgaa tcgccagcgg    1620
catcagcacc ttgtcgcctt gcgtataata tttgcccata gtgaaaacgg gggcgaagaa    1680
gttgtccata ttggccacgt ttaaatcaaa actggtgaaa ctcacccagg gattggctga    1740
gacgaaaaac atattctcaa taaacccttt agggaaatag gccaggtttt caccgtaaca    1800
cgccacatct gcgaatata tgtgtagaaa ctgccggaaa tcgtcgtggt attcactcca    1860
gagcgatgaa aacgtttcag tttgctcatg gaaaacggtg taacaagggt gaacactatc    1920
ccatatcacc agctcaccgt ctttcattgc catacggaac tccggatgag cattcatcag    1980
gcgggcaaga atgtgaataa aggccggata aaacttgtgc ttattttct ttacggtctt    2040 taaaaaggcc gtaatatcca gctgaacggt ctggttatag gtacattgag caactgactg    2100
aaatgcctca aatgttctt tacgatgcca ttgggatata tcaacggtgg tatatccagt    2160
gatttttttc tccattttag cttccttagc tcctgaaaat ctcgataact caaaaaatac    2220
gcccggtagt gatcttattt cattatggtg aaagttggaa cctcttacgt gccgatcaac    2280
gtctcatttt cgccaaaagt tggcccaggg cttcccggta tcaacaggga caccaggatt    2340
tatttattct gcgaagtgat cttccgtcac aggtatttat tcggcgcaaa gtgcgtcggg    2400
tgatgctgcc aacttactga tttagtgtat gatggtgttt ttgaggtgct ccagtggctt    2460
ctgtttctat cagctgtccc tcctgttcag ctactgacgg ggtggtgcgt aacggcaaaa    2520
gcaccgccgg acatcagcgc tagcggagtg tatactggct tactatgttg gcactgatga    2580
gggtgtcagt gaagtgcttc atgtggcagg agaaaaaagg ctgcaccggt gcgtcagcag    2640
aatatgtgat acaggatata ttccgcttcc tcgctcactg actcgctacg ctcggtcgtt    2700
cgactgcggc gagcggaaat ggcttacgaa cggggcggag atttcctgga agatgccagg    2760
aagatactta acagggaagt gagagggccg cggcaaagcc gttttccat aggctccgcc    2820 cccctgacaa gcatcacgaa atctgacgct caaatcagtg gtggcgaaac ccgacaggac    2880
tataaagata ccaggcgttt ccctggcgg ctccctcgtg cgctctcctg ttcctgcctt    2940
tcggtttacc ggtgtcattc cgctgttatg gccgcgtttg tctcattcca gcctgacac    3000 tcagttccgg gtaggcagtt cgctccaagc tggactgtat gcacgaaccc cccgttcagt    3060
ccgaccgctg cgccttatcc ggtaactatc gtcttgagtc caacccggaa agacatgcaa    3120
aagcaccact ggcagcagcc actggtaatt gatttagagg agttagtctt gaagtcatgc    3180
gccggttaag gctaaactga aaggacaagt tttggtgact gcgctcctcc aagccagtta    3240
cctcggttca aagagttggt agctcagaga accttgaaa aaccgccctg caaggcggtt    3300
ttttcgtttt cagagcaaga gattacgcgc agaccaaaac gatctcaaga agatcatctt    3360
attaatcaga taaatatttt ctagatttca gtgcaattta tctcttcaaa tgtagcacct    3420
gaagtcagcc ccatacgata taagttgtaa ttctcatgtt agtcatgccc cgcgcccacc    3480
ggaaggagct gactgggttg aaggctctca agggcatcgg tcgagatccc ggtgcctaat    3540
gagtgagcta acttacatta attgcgttgc gctcactgcc cgctttccag tcgggaaacc    3600
tgtcgtgcca gctgcattaa tgaatcggcc aacgcgcggg gagaggcggt ttgcgtattg    3660
```

```
ggcgccaggg tggtttttct tttcaccagt gagacgggca acagctgatt gcccttcacc      3720
gcctggccct gagagagttg cagcaagcgg tccacgctgg tttgcccag  caggcgaaaa      3780 tcctgtttga tggtggttaa cggcgggata taacatgagc tgtcttcggt atcgtcgtat      3840
cccactaccg agatgtccgc accaacgcgc agcccggact cggtaatggc gcgcattgcg      3900
cccagcgcca tctgatcgtt ggcaaccagc atcgcagtgg gaacgatgcc ctcattcagc      3960
atttgcatgg tttgttgaaa accggacatg gcactccagt cgccttcccg ttccgctatc      4020
ggctgaattt gattgcgagt gagatattta tgccagccag ccagacgcag acgcgccgag      4080
acagaactta atgggcccgc taacagcgcg atttgctggt gacccaatgc gaccagatgc      4140
tccacgccca gtcgcgtacc gtcttcatgg gagaaaataa tactgttgat gggtgtctgg      4200
tcagagacat caagaaataa cgccggaaca ttagtgcagg cagcttccac agcaatggca      4260
tcctggtcat ccagcggata gttaatgatc agcccactga cgcgttgcgc gagaagattg      4320
tgcaccgccg ctttacaggc ttcgacgccc cttcgttcta ccatcgacac caccacgctg      4380
gcacccagtt gatcggcgcg agatttaatc gccgcgacaa tttgcgacgg cgcgtgcagg      4440
gccagactgg aggtggcaac gccaatcagc aacgactgtt tgcccgccag ttgttgtgcc      4500
acgcggttgg gaatgtaatt cagctccgcc atcgccgctt ccacttttc  ccgcgttttc      4560 gcagaaacgt ggctggcctg gttcaccacg cgggaaacgg tctgataaga gacaccggca      4620
tactctgcga catcgtataa cgttactggt ttcacattca ccaccctgaa ttgactctct      4680
tccgggcgct atcatgccat accgcgaaag gttttgcgcc attcgatggt gtccgggatc      4740
tcgacgctct cccttatgcg actcctgcat taggaaatta tacgactca  ctata           4795
```

<210> SEQ ID NO 20
<211> LENGTH: 6383
<212> TYPE: DNA
<213> ORGANISM: Artificial Sequence
<220> FEATURE:
<223> OTHER INFORMATION: construct pET-PmnagT

<400> SEQUENCE: 20

```
ggggaattgt gagcggataa caattcccct ctagaaataa ttttgtttaa ctttaagaag        60
gagatatacc atgggcagca gccatcacca tcatcaccac agccaggatc cgaattcgag       120
ctcggcgcgc ctgcaggtcg acaagcttgc ggccgcataa tgcttaagtc gaacagaaag       180
taatcgtatt gtacacggcc gcataatcga aattaatacg actcactata ggggaattgt       240
gagcggataa caattcccca tcttagtata ttagttaagt ataagaagga gatatacata       300
tggaaaataa acctttagtt tcagttttga tttgtgctta taatgtcgag aaatatattg       360
aagaatgtat taatgcagtg attaatcaga catataagaa cttagaaatt attattgtga       420
atgatggttc ttctgataat acttatttc  ttttaaaaaa gttagctgaa aaagataatc       480
gtataaaaat attaaatttc aataatcata ttggaataat ttctgcttta atgaaggtt        540 taaaagagat agctggagaa tatattgctc gaacagattc tgatgatata actaagccag       600
attggattga gaaatatta  acttgtatgc aaaatgatcc taaaatcatc gctatgggat       660
cttatcttac tgtcttgtca gaagaaaata tggtagtgt  gcttgctaat catcataaaa       720
ataaagttga atggaaaaat ccattagagc acaaagatat tgttgagaaa atgttatttg       780
gtaatcctat tcataataat tcaatggtta tgagaagtga gatatataca aagtatcact       840
taatttatga tccagattat cattatgctg aagattataa attttggctg gaagttagtc       900
gaattgggaa attagcaaat tatcctgagt cactcgtata ttatagactt caccgaaatc       960
```

```
aaacatcttc tattcataat agccaacaag aaataaatgg taaaaaatta cgtttacaag   1020
ctcttaatta ttatttaaaa gatcttggta ttgattatca gttacctgaa aaatttttat   1080
tcaaagatat agcgttattg caagaaatat tttatgaacg aggtatgttt agagaaaata   1140
taataaggcg tatcatctac gaatgttatc tttccttggg agagtataat tataaagata   1200
tttattattt tttaataaat aaaaataact ttctttctat aaaagacaaa tttaaaataa   1260
taaaaaaata tcttcgtcct gataaatatt catctactta ttaggacgtc ggtaccctcg   1320
agtctggtaa agaaaccgct gctgcgaaat tgaacgcca gcacatggac tcgtctacta   1380
gcgcagctta attaacctag gctgctgcca ccgctgagca ataactagca taacccttg    1440 gggcctctaa acgggtcttg aggggttttt tgctgaaagg aggaactata tccggattgg   1500
cgaatgggac gcgccctgta gcggcgcatt aagcgcggcg ggtgtggtgg ttacgcgcag   1560
cgtgaccgct acacttgcca gcgccctagc gcccgctcct ttcgctttct tcccttcctt   1620
tctcgccacg ttcgccggct ttccccgtca agctctaaat cggggggctcc ctttagggtt   1680 ccgatttagt gctttacggc acctcgaccc caaaaaactt gattagggtg atggttcacg   1740
tagtgggcca tcgccctgat agacggtttt tcgccctttg acgttggagt ccacgttctt   1800
taatagtgga ctcttgttcc aaactggaac aacactcaac cctatctcgg tctattcttt   1860
tgatttataa gggattttgc cgatttcggc ctattggtta aaaaatgagc tgatttaaca   1920
aaaatttaac gcgaattta caaaatatt aacgtttaca atttctggcg gcacgatggc    1980
atgagattat caaaaaggat cttcacctag atccttttaa attaaaaatg aagttttaaa   2040
tcaatctaaa gtatatatga gtaaacttgg tctgacagtt accaatgctt aatcagtgag   2100
gcacctatct cagcgatctg tctatttcgt tcatccatag ttgcctgact ccccgtcgtg   2160
tagataacta cgatacggga gggcttacca tctggcccca gtgctgcaat gataccgcga   2220
gacccacgct caccggctcc agatttatca gcaataaacc agccagcgg aagggccgag    2280 cgcagaagtg gtcctgcaac tttatccgcc tccatccagt ctattaattg ttgccgggaa   2340
gctagagtaa gtagttcgcc agttaatagt ttgcgcaacg ttgttgccat tgctacaggc   2400
atcgtggtgt cacgctcgtc gtttggtatg gcttcattca gctccggttc ccaacgatca   2460
aggcgagtta catgatcccc catgttgtgc aaaaaagcgg ttagctcctt cggtcctccg   2520
atcgttgtca agtaagtt ggccgcagtg ttatcactca tggttatggc agcactgcat     2580
aattctctta ctgtcatgcc atccgtaaga tgcttttctg tgactggtga gtactcaacc   2640
aagtcattct gagaatagtg tatgcggcga ccgagttgct cttgcccggc gtcaatacgg   2700
gataataccg cgccacatag cagaacttta aaagtgctca tcattggaaa acgttcttcg   2760
gggcgaaaac tctcaaggat cttaccgctg ttgagatcca gttcgatgta acccactcgt   2820
gcacccaact gatcttcagc atcttttact ttcaccagcg tttctgggtg agcaaaaaca   2880
ggaaggcaaa atgccgcaaa aaagggaata agggcgacac ggaaatgttg aatactcata   2940
ctcttccttt ttcaatcatg attgaagcat ttatcagggt tattgtctca tgagcggata   3000
catatttgaa tgtatttaga aaaataaaca aataggtcat gaccaaaatc ccttaacgtg   3060
agttttcgtt ccactgagcg tcagaccccg tagaaaagat caaaggatct tcttgagatc   3120 cttttttct gcgcgtaatc tgctgcttgc aaacaaaaaa accaccgcta ccagcggtgg    3180 tttgttgcc ggatcaagag ctaccaactc ttttccgaa ggtaactggc ttcagcagag     3240
cgcagatacc aaatactgtc cttctagtgt agccgtagtt aggccaccac ttcaagaact   3300
```

```
ctgtagcacc gcctacatac ctcgctctgc taatcctgtt accagtggct gctgccagtg      3360
gcgataagtc gtgtcttacc gggttggact caagacgata gttaccggat aaggcgcagc      3420
ggtcgggctg aacggggggt tcgtgcacac agcccagctt ggagcgaacg acctacaccg      3480
aactgagata cctacagcgt gagctatgag aaagcgccac gcttcccgaa gggagaaagg      3540
cggacaggta tccggtaagc ggcagggtcg gaacaggaga gcgcacgagg gagcttccag      3600
ggggaaacgc ctggtatctt tatagtcctg tcgggtttcg ccacctctga cttgagcgtc      3660
gatttttgtg atgctcgtca ggggggcgga gcctatggaa aaacgccagc aacgcggcct      3720
ttttacggtt cctggccttt tgctggcctt tgctcacat gttctttcct gcgttatccc      3780
ctgattctgt ggataaccgt attaccgcct ttgagtgagc tgataccgct cgccgcagcc      3840
gaacgaccga gcgcagcgag tcagtgagcg aggaagcgga agagcgcctg atgcggtatt      3900
ttctccttac gcatctgtgc ggtatttcac accgcatata tggtgcactc tcagtacaat      3960
ctgctctgat gccgcatagt taagccagta tacactccgc tatcgctacg tgactgggtc      4020
atggctgcgc cccgacaccc gccaacaccc gctgacgcgc cctgacgggc ttgtctgctc      4080
ccggcatccg cttacagaca agctgtgacc gtctccggga gctgcatgtg tcagaggttt      4140
tcaccgtcat caccgaaacg cgcgaggcag ctgcggtaaa gctcatcagc gtggtcgtga      4200
agcgattcac agatgtctgc ctgttcatcc gcgtccagct cgttgagttt ctccagaagc      4260
gttaatgtct ggcttctgat aaagcgggcc atgttaaggg cggttttttc ctgtttggtc      4320
actgatgcct ccgtgtaagg gggatttctg ttcatggggg taatgatacc gatgaaacga      4380
gagaggatgc tcacgatacg ggttactgat gatgaacatg cccggttact ggaacgttgt      4440
gagggtaaac aactggcggt atggatgcgg cgggaccaga gaaaaatcac tcagggtcaa      4500
tgccagcgct tcgttaatac agatgtaggt gttccacagg gtagccagca gcatcctgcg      4560
atgcagatcc ggaacataat ggtgcagggc gctgacttcc gcgtttccag actttacgaa      4620
acacggaaac cgaagaccat tcatgttgtt gctcaggtcg cagacgtttt gcagcagcag      4680
tcgcttcacg ttcgctcgcg tatcggtgat tcattctgct aaccagtaag gcaaccccgc      4740
cagcctagcc gggtcctcaa cgacaggagc acgatcatgc tagtcatgcc ccgcgcccac      4800
cggaaggagc tgactgggtt gaaggctctc aagggcatcg gtcgagatcc cggtgcctaa      4860
tgagtgagct aacttacatt aattgcgttg cgctcactgc ccgctttcca gtcgggaaac      4920
ctgtcgtgcc agctgcatta atgaatcggc caacgcgcgg ggagaggcgg tttgcgtatt      4980
gggcgccagg gtggtttttc ttttcaccag tgagacgggc aacagctgat tgcccttcac      5040
cgcctggccc tgagagagtt gcagcaagcg gtccacgctg gtttgcccca gcaggcgaaa      5100
atcctgtttg atggtggtta acggcgggat ataacatgag ctgtcttcgg tatcgtcgta      5160
tcccactacc gagatgtccg caccaacgcg cagcccggac tcggtaatgg cgcgcattgc      5220
gcccagcgcc atctgatcgt tggcaaccag catcgcagtg ggaacgatgc cctcattcag      5280
catttgcatg gtttgttgaa aaccggacat ggcactccag tcgccttccc gttccgctat      5340
cggctgaatt tgattgcgag tgagatattt atgccagcca gccagacgca gacgcgccga      5400
gacagaactt aatgggcccg ctaacagcgc gatttgctgg tgacccaatg cgaccagatg      5460
ctccacgccc agtcgcgtac cgtcttcatg ggagaaaata atactgttga tgggtgtctg      5520
gtcagagaca tcaagaaata acgccggaac attagtgcag gcagcttcca cagcaatggc      5580
atcctggtca tccagcggat agttaatgat cagcccactg acgcgttgcg cgagaagatt      5640
gtgcaccgcc gctttacagg cttcgacgcc gcttcgttct accatcgaca ccaccacgct      5700
```

```
ggcacccagt tgatcggcgc gagatttaat cgccgcgaca atttgcgacg gcgcgtgcag    5760
ggccagactg gaggtggcaa cgccaatcag caacgactgt tgcccgcca gttgttgtgc      5820 cacgcggttg ggaatgtaat tcagctccgc catcgccgct tccactttt cccgcgtttt      5880 cgcagaaacg tggctggcct ggttcaccac gcgggaaacg gtctgataag agacaccggc    5940
atactctgcg acatcgtata acgttactgg tttcacattc accaccctga attgactctc    6000
ttccgggcgc tatcatgcca taccgcgaaa ggttttgcgc cattcgatgg tgtccgggat    6060
ctcgacgctc tcccttatgc gactcctgca ttaggaagca gcccagtagt aggttgaggc    6120
cgttgagcac cgccgccgca aggaatggtg catgcaagga gatggcgccc aacagtcccc    6180
cggccacggg gcctgccacc atacccacgc cgaaacaagc gctcatgagc ccgaagtggc    6240
gagcccgatc ttccccatcg gtgatgtcgg cgatataggc gccagcaacc gcacctgtgg    6300
cgccggtgat gccggccacg atgcgtccgg cgtagaggat cgagatcgat ctcgatcccg    6360
cgaaattaat acgactcact ata                                             6383

<210> SEQ ID NO 21
<211> LENGTH: 6711
<212> TYPE: DNA
<213> ORGANISM: Artificial Sequence
<220> FEATURE:
<223> OTHER INFORMATION: construct pINT-yjhB

<400> SEQUENCE: 21
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgaagatcct ttgatctttt    420
ctacggggtc tgacgctcag tggaacgaaa actcacgtta agggattttg gtcatgagat    480
tatcaaaaag gatcttcacc tagatccttt taaactagtg aagttaccat cacggaaaaa    540
ggttatgctg cttttaagac ccactttcac atttaagttg ttttctaat ccgcatatga     600 tcaattcaag gccgaataag aaggctggct ctgcaccttg gtgatcaaat aattcgatag    660
cttgtcgtaa taatggcggc atactatcag tagtaggtgt tcccttttct tctttagcga    720
cttgatgctc ttgatcttcc aatacgcaac ctaaagtaaa atgccccact gcgctgagtg    780
catataatgc attctctagt gaaaaacctt gttggcataa aaaggctaat tgattttcga    840
gagtttcata ctgtttttct gtaggccgtg tacctaaatg tacttttgct ccatcgcgat    900
gacttagtaa agcacatcta aaactttag cgttattacg taaaaaatct tgccagcttt     960 cccccttctaa agggcaaaag tgagtatggt gcctatctaa catctcaatg ctaaggcgt    1020 cgagcaaagc ccgcttattt tttacatgcc aatacaatgt aggctgctct acacctagct    1080
tctgggcgag tttacgggtt gttaaacctt cgattccgac ctcattaagc agctctaatg    1140
cgctgttaat cactttactt ttatctaaac gagacatact cttcctttt caatattatt    1200 gaagcattta tcagggttat tgtctcatga gcggatacat atttgaatgt atttagaaaa    1260
ataaacaaat aggggttccg cgcacatttc cccgaaaagt gccacctgaa attggccaga    1320
```

```
tgattaattc ctaattttg ttgacactct atcattgata gagttatttt accactccct    1380
atcagtgata gagaaaagtg aaatgaatag ttcgacaaaa atctagaaat aattttgttt    1440
aactttaaga aggagatata caagagctcg agtcgaagga gatagaacca tggcaacagc    1500
atggtataaa caagttaatc caccacaacg gaaagctctt ttttccgcat ggcttggata    1560
tgtatttgat ggctttgatt ttatgatgat attttacatt cttcatatta taaaagcaga    1620
tcttggcatt acggatattc aggctacttt aatagggaca gtggccttca tagccagacc    1680
tattggaggt ggttttttg gtgccatggc tgataaatat ggtcgtaagc caatgatgat    1740
gtgggcaatt ttcatttact cagtcggaac aggccttagc ggtattgcta caaacttata    1800
tatgctcgca gtttgccgtt ttattgttgg cttagggatg tctggtgaat atgcatgtgc    1860
ttcaacttat gcggtagaaa gttggcctaa aaatcttcaa tctaaagcta gtgcttttt     1920
ggtaagtggt tttctgttg gaaatattat tgcggcacaa ataatccctc agtttgctga    1980
agtatatgga tggagaaact ctttttttat aggcctgtta ccagttttac tagttctttg    2040
gatcagaaaa agtgctccag aaagtcagga gtggattgaa gataaatata aggataaatc    2100
aacattttg tctgtcttca gaaaaccaca tctttcaatc tctatgatcg ttttcctcgt    2160
ctgtttttgt ctatttggtg caaactggcc gataaacgga ctacttcctt cctacctggc    2220
agataatgga gttaatacag tggtcatttc aactctgatg acaatagcag gtttaggaac    2280
actgacaggt acaatatttt ttggttttgt tggtgataag attggtgtaa aaaaagcctt    2340
tgtagtcggt ctaataactt catttatttt cctttgtcct cttttttta tttctgtgaa    2400
aaactcttct cttataggat tatgtctctt tggattaatg tttacaaatt taggtattgc    2460
agggttggtt ccaaaattta tatgatgatta cttttccaaca aaattaagag gattagggac    2520
cggtcttatt tataacttag gggcaactgg aggaatggcc gcacctgtat tagctacata    2580
catttcagga tattatggct taggtgtttc attattcatt gttacggttg cattctctgc    2640
cttattaatt ttgttagttg gttttgatat tccaggtaaa atttataaac tatccgtggc    2700
taaatgataa atcgatacta gcataacccc ttggggcctc taaacgcgtc gacacgcaaa    2760
aaggccatcc gtcaggatgg ccttctgctt aatttgatgc ctggcagttt atggcgggcg    2820
tcctgcccgc caccctccgg gccgttgctt cgcaacgttc aaatccgctc ccggcggatt    2880
tgtcctactc aggagagcgt tcaccgacaa acaacagata aaacgaaagg cccagtcttt    2940
cgactgagcc tttcgtttta tttgatgcct ggcagttccc tactctcgca tggggagacc    3000
ccacactacc atcatgtatg aatatcctcc ttagttccta ttccgaagtt cctattctct    3060
agaaagtata ggaacttcgg cgcgtcctac ctgtgacgga agatcacttc gcagaataaa    3120
taaatcctgg tgtccctgtt gataccggga agccctgggc caacttttgg cgaaaatgag    3180
acgttgatcg gcacgtaaga ggttccaact ttcaccataa tgaaataaga tcactaccgg    3240
gcgtattttt tgagttgtcg agattttcag gagctaagga agctaaaatg gagaaaaaaa    3300
tcactggata taccaccgtt gatatatccc aatggcatcg taaagaacat tttgaggcat    3360
ttcagtcagt tgctcaatgt acctataacc agaccgttca gctggatatt acggcctttt    3420
taaagaccgt aaagaaaaat aagcacaagt tttatccggc ctttattcac attcttgccc    3480
gcctgatgaa tgctcatccg gaattacgta tggcaatgaa agacggtgag ctggtgatat    3540
gggatagtgt tcacccttgt tacaccgttt tccatgagca aactgaaacg ttttcatcgc    3600
tctggagtga ataccacgac gatttccggc agtttctaca catatattcg caagatgtgg    3660
cgtgttacgg tgaaaacctg gcctatttcc ctaaagggtt tattgagaat atgtttttcg    3720
```

```
tctcagccaa tccctgggtg agtttcacca gttttgattt aaacgtggcc aatatggaca      3780
acttcttcgc ccccgttttc accatgggca aatattatac gcaaggcgac aaggtgctga      3840
tgccgctggc gattcaggtt catcatgccg tttgtgatgg cttccatgtc ggcagatgct      3900
taatgaatac aacagtactg cgatgagtgg cagggcgggg cgtaaggcgc gccatttaaa      3960
tgaagttcct attccgaagt tcctattctc tagaaagtat aggaacttcg aagcagctcc      4020
agcctacaca atcgctcaag acgtgtaatg ctgcaatctg catgcaagct ggcactggc       4080
cacgcaaaaa ggccatccgt caggatggcc ttctgcttaa tttgatgcct ggcagtttat      4140
ggcgggcgtc ctgcccgcca ccctccgggc cgttgcttcg caacgttcaa atccgctccc      4200
ggcggatttg tcctactcag gagagcgttc accgacaaac aacagataaa acgaaaggcc      4260
cagtctttcg actgagcctt tcgttttatt tgatgcctgg cagttcccta ctctcgcatg      4320
gggagacccc acactaccat cggggggcca tcgatgcagg tggcactttt cggggaaatg      4380
tgcgcggaac ccctatttgt ttatttttct aaatacattc aaatatgtat ccgctcatga      4440
gacaataacc ctgctgcaga ggcctgcatg caagcttggc gtaatcatgg tcatagctgt      4500
ttcctgtgtg aaattgttat ccgctcacaa ttccacacaa catacgagcc ggaagcataa      4560
agtgtaaagc ctggggtgcc taatgagtga gctaactcac attaattgcg ttgcgctcac      4620
tgcccgcttt ccagtcggga aacctgtcgt gccagctgca ttaatgaatc ggccaacgcg      4680
cggggagagg cggtttgcgt attgggcgct cttccgcttc ctcgctcact gactcgctgc      4740
gctcggtcgt tcggctgcgg cgagcggtat cagctcactc aaaggcggta atacggttat      4800
ccacagaatc aggggataac gcaggaaaga acatgtgagc aaaaggccag caaaaggcca      4860
ggaaccgtaa aaaggccgcg ttgctggcgt ttttccatag gctccgcccc cctgacgagc      4920
atcacaaaaa tcgacgctca agtcagaggt ggcgaaaccc gacaggacta taaagatacc      4980
aggcgtttcc ccctggaagc tccctcgtgc gctctcctgt tccgaccctg ccgcttaccg      5040
gatacctgtc cgcctttctc ccttcgggaa gcgtggcgct ttctcatagc tcacgctgta      5100
ggtatctcag ttcggtgtag tcgttcgct ccaagctggg ctgtgtgcac gaaccccccg       5160
ttcagcccga ccgctgcgcc ttatccggta actatcgtct tgagtccaac ccggtaagac      5220
acgacttatc gccactggca gcagccactg gtaacaggat tagcagagcg aggtatgtag      5280
gcggtgctac agagttcttg aagtggtggc ctaactacgg ctacactaga agaacagtat      5340
ttggtatctg cgctctgctg aagccagtta ccttcggaaa aagagttggt agctcttgat      5400
ccggcaaaca aaccaccgct ggtagcggtg gttttttgt ttgcaagcag cagattacgc        5460
gcagaaaaaa aggatctcaa gaagatcctt tgatctttc tacggggtct gacgctcagt       5520
ggaacgaaaa ctcacgttaa gggattttgg tcatgagatt atcaaaaagg atcttcacct      5580
agatcctttt aaattaaaaa tgaagtttta atcaatcta aagtatatat gagtaaactt        5640
ggtctgacag ttaccaatgc ttaatcagtg aggcacctat ctcagcgatc tgtctatttc      5700
gttcatccat agttgcctga ctccccgtcg tgtagataac tacgatacgg gagggcttac      5760
catctggccc cagtgctgca atgataccgc gagacccacg ctcaccggct ccagatttat      5820
cagcaataaa ccagccagcc ggaagggccg agcgcagaag tggtcctgca actttatccg      5880
cctccatcca gtctattaat tgttgccggg aagctagagt aagtagttcg ccagttaata      5940
gtttgcgcaa cgttgttgcc attgctacag gcatcgtggt gtcacgctcg tcgtttggta      6000
tggcttcatt cagctccggt tcccaacgat caaggcgagt tacatgatcc cccatgttgt      6060
```

| | | | | | |
|---|---|---|---|---|---|
| gcaaaaaagc | ggttagctcc | ttcggtcctc | cgatcgttgt | cagaagtaag | ttggccgcag | 6120 |
| tgttatcact | catggttatg | gcagcactgc | ataattctct | tactgtcatg | ccatccgtaa | 6180 |
| gatgcttttc | tgtgactggt | gagtactcaa | ccaagtcatt | ctgagaatag | tgtatgcggc | 6240 |
| gaccgagttg | ctcttgcccg | gcgtcaatac | gggataatac | cgcgccacat | agcagaactt | 6300 |
| taaaagtgct | catcattgga | aaacgttctt | cggggcgaaa | actctcaagg | atcttaccgc | 6360 |
| tgttgagatc | cagttcgatg | taacccactc | gtgcacccaa | ctgatcttca | gcatctttta | 6420 |
| ctttcaccag | cgtttctggg | tgagcaaaaa | caggaaggca | aaatgccgca | aaaagggaa | 6480 |
| taagggcgac | acgaaatgt | tgaatactca | tactcttcct | ttttcaatat | tattgaagca | 6540 |
| tttatcaggg | ttattgtctc | atgagcggat | acatatttga | atgtatttag | aaaaataaac | 6600 |
| aaataggggt | tccgcgcaca | tttccccgaa | aagtgccacc | tgacgtctaa | gaaaccatta | 6660 |
| ttatcatgac | attaacctat | aaaaataggc | gtatcacgag | gccctttcgt | c | 6711 |

<210> SEQ ID NO 22
<211> LENGTH: 6867
<212> TYPE: DNA
<213> ORGANISM: Artificial Sequence
<220> FEATURE:
<223> OTHER INFORMATION: construct pINT-yebQ

<400> SEQUENCE: 22

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcgggctgg | cttaactatg | cggcatcaga | gcagattgta | ctgagagtgc | 180 |
| accatatgcg | gtgtgaaata | ccgcacagat | gcgtaaggag | aaaataccgc | atcaggcgcc | 240 |
| attcgccatt | caggctgcgc | aactgttggg | aagggcgatc | ggtgcgggcc | tcttcgctat | 300 |
| tacgccagct | ggcgaaaggg | ggatgtgctg | caaggcgatt | aagttgggta | acgccagggt | 360 |
| tttcccagtc | acgacgttgt | aaaacgacgg | ccagtgaatt | cgaagatcct | ttgatctttt | 420 |
| ctacggggtc | tgacgctcag | tggaacgaaa | actcacgtta | agggattttg | gtcatgagat | 480 |
| tatcaaaaag | gatcttcacc | tagatccttt | taaactagtg | aagttaccat | cacggaaaaa | 540 |
| ggttatgctg | cttttaagac | ccactttcac | atttaagttg | ttttctaat | ccgcatatga | 600 |
| tcaattcaag | gccgaataag | aaggctggct | ctgcaccttg | gtgatcaaat | aattcgatag | 660 |
| cttgtcgtaa | taatggcggc | atactatcag | tagtaggtgt | ttccctttct | tctttagcga | 720 |
| cttgatgctc | ttgatcttcc | aatacgcaac | ctaaagtaaa | atgccccact | gcgctgagtg | 780 |
| catataatgc | attctctagt | gaaaaacctt | gttggcataa | aaaggctaat | tgattttcga | 840 |
| gagtttcata | ctgttttttct | gtaggccgtg | tacctaaatg | tacttttgct | ccatcgcgat | 900 |
| gacttagtaa | agcacatcta | aaactttag | cgttattacg | taaaaaatct | tgccagcttt | 960 |
| ccccttctaa | agggcaaaag | tgagtatggt | gcctatctaa | catctcaatg | gctaaggcgt | 1020 |
| cgagcaaagc | ccgcttattt | tttacatgcc | aatacaatgt | aggctgctct | acacctagct | 1080 |
| tctgggcgag | tttacgggtt | gttaaacctt | cgattccgac | ctcattaagc | agctctaatg | 1140 |
| cgctgttaat | cactttactt | ttatctaaac | gagacatact | cttccttttt | caatattatt | 1200 |
| gaagcattta | tcagggttat | tgtctcatga | gcggatacat | atttgaatgt | atttagaaaa | 1260 |
| ataaacaaat | aggggttccg | cgcacatttc | cccgaaaagt | gccacctgaa | attggccaga | 1320 |
| tgattaattc | ctaattttg | ttgacactct | atcattgata | gagttatttt | accactccct | 1380 |
| atcagtgata | gagaaaagtg | aaatgaatag | ttcgacaaaa | atctagaaat | aattttgttt | 1440 |

```
aactttaaga aggagatata caagagctcg agtcgaagga gatagaacca tgccaaaagt    1500
tcaggccgac ggcctgccat tgccccagcg atacggtgcg atattaacca ttgtgattgg    1560
tatttcgatg ccgtccttg acggcgcaat cgccaacgtc gccctgccaa caatcgccac     1620
ggaccttcat gccacgccag ccagttccat ctgggtagtg aacgcctatc aaatcgccat    1680
tgtcatctcc ctgctctcgt tttcgtttct gggcgatatg tttggctatc gacgtattta    1740
taaatgcggt ctggtcgttt ttctgttgtc ttcactgttc tgcgcccttt ctgattcgct    1800
gcaaatgctc acccttgcgc gtgtcataca aggtttcggc ggtgcagcgt tgatgagcgt    1860
taataccgca cttatccgcc tgatctatcc acaacgtttt ctgggtagag ggatgggcat    1920
aaactcgttt attgttgccg tctcttctgc tgccgggccg acaattgctg cagcaatcct    1980
ctccatcgca tcctggaaat ggttattttt aatcaacgta ccgttaggta ttatcgccct    2040
gcttctggcg atgcgttttc tgccacccaa tggttctcgc gccagtaaac cccgtttcga    2100
cctgcccagc gccgtgatga acgcgttaac cttcggcctg cttatcactg cgttgagtgg    2160
tttcgctcag gggcaatcgc tgacgttaat tgctgcggaa ctggtggtaa tggttgttgt    2220
tggtattttc tttattcgcc gccagctttc tcttcccgta ccgctgctac cggtggattt    2280
actgcgtatc ccgctgtttt cactttctat ttgcacatct gtttgctctt tctgcgcaca    2340
aatgctggca atggtttccc tgccctttta cctgcaaacc gtgctcgggc gtagtgaagt    2400
cgaaacaggt ttacttctga caccgtggcc gttagcaacg atggtgatgg ctccgctggc    2460
aggctatttg attgaacgcg tacatgcagg attgctgggg ctttagggt tgttcatcat     2520 ggctgcgggg ctttttttccc tggttctgct gcccgcgtca cctgcggata tcaatattat    2580
ctggccgatg atcttatgtg gtgctggatt tggcttattc cagtcaccca ataaccacac    2640
cattattacc tccgcgcctc gcgaacgtag cggtggagcc agtggcatgt taggaacggc    2700
tcgtctactg ggtcagagta gcggcgcggc gctggtggcg ctgatgctaa atcagtttgg    2760
agataatggt acacacgtct cgctgatggc tgcggctatt ctggcagtga ttgctgcctg    2820
tgtcagtggt ttacgtatca ctcagccacg atccagggca taataaatcg atactagcat    2880
aaccccttgg ggcctctaaa cgcgtcgaca cgcaaaaagg ccatccgtca ggatggcctt    2940
ctgcttaatt tgatgcctgg cagtttatgg cgggcgtcct gcccgccacc ctccgggccg    3000
ttgcttcgca acgttcaaat ccgctcccgg cggatttgtc ctactcagga gagcgttcac    3060
cgacaaacaa cagataaaac gaaaggccca gtctttcgac tgagcctttc gttttatttg    3120
atgcctggca gttccctact ctcgcatggg gagaccccac actaccatca tgtatgaata    3180
tcctccttag ttcctattcc gaagttccta ttctctagaa agtataggaa cttcggcgcg    3240
tcctacctgt gacggaagat cacttcgcag aataaataaa tcctggtgtc cctgttgata    3300
ccgggaagcc ctgggccaac ttttggcgaa aatgagacgt tgatcggcac gtaagaggtt    3360
ccaactttca ccataatgaa ataagatcac taccgggcgt attttttgag ttgtcgagat    3420
tttcaggagc taaggaagct aaaatggaga aaaaaatcac tggatatacc accgttgata    3480
tatcccaatg gcatcgtaaa gaacattttg aggcatttca gtcagttgct caatgtacct    3540
ataaccagac cgttcagctg gatattacgg ccttttttaaa gaccgtaaag aaaaataagc    3600
acaagtttta tccggccttt attcacattc ttgcccgcct gatgaatgct catccggaat    3660
tacgtatggc aatgaaagac ggtgagctgg tgatatggga tagtgttcac ccttgttaca    3720
ccgttttcca tgagcaaact gaaacgtttt catcgctctg gagtgaatac cacgacgatt    3780
```

```
tccggcagtt tctacacata tattcgcaag atgtggcgtg ttacggtgaa aacctggcct   3840
atttccctaa agggtttatt gagaatatgt ttttcgtctc agccaatccc tgggtgagtt   3900
tcaccagttt tgatttaaac gtggccaata tggacaactt cttcgccccc gttttcacca   3960
tgggcaaata ttatacgcaa ggcgacaagg tgctgatgcc gctggcgatt caggttcatc   4020
atgccgtttg tgatggcttc catgtcggca gatgcttaat gaatacaaca gtactgcgat   4080
gagtggcagg gcggggcgta aggcgcgcca tttaaatgaa gttcctattc cgaagttcct   4140
attctctaga aagtatagga acttcgaagc agctccagcc tacacaatcg ctcaagacgt   4200
gtaatgctgc aatctgcatg caagcttggc actggccacg caaaaaggcc atccgtcagg   4260
atggccttct gcttaatttg atgcctggca gtttatggcg ggcgtcctgc ccgccaccct   4320
ccgggccgtt gcttcgcaac gttcaaatcc gctcccggcg gatttgtcct actcaggaga   4380
gcgttcaccg acaaacaaca gataaaacga aaggcccagt ctttcgactg agcctttcgt   4440
tttatttgat gcctggcagt tccctactct cgcatgggga gacccacac taccatcggg    4500
gggccatcga tgcaggtggc acttttcggg gaaatgtgcg cggaacccct atttgtttat   4560
ttttctaaat acattcaaat atgtatccgc tcatgagaca ataaccctgc tgcagaggcc   4620
tgcatgcaag cttggcgtaa tcatggtcat agctgtttcc tgtgtgaaat tgttatccgc   4680
tcacaattcc acacaacata cgagccggaa gcataaagtg taaagcctgg ggtgcctaat   4740
gagtgagcta actcacatta attgcgttgc gctcactgcc cgctttccag tcgggaaacc   4800
tgtcgtgcca gctgcattaa tgaatcggcc aacgcgcggg gagaggcggt ttgcgtattg   4860
ggcgctcttc cgcttcctcg ctcactgact cgctgcgctc ggtcgttcgg ctgcggcgag   4920
cggtatcagc tcactcaaag gcggtaatac ggttatccac agaatcaggg gataacgcag   4980
gaaagaacat gtgagcaaaa ggccagcaaa aggccaggaa ccgtaaaaag gccgcgttgc   5040
tggcgttttt ccataggctc cgcccccctg acgagcatca caaaaatcga cgctcaagtc   5100
agaggtggcg aaacccgaca ggactataaa gataccaggc gtttccccct ggaagctccc   5160
tcgtgcgctc tcctgttccg accctgccgc ttaccggata cctgtccgcc tttctccctt   5220
cgggaagcgt ggcgctttct catagctcac gctgtaggta tctcagttcg gtgtaggtcg   5280
ttcgctccaa gctgggctgt gtgcacgaac cccccgttca gcccgaccgc tgcgccttat   5340
ccggtaacta tcgtcttgag tccaacccgg taagacacga cttatcgcca ctggcagcag   5400
ccactggtaa caggattagc agagcgaggt atgtaggcgg tgctacagag ttcttgaagt   5460
ggtggcctaa ctacggctac actagaagaa cagtatttgg tatctgcgct ctgctgaagc   5520
cagttacctt cggaaaaaga gttggtagct cttgatccgg caaacaaacc accgctggta   5580
gcggtggttt ttttgtttgc aagcagcaga ttacgcgcag aaaaaaagga tctcaagaag   5640
atcctttgat cttttctacg gggtctgacg ctcagtggaa cgaaaactca cgttaaggga   5700
ttttggtcat gagattatca aaaaggatct tcacctagat ccttttaaat taaaaatgaa   5760
gttttaaatc aatctaaagt atatatgagt aaacttggtc tgacagttac caatgcttaa   5820
tcagtgaggc acctatctca gcgatctgtc tatttcgttc atccatagtt gcctgactcc   5880
ccgtcgtgta gataactacg atacgggagg gcttaccatc tggccccagt gctgcaatga   5940
taccgcgaga cccacgctca ccggctccag atttatcagc aataaaccag ccagccggaa   6000
gggccgagcg cagaagtggt cctgcaactt tatccgcctc catccagtct attaattgtt   6060
gccgggaagc tagagtaagt agttcgccag ttaatagttt gcgcaacgtt gttgccattg   6120
ctacaggcat cgtggtgtca cgctcgtcgt ttggtatggc ttcattcagc tccggttccc   6180
```

```
aacgatcaag gcgagttaca tgatccccca tgttgtgcaa aaaagcggtt agctccttcg    6240
gtcctccgat cgttgtcaga agtaagttgg ccgcagtgtt atcactcatg gttatggcag    6300
cactgcataa ttctcttact gtcatgccat ccgtaagatg cttttctgtg actggtgagt    6360
actcaaccaa gtcattctga aatagtgta tgcggcgacc gagttgctct tgcccggcgt     6420
caatacggga taataccgcg ccacatagca gaactttaaa agtgctcatc attggaaaac    6480
gttcttcggg gcgaaaactc tcaaggatct taccgctgtt gagatccagt tcgatgtaac    6540
ccactcgtgc acccaactga tcttcagcat ctttactttt caccagcgtt tctgggtgag    6600
caaaaacagg aaggcaaaat gccgcaaaaa agggaataag ggcgacacgg aaatgttgaa    6660
tactcatact cttcctttt caatattatt gaagcattta tcagggttat tgtctcatga     6720
gcggatacat atttgaatgt atttagaaaa ataaacaaat aggggttccg cgcacatttc    6780
cccgaaaagt gccacctgac gtctaagaaa ccattattat catgacatta acctataaaa    6840
ataggcgtat cacgaggccc tttcgtc                                        6867

<210> SEQ ID NO 23
<211> LENGTH: 6768
<212> TYPE: DNA
<213> ORGANISM: Artificial Sequence
<220> FEATURE:
<223> OTHER INFORMATION: construct pINT-proP

<400> SEQUENCE: 23
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgaagatcct ttgatctttt     420
ctacggggtc tgacgctcag tggaacgaaa actcacgtta agggattttg gtcatgagat     480
tatcaaaaag gatcttcacc tagatccttt taaactagtg aagttaccat cacggaaaaa     540
ggttatgctg ctttaagac ccactttcac atttaagttg tttttctaat ccgcatatga      600
tcaattcaag gccgaataag aaggctggct ctgcaccttg gtgatcaaat aattcgatag     660
cttgtcgtaa taatggcggc atactatcag tagtaggtgt ttccctttct tctttagcga    720
cttgatgctc ttgatcttcc aatacgcaac ctaaagtaaa atgccccact gcgctgagtg    780
catataatgc attctctagt gaaaaaccctt gttggcataa aaaggctaat tgattttcga   840
gagtttcata ctgttttttct gtaggccgtg tacctaaatg tacttttgct ccatcgcgat    900
gacttagtaa agcacatcta aaactttag cgttattacg taaaaaatct tgccagcttt     960 cccttctaa agggcaaaag tgagtatggt gcctatctaa catctcaatg gctaaggcgt    1020
cgagcaaagc ccgcttattt tttacatgcc aatacaatgt aggctgctct acacctagct   1080
tctgggcgag tttacgggtt gttaaacctt cgattccgac ctcattaagc agctctaatg   1140
cgctgttaat cactttactt ttatctaaac gagacatact cttcctttt caatattatt    1200 gaagcattta tcagggttat tgtctcatga gcggatacat atttgaatgt atttagaaaa   1260
ataaacaaat aggggttccg cgcacatttc cccgaaaagt gccacctgaa attggccaga   1320
```

```
tgattaattc ctaattttg ttgacactct atcattgata gagttatttt accactccct      1380
atcagtgata gagaaaagtg aaatgaatag ttcgacaaaa atctagaaat aattttgttt      1440
aactttaaga aggagatata caagagctcg agtcgaagga gatagaacca tgccgaacaa      1500
agctgaaacc tccccggcga aactgcgtct gaaagccttc ctgaaacgta tcaagattat      1560
gaacaccacc gaaaacagca aacagaagcc ggttaacgtg gttgcatttg ctttcctgct      1620
gaccgcgttt ctgacgggta tcgccagctc tttccaaacc ccgacgctga gcctgttcct      1680
ggcgcaggaa attcaagtct ctccgtttat ggtgggcatg ttctatacct caaatgcagt      1740
gctgggcatc gttctgtcgc agattctggc taaatacagt gattcccaag atgaccgtcg      1800
caagattatc attttctgca gtctgctggc gatcggcggt tgtatcacct tcgcctacaa      1860
ccgtaactac tacgtgctga tgtttttcgc gacgttcctg ctgtccctgg gtagttccgc      1920
aaacccgcag gcatttgcac tggcacgtga atatgcagac tacaccaaac gcgaagctat      1980
catgtttacc acgattatgc gcacgcagat cagcctggca tggattgttg gcccgccgct      2040
gtcattctcg attgcgctgg gctggggttt tgaatatatg tacatggtcg cggcctcagc      2100
atttctgctg tgcgctatca ttgctaaagc gctgctgccg tatgtgccgc gtaaagccgt      2160
cgtgccgctg accaagccgg atgaagttgc gggtctgccg gccaaaaata aaaagcagag      2220
tgacaagcaa tccatccgcc tgctgtttat tacgtgcttc ctgatgtgga gttgtaacgg      2280
catgtatctg atctccatgc cgctgcatgt tattaatgaa ctgcacctga gtgaacgtct      2340
ggcgggcatt ctgatgggta ccgcagctgg cctggaaatc ccggtgatgc tgattgccgg      2400
ctatctgacc aaatacctga cgaaaaagtc tctgatcctg accgccctgt tcatgggtct      2460
gtttttctat attggcatgc tgtttgcaga acagacgtgg caactggtcg ccctgcaggc      2520
atttaacgct atcttcattg gtatcattgc gaccctgggc atggtgtact ttcaagatct      2580
gatgccgggc aaaatgggtt cagccaccac gctgttctcg aacgcggcca atcatcgtg      2640
gatcgttgca ggtccgtttg tcggcatcat tgctcagatt tggaattata gctcgtgtt      2700
ctacatcagc attgttctgg tcgcggtgtc tctgtttagc atgtctaaag ttaagagcgt      2760
ctaataaatc gatactagca taaccccttg gggcctctaa acgcgtcgac acgcaaaag      2820
gccatccgtc aggatggcct tctgcttaat ttgatgcctg gcagtttatg gcgggcgtcc      2880
tgcccgccac cctccggcc gttgcttcgc aacgttcaaa tccgctcccg gcggatttgt      2940
cctactcagg agagcgttca ccgacaaaca acagataaaa cgaaaggccc agtctttcga      3000
ctgagccttt cgtttatttt gatgcctggc agttccctac tctcgcatgg ggagaccca      3060
cactaccatc atgtatgaat atcctcctta gttcctattc gaagttcct attctctaga      3120
aagtatagga acttcggcgc gtcctacctg tgacggaaga tcacttcgca gaataaataa      3180
atcctggtgt ccctgttgat accgggaagc cctgggccaa cttttggcga aaatgagacg      3240
ttgatcggca cgtaagaggt tccaactttc accataatga aataagatca ctaccgggcg      3300
tatttttga gttgtcgaga ttttcaggag ctaaggaagc taaaatggag aaaaaaatca      3360
ctggatatac caccgttgat atatcccaat ggcatcgtaa agaacatttt gaggcatttc      3420
agtcagttgc tcaatgtacc tataaccaga ccgttcagct ggatattacg gcctttttaa      3480
agaccgtaaa gaaaaataag cacaagtttt atccggcctt tattcacatt cttgcccgcc      3540
tgatgaatgc tcatccggaa ttacgtatgg caatgaaaga cggtgagctg gtgatatggg      3600
atagtgttca cccttgttac accgttttcc atgagcaaac tgaaacgttt tcatcgctct      3660
ggagtgaata ccacgacgat ttccggcagt ttctacacat atattcgcaa gatgtggcgt      3720
```

```
gttacggtga aaacctggcc tatttcccta aagggtttat tgagaatatg ttttcgtct     3780
cagccaatcc ctgggtgagt ttcaccagtt ttgatttaaa cgtggccaat atggacaact    3840
tcttcgcccc cgttttcacc atgggcaaat attatacgca aggcgacaag gtgctgatgc    3900
cgctggcgat tcaggttcat catgccgttt gtgatggctt ccatgtcggc agatgcttaa    3960
tgaatacaac agtactgcga tgagtggcag ggcggggcgt aaggcgcgcc atttaaatga    4020
agttcctatt ccgaagttcc tattctctag aaagtatagg aacttcgaag cagctccagc    4080
ctacacaatc gctcaagacg tgtaatgctg caatctgcat gcaagcttgg cactggccac    4140
gcaaaaaggc catccgtcag gatggccttc tgcttaattt gatgcctggc agtttatggc    4200
gggcgtcctg cccgccaccc tccgggccgt tgcttcgcaa cgttcaaatc cgctcccggc    4260
ggatttgtcc tactcaggag agcgttcacc gacaaacaac agataaaacg aaaggcccag    4320
tctttcgact gagcctttcg ttttatttga tgcctggcag ttccctactc tcgcatgggg    4380
agacccaca  ctaccatcgg ggggccatcg atgcaggtgg cacttttcgg ggaaatgtgc    4440
gcggaacccc tatttgttta ttttctaaa  tacattcaaa tatgtatccg ctcatgagac    4500
aataaccctg ctgcagaggc ctgcatgcaa gcttggcgta atcatggtca tagctgtttc    4560
ctgtgtgaaa ttgttatccg ctcacaattc cacacaacat acgagccgga agcataaagt    4620
gtaaagcctg gggtgcctaa tgagtgagct aactcacatt aattgcgttg cgctcactgc    4680
ccgctttcca gtcgggaaac ctgtcgtgcc agctgcatta atgaatcggc caacgcgcgg    4740
ggagaggcgg tttgcgtatt gggcgctctt ccgcttcctc gctcactgac tcgctgcgct    4800
cggtcgttcg gctgcggcga gcggtatcag ctcactcaaa ggcggtaata cggttatcca    4860
cagaatcagg ggataacgca ggaaagaaca tgtgagcaaa aggccagcaa aaggccagga    4920
accgtaaaaa ggccgcgttg ctggcgtttt tccataggct ccgcccccct gacgagcatc    4980
acaaaaatcg acgctcaagt cagaggtggc gaaacccgac aggactataa agataccagg    5040
cgtttccccc tggaagctcc ctcgtgcgct ctcctgttcc gaccctgccg cttaccggat    5100
acctgtccgc ctttctccct tcgggaagcg tggcgctttc tcatagctca cgctgtaggt    5160
atctcagttc ggtgtaggtc gttcgctcca agctgggctg tgtgcacgaa ccccccgttc    5220
agcccgaccg ctgcgcctta tccggtaact atcgtcttga gtccaacccg gtaagacacg    5280
acttatcgcc actggcagca gccactggta acaggattag cagagcgagg tatgtaggcg    5340
gtgctacaga gttcttgaag tggtggccta actacggcta cactagaaga acagtatttg    5400
gtatctgcgc tctgctgaag ccagttacct tcggaaaaag agttggtagc tcttgatccg    5460
gcaaacaaac caccgctggt agcggtggtt tttttgtttg caagcagcag attacgcgca    5520
gaaaaaaagg atctcaagaa gatcctttga tcttttctac ggggtctgac gctcagtgga    5580
acgaaaactc acgttaaggg attttggtca tgagattatc aaaaggatc  ttcacctaga    5640
tccttttaaa ttaaaaatga agttttaaat caatctaaag tatatatgag taaacttggt    5700
ctgacagtta ccaatgctta atcagtgagg cacctatctc agcgatctgt ctatttcgtt    5760
catccatagt tgcctgactc cccgtcgtgt agataactac gatacgggag ggcttaccat    5820
ctggccccag tgctgcaatg ataccgcgag acccacgctc accggctcca gatttatcag    5880
caataaacca gccagccgga agggccgagc gcagaagtgg tcctgcaact ttatccgcct    5940
ccatccagtc tattaattgt tgccgggaag ctagagtaag tagttcgcca gttaatagtt    6000
tgcgcaacgt tgttgccatt gctacaggca tcgtggtgtc acgctcgtcg tttggtatgg    6060
```

```
cttcattcag ctccggttcc caacgatcaa ggcgagttac atgatccccc atgttgtgca    6120
aaaaagcggt tagctccttc ggtcctccga tcgttgtcag aagtaagttg gccgcagtgt    6180
tatcactcat ggttatggca gcactgcata attctcttac tgtcatgcca tccgtaagat    6240
gcttttctgt gactggtgag tactcaacca agtcattctg agaatagtgt atgcggcgac    6300
cgagttgctc ttgcccggcg tcaatacggg ataataccgc gccacatagc agaactttaa    6360
aagtgctcat cattggaaaa cgttcttcgg ggcgaaaact ctcaaggatc ttaccgctgt    6420
tgagatccag ttcgatgtaa cccactcgtg cacccaactg atcttcagca tcttttactt    6480
tcaccagcgt ttctgggtga gcaaaaacag gaaggcaaaa tgccgcaaaa agggaataa     6540
gggcgacacg gaaatgttga atactcatac tcttcctttt tcaatattat tgaagcattt    6600
atcaggggtta ttgtctcatg agcggataca tatttgaatg tatttagaaa aataaacaaa   6660
tagggggttcc gcgcacattt ccccgaaaag tgccacctga cgtctaagaa accattatta   6720
tcatgacatt aacctataaa aataggcgta tcacgaggcc ctttcgtc                 6768

<210> SEQ ID NO 24
<211> LENGTH: 6672
<212> TYPE: DNA
<213> ORGANISM: Artificial Sequence
<220> FEATURE:
<223> OTHER INFORMATION: construct pINT-Cn-setA

<400> SEQUENCE: 24
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgaagatcct ttgatctttt     420
ctacggggtc tgacgctcag tggaacgaaa actcacgtta agggattttg gtcatgagat     480
tatcaaaaag gatcttcacc tagatccttt taaactagtg aagttaccat cacggaaaaa     540
ggttatgctg cttttaagac ccactttcac atttaagttg tttttctaat ccgcatatga     600
tcaattcaag gccgaataag aaggctggct ctgcaccttg gtgatcaaat aattcgatag     660
cttgtcgtaa taatggcggc atactatcag tagtaggtgt ttccctttct tctttagcga     720
cttgatgctc ttgatcttcc aatacgcaac ctaaagtaaa atgccccact gcgctgagtg     780
catataatgc attctctagt gaaaaacctt gttggcataa aaaggctaat tgattttcga     840
gagtttcata ctgtttttct gtaggccgtg tacctaaatg tacttttgct ccatcgcgat     900
gacttagtaa agcacatcta aaactttag  cgttattacg taaaaaatct tgccagcttt     960
cccccttctaa agggcaaaag tgagtatggt gcctatctaa catctcaatg ctaaggcgt    1020
cgagcaaagc ccgcttattt tttacatgcc aatacaatgt aggctgctct acacctagct    1080
tctgggcgag tttacgggtt gttaaacctt cgattccgac ctcattaagc agctctaatg    1140
cgctgttaat cactttactt ttatctaaac gagacatact cttcctttt  caatattatt   1200
gaagcattta tcagggttat tgtctcatga gcggatacat atttgaatgt atttagaaaa   1260
ataaacaaat aggggttccg cgcacatttc cccgaaaagt gccacctgaa attggccaga   1320
tgattaattc ctaattttg ttgacactct atcattgata gagttatttt accactccct    1380
```

```
atcagtgata gagaaaagtg aaatgaatag ttcgacaaaa atctagaaat aatttgttt    1440 aactttaaga aggagatata caagagctcg agtcgaagga gatagaacca tgctgtggtt   1500
tctgacccgt gctcgtcgct tcaatccggt ttatgcggcc tttatggccg tcagcttcat   1560
gattggtgtg gccggtgcac tgcaggcacc gaccctgtct ctgtttctga cgcgtgaagt   1620
tgaagtccgc ccgttttggg ttggtctgtt ctacacggtc aacgcaattg ctggcatcgg   1680
tgtgagtctg ctgctggcca aacgtagtga ttcccaaggc gaccgtcgca aactgattat   1740
ggtgtgctgt gttatggcgg tcgccaactg cgtcctgttt gcattcaatc gccattatct   1800
gaccctgatc acgctgggtg tgatgtttgc aagcattgct aataccgcga tgccgcagat   1860
cttcgcactg gctcgtgaat acgccgatcg ttctgcacgc gaagtggtta tgtttagctc   1920
tattatgcgc gcccaactga gtctggcatg ggttattggc cgccgctgt ccttcatgct    1980 ggccctgaaa tatggtttta ccacgatgtt cctgattgca gctggcattt tgtgatctc    2040 actggctctg attatcttcg cgctgccgtc ggtgccgcgt gttgaacagc cggccgaagt   2100
ggcaattacc caagttagcg gttggaaaga ttctaacgtt cgcatgctgt ttatcgcctc   2160
aatgctgatg tggacctgta atacgatgta tattatcgac atgccgctgt ggatttcgca   2220
ggatctgggt ctgccggatg aactggccgg tctgctgatg ggtaccgccg caggcattga   2280
aatcccggct atgatcctgg cgggttatta cgtgaaacgt tttggcaaac gcaacatgat   2340
ggtcgcagct gtggcggccg gtattctgtt ttacgttggc ctgatcctgt ccatagcaa    2400 aacgcgctg gtcgtgctgc agctgtttaa tgccgtcttc attggtatta tcgcaggcat   2460
cggtatgctg tggtttcaag atctgatgcc gggtcgtccg ggtagcgcaa ccaccctgtt   2520
caccaactca atttcgacgg gcgtgattct ggccggtatt ctgcagggtg ccctggcaga   2580
aggttttggt cactatagtg tgtactggct gatggcagct ctggctgtta tcgcgctgtt   2640
cctgaccagc cgcgttaaaa acgtctaata aatcgatact agcataaccc cttgggcct    2700 ctaaacgcgt cgacacgcaa aaaggccatc cgtcaggatg gccttctgct taatttgatg   2760
cctggcagtt tatggcgggc gtcctgcccg ccaccctccg ggccgttgct tcgcaacgtt   2820
caaatccgct cccggcggat ttgtcctact caggagagcg ttcaccgaca aacaacagat   2880
aaaacgaaag gcccagtctt tcgactgagc ctttcgtttt atttgatgcc tggcagttcc   2940
ctactctcgc atgggagac cccacactac catcatgtat gaatatcctc cttagttcct   3000
attccgaagt tcctattctc tagaaagtat aggaacttcg gcgcgtccta cctgtgacgg   3060
aagatcactt cgcagaataa ataaatcctg gtgtccctgt tgataccggg aagccctggg   3120 ccaactttg gcgaaaatga gacgttgatc ggcacgtaag aggttccaac tttcaccata    3180
atgaaataag atcactaccg gcgtattttt tgagttgtc gagattttca ggagctaagg    3240
aagctaaaat ggagaaaaaa atcactggat ataccaccgt tgatatatcc caatggcatc   3300
gtaaagaaca ttttgaggca tttcagtcag ttgctcaatg tacctataac cagaccgttc   3360
agctggatat tacggccttt ttaaagaccg taaagaaaaa taagcacaag ttttatccgg   3420
cctttattca cattcttgcc cgcctgatga atgctcatcc ggaattacgt atggcaatga   3480
aagacggtga gctggtgata tgggatagtg ttcacccttg ttacaccgtt ttccatgagc   3540
aaactgaaac gttttcatcg ctctggagtg aataccacga cgatttccgg cagtttctac   3600
acatatattc gcaagatgtg gcgtgttacg gtgaaaacct ggcctatttc cctaaagggt   3660
ttattgagaa tatgtttttc gtctcagcca atccctgggt gagtttcacc agttttgatt   3720
```

```
taaacgtggc caatatggac aacttcttcg cccccgtttt caccatgggc aaatattata    3780
cgcaaggcga caaggtgctg atgccgctgg cgattcaggt tcatcatgcc gtttgtgatg    3840
gcttccatgt cggcagatgc ttaatgaata caacagtact gcgatgagtg gcagggcggg    3900
gcgtaaggcg cgccatttaa atgaagttcc tattccgaag ttcctattct ctagaaagta    3960
taggaacttc gaagcagctc cagcctacac aatcgctcaa gacgtgtaat gctgcaatct    4020
gcatgcaagc ttggcactgg ccacgcaaaa aggccatccg tcaggatggc cttctgctta    4080
atttgatgcc tggcagttta tggcgggcgt cctgcccgcc accctccggg ccgttgcttc    4140
gcaacgttca aatccgctcc cggcggattt gtcctactca ggagagcgtt caccgacaaa    4200
caacagataa aacgaaaggc ccagtctttc gactgagcct ttcgttttat ttgatgcctg    4260
gcagttccct actctcgcat ggggagaccc cacactacca tcgggggcc atcgatgcag    4320
gtggcacttt tcggggaaat gtgcgcggaa cccctatttg tttattttc taaatacatt    4380
caaatatgta tccgctcatg agacaataac cctgctgcag aggcctgcat gcaagcttgg    4440
cgtaatcatg gtcatagctg tttcctgtgt gaaattgtta tccgctcaca attccacaca    4500
acatacgagc cggaagcata aagtgtaaag cctggggtgc ctaatgagtg agctaactca    4560
cattaattgc gttgcgctca ctgcccgctt tccagtcggg aaacctgtcg tgccagctgc    4620
attaatgaat cggccaacgc gcggggagag gcggtttgcg tattgggcgc tcttccgctt    4680
cctcgctcac tgactcgctg cgctcggtcg ttcggctgcg gcgagcggta tcagctcact    4740
caaaggcggt aatacggtta tccacagaat caggggataa cgcaggaaag aacatgtgag    4800
caaaaggcca gcaaaaggcc aggaaccgta aaaaggccgc gttgctggcg ttttttccata    4860
ggctccgccc ccctgacgag catcacaaaa atcgacgctc aagtcagagg tggcgaaacc    4920
cgacaggact ataaagatac caggcgtttc ccctggaag ctccctcgtg cgctctcctg    4980
ttccgaccct gccgcttacc ggatacctgt ccgcctttct cccttcggga agcgtggcgc    5040
tttctcatag ctcacgctgt aggtatctca gttcggtgta ggtcgttcgc tccaagctgg    5100
gctgtgtgca cgaaccccc gttcagcccg accgctgcgc cttatccggt aactatcgtc    5160
ttgagtccaa cccggtaaga cacgacttat cgccactggc agcagccact ggtaacagga    5220
ttagcagagc gaggtatgta ggcggtgcta cagagttctt gaagtggtgg cctaactacg    5280
gctacactag aagaacagta tttggtatct gcgctctgct gaagccagtt accttcggaa    5340
aaagagttgg tagctcttga tccggcaaac aaaccaccgc tggtagcggt ggttttttg    5400
tttgcaagca gcagattacg cgcagaaaaa aaggatctca agaagatcct ttgatctttt    5460
ctacggggtc tgacgctcag tggaacgaaa actcacgtta agggattttg gtcatgagat    5520
tatcaaaaag gatcttcacc tagatccttt taaattaaaa atgaagtttt aaatcaatct    5580
aaagtatata tgagtaaact tggtctgaca gttaccaatg cttaatcagt gaggcaccta    5640
tctcagcgat ctgtctattt cgttcatcca tagttgcctg actccccgtc gtgtagataa    5700
ctacgatacg ggagggctta ccatctggcc ccagtgctgc aatgataccg cgagacccac    5760
gctcaccggc tccagattta tcagcaataa accagccagc cggaagggcc gagcgcagaa    5820
gtggtcctgc aactttatcc gcctccatcc agtctattaa ttgttgccgg gaagctagag    5880
taagtagttc gccagttaat agtttgcgca acgttgttgc cattgctaca ggcatcgtgg    5940
tgtcacgctc gtcgtttggt atggcttcat tcagctccgg ttcccaacga tcaaggcgag    6000
ttacatgatc ccccatgttg tgcaaaaaag cggttagctc cttcggtcct ccgatcgttg    6060
tcagaagtaa gttggccgca gtgttatcac tcatggttat ggcagcactg cataattctc    6120
```

```
ttactgtcat gccatccgta agatgctttt ctgtgactgg tgagtactca accaagtcat    6180
tctgagaata gtgtatgcgg cgaccgagtt gctcttgccc ggcgtcaata cgggataata    6240
ccgcgccaca tagcagaact ttaaaagtgc tcatcattgg aaaacgttct tcggggcgaa    6300
aactctcaag gatcttaccg ctgttgagat ccagttcgat gtaacccact cgtgcaccca    6360
actgatcttc agcatctttt actttcacca gcgtttctgg gtgagcaaaa acaggaaggc    6420
aaaatgccgc aaaaaaggga ataagggcga cacggaaatg ttgaatactc atactcttcc    6480
tttttcaata ttattgaagc atttatcagg gttattgtct catgagcgga tacatatttg    6540
aatgtattta gaaaaataaa caataggggg ttccgcgcac atttccccga aaagtgccac    6600
ctgacgtcta agaaaccatt attatcatga cattaaccta taaaaatagg cgtatcacga    6660
ggccctttcg tc                                                        6672
```

<210> SEQ ID NO 25  
<211> LENGTH: 7074  
<212> TYPE: DNA  
<213> ORGANISM: Artificial Sequence  
<220> FEATURE:  
<223> OTHER INFORMATION: construct pINT-spoVB

<400> SEQUENCE: 25

```
tcgcgcgttt cggtgatgac ggtgaaaacc tctgacacat gcagctcccg gagacggtca      60
cagcttgtct gtaagcggat gccggagca  gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgaagatcct ttgatctttt     420
ctacggggtc tgacgctcag tggaacgaaa actcacgtta agggattttg gtcatgagat     480
tatcaaaaag gatcttcacc tagatccttt taaactagtg aagttaccat cacggaaaaa     540
ggttatgctg ctttaagac ccactttcac atttaagttg ttttctaat ccgcatatga      600 tcaattcaag gccgaataag aaggctggct ctgcaccttg gtgatcaaat aattcgatag     660
cttgtcgtaa taatggcggc atactatcag tagtaggtgt ttccctttct tctttagcga    720
cttgatgctc ttgatcttcc aatacgcaac ctaaagtaaa atgccccact gcgctgagtg    780
catataatgc attctctagt gaaaaacctt gttggcataa aaaggctaat tgattttcga    840
gagtttcata ctgtttttct gtaggccgtg tacctaaatg tactttgct ccatcgcgat     900 gacttagtaa agcacatcta aaactttag cgttattacg taaaaaatct tgccagcttt     960
ccccttctaa agggcaaaag tgagtatggt gcctatctaa catctcaatg gctaaggcgt   1020
cgagcaaagc ccgcttattt tttacatgcc aatacaatgt aggctgctct acacctagct   1080
tctgggcgag tttacgggtt gttaaacctt cgattccgac ctcattaagc agctctaatg   1140
cgctgttaat cacttacttt ttatctaaac gagacatact cttccttttt caatattatt   1200
gaagcattta tcagggttat tgtctcatga gcggatacat atttgaatgt atttagaaaa   1260
ataaacaaat aggggttccg cgcacatttc cccgaaaagt gccacctgaa attggccaga   1320
tgattaattc ctaatttttg ttgacactct atcattgata gagttatttt accactccct   1380
atcagtgata gagaaaagtg aaatgaatag ttcgacaaaa atctagaaat aattttgttt   1440
```

```
aactttaaga aggagatata caagagctcg agtcgaagga gatagaacca tgaatgactc    1500
ggtcggtgct aagcgtcaaa gtgcgtggaa gggtgcgttc gtcctggtcg ttgcgggcat    1560
cgttaccaag atcctgtctg ccgtgtatcg tgttccgttt cagaacattg tcggcgatgt    1620
gggtttctat atctaccagc aagtttaccc gtttctgggc attgcggtca tgctgagtac    1680
ctccggtttt ccggtgatca tctcgaagct gatgaacgat tacagcgacc ataaacagaa    1740
gattatgaag atcagtgcac tgtatgtgac ggcagcaggt ctggttctgt ttgccctgat    1800
gtacgcaggt gcagctccgc tggcgggctt catgggtgat gaccgtctgg tcatgctgat    1860
tcgcgtggcg gcctttgctt tcatcctgtt tccgttcacc gcggtttttc gcggctattt    1920
ccagggtgtg cacgacatga tgccgtctgc tctgagtcag attacggaac aactgctgcg    1980
tgtggcagtt ctgctgggcc tgtcttttg gctgctgaaa tccggtcgtt cactgtacgc    2040
agctggtgca ggtgcagcat caggttcgat tgcaggtagt ctggcagctc tgtgcgttct    2100
ggcagtcttc tggtataaac gtgaagaaac caaaaaggat ggcggtcata tcgaaacggc    2160
ggttattatc aaaaagctgc tgctgtactc cgtgaccatt tgtatcagct ctgttctgat    2220
gctgctgctg cagctggttg atgcgctgaa cctgtattcg ctgctgagcg acggcaccga    2280
atcacatgcg gccaaacaac tgaagggcat ttacgaccgt ggtcagccgc tgctgcaact    2340
gggtacggtg tttgcggttt ccattgcagc ttcactggtc ccgagcatct ctaaagccgt    2400
gcacgaaaat aagccgttca ttatcaaaga aaaggctacc tctgcggtca aactgtgcct    2460
ggcggtgggc attggtgcta gtgcgggcct gttttgtatt ctggaaccgg ttaacatcat    2520
gctgttccag aattccgaag gtacccgac gctgcaaatc tttagtctgt ccattttctt    2580
tgcctcaatc gcactgaccg cagcagcaat cctgcaaggt gcaggtcata cggtgttccc    2640
ggcagtcagc gtgctggctg gcggtgcgct gaaatgggtc ctgaacgtgt ggctggttcc    2700
gggttggggt attaccggtg ctgcactggc tacggttctg gcatttgcag cagtcgcatg    2760
cctgaacctg cgtcgcatct ggtcgaaagg ttggctgacc aatattggcg gtgtgatcgc    2820
acgtctgtgc tggtgtagcc tgctgatggt gtttttcctg ctggtctata tgaaactgtg    2880
gcagctgttt gttccggtca gccgtgccgg cgcagtttgc gaatcactgt cggccagcgt    2940
gattggcggt ctgctgttca tctactgtat gatccgcatg aagatcttca ccgatgaaga    3000
actgagcggc ctgccgttcg gttctgcgct gagtaaactg aaaaagcgtc gcgaaaagca    3060
cggtcgctaa taaatcgata ctagcataac cccttggggc ctctaaacgc gtcgacacgc    3120
aaaaaggcca tccgtcagga tggccttctg cttaatttga tgcctggcag tttatggcgg    3180
gcgtcctgcc cgccaccctc cgggccgttg cttcgcaacg ttcaaatccg ctcccggcgg    3240
atttgtccta ctcaggagag cgttcaccga caaacaacag ataaaacgaa aggcccagtc    3300
tttcgactga gcctttcgtt ttatttgatg cctggcagtt ccctactctc gcatggggag    3360
accccacact accatcatgt atgaatatcc tccttagttc ctattccgaa gttcctattc    3420
tctagaaagt ataggaactt cggcgcgtcc tacctgtgac ggaagatcac ttcgcagaat    3480
aaataaatcc tggtgtccct gttgataccg ggaagccctg gccaactttt ggcgaaaat    3540 gagacgttga tcggcacgta agaggttcca actttcacca taatgaaata agatcactac    3600
cgggcgtatt ttttgagttg tcgagatttt caggagctaa ggaagctaaa atggagaaaa    3660
aaatcactgg atataccacc gttgatatat cccaatggca tcgtaaagaa cattttgagg    3720
catttcagtc agttgctcaa tgtacctata accagaccgt tcagctggat attacggcct    3780
ttttaaagac cgtaaagaaa aataagcaca agttttatcc ggcctttatt cacattcttg    3840
```

```
cccgcctgat gaatgctcat ccggaattac gtatggcaat gaaagacggt gagctggtga    3900
tatgggatag tgttcaccct tgttacaccg ttttccatga gcaaactgaa acgttttcat    3960
cgctctggag tgaataccac gacgatttcc ggcagtttct acacatatat tcgcaagatg    4020
tggcgtgtta cggtgaaaac ctggcctatt tccctaaagg gtttattgag aatatgtttt    4080
tcgtctcagc caatccctgg gtgagtttca ccagttttga tttaaacgtg gccaatatgg    4140
acaacttctt cgcccccgtt ttcaccatgg gcaaatatta tacgcaaggc gacaaggtgc    4200
tgatgccgct ggcgattcag gttcatcatg ccgtttgtga tggcttccat gtcggcagat    4260
gcttaatgaa tacaacagta ctgcgatgag tggcagggcg gggcgtaagg cgcgccattt    4320
aaatgaagtt cctattccga agttcctatt ctctagaaag tataggaact tcgaagcagc    4380
tccagcctac acaatcgctc aagacgtgta atgctgcaat ctgcatgcaa gcttggcact    4440
ggccacgcaa aaaggccatc cgtcaggatg gccttctgct taatttgatg cctggcagtt    4500
tatggcgggt gtcctgcccg ccaccctccg ggccgttgct tcgcaacgtt caaatccgct    4560
cccggcggat ttgtcctact caggagagcg ttcaccgaca acaacagat aaaacgaaag    4620 gcccagtctt tcgactgagc cttcgttttt atttgatgcc tggcagttcc ctactctcgc    4680
atggggagac cccacactac catcgggggg ccatcgatgc aggtggcact tttcggggaa    4740
atgtgcgcgg aaccctatt tgtttatttt tctaaataca ttcaaatatg tatccgctca    4800
tgagacaata accctgctgc agaggcctgc atgcaagctt ggcgtaatca tggtcatagc    4860
tgtttcctgt gtgaaattgt tatccgctca caattccaca caacatacga gccggaagca    4920
taaagtgtaa agcctggggt gcctaatgag tgagctaact cacattaatt gcgttgcgct    4980
cactgcccgc tttccagtcg ggaaacctgt cgtgccagct gcattaatga atcggccaac    5040
gcgcggggag aggcggtttg cgtattgggc gctcttccgc ttcctcgctc actgactcgc    5100
tgcgctcggt cgttcggctg cggcgagcgg tatcagctca ctcaaaggcg gtaatacggt    5160
tatccacaga atcagggggat aacgcaggaa agaacatgtg agcaaaaggc cagcaaaagg    5220
ccaggaaccg taaaaaggcc gcgttgctgg cgttttttcca taggctccgc cccctgacg    5280 agcatcacaa aaatcgacgc tcaagtcaga ggtggcgaaa cccgacagga ctataaagat    5340
accaggcgtt tccccctgga agctccctcg tgcgctctcc tgttccgacc ctgccgctta    5400
ccggatacct gtccgccttt ctcccttcgg aagcgtggc gctttctcat agctcacgct    5460
gtaggtatct cagttcggtg taggtcgttc gctccaagct gggctgtgtg cacgaacccc    5520
ccgttcagcc cgaccgctgc gccttatccg gtaactatcg tcttgagtcc aacccggtaa    5580
gacacgactt atcgccactg gcagcagcca ctggtaacag gattagcaga gcgaggtatg    5640
taggcggtgc tacagagttc ttgaagtggt ggcctaacta cggctacact agaagaacag    5700
tatttggtat ctgcgctctg ctgaagccag ttaccttcgg aaaaagagtt ggtagctctt    5760
gatccggcaa acaaaccacc gctggtagcg gtggtttttt tgtttgcaag cagcagatta    5820
cgcgcagaaa aaaaggatct caagaagatc ctttgatctt ttctacgggg tctgacgctc    5880
agtggaacga aaactcacgt taagggattt tggtcatgag attatcaaaa aggatcttca    5940
cctagatcct tttaaattaa aaatgaagtt ttaaatcaat ctaaagtata tatgagtaaa    6000
cttggtctga cagttaccaa tgcttaatca gtgaggcacc tatctcagcg atctgtctat    6060
ttcgttcatc catagttgcc tgactccccg tcgtgtagat aactacgata cgggagggct    6120
taccatctgg ccccagtgct gcaatgatac cgcgagaccc acgctcaccg gctccagatt    6180
```

| | |
|---|---|
| tatcagcaat aaaccagcca gccggaaggg ccgagcgcag aagtggtcct gcaactttat | 6240 |
| ccgcctccat ccagtctatt aattgttgcc gggaagctag agtaagtagt tcgccagtta | 6300 |
| atagtttgcg caacgttgtt gccattgcta caggcatcgt ggtgtcacgc tcgtcgtttg | 6360 |
| gtatggcttc attcagctcc ggttcccaac gatcaaggcg agttacatga tcccccatgt | 6420 |
| tgtgcaaaaa agcggttagc tccttcggtc ctccgatcgt tgtcagaagt aagttggccg | 6480 |
| cagtgttatc actcatggtt atggcagcac tgcataattc tcttactgtc atgccatccg | 6540 |
| taagatgctt ttctgtgact ggtgagtact caaccaagtc attctgagaa tagtgtatgc | 6600 |
| ggcgaccgag ttgctcttgc ccggcgtcaa tacgggataa taccgcgcca catagcagaa | 6660 |
| ctttaaaagt gctcatcatt ggaaaacgtt cttcggggcg aaaactctca aggatcttac | 6720 |
| cgctgttgag atccagttcg atgtaaccca ctcgtgcacc caactgatct tcagcatctt | 6780 |
| ttactttcac cagcgtttct gggtgagcaa aaacaggaag gcaaaatgcc gcaaaaaagg | 6840 |
| gaataagggc gacacggaaa tgttaatac tcatactctt ccttttcaa tattattgaa | 6900 |
| gcatttatca gggttattgt ctcatgagcg gatacatatt tgaatgtatt tagaaaaata | 6960 |
| aacaaatagg ggttccgcgc acatttcccc gaaaagtgcc acctgacgtc taagaaacca | 7020 |
| ttattatcat gacattaacc tataaaaata ggcgtatcac gaggcccttt cgtc | 7074 |

<210> SEQ ID NO 26
<211> LENGTH: 6699
<212> TYPE: DNA
<213> ORGANISM: Artificial Sequence
<220> FEATURE:
<223> OTHER INFORMATION: construct pINT-yabM

<400> SEQUENCE: 26

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cgaagatcct ttgatctttt | 420 |
| ctacggggtc tgacgctcag tggaacgaaa actcacgtta agggattttg gtcatgagat | 480 |
| tatcaaaaag gatcttcacc tagatccttt taaactagtg aagttaccat cacggaaaaa | 540 |
| ggttatgctg cttttaagac ccactttcac atttaagttg ttttttctaat ccgcatatga | 600 |
| tcaattcaag gccgaataag aaggctggct ctgcaccttg gtgatcaaat aattcgatag | 660 |
| cttgtcgtaa taatggcggc atactatcag tagtaggtgt ttccctttct tctttagcga | 720 |
| cttgatgctc ttgatcttcc aatacgcaac ctaaagtaaa atgccccact gcgctgagtg | 780 |
| catataatgc attctctagt gaaaaacctt gttggcataa aaaggctaat tgattttcga | 840 |
| gagtttcata ctgttttct gtaggccgtg tacctaaatg tacttttgct ccatcgcgat | 900 |
| gacttagtaa agcacatcta aaactttag cgttattacg taaaaaatct tgccagcttt | 960 |
| ccccttctaa agggcaaaag tgagtatggt gcctatctaa catctcaatg gctaaggcgt | 1020 |
| cgagcaaagc ccgcttattt tttacatgcc aatacaatgt aggctgctct acacctagct | 1080 |
| tctgggcgag tttacgggtt gttaaacctt cgattccgac ctcattaagc agctctaatg | 1140 |
| cgctgttaat cactttactt ttatctaaac gagacatact cttcctttt caatattatt | 1200 |

```
gaagcattta tcagggttat tgtctcatga gcggatacat atttgaatgt atttagaaaa    1260
ataaacaaat aggggttccg cgcacatttc cccgaaaagt gccacctgaa attggccaga    1320
tgattaattc ctaattttg ttgacactct atcattgata gagttatttt accactccct    1380
atcagtgata gagaaaagtg aaatgaatag ttcgacaaaa atctagaaat aattttgttt    1440
aactttaaga aggagatata caagagctcg agtcgaagga gatagaacca tgaaggctct    1500
gtggtcgcgt cgccgtcgta tccacccggt ctatctggct tttatggcag tttcgtttat    1560
ggttggcatc gcaggtgcgc tgcagtcacc gaccctgtcg ctgtttctga gccgtgaagt    1620
gggtgttcgc ccgttttggg tgggcctgtt ctatacggtt aacgcagtcg ctggtattat    1680
cgtttccctg ctgctggcca aacgttcaga taatcagggc gaccgtcgca tgctgattct    1740
gttctgctgt gttatggcga tcgccaacgc agtcctgttt gccttcaatc gccattatct    1800
gaccctggtc attgcaggtg tgctgctgag ctctatcgct agcgtggcga tgccgcagat    1860
ttttgctctg gcgcgtgaat acgcagatag ttccgcccgc gaagcagtca tgttctcatc    1920
ggtgatgcgt gcccaactgt cgctggcatg ggttatcggt ccgccgctga gctttgccat    1980
tgcactgaac tacggcttta ccgcgatgtt cctggtggcg gccctgctgt ttttcgtctg    2040
cgtggctctg atttggttca ccctgccgag cgttccgcgt gcagaaaaca cggcagctga    2100
accgctgagt gatatctccg gttggaaaca ccgtgacgtg cgcatgctgt ttattgcctc    2160
tgttttcatg tggacctgta atacgatgta tgttatcgat atgccgctgt acattagtat    2220
cgtcctgggc ctgccggaca agctggcagg tctgctgatg ggtaccgcag caggcctgga    2280
aattccggtc atgctgctgg ctggtcatta tgtgaaacgt tttggcaagc gcccgatgat    2340
gctgctggcg gttggctgcg gtgtcctgtt ttacctgggt ctggtgctgt tccacggccg    2400
tacggaactg atgctgctgc agctgctgaa cgctctgttt atcggcatta tcgcgggcat    2460
tggtatgatc tggttccaag atctgatgcc gggtcgtccg ggttctgcaa ccacgctgtt    2520
taccaatagc atttctacgg gtgtgatcct ggcaggtgtg ctgcagggcg ttatggccga    2580
aaccttggc catcacgcag tctattggct ggcttccctg ctggcgctga tttcttcgc    2640
tctgagttgg caagttcgtg aagcgcgcac ggtgaagagt gttccgctgg cctaataaat    2700
cgatactagc ataacccctt ggggcctcta aacgcgtcga cacgcaaaaa ggccatccgt    2760
caggatggcc ttctgcttaa tttgatgcct ggcagtttat ggcgggcgtc ctgcccgcca    2820
ccctccgggc cgttgcttcg caacgttcaa atccgctccc ggcggatttg tcctactcag    2880
gagagcgttc accgacaaac aacagataaa acgaaaggcc cagtctttcg actgagcctt    2940
tcgttttatt tgatgcctgg cagttcccta ctctcgcatg gggagacccc acactaccat    3000
catgtatgaa tatcctcctt agttcctatt ccgaagttcc tattctctag aaagtatagg    3060
aacttcggcg cgtcctacct gtgacggaag atcacttcgc agaataaata aatcctggtg    3120
tccctgttga taccgggaag ccctgggcca acttttggcg aaaatgagac gttgatcggc    3180
acgtaagagg ttccaacttt caccataatg aaataagatc actaccgggc gtatttttg    3240
agttgtcgag attttcagga gctaaggaag ctaaaatgga gaaaaaatc actggatata    3300
ccaccgttga tatatcccaa tggcatcgta agaacatttt tgaggcattt cagtcagttg    3360
ctcaatgtac ctataaccag accgttcagc tggatattac ggcctttta aagaccgtaa    3420
agaaaaataa gcacaagttt tatccggcct ttattcacat tcttgcccgc ctgatgaatg    3480
ctcatccgga attacgtatg gcaatgaaag acggtgagct ggtgatatgg gatagtgttc    3540
```

```
accccttgtta caccgttttc catgagcaaa ctgaaacgtt ttcatcgctc tggagtgaat    3600
accacgacga tttccggcag tttctacaca tatattcgca agatgtggcg tgttacggtg    3660
aaaacctggc ctatttccct aaagggttta ttgagaatat gttttcgtc tcagccaatc    3720
cctgggtgag tttcaccagt tttgatttaa acgtggccaa tatggacaac ttcttcgccc    3780
ccgttttcac catgggcaaa tattatacgc aaggcgacaa ggtgctgatg ccgctggcga    3840
ttcaggttca tcatgccgtt tgtgatggct tccatgtcgg cagatgctta atgaatacaa    3900
cagtactgcg atgagtggca gggcggggcg taaggcgcgc catttaaatg aagttcctat    3960
tccgaagttc ctattctcta gaaagtatag gaacttcgaa gcagctccag cctacacaat    4020
cgctcaagac gtgtaatgct gcaatctgca tgcaagcttg gcactggcca cgcaaaaagg    4080
ccatccgtca ggatggcctt ctgcttaatt tgatgcctgg cagtttatgg cgggcgtcct    4140
gcccgccacc ctccgggccg ttgcttcgca acgttcaaat ccgctcccgg cggatttgtc    4200
ctactcagga gagcgttcac cgacaaacaa cagataaaac gaaaggccca gtctttcgac    4260
tgagcctttc gttttatttg atgcctggca gttccctact ctcgcatggg gagacccccac    4320
actaccatcg gggggccatc gatgcaggtg gcacttttcg gggaaatgtg cgcggaaccc    4380
ctatttgttt atttttctaa atacattcaa atatgtatcc gctcatgaga caataaccct    4440
gctgcagagg cctgcatgca agcttggcgt aatcatggtc atagctgttt cctgtgtgaa    4500
attgttatcc gctcacaatt ccacacaaca tacgagccgg aagcataaag tgtaaagcct    4560
ggggtgccta atgagtgagc taactcacat taattgcgtt gcgctcactg cccgctttcc    4620
agtcgggaaa cctgtcgtgc cagctgcatt aatgaatcgg ccaacgcgcg gggagaggcg    4680
gtttgcgtat tgggcgctct tccgcttcct cgctcactga ctcgctgcgc tcggtcgttc    4740
ggctgcggcg agcggtatca gctcactcaa aggcggtaat acggttatcc acagaatcag    4800
gggataacgc aggaaagaac atgtgagcaa aaggccagca aaaggccagg aaccgtaaaa    4860
aggccgcgtt gctggcgttt ttccataggc tccgcccccc tgacgagcat cacaaaaatc    4920
gacgctcaag tcagaggtgg cgaaacccga caggactata agataccagg cgtttcccc    4980
ctggaagctc cctcgtgcgc tctcctgttc cgaccctgcc gcttaccgga tacctgtccg    5040
cctttctccc ttcgggaagc gtggcgcttt ctcatagctc acgctgtagg tatctcagtt    5100
cggtgtaggt cgttcgctcc aagctgggct gtgtgcacga accccccgtt cagcccgacc    5160
gctgcgcctt atccggtaac tatcgtcttg agtccaaccc ggtaagacac gacttatcgc    5220
cactggcagc agccactggt aacaggatta gcagagcgag gtatgtaggc ggtgctacag    5280
agttcttgaa gtggtggcct aactacggct acactagaag aacagtattt ggtatctgcg    5340
ctctgctgaa gccagttacc ttcggaaaaa gagttggtag ctcttgatcc ggcaaacaaa    5400
ccaccgctgg tagcggtggt ttttttgttt gcaagcagca gattacgcgc agaaaaaaag    5460
gatctcaaga agatccttg atcttttcta cggggtctga cgctcagtgg aacgaaaact    5520
cacgttaagg gattttggtc atgagattat caaaaaggat cttcacctag atccttttaa    5580
attaaaaatg aagttttaaa tcaatctaaa gtatatatga gtaaacttgg tctgacagtt    5640
accaatgctt aatcagtgag gcacctatct cagcgatctg tctatttcgt tcatccatag    5700
ttgcctgact ccccgtcgtg tagataacta cgatacggga gggcttacca tctggcccca    5760
gtgctgcaat gataccgcga gacccacgct caccggctcc agatttatca gcaataaacc    5820
agccagccgg aagggccgag cgcagaagtg gtcctgcaac tttatccgcc tccatccagt    5880
ctattaattg ttgccgggaa gctagagtaa gtagttcgcc agttaatagt ttgcgcaacg    5940
```

| | |
|---|---:|
| ttgttgccat tgctacaggc atcgtggtgt cacgctcgtc gtttggtatg gcttcattca | 6000 |
| gctccggttc ccaacgatca aggcgagtta catgatcccc catgttgtgc aaaaaagcgg | 6060 |
| ttagctcctt cggtcctccg atcgttgtca gaagtaagtt ggccgcagtg ttatcactca | 6120 |
| tggttatggc agcactgcat aattctctta ctgtcatgcc atccgtaaga tgcttttctg | 6180 |
| tgactggtga gtactcaacc aagtcattct gagaatagtg tatgcggcga ccgagttgct | 6240 |
| cttgcccggc gtcaatacgg gataataccg cgccacatag cagaaccttta aaagtgctca | 6300 |
| tcattggaaa acgttcttcg gggcgaaaac tctcaaggat cttaccgctg ttgagatcca | 6360 |
| gttcgatgta acccactcgt gcacccaact gatcttcagc atcttttact ttcaccagcg | 6420 |
| tttctgggtg agcaaaaaca ggaaggcaaa atgccgcaaa aaagggaata agggcgacac | 6480 |
| ggaaatgttg aatactcata ctcttccttt ttcaatatta ttgaagcatt tatcagggtt | 6540 |
| attgtctcat gagcggatac atatttgaat gtatttagaa aaataaacaa ataggggttc | 6600 |
| cgcgcacatt tccccgaaaa gtgccacctg acgtctaaga accattatt atcatgacat | 6660 |
| taacctataa aaataggcgt atcacgaggc cctttcgtc | 6699 |

```
<210> SEQ ID NO 27
<211> LENGTH: 6684
<212> TYPE: DNA
<213> ORGANISM: Artificial Sequence
<220> FEATURE:
<223> OTHER INFORMATION: construct pINT-ydeA

<400> SEQUENCE: 27
```

| | |
|---|---:|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cgaagatcct ttgatctttt | 420 |
| ctacggggtc tgacgctcag tggaacgaaa actcacgtta agggattttg gtcatgagat | 480 |
| tatcaaaaag gatcttcacc tagatccttt taaactagtg aagttaccat cacgaaaaaa | 540 |
| ggttatgctg cttttaagac ccactttcac atttaagttg ttttctaat ccgcatatga | 600 |
| tcaattcaag gccgaataag aaggctggct ctgcaccttg gtgatcaaat aattcgatag | 660 |
| cttgtcgtaa taatggcggc atactatcag tagtaggtgt ttccctttct tctttagcga | 720 |
| cttgatgctc ttgatcttcc aatacgcaac ctaaagtaaa atgccccact gcgctgagtg | 780 |
| catataatgc attctctagt gaaaaacctt gttggcataa aaaggctaat tgattttcga | 840 |
| gagtttcata ctgtttttct gtaggccgtg tacctaaatg tacttttgct ccatcgcgat | 900 |
| gacttagtaa agcacatcta aaacttttag cgttattacg taaaaaatct tgccagcttt | 960 |
| cccccttctaa agggcaaaag tgagtatggt gcctatctaa catctcaatg gctaaggcgt | 1020 |
| cgagcaaagc ccgcttattt tttacatgcc aatacaatgt aggctgctct acacctagct | 1080 |
| tctgggcgag tttacgggtt gttaaacctt cgattccgac ctcattaagc agctctaatg | 1140 |
| cgctgttaat cactttactt ttatctaaac gagacatact cttccttttt caatattatt | 1200 |
| gaagcattta tcagggttat tgtctcatga gcggatacat atttgaatgt atttagaaaa | 1260 |

```
ataaacaaat agggggttccg cgcacatttc cccgaaaagt gccacctgaa attggccaga    1320
tgattaattc ctaattttg ttgacactct atcattgata gagttatttt accactccct    1380
atcagtgata gagaaaagtg aaatgaatag ttcgacaaaa atctagaaat aattttgttt    1440
aactttaaga aggagatata caagagctcg agtcgaagga gatagaacca tgacaacaaa    1500
cactgtttcc cgcaaagtgg cgtggctacg ggtcgttacg ctggcagtcg ccgccttcat    1560
cttcaacacc accgaatttg tccctgttgg cctgctctct gacattgcgc aaagttttca    1620
catgcaaacc gctcaggtcg gcatcatgtt gaccatttac gcatgggtag tagcgctaat    1680
gtcattgcct tttatgttaa tgaccagtca ggttgaacgg cgcaaattac tgatctgcct    1740
gtttgtggtg tttattgcca gccacgtact gtcgttttg tcgtggagct ttaccgttct    1800
ggtgatcagt cgcattggtg tggcttttgc acatgcgatt ttctggtcga ttacggcgtc    1860
tctggcgatc cgtatggctc cggccgggaa gcagcacag gcattgagtt taattgccac    1920
cggtacagca ctggcgatgg tcttaggttt acctctcggg cgcattgtgg gccagtattt    1980
cggttggcga atgaccttct tcgcgattgg tattggggcg cttatcaccc ttttgtgcct    2040
gattaagtta cttcccttac tgcccagtga gcattccggt tcactgaaaa gcctcccgct    2100
attgttccgc cgcccggcat tgatgagcat ttatttgtta actgtggtgg ttgtcaccgc    2160
ccattacacg gcatacagct atatcgagcc ttttgtacaa acattgcgg gattcagcgc    2220
caactttgcc acggcattac tgttattact cggtggtgcg ggcattattg cagcgtgat    2280
tttcggtaaa ctgggtaatc agtatgcgtc tgcgttggtg agtacggcga ttgcgctgtt    2340
gctggtgtgc ctggcattgc tgttacctgc ggcgaacagt gaaatacacc tcggggtgct    2400
gagtattttc tgggggatcg cgatgatgat catcgggctt ggtatgcagg ttaaagtgct    2460
ggcgctggca ccagatgcta ccgacgtcgc gatggcgcta ttctccggca tatttaatat    2520
tggaatcggg gcgggtgcgt tggtaggtaa tcaggtgagt ttgcactggt caatgtcgat    2580
gattggttat gtgggcgcgg tgcctgcttt tgccgcgtta atttggtcaa tcattatatt    2640
tcgccgctgg ccagtgacac tcgaagaaca gacgcaatag taaatcgata ctagcataac    2700
cccttggggc ctctaaacgc gtcgacacgc aaaaaggcca tccgtcagga tggccttctg    2760
cttaatttga tgcctggcag tttatggcgg gcgtcctgcc cgccaccctc cgggccgttg    2820
cttcgcaacg ttcaaatccg ctcccggcgg atttgtccta ctcaggagag cgttcaccga    2880
caaacaacag ataaaacgaa aggcccagtc tttcgactga gcctttcgtt ttatttgatg    2940
cctggcagtt ccctactctc gcatggggag accccacact accatcatgt atgaatatcc    3000
tccttagttc ctattccgaa gttcctattc tctagaaagt ataggaactt cggcgcgtcc    3060
tacctgtgac ggaagatcac ttcgcagaat aaataaatcc tggtgtccct gttgataccg    3120
ggaagccctg ggccaacttt tggcgaaaat gagacgttga tcggcacgta agaggttcca    3180
actttcacca taatgaaata agatcactac cgggcgtatt ttttgagttg tcgagatttt    3240
caggagctaa ggaagctaaa atggagaaaa aaatcactgg atataccacc gttgatatat    3300
cccaatggca tcgtaaagaa cattttgagg catttcagtc agttgctcaa tgtacctata    3360
accagaccgt tcagctggat attacggcct ttttaaagac cgtaaagaaa aataagcaca    3420
agttttatcc ggcctttatt cacattcttg cccgcctgat gaatgctcat ccggaattac    3480
gtatggcaat gaaagacggt gagctggtga tatgggatag tgttcaccct tgttacaccg    3540
ttttccatga gcaaactgaa acgttttcat cgctctggag tgaataccac gacgatttcc    3600
ggcagtttct acacatatat tcgcaagatg tggcgtgtta cggtgaaaac ctggcctatt    3660
```

```
tccctaaagg gtttattgag aatatgtttt tcgtctcagc caatccctgg gtgagtttca   3720
ccagttttga tttaaacgtg gccaatatgg acaacttctt cgcccccgtt ttcaccatgg   3780
gcaaatatta tacgcaaggc gacaaggtgc tgatgccgct ggcgattcag gttcatcatg   3840
ccgtttgtga tggcttccat gtcggcagat gcttaatgaa tacaacagta ctgcgatgag   3900
tggcagggcg gggcgtaagg cgcgccattt aaatgaagtt cctattccga agttcctatt   3960
ctctagaaag tataggaact tcgaagcagc tccagcctac acaatcgctc aagacgtgta   4020
atgctgcaat ctgcatgcaa gcttggcact ggccacgcaa aaaggccatc cgtcaggatg   4080
gccttctgct taatttgatg cctggcagtt tatggcgggc gtcctgcccg ccaccctccg   4140
ggccgttgct tcgcaacgtt caaatccgct cccggcggat ttgtcctact caggagagcg   4200
ttcaccgaca acaacagat aaaacgaaag gcccagtctt tcgactgagc ctttcgtttt   4260
atttgatgcc tggcagttcc ctactctcgc atggggagac cccacactac catcgggggg   4320
ccatcgatgc aggtggcact tttcggggaa atgtgcgcgg aacccctatt tgtttatttt   4380
tctaaataca ttcaaatatg tatccgctca tgagacaata accctgctgc agaggcctgc   4440
atgcaagctt ggcgtaatca tggtcatagc tgtttcctgt gtgaaattgt tatccgctca   4500
caattccaca acatacga gccggaagca taaagtgtaa agcctggggt gcctaatgag   4560
tgagctaact cacattaatt gcgttgcgct cactgcccgc tttccagtcg ggaaacctgt   4620
cgtgccagct gcattaatga atcggccaac gcgcgggag aggcggtttg cgtattgggc   4680
gctcttccgc ttcctcgctc actgactcgc tgcgctcggt cgttcggctg cggcgagcgg   4740
tatcagctca ctcaaaggcg gtaatacggt tatccacaga atcaggggat aacgcaggaa   4800
agaacatgtg agcaaaaggc cagcaaaagg ccaggaaccg taaaaaggcc gcgttgctgg   4860
cgttttcca taggctccgc ccccctgacg agcatcacaa aaatcgacgc tcaagtcaga   4920
ggtggcgaaa cccgacagga ctataaagat accaggcgtt tcccctgga agctccctcg   4980
tgcgctctcc tgttccgacc ctgccgctta ccggatacct gtccgccttt ctcccttcgg   5040
gaagcgtggc gctttctcat agctcacgct gtaggtatct cagttcggtg taggtcgttc   5100
gctccaagct gggctgtgtg cacgaacccc cgttcagcc cgaccgctgc gccttatccg   5160
gtaactatcg tcttgagtcc aacccggtaa gacacgactt atcgccactg gcagcagcca   5220
ctggtaacag gattagcaga gcgaggtatg taggcggtgc tacagagttc ttgaagtggt   5280
ggcctaacta cggctacact agaagaacag tatttggtat ctgcgctctg ctgaagccag   5340
ttaccttcgg aaaaagagtt ggtagctctt gatccggcaa acaaaccacc gctggtagcg   5400
gtggtttttt tgtttgcaag cagcagatta cgcgcagaaa aaaggatct caagaagatc   5460
ctttgatctt ttctacgggg tctgacgctc agtggaacga aaactcacgt taagggattt   5520
tggtcatgag attatcaaaa aggatcttca cctagatcct tttaaattaa aaatgaagtt   5580
ttaaatcaat ctaaagtata tatgagtaaa cttggtctga cagttaccaa tgcttaatca   5640
gtgaggcacc tatctcagcg atctgtctat ttcgttcatc catagttgcc tgactccccg   5700
tcgtgtagat aactacgata cgggagggct taccatctgg ccccagtgct gcaatgatac   5760
cgcgagaccc acgctcaccg gctccagatt tatcagcaat aaaccagcca gccggaaggg   5820
ccgagcgcag aagtggtcct gcaactttat ccgcctccat ccagtctatt aattgttgcc   5880
gggaagctag agtaagtagt tcgccagtta atagtttgcg caacgttgtt gccattgcta   5940
caggcatcgt ggtgtcacgc tcgtcgtttg gtatggcttc attcagctcc ggttcccaac   6000
```

```
gatcaaggcg agttacatga tcccccatgt tgtgcaaaaa agcggttagc tccttcggtc    6060
ctccgatcgt tgtcagaagt aagttggccg cagtgttatc actcatggtt atggcagcac    6120
tgcataattc tcttactgtc atgccatccg taagatgctt ttctgtgact ggtgagtact    6180
caaccaagtc attctgagaa tagtgtatgc ggcgaccgag ttgctcttgc ccggcgtcaa    6240
tacgggataa taccgcgcca catagcagaa ctttaaaagt gctcatcatt ggaaaacgtt    6300
cttcggggcg aaaactctca aggatcttac cgctgttgag atccagttcg atgtaaccca    6360
ctcgtgcacc caactgatct tcagcatctt ttactttcac cagcgtttct gggtgagcaa    6420
aaacaggaag gcaaaatgcc gcaaaaaagg aataagggc gacacggaaa tgttgaatac     6480
tcatactctt cctttttcaa tattattgaa gcatttatca gggttattgt ctcatgagcg    6540
gatacatatt tgaatgtatt tagaaaaata acaaataggg gttccgcgc acatttcccc     6600 gaaaagtgcc acctgacgtc taagaaacca ttattatcat gacattaacc tataaaaata    6660
ggcgtatcac gaggcccttt cgtc                                           6684

<210> SEQ ID NO 28
<211> LENGTH: 6738
<212> TYPE: DNA
<213> ORGANISM: Artificial Sequence
<220> FEATURE:
<223> OTHER INFORMATION: construct pINT-propP2

<400> SEQUENCE: 28
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgaagatcct tgatctttt      420 ctacggggtc tgacgctcag tggaacgaaa actcacgtta agggattttg gtcatgagat     480
tatcaaaaag gatcttcacc tagatccttt taaactagtg aagttaccat cacggaaaaa     540
ggttatgctg ctttaagac ccactttcac atttaagttg ttttctaat ccgcatatga       600 tcaattcaag gccgaataag aaggctggct ctgcaccttg gtgatcaaat aattcgatag     660
cttgtcgtaa taatggcggc atactatcag tagtaggtgt ttcccttcct tctttagcga    720
cttgatgctc ttgatcttcc aatacgcaac ctaaagtaaa atgccccact gcgctgagtg     780
catataatgc attctctagt gaaaaacctt gttggcataa aaaggctaat tgattttcga     840
gagtttcata ctgttttct gtaggccgtg tacctaaatg tacttttgct ccatcgcgat      900
gacttagtaa agcacatcta aaactttag cgttattacg taaaaaatct tgccagcttt      960
ccccttctaa agggcaaaag tgagtatggt gcctatctaa catctcaatg ctaaggcgt     1020 cgagcaaagc ccgcttattt tttacatgcc aatacaatgt aggctgctct acacctagct    1080
tctgggcgag tttacgggtt gttaaacctt cgattccgac ctcattaagc agctctaatg    1140
cgctgttaat cactttactt ttatctaaac gagacatact cttccttttt caatattatt    1200
gaagcattta tcagggttat tgtctcatga gcggatacat atttgaatgt atttagaaaa    1260
ataaacaaat aggggttccg cgcacatttc cccgaaaagt gccacctgaa attggcaga    1320 tgattaattc ctaattttg ttgacactct atcattgata gagttatttt accactccct    1380
```

```
atcagtgata gagaaaagtg aaatgaatag ttcgacaaaa atctagaaat aattttgttt    1440
aactttaaga aggagatata caagagctcg agtcgaagga gatagaacca tgaatgaatc    1500
cgccgtgaaa atcaaccgca cctttatctc ccactatgct ctgctgctga aactgatgac    1560
catgttcgtc caacaacaga acagtacccc gtccaatatt gtggcgttta acttcctgct    1620
gatcgccttt ctgacgggta ttgcgagcgc cttccagacc ccgacgctgt cactgtatct    1680
gtcgcaagaa atcaatgtta gtccgttttt cgttggtctg ttttactccg ttaacgcgat    1740
tatcggcatt atcctgagcc agattctggc caaatattct gataagcaag atgaccgtcg    1800
caaagtcatg attgtgtgct gtctgatcgc agtgctgggt tgcctgatct ttgcttacag    1860
ccgtaattat tacgttctga ttatcattgg caccacgctg ctgggcctgg gtagctctgc    1920
aaacccgcag tcatttgcac tggctcgtga atatgcagaa agttcccatc gcgaagctgt    1980
tatgttcacc acgattatgc gcacccagat cagtctggca tggattgtcg gtccgccgct    2040
gtcctttttc attgctctga attggggctt tgattatatg tacctggtcg caggttcagc    2100
tttcctgctg tgcgccggcg tgtcgaaact gctgccgaag atcccgcgtc agtctgcagt    2160
caaaaatcaa gaaattctgg acaacacccc gccgcgtcgc agtgtgattt acctgtttat    2220
cgccaatctg ctgctgtgga cgtgtaattc catgtacctg atcaacatgc cgctgttcgt    2280
gattaacgaa ctgcacctgg gtaaagaact ggcaggtacc ctgatgggta cggcagcagg    2340
cctggaaatt ccggtgatga tctttgccgg ctatctgacc aaatacttct caaaaaagcg    2400
cctgatgatg attgcactgg tttcgggtct ggcttttttat tcatcgctgc tgttcagcga    2460
tcagacctgg caactgatcg gcctgcagat gctgaacgcg atctttattg gtatcaccgc    2520
cacgattggc atggtttatt ccaagacct gatgccgacc aaaatgggta cggcgaccac    2580
gctgtttagt aatgcagcta agagctcttg gatcattggc ggtccgatcg cgggcatcat    2640
tgccgaaatc tggcattaca actctgtgtt ttatgtggcg gttgccctga ttttcatcag    2700
cgtcggctgt atgtggaagg ttaagtctgt ctaataaatc gatactagca taacccttg    2760 gggcctctaa acgcgtcgac acgcaaaaag gccatccgtc aggatggcct tctgcttaat    2820
ttgatgcctg gcagtttatg gcgggcgtcc tgcccgccac cctccgggcc gttgcttcgc    2880
aacgttcaaa tccgctcccg gcggatttgt cctactcagg agagcgttca ccgacaaaca    2940
acagataaaa cgaaaggccc agtctttcga ctgagccttt cgttttattt gatgcctggc    3000
agttccctac tctcgcatgg ggagaccccca cactaccatc atgtatgaat atcctcctta    3060
gttcctattc cgaagttcct attctctaga agtataagga acttcggcgc gtcctacctg    3120
tgacggaaga tcacttcgca gaataaataa atcctggtgt ccctgttgat accgggaagc    3180
cctgggccaa cttttggcga aaatgagacg ttgatcggca cgtaagaggt tccaactttc    3240
accataatga aataagatca ctaccgggcg tattttttga gttgtcgaga ttttcaggag    3300
ctaaggaagc taaatggag aaaaaaatca ctggatatac caccgttgat atatcccaat    3360
ggcatcgtaa agaacatttt gaggcatttc agtcagttgc tcaatgtacc tataaccaga    3420
ccgttcagct ggatattacg gcctttttaa agaccgtaaa gaaaaataag cacaagtttt    3480
atccggcctt tattcacatt cttgcccgcc tgatgaatgc tcatccggaa ttacgtatgg    3540
caatgaaaga cggtgagctg gtgatatggg atagtgttca cccttgttac accgttttcc    3600
atgagcaaac tgaaacgttt tcatcgctct ggagtgaata ccacgacgat ttccggcagt    3660
ttctacacat atattcgcaa gatgtggcgt gttacggtga aaacctggcc tatttcccta    3720
```

```
aagggtttat tgagaatatg tttttcgtct cagccaatcc ctgggtgagt ttcaccagtt    3780
ttgatttaaa cgtggccaat atggacaact tcttcgcccc cgttttcacc atgggcaaat    3840
attatacgca aggcgacaag gtgctgatgc cgctggcgat tcaggttcat catgccgttt    3900
gtgatggctt ccatgtcggc agatgcttaa tgaatacaac agtactgcga tgagtggcag    3960
ggcggggcgt aaggcgcgcc atttaaatga agttcctatt ccgaagttcc tattctctag    4020
aaagtatagg aacttcgaag cagctccagc ctacacaatc gctcaagacg tgtaatgctg    4080
caatctgcat gcaagcttgg cactggccac gcaaaaaggc catccgtcag gatggccttc    4140
tgcttaattt gatgcctggc agtttatggc gggcgtcctg cccgccaccc tccgggccgt    4200
tgcttcgcaa cgttcaaatc cgctcccggc ggatttgtcc tactcaggag agcgttcacc    4260
gacaaacaac agataaaacg aaaggcccag tctttcgact gagcctttcg ttttatttga    4320
tgcctggcag ttccctactc tcgcatgggg agacccacac ctaccatcgg ggggccatcg    4380
atgcaggtgg cacttttcgg ggaaatgtgc gcggaacccc tatttgttta ttttctaaa    4440
tacattcaaa tatgtatccg ctcatgagac aataaccctg ctgcagaggc ctgcatgcaa    4500
gcttggcgta atcatggtca tagctgtttc ctgtgtgaaa ttgttatccg ctcacaattc    4560
cacacaacat acgagccgga agcataaagt gtaaagcctg gggtgcctaa tgagtgagct    4620
aactcacatt aattgcgttg cgctcactgc ccgctttcca gtcgggaaac ctgtcgtgcc    4680
agctgcatta atgaatcggc caacgcgcgg ggagaggcgg tttgcgtatt gggcgctctt    4740
ccgcttcctc gctcactgac tcgctgcgct cggtcgttcg gctgcggcga gcggtatcag    4800
ctcactcaaa ggcggtaata cggttatcca cagaatcagg ggataacgca ggaaagaaca    4860
tgtgagcaaa aggccagcaa aaggccagga accgtaaaaa ggccgcgttg ctggcgtttt    4920
tccataggct ccgcccccct gacgagcatc acaaaaatcg acgctcaagt cagaggtggc    4980
gaaacccgac aggactataa agataccagg cgtttccccc tggaagctcc ctcgtgcgct    5040
ctcctgttcc gaccctgccg cttaccggat acctgtccgc ctttctccct tcgggaagcg    5100
tggcgctttc tcatagctca cgctgtaggt atctcagttc ggtgtaggtc gttcgctcca    5160
agctgggctg tgtgcacgaa ccccccgttc agcccgaccg ctgcgcctta tccggtaact    5220
atcgtcttga gtccaacccg gtaagacacg acttatcgcc actggcagca gccactggta    5280
acaggattag cagagcgagg tatgtaggcg gtgctacaga gttcttgaag tggtggccta    5340
actacggcta cactagaaga acagtatttg gtatctgcgc tctgctgaag ccagttacct    5400
tcggaaaaag agttggtagc tcttgatccg gcaaacaaac caccgctggt agcggtggtt    5460
tttttgtttg caagcagcag attacgcgca gaaaaaaagg atctcaagaa gatcctttga    5520
tcttttctac ggggtctgac gctcagtgga acgaaaactc acgttaaggg attttggtca    5580
tgagattatc aaaaaggatc ttcacctaga tccttttaaa ttaaaaatga agttttaaat    5640
caatctaaag tatatatgag taaacttggt ctgacagtta ccaatgctta atcagtgagg    5700
cacctatctc agcgatctgt ctatttcgtt catccatagt tgcctgactc cccgtcgtgt    5760
agataactac gatacgggag ggcttaccat ctggccccag tgctgcaatg ataccgcgag    5820
acccacgctc accggctcca gatttatcag caataaacca gccagccgga agggccgagc    5880
gcagaagtgg tcctgcaact ttatccgcct ccatccagtc tattaattgt tgccgggaag    5940
ctagagtaag tagttcgcca gttaatagtt tgcgcaacgt tgttgccatt gctacaggca    6000
tcgtggtgtc acgctcgtcg tttggtatgg cttcattcag ctccggttcc caacgatcaa    6060
ggcgagttac atgatccccc atgttgtgca aaaaagcggt tagctccttc ggtcctccga    6120
```

```
tcgttgtcag aagtaagttg gccgcagtgt tatcactcat ggttatggca gcactgcata    6180
attctcttac tgtcatgcca tccgtaagat gcttttctgt gactggtgag tactcaacca    6240
agtcattctg agaatagtgt atgcggcgac cgagttgctc ttgcccggcg tcaatacggg    6300
ataataccgc gccacatagc agaactttaa aagtgctcat cattggaaaa cgttcttcgg    6360
ggcgaaaact ctcaaggatc ttaccgctgt tgagatccag ttcgatgtaa cccactcgtg    6420
cacccaactg atcttcagca tcttttactt tcaccagcgt ttctgggtga gcaaaaacag    6480
gaaggcaaaa tgccgcaaaa aagggaataa gggcgacacg gaaatgttga atactcatac    6540
tcttcctttt tcaatattat tgaagcattt atcaggggta ttgtctcatg agcggataca    6600
tatttgaatg tatttagaaa aataaacaaa taggggttcc gcgcacattt ccccgaaaag    6660
tgccacctga cgtctaagaa accattatta tcatgacatt aacctataaa aataggcgta    6720
tcacgaggcc ctttcgtc                                                  6738
```

<210> SEQ ID NO 29
<211> LENGTH: 6513
<212> TYPE: DNA
<213> ORGANISM: Artificial Sequence
<220> FEATURE:
<223> OTHER INFORMATION: construct pINT-Pc-setA

<400> SEQUENCE: 29

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgaagatcct tgatcttttc     420
ctacggggtc tgacgctcag tggaacgaaa actcacgtta agggattttg gtcatgagat     480
tatcaaaaag gatcttcacc tagatccttt taaactagtg aagttaccat cacggaaaaa     540
ggttatgctg cttttaagac ccactttcac atttaagttg ttttttctaat ccgcatatga     600 tcaattcaag gccgaataag aaggctggct ctgcaccttg gtgatcaaat aattcgatag     660
cttgtcgtaa taatggcggc atactatcag tagtaggtgt ttccctttct tctttagcga     720
cttgatgctc ttgatcttcc aatacgcaac ctaaagtaaa atgccccact gcgctgagtg     780
catataatgc attctctagt gaaaaacctt gttggcataa aaaggctaat tgattttcga     840
gagtttcata ctgtttttct gtaggccgtg tacctaaatg tacttttgct ccatcgcgat     900
gacttagtaa agcacatcta aaactttag cgttattacg taaaaaatct tgccagcttt     960 cccttctaa agggcaaaag tgagtatggt gcctatctaa catctcaatg gctaaggcgt    1020
cgagcaaagc ccgcttattt tttacatgcc aatacaatgt aggctgctct acacctagct    1080
tctgggcgag tttacgggtt gttaaacctt cgattccgac ctcattaagc agctctaatg    1140
cgctgttaat cactttactt ttatctaaac gagacatact cttccttttt caatattatt    1200
gaagcattta tcagggttat tgtctcatga gcggatacat atttgaatgt atttagaaaa    1260
ataaacaaat aggggttccg cgcacatttc cccgaaaagt gccacctgaa attggccaga    1320
tgattaattc ctaattttg ttgacactct atcattgata gagttatttt accactccct    1380
```

```
atcagtgata gagaaaagtg aaatgaatag ttcgacaaaa atctagaaat aattttgttt    1440
aactttaaga aggagatata caagagctcg agtcgaagga gatagaacca tgttctacac    1500
gggctcggca gttattggta tcgtcgtctc gcagatgctg gctacgcgct cggatcgtca    1560
gggtgaccgc aagtcgctga tcttcgtttg ctgtctgctg ggtgcgctgg cctgcatgct    1620
gtttgcgtgg aaccgcaatt atttcatcct gctgtttatt ggtgtgctgc tgagctcttt    1680
cggcagtacc gccaacccgc agctgtttgc actggctcgc gaacatgcag ataaaacggg    1740
tcgtgaagcg gccatgttca gttccatcct gcgtgcccaa atttccctgg catgggtggt    1800
tggtccgccg attgcgtttg ccctggcact gggcttcggt tttaccacga tgtacctgac    1860
cgcagctgtc gtgttcatcc tgtgtggtat tctggtgaag ctgtttctgc cgagcatgcc    1920
gaaagccgtt gaaagacca cgagcaccct ggaatctccg cgtcgcaatc gtcgcgacac    1980
gctgctgctg tttgttgcgt gcaccctgat gtggacgtgt aacggcatct atctgattaa    2040
tatgccgctg tacctggttc atgaactgca cctgccggaa aaactggcag gtatcatgat    2100
gggtgtcgca gcaggtctgg aaatcccggt tatgctgatt gccggttatg tcgcaaaacg    2160
tttcggcaag cgcttctga tgcgtctggc tgtcgcgagc ggtctgctgt ttttcggcgg    2220
tctgctggtg ctggatggcg aaatcgccct gctggcactg caggctctga acgcgatttt    2280
catcggcatt ctggctggca ttggtatgct gtactttcag gacctgatgc cgggccaagc    2340
aggtgcagct accacgctgt taccaacac acgcgcgtg ggttggatta tctcaggttc    2400
gctggctggc atcgtggcgg aaatttggaa ttatcacgct gtgttttct ttgcgctgct    2460 gatgatcgtc ggctctatttt actgcatgtg gcgtattaaa gatgcgtaat aaatcgatac    2520
tagcataacc ccttggggcc tctaaacgcg tcgacacgca aaaggccat ccgtcaggat    2580 ggccttctgt ttaatttgat gcctggcagt ttatggcggg cgtcctgccc gccaccctcc    2640
gggccgttgc ttcgcaacgt tcaaatccgc tcccggcgga tttgtcctac tcaggagagc    2700
gttcaccgac aaacaacaga taaaacgaaa ggcccagtct ttcgactgag cctttcgttt    2760
tatttgatgc ctggcagttc cctactctcg catggggaga ccccacacta ccatcatgta    2820
tgaatatcct ccttagttcc tattccgaag ttcctattct ctagaaagta taggaacttc    2880
ggcgcgtcct acctgtgacg gaagatcact tcgcagaata aataaatcct ggtgtccctg    2940
ttgataccgg gaagccctgg gccaactttt ggcgaaaatg agacgttgat cggcacgtaa    3000
gaggttccaa ctttcaccat aatgaaataa gatcactacc gggcgtattt tttgagttgt    3060
cgagattttc aggagctaag gaagctaaaa tggagaaaaa atcactgga tataccaccg    3120 ttgatatatc ccaatggcat cgtaaagaac attttgaggc atttcagtca gttgctcaat    3180
gtacctataa ccagaccgtt cagctggata ttacggcctt tttaaagacc gtaaagaaaa    3240
ataagcacaa gttttatccg gcctttattc acattcttgc ccgcctgatg aatgctcatc    3300
cggaattacg tatggcaatg aaagacggtg agctggtgat atgggatagt gttcacccttt    3360 gttacaccgt tttccatgag caaactgaaa cgttttcatc gctctggagt gaataccacg    3420
acgatttccg gcagtttcta cacatatatt cgcaagatgt ggcgtgttac ggtgaaaacc    3480
tggcctattt ccctaaaggg tttattgaga atatgttttt cgtctcagcc aatccctggg    3540
tgagtttcac cagttttgat ttaaacgtgg ccaatatgga caacttcttc gcccccgttt    3600
tcaccatggg caaatattat acgcaaggcg acaaggtgct gatgccgctg gcgattcagg    3660
ttcatcatgc cgtttgtgat ggcttccatg tcggcagatg cttaatgaat acaacagtac    3720
tgcgatgagt ggcagggcgg ggcgtaaggc gcgccattta aatgaagttc ctattccgaa    3780
```

```
gttcctattc tctagaaagt ataggaactt cgaagcagct ccagcctaca caatcgctca    3840
agacgtgtaa tgctgcaatc tgcatgcaag cttggcactg gccacgcaaa aaggccatcc    3900
gtcaggatgg ccttctgctt aatttgatgc ctggcagttt atggcgggcg tcctgcccgc    3960
caccctccgg gccgttgctt cgcaacgttc aaatccgctc ccggcggatt tgtcctactc    4020
aggagagcgt tcaccgacaa acaacagata aaacgaaagg cccagtcttt cgactgagcc    4080
tttcgtttta tttgatgcct ggcagttccc tactctcgca tggggagacc ccacactacc    4140
atcgggggc catcgatgca ggtggcactt tcggggaaa tgtgcgcgga acccctattt    4200
gtttattttt ctaaatacat tcaaatatgt atccgctcat gagacaataa ccctgctgca    4260
gaggcctgca tgcaagcttg gcgtaatcat ggtcatagct gtttcctgtg tgaaattgtt    4320
atccgctcac aattccacac aacatacgag ccggaagcat aaagtgtaaa gcctggggtg    4380
cctaatgagt gagctaactc acattaattg cgttgcgctc actgcccgct ttccagtcgg    4440
gaaacctgtc gtgccagctg cattaatgaa tcggccaacg cgcggggaga ggcggtttgc    4500
gtattgggcg ctcttccgct tcctcgctca ctgactcgct gcgctcggtc gttcggctgc    4560
ggcgagcgg atcagctcac tcaaaggcgg taatacggtt atccacagaa tcaggggata    4620
acgcaggaaa gaacatgtga gcaaaaggcc agcaaaaggc caggaaccgt aaaaaggccg    4680
cgttgctggc gtttttccat aggctccgcc cccctgacga gcatcacaaa aatcgacgct    4740
caagtcagag gtggcgaaac ccgacaggac tataaagata ccaggcgttt ccccctggaa    4800
gctccctcgt gcgctctcct gttccgaccc tgccgcttac cggatacctg tccgcctttc    4860
tcccttcggg aagcgtggcg ctttctcata gctcacgctg taggtatctc agttcggtgt    4920
aggtcgttcg ctccaagctg ggctgtgtgc acgaaccccc cgttcagccc gaccgctgcg    4980
ccttatccgg taactatcgt cttgagtcca acccggtaag acacgactta tcgccactgg    5040
cagcagccac tggtaacagg attagcagag cgaggtatgt aggcggtgct acagagttct    5100
tgaagtggtg gcctaactac ggctacacta gaagaacagt atttggtatc tgcgctctgc    5160
tgaagccagt taccttcgga aaaagagttg gtagctcttg atccggcaaa caaaccaccg    5220
ctggtagcgg tggttttttt gtttgcaagc agcagattac gcgcagaaaa aaaggatctc    5280
aagaagatcc tttgatcttt tctacggggt ctgacgctca gtggaacgaa aactcacgtt    5340
aagggatttt ggtcatgaga ttatcaaaaa ggatcttcac ctagatcctt ttaaattaaa    5400
aatgaagttt taaatcaatc taaagtatat atgagtaaac ttggtctgac agttaccaat    5460
gcttaatcag tgaggcacct atctcagcga tctgtctatt tcgttcatcc atagttgcct    5520
gactccccgt cgtgtagata actacgatac gggagggctt accatctggc cccagtgctg    5580
caatgatacc gcgagaccca cgctcaccgg ctccagattt atcagcaata aaccagccag    5640
ccggaagggc cgagcgcaga agtggtcctg caactttatc cgcctccatc cagtctatta    5700
attgttgccg ggaagctaga gtaagtagtt cgccagttaa tagtttgcgc aacgttgttg    5760
ccattgctac aggcatcgtg gtgtcacgct cgtcgtttgg tatggcttca ttcagctccg    5820
gttcccaacg atcaaggcga gttacatgat cccccatgtt gtgcaaaaaa gcggttagct    5880
ccttcggtcc tccgatcgtt gtcagaagta agttggccgc agtgttatca ctcatggtta    5940
tggcagcact gcataattct cttactgtca tgccatccgt aagatgcttt tctgtgactg    6000
gtgagtactc aaccaagtca ttctgagaat agtgtatgcg gcgaccgagt tgctcttgcc    6060
cggcgtcaat acgggataat accgcgccac atagcagaac tttaaaagtg ctcatcattg    6120
```

| | |
|---|---|
| gaaaacgttc ttcggggcga aaactctcaa ggatcttacc gctgttgaga tccagttcga | 6180 |
| tgtaacccac tcgtgcaccc aactgatctt cagcatcttt tactttcacc agcgtttctg | 6240 |
| ggtgagcaaa acaggaagg caaaatgccg caaaaaggg aataagggcg acacggaaat | 6300 |
| gttgaatact catactcttc ctttttcaat attattgaag catttatcag ggttattgtc | 6360 |
| tcatgagcgg atacatattt gaatgtattt agaaaaataa acaaataggg gttccgcgca | 6420 |
| catttccccg aaaagtgcca cctgacgtct aagaaaccat tattatcatg acattaacct | 6480 |
| ataaaaatag gcgtatcacg aggccctttc gtc | 6513 |

<210> SEQ ID NO 30
<211> LENGTH: 6810
<212> TYPE: DNA
<213> ORGANISM: Artificial Sequence
<220> FEATURE:
<223> OTHER INFORMATION: construct pINT-fucP

<400> SEQUENCE: 30

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cgaagatcct ttgatctttt | 420 |
| ctacggggtc tgacgctcag tggaacgaaa actcacgtta agggattttg gtcatgagat | 480 |
| tatcaaaaag gatcttcacc tagatccttt taaactagtg aagttaccat cacggaaaaa | 540 |
| ggttatgctg cttttaagac ccactttcac atttaagttg tttttctaat ccgcatatga | 600 |
| tcaattcaag gccgaataag aaggctggct ctgcaccttg gtgatcaaat aattcgatag | 660 |
| cttgtcgtaa taatggcggc atactatcag tagtaggtgt ttccctttct tctttagcga | 720 |
| cttgatgctc ttgatcttcc aatacgcaac ctaaagtaaa atgccccact cgctgagtg | 780 |
| catataatgc attctctagt gaaaaacctt gttggcataa aaaggctaat tgattttcga | 840 |
| gagtttcata ctgtttttct gtaggccgtg tacctaaatg tacttttgct ccatcgcgat | 900 |
| gacttagtaa agcacatcta aaactttag cgttattacg taaaaaatct tgccagcttt | 960 |
| ccccttctaa agggcaaaag tgagtatggt gcctatctaa catctcaatg gctaaggcgt | 1020 |
| cgagcaaagc ccgcttattt tttacatgcc aatacaatgt aggctgctct acacctagct | 1080 |
| tctgggcgag tttacgggtt gttaaacctt cgattccgac ctcattaagc agctctaatg | 1140 |
| cgctgttaat cactttactt ttatctaaac gagacatact cttcctttt caatattatt | 1200 |
| gaagcattta tcagggttat tgtctcatga gcggatacat atttgaatgt atttagaaaa | 1260 |
| ataaacaaat agggggttccg cgcacatttc cccgaaaagt gccacctgaa attggccaga | 1320 |
| tgattaattc ctaattttg ttgacactct atcattgata gagttatttt accactccct | 1380 |
| atcagtgata gagaaaagtg aaatgaatag ttcgacaaaa atctagaaat aattttgttt | 1440 |
| aactttaaga aggagatata caagagctcg agtcgaagga gatagaacca tgggaaacac | 1500 |
| atcaatacaa acgcagagtt accgtgcggt agataaagat gcagggcaaa gcagaagtta | 1560 |
| cattattcca ttcgcgctgc tgtgctcact gtttttctt tgggcggtag ccaataacct | 1620 |
| taacgacatt ttattacctc aattccagca ggcttttacg ctgacaaatt tccaggctgg | 1680 |

```
cctgatccaa tcggccttttt actttggtta tttcattatc ccaatccctg ctgggatatt    1740
gatgaaaaaa ctcagttata aagcagggat tattaccggg ttatttttat atgccttggg    1800
tgctgcatta ttctggcccg ccgcagaaat aatgaactac accttgtttt tagttggcct    1860
atttattatt gcagccggat taggttgtct ggaaactgcc gcaaacccctt ttgttacggt    1920 attagggccg gaaagtagtg gtcacttccg cttaaatctt gcgcaaacat ttaactcgtt    1980
tggcgcaatt atcgcggttg tctttgggca aagtcttatt ttgtctaacg tgccacatca    2040
atcgcaagac gttctcgata aaatgtctcc agagcaattg agtgcgtata aacacagcct    2100
ggtattatcg gtacagacac cttatatgat catcgtggct atcgtgttac tggtcgccct    2160
gctgatcatg ctgacgaaat tcccggcatt gcagagtgat aatcacagtg acgccaaaca    2220
aggatcgttc tccgcatcgc tttctcgcct ggcgcgtatt cgccactggc gctgggcggt    2280
attagcgcaa ttctgctatg tcggcgcaca aacggcctgc tggagctatt tgattcgcta    2340
cgctgtagaa gaaattccag gtatgactgc aggctttgcc gctaactatt taaccggaac    2400
catggtgtgc ttctttattg gtcgtttcac cggtacctgg ctcatcagtc gcttcgcacc    2460
acacaaagtc ctgccgcct acgcattaat cgctatggca ctgtgcctga tctcagcctt    2520
cgctggcggt catgtgggct taatagccct gactttatgc agcgcctttta tgtcgattca    2580 gtacccaaca atcttctcgc tgggcattaa gaatctcggc caggacacca atatggttc    2640 gtccttcatc gttatgacca ttattggcgg cggtattgtc actccggtca tgggttttgt    2700
cagtgacgcg gcgggcaaca tccccactgc tgaactgatc cccgcactct gcttcgcggt    2760
catctttatc tttgcccgtt ccgttctca aacggcaact aactgataaa tcgatactag    2820 cataaccccct tggggcctct aaacgcgtcg acacgcaaaa aggccatccg tcaggatggc    2880
cttctgctta atttgatgcc tggcagttta tggcgggcgt cctgcccgcc accctccggg    2940
ccgttgcttc gcaacgttca aatccgctcc cggcggattt gtcctactca ggagagcgtt    3000
caccgacaaa caacagataa acgaaaggc ccagtctttc gactgagcct ttcgttttat    3060
ttgatgcctg gcagttccct actctcgcat ggggagaccc cacactacca tcatgtatga    3120
atatcctcct tagttcctat tccgaagttc ctattctcta gaaagtatag gaacttcggc    3180
gcgtcctacc tgtgacggaa gatcacttcg cagaataaat aaatcctggt gtccctgttg    3240
ataccgggaa gccctgggcc aacttttggc gaaaatgaga cgttgatcgg cacgtaagag    3300
gttccaactt tcaccataat gaaataagat cactaccggg cgtatttttt gagttgtcga    3360
gattttcagg agctaaggaa gctaaaatgg agaaaaaat cactggatat accaccgttg    3420
atatatccca atggcatcgt aaagaacatt ttgaggcatt tcagtcagtt gctcaatgta    3480
cctataacca gaccgttcag ctggatatta cggcctttttt aaagaccgta agaaaaata    3540 agcacaagtt ttatccggcc tttattcaca ttcttgcccg cctgatgaat gctcatccgg    3600
aattacgtat ggcaatgaaa gacggtgagc tggtgatatg ggatagtgtt cacccttgtt    3660
acaccgtttt ccatgagcaa actgaaacgt tttcatcgct ctggagtgaa taccacgacg    3720
atttccggca gtttctacac atatattcgc aagatgtggc gtgttacggt gaaaacctgg    3780
cctatttccc taaagggttt attgagaata tgttttttcgt ctcagccaat ccctgggtga    3840
gtttcaccag ttttgattta aacgtggcca atatggacaa cttcttcgcc cccgttttca    3900
ccatgggcaa atattatacg caaggcgaca aggtgctgat gccgctggcg attcaggttc    3960
atcatgccgt ttgtgatggc ttccatgtcg gcagatgctt aatgaataca acagtactgc    4020
```

```
gatgagtggc agggcggggc gtaaggcgcg ccatttaaat gaagttccta ttccgaagtt    4080
cctattctct agaaagtata ggaacttcga agcagctcca gcctacacaa tcgctcaaga    4140
cgtgtaatgc tgcaatctgc atgcaagctt ggcactggcc acgcaaaaag gccatccgtc    4200
aggatggcct tctgcttaat ttgatgcctg gcagtttatg gcgggcgtcc tgcccgccac    4260
cctccgggcc gttgcttcgc aacgttcaaa tccgctcccg gcggatttgt cctactcagg    4320
agagcgttca ccgacaaaca acagataaaa cgaaaggccc agtctttcga ctgagccttt    4380
cgttttattt gatgcctggc agttccctac tctcgcatgg ggagacccca cactaccatc    4440
gggggggccat cgatgcaggt ggcacttttc ggggaaatgt gcgcggaacc cctatttgtt    4500
tatttttcta aatacattca aatatgtatc cgctcatgag acaataaccc tgctgcagag    4560
gcctgcatgc aagcttggcg taatcatggt catagctgtt tcctgtgtga aattgttatc    4620
cgctcacaat tccacacaac atacgagccg aagcataaa gtgtaaagcc tggggtgcct    4680
aatgagtgag ctaactcaca ttaattgcgt tgcgctcact gcccgctttc cagtcgggaa    4740
acctgtcgtg ccagctgcat taatgaatcg gccaacgcgc ggggagaggc ggtttgcgta    4800
ttgggcgctc ttccgcttcc tcgctcactg actcgctgcg ctcggtcgtt cggctgcggc    4860
gagcggtatc agctcactca aaggcggtaa tacggttatc cacagaatca ggggataacg    4920
caggaaagaa catgtgagca aaaggccagc aaaaggccag gaaccgtaaa aaggccgcgt    4980
tgctggcgtt tttccatagg ctccgccccc ctgacgagca tcacaaaaat cgacgctcaa    5040
gtcagaggtg gcgaaacccg acaggactat aaagatacca ggcgtttccc cctggaagct    5100
ccctcgtgcg ctctcctgtt ccgaccctgc cgcttaccgg atacctgtcc gcctttctcc    5160
cttcgggaag cgtggcgctt tctcatagct cacgctgtag gtatctcagt tcggtgtagg    5220
tcgttcgctc caagctgggc tgtgtgcacg aaccccccgt tcagcccgac cgctgcgcct    5280
tatccggtaa ctatcgtctt gagtccaacc cggtaagaca cgacttatcg ccactggcag    5340
cagccactgg taacaggatt agcagagcga ggtatgtagg cggtgctaca gagttcttga    5400
agtggtggcc taactacggc tacactagaa gaacagtatt tggtatctgc gctctgctga    5460
agccagttac cttcggaaaa agagttggta gctcttgatc cggcaaacaa accaccgctg    5520
gtagcggtgg tttttttgtt tgcaagcagc agattacgcg cagaaaaaaa ggatctcaag    5580
aagatccttt gatcttttct acggggtctg acgctcagtg gaacgaaaac tcacgttaag    5640
ggattttggt catgagatta tcaaaaagga tcttcaccta gatcctttta aattaaaaat    5700
gaagttttaa atcaatctaa agtatatatg agtaaacttg gtctgacagt taccaatgct    5760
taatcagtga ggcacctatc tcagcgatct gtctatttcg ttcatccata gttgcctgac    5820
tccccgtcgt gtagataact acgatacggg agggcttacc atctggcccc agtgctgcaa    5880
tgataccgcg agacccacgc tcaccggctc cagatttatc agcaataaac cagccagccg    5940
gaagggccga gcgcagaagt ggtcctgcaa ctttatccgc ctccatccag tctattaatt    6000
gttgccggga agctagagta agtagttcgc cagttaatag tttgcgcaac gttgttgcca    6060
ttgctacagg catcgtggtg tcacgctcgt cgtttggtat ggcttcattc agctccggtt    6120
cccaacgatc aaggcgagtt acatgatccc ccatgttgtg caaaaaagcg gttagctcct    6180
tcggtcctcc gatcgttgtc agaagtaagt tggccgcagt gttatcactc atggttatgg    6240
cagcactgca taattctctt actgtcatgc catccgtaag atgcttttct gtgactggtg    6300
agtactcaac caagtcattc tgagaatagt gtatgcggcg accgagttgc tcttgcccgg    6360
cgtcaatacg ggataatacc gcgccacata gcagaacttt aaaagtgctc atcattggaa    6420
```

```
aacgttcttc ggggcgaaaa ctctcaagga tcttaccgct gttgagatcc agttcgatgt    6480
aacccactcg tgcacccaac tgatcttcag catcttttac tttcaccagc gtttctgggt    6540
gagcaaaaac aggaaggcaa aatgccgcaa aaagggaat aagggcgaca cggaaatgtt     6600
gaatactcat actcttcctt tttcaatatt attgaagcat ttatcagggt tattgtctca    6660
tgagcggata catatttgaa tgtatttaga aaaataaaca aatagggggtt ccgcgcacat   6720 ttccccgaaa agtgccacct gacgtctaag aaaccattat tatcatgaca ttaacctata   6780
aaaataggcg tatcacgagg ccctttcgtc                                    6810
```

<210> SEQ ID NO 31
<211> LENGTH: 6933
<212> TYPE: DNA
<213> ORGANISM: Artificial Sequence
<220> FEATURE:
<223> OTHER INFORMATION: construct pINT-mdeA

<400> SEQUENCE: 31

```
tcgcgcgttt cggtgatgac ggtgaaaacc tctgacacat gcagctcccg gagacggtca     60
cagcttgtct gtaagcggat gccgggagca gacaagcccg tcaggcgcg tcagcgggtg     120 ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgaagatcct tgatcttttt    420
ctacggggtc tgacgctcag tggaacgaaa actcacgtta agggattttg gtcatgagat    480
tatcaaaaag gatcttcacc tagatccttt taaactagtg aagttaccat cacggaaaaa    540
ggttatgctg cttttaagac ccactttcac atttaagttg ttttttctaat ccgcatatga    600 tcaattcaag gccgaataag aaggctggct ctgcaccttg gtgatcaaat aattcgatag    660
cttgtcgtaa taatggcggc atactatcag tagtaggtgt ttccctttct tctttagcga    720
cttgatgctc ttgatcttcc aatacgcaac ctaaagtaaa atgccccact gcgctgagtg    780
catataatgc attctctagt gaaaaacctt gttggcataa aaaggctaat tgattttcga    840
gagtttcata ctgtttttct gtaggccgtg tacctaaatg tacttttgct ccatcgcgat    900
gacttagtaa agcacatcta aaacttttag cgttattacg taaaaaatct gccagctttt    960
ccccttctaa agggcaaaag tgagtatggt gcctatctaa catctcaatg gctaaggcgt   1020
cgagcaaagc ccgcttattt tttacatgcc aatacaatgt aggctgctct acacctagct   1080
tctgggcgag tttacgggtt gttaaacctt cgattccgac ctcattaagc agctctaatg   1140
cgctgttaat cactttactt ttatctaaac gagacatact cttccttttt caatattatt   1200
gaagcattta tcagggttat tgtctcatga gcggatacat atttgaatgt atttagaaaa   1260
ataaacaaat agggggttccg cgcacatttc cccgaaaagt gccacctgaa attggccaga   1320
tgattaattc ctaatttttg ttgacactct atcattgata gagttatttt accactccct   1380
atcagtgata gagaaaagtg aaatgaatag ttcgacaaaa atctagaaat aattttgttt   1440
aactttaaga aggagatata caagagctcg agtcgaagga gatagaacca tgtccaaaaa   1500
acaaaaactg acgatgatta ttacgatgct gatgggtggc ttcttcggtc tgctgaatga   1560
aacgctgctg gtgacggcac tgccgagcat catgaaagac ttcgaaattt cttatacgca   1620
```

```
ggttcaatgg ctgaccacgg catttctgct gaccaacggc atcgttattc cgctgtcagc    1680
tctggtcatt cagcgttaca ccacgcgcca agttttcctg gtcggtatct ctattttctt    1740
tctgggcacg ctgctgtcag gtctgtcgcc gcattttgcg accctgctgg ttgcgcgtat    1800
tatccaggca ctgggcgctg gtatcatgat gccgctgatg atgaccacga ttctggatgt    1860
cttccaaccg cacgaacgcg gcaaatatat gggcattttt ggtctggtga tcggtctggc    1920
accggcaatc ggtccgaccc tgagtggtta tctggttgaa tacttcaact ggcgttccct    1980
gtttcatgtg gttgcgccga tcgcggccgt tacctttctg attggcttca aaacgatcaa    2040
aaatgtgggt accacgatta aagttccgat cgactttatt tcagtcatct ctcggtgct     2100 gggctttggc ggtctgctgt atggtaccag ctctatttca gaaaaaggct tcgataatcc    2160
gatcgtcctg gtgtcgatga ttggcggtgt cgtgctggtt gcactgtttg tcctgcgtca    2220
gtaccgcctg agcacccgc tgctgaactt cgctgtgttc aaaaacaaac aattcaccgt      2280
tggcattatc attatgggtg tgacgatggt tagcatgatc ggctctgaaa ccattctgcc    2340
gatctttgtt cagaacctgc tgcatcgtag tgcactggac tccggtctga cgctgctgcc    2400
gggtgcaatt gtgatggcct tcatgagcat gacctctggc gccctgtatg aaaaatttgg    2460
tccgcgcaat ctggcactgg tgggtatggc tattgttgtc atcaccacgg catattttgt    2520
ggttatggat gaacagacca gtacgattat gctggcaacc gtctacgcta ttcgcatggt    2580
gggcatcgcg ctgggtctga ttccggttat gacccatacg atgaaccagc tgaaaccgga    2640
aatgaatgcg cacggcagtt ccatgaccaa cacggtgcag caaattgccg gcagcatcgg    2700
taccgcagct ctgatcacga ttctgagtca cgcctccaaa aacttttcac cgaccatgtc    2760
ggattacaac ggtatgaaca aaatcgacat gatgaaccag atcaaagtcg ataccatgct    2820
gcatggctac cacgcgggtt ttctgttcgc cctgctgatt accgtggtgt cgttcttctg    2880
ttcatttatg ctgcaaggca aaagaaaga agtggattcc cgccagtaat aaatcgatac     2940
tagcataacc ccttggggcc tctaaacgcg tcgacacgca aaaaggccat ccgtcaggat    3000
ggccttctgc ttaatttgat gcctggcagt ttatggcggg cgtcctgccc gccaccctcc    3060
gggccgttgc ttcgcaacgt tcaaatccgc tcccggcgga tttgtcctac tcaggagagc    3120
gttcaccgac aaacaacaga taaaacgaaa ggcccagtct ttcgactgag cctttcgttt    3180
tatttgatgc ctggcagttc cctactctcg catggggaga ccccacacta ccatcatgta    3240
tgaatatcct ccttagttcc tattccgaag ttcctattct ctagaaagta taggaacttc    3300
ggcgcgtcct acctgtgacg gaagatcact tcgcagaata aataaatcct ggtgtccctg    3360
ttgataccgg gaagccctgg gccaactttt ggcgaaaatg agacgttgat cggcacgtaa    3420
gaggttccaa ctttcaccat aatgaaataa gatcactacc gggcgtattt tttgagttgt    3480
cgagattttc aggagctaag gaagctaaaa tggagaaaaa aatcactgga tataccaccg    3540
ttgatatatc ccaatggcat cgtaaagaac attttgaggc atttcagtca gttgctcaat    3600
gtacctataa ccagaccgtt cagctggata ttacggcctt tttaaagacc gtaaagaaaa    3660
ataagcacaa gttttatccg gcctttattc acattcttgc ccgcctgatg aatgctcatc    3720
cggaattacg tatggcaatg aaagacggtg agctggtgat atgggatagt gttcacccTT    3780
gttacaccgt tttccatgag caaactgaaa cgttttcatc gctctggagt gaataccacg    3840
acgatttccg gcagtttcta cacatatatt cgcaagatgt ggcgtgttac ggtgaaaacc    3900
tggcctattt ccctaaaggg tttattgaga atatgttttt cgtctcagcc aatccctggg    3960
tgagtttcac cagttttgat ttaaacgtgg ccaatatgga caacttcttc gcccccgttt    4020
```

```
tcaccatggg caaatattat acgcaaggcg acaaggtgct gatgccgctg gcgattcagg    4080
ttcatcatgc cgtttgtgat ggcttccatg tcggcagatg cttaatgaat acaacagtac    4140
tgcgatgagt ggcagggcgg ggcgtaaggc gcgccattta aatgaagttc ctattccgaa    4200
gttcctattc tctagaaagt ataggaactt cgaagcagct ccagcctaca caatcgctca    4260
agacgtgtaa tgctgcaatc tgcatgcaag cttggcactg ccacgcaaa aaggccatcc    4320 gtcaggatgg ccttctgctt aatttgatgc ctggcagttt atggcgggcg tcctgcccgc    4380
caccctccgg gccgttgctt cgcaacgttc aaatccgctc ccggcggatt tgtcctactc    4440
aggagagcgt tcaccgacaa acaacagata aaacgaaagg cccagtcttt cgactgagcc    4500
tttcgtttta tttgatgcct ggcagttccc tactctcgca tggggagacc ccacactacc    4560 atcgggggc catcgatgca ggtggcactt ttcggggaaa tgtgcgcgga accctatt     4620 gtttattttt ctaaatacat tcaaatatgt atccgctcat gagacaataa ccctgctgca    4680
gaggcctgca tgcaagcttg gcgtaatcat ggtcatagct gtttcctgtg tgaaattgtt    4740
atccgctcac aattccacac aacatacgag ccggaagcat aaagtgtaaa gcctggggtg    4800
cctaatgagt gagctaactc acattaattg cgttgcgctc actgcccgct ttccagtcgg    4860
gaaacctgtc gtgccagctg cattaatgaa tcggccaacg cgcggggaga ggcggtttgc    4920
gtattgggcg ctcttccgct tcctcgctca ctgactcgct gcgctcggtc gttcggctgc    4980
ggcgagcggt atcagctcac tcaaaggcgg taatacggtt atccacagaa tcaggggata    5040
acgcaggaaa gaacatgtga gcaaaaggcc agcaaaaggc caggaaccgt aaaaaggccg    5100
cgttgctggc gtttttccat aggctccgcc cccctgacga gcatcacaaa aatcgacgct    5160
caagtcagag gtggcgaaac ccgacaggac tataaagata ccaggcgttt ccccctggaa    5220
gctccctcgt gcgctctcct gttccgaccc tgccgcttac cggatacctg tccgcctttc    5280
tcccttcggg aagcgtggcg ctttctcata gctcacgctg taggtatctc agttcggtgt    5340
aggtcgttcg ctccaagctg ggctgtgtgc acgaacccc cgttcagccc gaccgctgcg    5400
ccttatccgg taactatcgt cttgagtcca acccggtaag acacgactta tcgccactgg    5460
cagcagccac tggtaacagg attagcagag cgaggtatgt aggcggtgct acagagttct    5520
tgaagtggtg gcctaactac ggctacacta agaacagt atttggtatc tgcgctctgc    5580
tgaagccagt taccttcgga aaagagttg gtagctcttg atccggcaaa caaaccaccg    5640
ctggtagcgg tggtttttt gtttgcaagc agcagattac gcgcagaaaa aaggatctc    5700 aagaagatcc tttgatcttt tctacggggt ctgacgctca gtggaacgaa aactcacgtt    5760
aagggatttt ggtcatgaga ttatcaaaaa ggatcttcac ctagatcctt ttaaattaaa    5820
aatgaagttt taaatcaatc taagtatat atgagtaaac ttggtctgac agttaccaat    5880
gcttaatcag tgaggcacct atctcagcga tctgtctatt tcgttcatcc atagttgcct    5940
gactccccgt cgtgtagata actacgatac gggagggctt accatctggc cccagtgctg    6000
caatgatacc gcgagaccca cgctcaccgg ctccagattt atcagcaata aaccagccag    6060
ccggaagggc cgagcgcaga agtggtcctg caactttatc cgcctccatc cagtctatta    6120
attgttgccg ggaagctaga gtaagtagtt cgccagttaa tagtttgcgc aacgttgttg    6180
ccattgctac aggcatcgtg gtgtcacgct cgtcgtttgg tatggcttca ttcagctccg    6240
gttcccaacg atcaaggcga gttacatgat ccccatgtt gtgcaaaaaa gcggttagct    6300
ccttcggtcc tccgatcgtt gtcagaagta agttggccgc agtgttatca ctcatggtta    6360
```

-continued

| | |
|---|---|
| tggcagcact gcataattct cttactgtca tgccatccgt aagatgcttt tctgtgactg | 6420 |
| gtgagtactc aaccaagtca ttctgagaat agtgtatgcg gcgaccgagt tgctcttgcc | 6480 |
| cggcgtcaat acgggataat accgcgccac atagcagaac tttaaaagtg ctcatcattg | 6540 |
| gaaaacgttc ttcggggcga aaactctcaa ggatcttacc gctgttgaga tccagttcga | 6600 |
| tgtaacccac tcgtgcaccc aactgatctt cagcatcttt tactttcacc agcgtttctg | 6660 |
| ggtgagcaaa aacaggaagg caaaatgccg caaaaaaggg aataagggcg acacggaaat | 6720 |
| gttgaatact catactcttc ctttttcaat attattgaag catttatcag ggttattgtc | 6780 |
| tcatgagcgg atacatattt gaatgtattt agaaaaataa acaaataggg gttccgcgca | 6840 |
| catttccccg aaaagtgcca cctgacgtct aagaaaccat tattatcatg acattaacct | 6900 |
| ataaaaatag gcgtatcacg aggccctttc gtc | 6933 |

<210> SEQ ID NO 32
<211> LENGTH: 7248
<212> TYPE: DNA
<213> ORGANISM: Artificial Sequence
<220> FEATURE:
<223> OTHER INFORMATION: construct pINT-lmrA

<400> SEQUENCE: 32

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cgaagatcct tgatcttttt | 420 |
| ctacggggtc tgacgctcag tggaacgaaa actcacgtta agggattttg gtcatgagat | 480 |
| tatcaaaaag gatcttcacc tagatccttt taaactagtg aagttaccat cacggaaaaa | 540 |
| ggttatgctg cttttaagac ccactttcac atttaagttg ttttttctaat ccgcatatga | 600 |
| tcaattcaag gccgaataag aaggctggct ctgcaccttg gtgatcaaat aattcgatag | 660 |
| cttgtcgtaa taatggcggc atactatcag tagtaggtgt ttccctttct ctttagcga | 720 |
| cttgatgctc ttgatcttcc aatacgcaac ctaaagtaaa atgccccact gcgctgagtg | 780 |
| catataatgc attctctagt gaaaaacctt gttggcataa aaaggctaat tgattttcga | 840 |
| gagtttcata ctgtttttct gtaggccgtg tacctaaatg tactttttgct ccatcgcgat | 900 |
| gacttagtaa agcacatcta aaactttttag cgttattacg taaaaaatct tgccagcttt | 960 |
| cccctttctaa agggcaaaag tgagtatggt gcctatctaa catctcaatg gctaaggcgt | 1020 |
| cgagcaaagc ccgcttattt tttacatgcc aatacaatgt aggctgctct acacctagct | 1080 |
| tctgggcgag tttacgggtt gttaaacctt cgattccgac ctcattaagc agctctaatg | 1140 |
| cgctgttaat cactttactt ttatctaaac gagacatact cttcctttttt caatattatt | 1200 |
| gaagcattta tcagggttat tgtctcatga gcggatacat atttgaatgt atttagaaaa | 1260 |
| ataaacaaat aggggttccg cgcacatttc cccgaaaagt gccacctgaa attggccaga | 1320 |
| tgattaattc ctaattttttg ttgacactct atcattgata gagttatttt accactccct | 1380 |
| atcagtgata gagaaaagtg aaatgaatag ttcgacaaaa atctagaaat aattttgttt | 1440 |
| aactttaaga aggagatata caagagctcg agtcgaagga gatagaacca tggcgaaccg | 1500 |

```
tatcgaaggc aaagctgtgg acaaaacctc aatcaaacat tcattaaac tgatccgtgc    1560 cgcaaaaccg cgttacctgt ttttcattat cggtattctg gcgggtatcg tgggcaccct    1620
gattcagctg caagtcccga aaatggtgca gccgctggtt aactcttttg gtcatggcgt    1680
taatggcggt aaagttgccc tggtcattgc actgtatatc ggtagtgcag cagtctccgc    1740
aattgcagct atcgtgctgg gtatctttgg cgaaagcgtg gttaaaaacc tgcgtacgcg    1800
cgtttgggat aaaatgattc acctgccggt gaaatacttc gacgaagtta aaaccggtga    1860
aatgagctct cgtctggcga atgataccac gcaagtgaaa aacctgattg caaatagcat    1920
cccgcaggct tttacgtcta ttctgctgct ggtcggcagt atcgtgttca tgctgcagat    1980
gcaatggcgc ctgaccctgg ctatgattat cgcggttccg gtcgtgatgc tgattatgtt    2040
tccgatcatg acgttcggtc agaaaattgg ccgtacccgc caagatagcc tggcgaactt    2100
tcagggtatt gcctcagaat cgctgagcga atccgtctg gtgaaaagtt ccaatgccga    2160
aaaacaggca tccaaaaaag ctgaaaacga cgttaatgca ctgtataaaa ttggtgtcaa    2220
agaagcgatc tttgatggcc tgatgagtcc ggtcatgatg ctgtccatga tgctgatgat    2280
cttcggtctg ctggcctatg gcatttacct gatcagcacg ggtgtgatgt ctctgggtac    2340
cctgctgggc atgatgatgt acctgatgaa cctgattggc gcggtgccga ccgttgccac    2400 gttttttcacc gaactggcga aagcctctgg tagtacgggc cgtctgaccg aactgctgga    2460
tgaagaacag gaagttctgc atcagggtga atcgctggat ctggaaggca aaaccctgag    2520
cgcacgtcac gtcgactttg cttatgatga ctctgaacaa attctgcgcg atatctcctt    2580
tgaagcgcag ccgaattcaa ttatcgcatt cgctggcccg agtggcggtg gcaaatcaac    2640
catcttttcg ctgctggaac gcttctacca accgacggcc ggtgaaatta ccatcgatgg    2700
ccagccgatt gacaacatct cactggaaaa ttggcgttcg cagattggtt tcgttagcca    2760
agactctgct attatggcgg gcacgatccg cgaaaacctg acctatggtc tggaaggcga    2820
ttacacggat gaagacctgt ggcaggtcct ggacctggcg tttgcccgtt cattcgtgga    2880
aaacatgccg gatcagctga ataccgaagt tggtgaacgc ggcgtcaaaa ttcgggtgg    2940 ccagcgtcaa cgcctggcaa tcgctcgtgc gtttctgcgc aatccgaaaa ttctgatgct    3000
ggatgaagcc accgcatctc tggactccga atcagaatcg atggtgcaga agcgctgga    3060 tagtctgatg aaaggtcgta ccacgctggt gattgcccat cgcctgtcca cgatcgttga    3120
tgcagacaaa atctacttca tcgaaaaagg ccagatcacc ggtagcggca acacaacga    3180 actggtcgca acccacccgc tgtacgcaaa atatgtctcg gaacaactga cggtcggcca    3240
ataataaatc gatactagca taaccccttg gggcctctaa acgcgtcgac acgcaaaaag    3300
gccatccgtc aggatggcct tctgcttaat ttgatgcctg gcagtttatg gcgggcgtcc    3360
tgcccgccac cctccgggcc gttgcttcgc aacgttcaaa tccgctcccg gcggatttgt    3420
cctactcagg agagcgttca ccgacaaaca acagataaaa cgaaaggccc agtctttcga    3480
ctgagccttt cgttttattt gatgcctggc agttccctac tctcgcatgg ggagacccca    3540
cactaccatc atgtatgaat atcctccta gttcctattc cgaagttcct attctctaga    3600
aagtatagga acttcggcgc gtcctacctg tgacggaaga tcacttcgca gaataaataa    3660
atcctggtgt ccctgttgat accgggaagc cctgggccaa cttttggcga aatgagacg    3720 ttgatcggca cgtaagaggt tccaactttc accataatga aataagatca ctaccgggcg    3780
tattttttga gttgtcgaga ttttcaggag ctaaggaagc taaaatggag aaaaaaatca    3840
```

```
ctggatatac caccgttgat atatcccaat ggcatcgtaa agaacatttt gaggcatttc    3900
agtcagttgc tcaatgtacc tataaccaga ccgttcagct ggatattacg gccttttaa     3960 agaccgtaaa gaaaaataag cacaagtttt atccggcctt tattcacatt cttgcccgcc    4020
tgatgaatgc tcatccggaa ttacgtatgg caatgaaaga cggtgagctg gtgatatggg    4080
atagtgttca cccttgttac accgttttcc atgagcaaac tgaaacgttt tcatcgctct    4140
ggagtgaata ccacgacgat ttccggcagt ttctacacat atattcgcaa gatgtggcgt    4200
gttacggtga aaacctggcc tatttcccta aagggtttat tgagaatatg tttttcgtct    4260
cagccaatcc ctgggtgagt ttcaccagtt ttgatttaaa cgtggccaat atggacaact    4320
tcttcgcccc cgttttcacc atgggcaaat attatacgca aggcgacaag gtgctgatgc    4380
cgctggcgat tcaggttcat catgccgttt gtgatggctt ccatgtcggc agatgcttaa    4440
tgaatacaac agtactgcga tgagtggcag ggcggggcgt aaggcgcgcc atttaaatga    4500
agttcctatt ccgaagttcc tattctctag aaagtatagg aacttcgaag cagctccagc    4560
ctacacaatc gctcaagacg tgtaatgctg caatctgcat gcaagcttgg cactggccac    4620
gcaaaaaggc catccgtcag gatggccttc tgcttaattt gatgcctggc agtttatggc    4680
gggcgtcctg cccgccaccc tccgggccgt tgcttcgcaa cgttcaaatc cgctcccggc    4740
ggatttgtcc tactcaggag agcgttcacc gacaaacaac agataaaacg aaaggcccag    4800
tctttcgact gagcctttcg ttttatttga tgcctgcag ttccctactc tcgcatgggg    4860
agaccccaca ctaccatcgg ggggccatcg atgcaggtgg cacttttcgg ggaaatgtgc    4920
gcggaacccc tatttgttta tttttctaaa tacattcaaa tatgtatccg ctcatgagac    4980
aataaccctg ctgcagaggc ctgcatgcaa gcttggcgta atcatggtca tagctgtttc    5040
ctgtgtgaaa ttgttatccg ctcacaattc cacacaacat acgagccgga agcataaagt    5100
gtaaagcctg gggtgcctaa tgagtgagct aactcacatt aattgcgttg cgctcactgc    5160
ccgctttcca gtcgggaaac ctgtcgtgcc agctgcatta atgaatcggc caacgcgcgg    5220
ggagaggcgg tttgcgtatt gggcgctctt ccgcttcctc gctcactgac tcgctgcgct    5280
cggtcgttcg gctgcggcga gcggtatcag ctcactcaaa ggcggtaata cggttatcca    5340
cagaatcagg ggataacgca ggaaagaaca tgtgagcaaa aggccagcaa aaggccagga    5400
accgtaaaaa ggccgcgttg ctggcgtttt tccataggct ccgcccccct gacgagcatc    5460
acaaaaatcg acgctcaagt cagaggtggc gaaacccgac aggactataa agataccagg    5520
cgtttccccc tggaagctcc ctcgtgcgct ctcctgttcc gaccctgccg cttaccggat    5580
acctgtccgc ctttctccct tcgggaagcg tggcgctttc tcatagctca cgctgtaggt    5640
atctcagttc ggtgtaggtc gttcgctcca agctgggctg tgtgcacgaa ccccccgttc    5700
agcccgaccg ctgcgcctta tccggtaact atcgtcttga gtccaacccg gtaagacacg    5760
acttatcgcc actggcagca gccactggta acaggattag cagagcgagg tatgtaggcg    5820
gtgctacaga gttcttgaag tggtggccta actacggcta cactagaaga acagtatttg    5880
gtatctgcgc tctgctgaag ccagttacct tcggaaaaag agttggtagc tcttgatccg    5940
gcaaacaaac caccgctggt agcggtggtt ttttgtttg caagcagcag attacgcgca    6000 gaaaaaagg atctcaagaa gatcctttga tcttttctac ggggtctgac gctcagtgga    6060
acgaaaactc acgttaaggg attttggtca tgagattatc aaaaaggatc ttcacctaga    6120
tccttttaaa ttaaaaatga agttttaaat caatctaaag tatatatgag taaacttggt    6180
ctgacagtta ccaatgctta atcagtgagg cacctatctc agcgatctgt ctatttcgtt    6240
```

```
catccatagt tgcctgactc cccgtcgtgt agataactac gatacgggag ggcttaccat    6300
ctggccccag tgctgcaatg ataccgcgag acccacgctc accggctcca gatttatcag    6360
caataaacca gccagccgga agggccgagc gcagaagtgg tcctgcaact ttatccgcct    6420
ccatccagtc tattaattgt tgccgggaag ctagagtaag tagttcgcca gttaatagtt    6480
tgcgcaacgt tgttgccatt gctacaggca tcgtggtgtc acgctcgtcg tttggtatgg    6540
cttcattcag ctccggttcc caacgatcaa ggcgagttac atgatccccc atgttgtgca    6600
aaaaagcggt tagctccttc ggtcctccga tcgttgtcag aagtaagttg gccgcagtgt    6660
tatcactcat ggttatggca gcactgcata attctcttac tgtcatgcca tccgtaagat    6720
gcttttctgt gactggtgag tactcaacca agtcattctg agaatagtgt atgcggcgac    6780
cgagttgctc ttgcccggcg tcaatacggg ataataccgc gccacatagc agaactttaa    6840
aagtgctcat cattggaaaa cgttcttcgg ggcgaaaact ctcaaggatc ttaccgctgt    6900
tgagatccag ttcgatgtaa cccactcgtg cacccaactg atcttcagca tcttttactt    6960
tcaccagcgt ttctgggtga gcaaaaacag gaaggcaaaa tgccgcaaaa aagggaataa    7020
gggcgacacg gaaatgttga atactcatac tcttcctttt tcaatattat tgaagcattt    7080
atcagggtta ttgtctcatg agcggataca tatttgaatg tatttagaaa aataaacaaa    7140
taggggttcc gcgcacattt ccccgaaaag tgccacctga cgtctaagaa accattatta    7200
tcatgacatt aacctataaa aataggcgta tcacgaggcc ctttcgtc                 7248

<210> SEQ ID NO 33
<211> LENGTH: 6684
<212> TYPE: DNA
<213> ORGANISM: Artificial Sequence
<220> FEATURE:
<223> OTHER INFORMATION: construct pINT-Ps-setA

<400> SEQUENCE: 33
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg     120 ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccaggt     360 tttcccagtc acgacgttgt aaaacgacgg ccagtgaatt cgaagatcct ttgatctttt     420
ctacggggtc tgacgctcag tggaacgaaa actcacgtta agggattttg gtcatgagat     480
tatcaaaaag gatcttcacc tagatccttt taaactagtg aagttaccat cacggaaaaa     540
ggttatgctg cttttaagac ccactttcac atttaagttg ttttctaat ccgcatatga      600 tcaattcaag gccgaataag aaggctggct ctgcaccttg gtgatcaaat aattcgatag     660
cttgtcgtaa taatggcggc atactatcag tagtaggtgt ttcccttctt ctttagcga     720 cttgatgctc ttgatcttcc aatacgcaac ctaaagtaaa atgccccact cgctgagtg     780 catataatgc attctctagt gaaaaacctt gttggcataa aaaggctaat tgattttcga    840
gagtttcata ctgttttct gtaggccgtg tacctaaatg tacttttgct ccatcgcgat     900
gacttagtaa agcacatcta aaactttag cgttattacg taaaaaatct tgccagcttt      960
ccccttctaa agggcaaaag tgagtatggt gcctatctaa catctcaatg gctaaggcgt    1020
```

```
cgagcaaagc ccgcttattt tttacatgcc aatacaatgt aggctgctct acacctagct    1080
tctgggcgag tttacgggtt gttaaacctt cgattccgac ctcattaagc agctctaatg    1140
cgctgttaat cactttactt ttatctaaac gagacatact cttccttttt caatattatt    1200
gaagcattta tcagggttat tgtctcatga gcggatacat atttgaatgt atttagaaaa    1260
ataaacaaat aggggttccg cgcacatttc cccgaaaagt gccacctgaa attggccaga    1320
tgattaattc ctaattttg ttgacactct atcattgata gagttatttt accactccct    1380
atcagtgata gagaaaagtg aaatgaatag ttcgacaaaa atctagaaat aattttgttt    1440
aactttaaga aggagatata caagagctcg agtcgaagga gatagaacca tgaacgaaag    1500
ccagagctct catggcggtt catggctgtc ggttattgcg ctggccctgg cggcctttat    1560
cttcaatacc acggaattcg ttccggtcgc gctgctgtca gatattggcc gttcgtttga    1620
catgccgcca tcacaagtgg gtctgatgct gaccatctat gcgtgggtgg ttgccctgat    1680
gtcgctgccg atgatgctgc tgacccgcaa cgtcgaacgt cgcacgctgc tgattttgt    1740 gttcgtcgtg ttcatcggca gtcatctggt gagttccgtg gcgtcatcgt ttagcatgct    1800
gatgattctt cgtattggta tcgcactgtc ccacgctgtg ttttggagta tcaccgcatc    1860
cctggctgtg cgtgttgcac cggctggtaa acaggcccag gcactgggtc tgctggcaac    1920
cggttcagca ctggctatgg tcctgggtat tccgctgggc cgtgttgtcg gtgaactgct    1980
ggattggcgc accacgttcc tgagcattgc catcgtggca gctctggtgg ttctgtgtct    2040
ggcacgtacc ctgccgctgc tgccgagtca gaatagtggt tccctgcgtt ccctgccgat    2100
gctgtttaaa cgtccggcgc tggttgcggc atatgttctg accgccctgg ttattacggc    2160
gcagtttacc gcctatacgt acattgaacc gttcgcacaa accatcgctc atctgtctgg    2220
caacatgacc acggcactgc tgctgctgtt tggcggtgct ggtattctgg gcacggtgct    2280
gttcagccgt tattctaatc gctacccgaa aggttttctg atcgcagcta ttagtatcat    2340
ggcaatgtgt ctgctgctgc tgctgccggc ctcccgcgat agctctctgc tggccgccct    2400
ggtcgtggtt tggggtattg cgggcatgtg tttcggcctg gcgctgcagg ccaaagttct    2460
gaacctggca agcgatgcta ccgacgtcgc gatggccctg ttttctggca tttataatgt    2520
tggtatcggc ggtggcgccc tgctgggttc actggttacg gcacacctgg gcctgtcgga    2580
cgttggtatt gtcggtggcc tgctggccct gagcggcgtc gtgctgtgct gttttgccac    2640
ctatcgcttt gcacgtccgg tgggttctgc agctctgtaa taaatcgata ctagcataac    2700
cccttggggc ctctaaacgc gtcgacacgc aaaaaggcca tccgtcagga tggccttctg    2760
cttaatttga tgcctggcag tttatggcgg gcgtcctgcc cgccaccctc cgggccgttg    2820
cttcgcaacg ttcaaatccg ctcccggcgg atttgtccta ctcaggagag cgttcaccga    2880
caaacaacag ataaaacgaa aggcccagtc tttcgactga gcctttcgtt ttatttgatg    2940
cctggcagtt ccctactctc gcatgggag accccacact accatcatgt atgaatatcc    3000
tccttagttc ctattccgaa gttcctattc tctagaaagt ataggaactt cggcgcgtcc    3060
tacctgtgac ggaagatcac ttcgcagaat aaataaatcc tggtgtccct gttgataccg    3120
ggaagccctg ggccaacttt tggcgaaaat gagacgttga tcggcacgta agaggttcca    3180
actttcacca taatgaaata agatcactac cgggcgtatt ttttgagttg tcgagatttt    3240
caggagctaa ggaagctaaa atggagaaaa aaatcactgg atataccacc gttgatatat    3300
cccaatggca tcgtaaagaa cattttgagg catttcagtc agttgctcaa tgtacctata    3360
accagaccgt tcagctggat attacggcct ttttaaagac cgtaaagaaa aataagcaca    3420
```

```
agttttatcc ggcctttatt cacattcttg cccgcctgat gaatgctcat ccggaattac    3480
gtatggcaat gaaagacggt gagctggtga tatgggatag tgttcaccct tgttacaccg    3540
ttttccatga gcaaactgaa acgttttcat cgctctggag tgaataccac gacgatttcc    3600
ggcagtttct acacatatat tcgcaagatg tggcgtgtta cggtgaaaac ctggcctatt    3660
tccctaaagg gtttattgag aatatgtttt tcgtctcagc caatccctgg gtgagtttca    3720
ccagttttga tttaaacgtg gccaatatgg acaacttctt cgcccccgtt ttcaccatgg    3780
gcaaatatta tacgcaaggc gacaaggtgc tgatgccgct ggcgattcag gttcatcatg    3840
ccgtttgtga tggcttccat gtcggcagat gcttaatgaa tacaacagta ctgcgatgag    3900
tggcagggcg gggcgtaagg cgcgccattt aaatgaagtt cctattccga agttcctatt    3960
ctctagaaag tataggaact tcgaagcagc tccagcctac acaatcgctc aagacgtgta    4020
atgctgcaat ctgcatgcaa gcttggcact ggccacgcaa aaaggccatc cgtcaggatg    4080
gccttctgct taatttgatg cctggcagtt tatggcgggc gtcctgcccg ccaccctccg    4140
ggccgttgct tcgcaacgtt caaatccgct cccgcggat ttgtcctact caggagagcg    4200
ttcaccgaca acaacagat aaaacgaaag gcccagtctt tcgactgagc ctttcgtttt    4260
atttgatgcc tggcagttcc ctactctcgc atggggagac cccacactac catcgggggg    4320
ccatcgatgc aggtggcact tttcggggaa atgtgcgcgg aacccctatt tgtttatttt    4380
tctaaataca ttcaaatatg tatccgctca tgagacaata accctgctgc agaggcctgc    4440
atgcaagctt ggcgtaatca tggtcatagc tgtttcctgt gtgaaattgt tatccgctca    4500
caattccaca acatacga gccggaagca taaagtgtaa agcctgggt gcctaatgag    4560 tgagctaact cacattaatt gcgttgcgct cactgcccgc tttccagtcg ggaaacctgt    4620
cgtgccagct gcattaatga atcggccaac gcgcgggag aggcggtttg cgtattgggc    4680
gctcttccgc ttcctcgctc actgactcgc tgcgctcggt cgttcggctg cggcgagcgg    4740
tatcagctca ctcaaaggcg gtaatacggt tatccacaga atcaggggat aacgcaggaa    4800
agaacatgtg agcaaaaggc cagcaaaagg ccaggaaccg taaaaaggcc gcgttgctgg    4860
cgtttttcca taggctccgc cccctgacg agcatcacaa aaatcgacgc tcaagtcaga    4920
ggtggcgaaa cccgacagga ctataaagat accaggcgtt tccccctgga agctccctcg    4980
tgcgctctcc tgttccgacc ctgccgctta ccggatacct gtccgccttt ctcccttcgg    5040
gaagcgtggc gctttctcat agctcacgct gtaggtatct cagttcggtg taggtcgttc    5100
gctccaagct gggctgtgtg cacgaacccc cgttcagcc cgaccgctgc gccttatccg    5160
gtaactatcg tcttgagtcc aacccggtaa gacacgactt atcgccactg gcagcagcca    5220
ctggtaacag gattagcaga gcgaggtatg taggcggtgc tacagagttc ttgaagtggt    5280
ggcctaacta cggctacact agaagaacag tatttggtat ctgcgctctg ctgaagccag    5340
ttaccttcgg aaaaagagtt ggtagctctt gatccggcaa acaaaccacc gctggtagcg    5400
gtggtttttt tgtttgcaag cagcagatta cgcgcagaaa aaaaggatct caagaagatc    5460
ctttgatctt ttctacgggg tctgacgctc agtggaacga aaactcacgt taagggattt    5520
tggtcatgag attatcaaaa aggatcttca cctagatcct tttaaattaa aaatgaagtt    5580
ttaaatcaat ctaaagtata tatgagtaaa cttggtctga cagttaccaa tgcttaatca    5640
gtgaggcacc tatctcagcg atctgtctat ttcgttcatc catagttgcc tgactccccg    5700
tcgtgtagat aactacgata cgggagggct taccatctgg ccccagtgct gcaatgatac    5760
```

| | |
|---|---|
| cgcgagaccc acgctcaccg gctccagatt tatcagcaat aaaccagcca gccggaaggg | 5820 |
| ccgagcgcag aagtggtcct gcaactttat ccgcctccat ccagtctatt aattgttgcc | 5880 |
| gggaagctag agtaagtagt tcgccagtta atagtttgcg caacgttgtt gccattgcta | 5940 |
| caggcatcgt ggtgtcacgc tcgtcgtttg gtatggcttc attcagctcc ggttcccaac | 6000 |
| gatcaaggcg agttacatga tcccccatgt tgtgcaaaaa agcggttagc tccttcggtc | 6060 |
| ctccgatcgt tgtcagaagt aagttggccg cagtgttatc actcatggtt atggcagcac | 6120 |
| tgcataattc tcttactgtc atgccatccg taagatgctt ttctgtgact ggtgagtact | 6180 |
| caaccaagtc attctgagaa tagtgtatgc ggcgaccgag ttgctcttgc ccggcgtcaa | 6240 |
| tacgggataa taccgcgcca catagcagaa ctttaaaagt gctcatcatt ggaaaacgtt | 6300 |
| cttcggggcg aaaactctca aggatcttac cgctgttgag atccagttcg atgtaaccca | 6360 |
| ctcgtgcacc caactgatct tcagcatctt ttactttcac cagcgtttct gggtgagcaa | 6420 |
| aaacaggaag gcaaaatgcc gcaaaaaagg gaataagggc gacacggaaa tgttgaatac | 6480 |
| tcatactctt cctttttcaa tattattgaa gcatttatca gggttattgt ctcatgagcg | 6540 |
| gatacatatt tgaatgtatt tagaaaaata aacaataggg gttccgcgc acatttcccc | 6600 |
| gaaaagtgcc acctgacgtc taagaaacca ttattatcat gacattaacc tataaaaata | 6660 |
| ggcgtatcac gaggcccttt cgtc | 6684 |

<210> SEQ ID NO 34
<211> LENGTH: 6692
<212> TYPE: DNA
<213> ORGANISM: Artificial Sequence
<220> FEATURE:
<223> OTHER INFORMATION: construct pINT-Bb-setA

<400> SEQUENCE: 34

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cgaagatcct tgatcttttt | 420 |
| ctacggggtc tgacgctcag tggaacgaaa actcacgtta agggattttg gtcatgagat | 480 |
| tatcaaaaag gatcttcacc tagatccttt taaactagtg aagttaccat cacggaaaaa | 540 |
| ggttatgctg cttttaagac ccactttcac atttaagttg ttttttctaat ccgcatatga | 600 |
| tcaattcaag gccgaataag aaggctggct ctgcaccttg gtgatcaaat aattcgatag | 660 |
| cttgtcgtaa taatggcggc atactatcag tagtaggtgt ttcccttcct tctttagcga | 720 |
| cttgatgctc ttgatcttcc aatacgcaac ctaaagtaaa atgccccact gcgctgagtg | 780 |
| catataatgc attctctagt gaaaaacctt gttggcataa aaaggctaat gattttcga | 840 |
| gagtttcata ctgttttct gtaggccgtg tacctaaatg tacttttgct ccatcgcgat | 900 |
| gacttagtaa agcacatcta aactttttag cgttattacg taaaaaatct tgccagcttt | 960 |
| cccccttcta aagggcaaaag tgagtatggt gcctatctaa catctcaatg gctaaggcgt | 1020 |
| cgagcaaagc ccgcttattt tttacatgcc aatacaatgt aggctgctct acacctagct | 1080 |
| tctgggcgag tttacggggtt gttaaacctt cgattccgac ctcattaagc agctctaatg | 1140 |

```
cgctgttaat cactttactt ttatctaaac gagacatact cttccttttt caatattatt    1200
gaagcattta tcagggttat tgtctcatga gcggatacat atttgaatgt atttagaaaa    1260
ataaacaaat aggggttccg cgcacatttc cccgaaaagt gccacctgaa attggccaga    1320
tgattaattc ctaatttttg ttgacactct atcattgata gagttatttt accactccct    1380
atcagtgata gagaaaagtg aaatgaatag ttcgacaaaa atctagaaat aattttgttt    1440
aactttaaga aggagatata caagagctcg agtcgaagga gatagaacca tgaccattgc    1500
aacggtttcc cgcaaaaccg cttggctgcg tgtggttacc ctggccgttg ccgcctttat    1560
cttcaacacc acgaaatttg tcccggtggg cctgctgagt gatattgcgc agtccttcgg    1620
catggaaacc gcccaagtgg gtattatgct gacgatctat gcctgggttg tggcactgat    1680
gagcctgccg tttatgctga tgacctctca ggtggaacgt cgccgtctgc tgattagcat    1740
ctttctgctg ttcatcgcaa gtcatgttct gtcctttctg gcgtggaatt tcaccgttct    1800
ggtcatttct cgcattggta tcgcgtttgc ccacgcaatt ttctggtcaa tcacggcttc    1860
gctggcgatt cgtatggctc cggcgggcaa gaaagcgcag gcactgagtc tgctggcgac    1920
cggtacggct ctggcgatgg ttctgggtct gccgatcggc cgcattgtcg gtcaatactt    1980
tggctggcgt accacgtttt tcgtgattgg cgttgtcgca gctatcaccc tgttctgcct    2040
gattaaactg ctgccgaaac tgccgagcga acatagtggt tccctgagct ctgtgccgaa    2100
actgtttcgc cgtccggcgc tggttaacat ctatgccctg attgcaatcg tggttaccgc    2160 acactcacg gcttatagtt acatcgaacc gttcgtgcag caaattgccg gcctgtccgc    2220
taactttgcg accctgctgc tgctgctgtt tggcggtgcg ggtattatcg gctctgttct    2280
gtttggtaaa tggggcaata acatgccag cggtctggtc tctggcgcca ttgcactgat    2340
ggccgcatgt ctggtgctgc tgctgccggc agctcagggt gaactgaccc tggccggcct    2400
gtcactgttt tggggtattt cgatcatgat tgtcgcactg ggtatgcaag tgaaagttct    2460
ggctctggcc ccggatgcca ccgatgttgc catgagcctg ttttctggca tcttcaacat    2520
cggcattggt gccggcgcac tgctgggtaa tcaggtgtca ctgcacattt caatgtcgga    2580
catcggtttt attggcgcca tcccggcaat tatcgctctg gtctggtcga ttctggtgtc    2640
cgccgttggc cggttgccct ggaagaacat ccgcaggcaa cccactaata aatcgatact    2700
agcataaccc cttggggcct ctaaacgcgt cgacacgcaa aaaggccatc cgtcaggatg    2760
gccttctgct taatttgatg cctggcagtt tatggcgggc gtcctgcccg ccaccctccg    2820
ggccgttgct tcgcaacgtt caaatccgct cccggcggat ttgtcctact caggagagcg    2880
ttcaccgaca acaacagat aaaacgaaag gcccagtctt tcgactgagc ctttcgtttt    2940
atttgatgcc tggcagttcc ctactctcgc atggggagac cccacactac catcatgtat    3000
gaatatcctc cttagttcct attccgaagt tcctattctc tagaaagtat aggaacttcg    3060
gcgcgtccta cctgtgacgg aagatcactt cgcagaataa ataaatcctg gtgtccctgt    3120
tgataccggg aagccctggg ccaacttttg gcgaaaatga cgttgatcg gcacgtaag    3180 aggttccaac tttcaccata atgaaataag atcactaccg ggcgtatttt ttgagttgtc    3240
gagattttca ggagctaagg aagctaaaat ggagaaaaaa atcactggat ataccaccgt    3300
tgatatatcc caatggcatc gtaaagaaca ttttgaggca tttcagtcag ttgctcaatg    3360
tacctataac cagaccgttc agctggatat tacggccttt ttaaagaccg taagaaaaaa    3420
taagcacaag ttttatccgg cctttattca cattcttgcc cgcctgatga atgctcatcc    3480
```

-continued

```
ggaattacgt atggcaatga aagacggtga gctggtgata tgggatagtg ttcacccttg    3540
ttacaccgtt ttccatgagc aaactgaaac gttttcatcg ctctggagtg aataccacga    3600
cgatttccgg cagtttctac acatatattc gcaagatgtg gcgtgttacg gtgaaaacct    3660
ggcctatttc cctaaagggt ttattgagaa tatgttttc gtctcagcca atccctgggt     3720
gagtttcacc agttttgatt taaacgtggc caatatggac aacttcttcg ccccgtttt    3780
caccatggga aaatattata cgcaaggcga caaggtgctg atgccgctgg cgattcaggt    3840
tcatcatgcc gtttgtgatg gcttccatgt cggcagatgc ttaatgaata caacagtact    3900
gcgatgagtg gcagggcggg gcgtaaggcg cgccatttaa atgaagttcc tattccgaag    3960
ttcctattct ctagaaagta taggaacttc gaagcagctc cagcctacac aatcgctcaa    4020
gacgtgtaat gctgcaatct gcatgcaagc ttggcactgg ccacgcaaaa aggccatccg    4080
tcaggatggc cttctgctta atttgatgcc tggcagttta tggcgggcgt cctgcccgcc    4140
accctccggg ccgttgcttc gcaacgttca atccgctcc cggcggattt gtcctactca     4200
ggagagcgtt caccgacaaa caacagataa aacgaaaggc ccagtctttc gactgagcct    4260
ttcgttttat ttgatgcctg gcagttccct actctcgcat ggggagaccc cacactacca    4320
tcgggggggcc atcgatgcag gtggcacttt tcggggaaat gtgcgcggaa ccctatttg    4380
tttattttc taaatacatt caaatatgta tccgctcatg agacaataac cctgctgcag    4440
aggcctgcat gcaagcttgg cgtaatcatg gtcatagctg tttcctgtgt gaattgtta    4500
tccgctcaca attccacaca acatacgagc cggaagcata agtgtaaag cctggggtgc     4560
ctaatgagtg agctaactca cattaattgc gttgcgctca ctgcccgctt ccagtcggg    4620
aaacctgtcg tgccagctgc attaatgaat cggccaacgc gcggggagag gcggtttgcg    4680
tattgggcgc tcttccgctt cctcgctcac tgactcgctg cgctcggtcg ttcggctgcg    4740
gcgagcggta tcagctcact caaaggcggt aatacggtta tccacagaat caggggataa    4800
cgcaggaaag aacatgtgag caaaaggcca gcaaaaggcc aggaaccgta aaaaggccgc    4860
gttgctggcg ttttttccata ggctccgccc ccctgacgag catcacaaaa atcgacgctc    4920
aagtcagagg tggcgaaacc cgacaggact ataaagatac caggcgtttc ccctggaag    4980
ctccctcgtg cgctctcctg ttccgaccct gccgcttacc ggatacctgt ccgcctttct    5040
cccttcggga agcgtggcgc tttctcatag ctcacgctgt aggtatctca gttcggtgta    5100
ggtcgttcgc tccaagctgg gctgtgtgca cgaaccccc gttcagcccg accgctgcgc     5160
cttatccggt aactatcgtc ttgagtccaa cccggtaaga cacgacttat cgccactggc    5220
agcagccact ggtaacagga ttagcagagc gaggtatgta ggcggtgcta cagagttctt    5280
gaagtggtgg cctaactacg gctacactag aagaacagta tttggtatct gcgctctgct    5340
gaagccagtt accttcggaa aaagagttgg tagctcttga tccggcaaac aaaccaccgc    5400
tggtagcggt ggtttttttg tttgcaagca gcagattacg cgcagaaaaa aaggatctca    5460
agaagatcct ttgatctttt ctacggggtc tgacgctcag tggaacgaaa actcacgtta    5520
agggattttg gtcatgagat tatcaaaaag gatcttcacc tagatccttt taaattaaaa    5580
atgaagtttt aaatcaatct aaagtatata tgagtaaact tggtctgaca gttaccaatg    5640
cttaatcagt gaggcaccta tctcagcgat ctgtctattt cgttcatcca tagttgcctg    5700
actccccgtc gtgtagataa ctacgatacg ggagggctta ccatctggcc ccagtgctgc    5760
aatgataccg cgagacccac gctcaccggc tccagattta tcagcaataa accagccagc    5820
cggaagggcc gagcgcagaa gtggtcctgc aactttatcc gcctccatcc agtctattaa    5880
```

```
ttgttgccgg gaagctagag taagtagttc gccagttaat agtttgcgca acgttgttgc      5940
cattgctaca ggcatcgtgg tgtcacgctc gtcgtttggt atggcttcat tcagctccgg      6000
ttcccaacga tcaaggcgag ttacatgatc ccccatgttg tgcaaaaaag cggttagctc      6060
cttcggtcct ccgatcgttg tcagaagtaa gttggccgca gtgttatcac tcatggttat      6120
ggcagcactg cataattctc ttactgtcat gccatccgta agatgctttt ctgtgactgg      6180
tgagtactca accaagtcat tctgagaata gtgtatgcgg cgaccgagtt gctcttgccc      6240
ggcgtcaata cgggataata ccgcgccaca tagcagaact ttaaaagtgc tcatcattgg      6300
aaaacgttct cggggcgaa aactctcaag gatcttaccg ctgttgagat ccagttcgat       6360
gtaacccact cgtgcaccca actgatcttc agcatctttt actttcacca gcgtttctgg      6420
gtgagcaaaa acaggaaggc aaaatgccgc aaaaaaggga ataagggcga cacggaaatg      6480
ttgaatactc atactcttcc ttttcaata ttattgaagc atttatcagg gttattgtct       6540
catgagcgga tacatatttg aatgtattta gaaaaataaa caatagggg ttccgcgcac       6600 atttccccga aaagtgccac ctgacgtcta agaaaccatt attatcatga cattaaccta     6660
taaaaatagg cgtatcacga ggccctttcg tc                                    6692

<210> SEQ ID NO 35
<211> LENGTH: 35
<212> TYPE: DNA
<213> ORGANISM: Artificial Sequence
<220> FEATURE:
<223> OTHER INFORMATION: Primer

<400> SEQUENCE: 35
ttactcagca ataaactgat attccgtcag gctgg                                 35

<210> SEQ ID NO 36
<211> LENGTH: 83
<212> TYPE: DNA
<213> ORGANISM: Artificial Sequence
<220> FEATURE:
<223> OTHER INFORMATION: Primer

<400> SEQUENCE: 36
ttgtaatctc gcgctcttca catcagactt tccatataga gcgtaatttc cgttaacgtc      60
ggtagtgctg accttgccgg agg                                              83

<210> SEQ ID NO 37
<211> LENGTH: 53
<212> TYPE: DNA
<213> ORGANISM: Artificial Squence
<220> FEATURE:
<223> OTHER INFORMATION: Primer

<400> SEQUENCE: 37
ctgtctctta tcacatctcc tgaaatggcc agatgtaatt cctaattttt gtt             53
```

<210> SEQ ID NO 38
<211> LENGTH: 44
<212> TYPE: DNA
<213> ORGANISM: Artificial Sequence
<220> FEATURE:
<223> OTHER INFORMATION: Primer

<400> SEQUENCE: 38
ctgtctctta tcacatctca cattacatct gagcgattgt tagg                44

<210> SEQ ID NO 39
<211> LENGTH: 30
<212> TYPE: DNA
<213> ORGANISM: Artificial Sequence
<220> FEATURE:
<223> OTHER INFORMATION: Primer

<400> SEQUENCE: 39
gatcacatat gagagttctg gttaccggtg                                30

<210> SEQ ID NO 40
<211> LENGTH: 40
<212> TYPE: DNA
<213> ORGANISM: Artificial Sequence
<220> FEATURE:
<223> OTHER INFORMATION: Primer

<400> SEQUENCE: 40
gatcactcga gtcattaatc gggatatccc tgtggatggc                     40

<210> SEQ ID NO 41
<211> LENGTH: 60
<212> TYPE: DNA
<213> ORGANISM: Artificial Sequence
<220> FEATURE:
<223> OTHER INFORMATION: Primer

<400> SEQUENCE: 41
gtcgatgaag ccctgaaaga cgcgcagact atgcacttca ttgaaaacaa aaacttcgtc    60

<210> SEQ ID NO 42
<211> LENGTH: 60
<212> TYPE: DNA
<213> ORGANISM: Artificial Sequence
<220> FEATURE:
<223> OTHER INFORMATION: Primer

<400> SEQUENCE: 42
gatggccttt ttgcgtgtcg acgcggccgc ctagataaac aggatgatat ttttgccttg    60

<210> SEQ ID NO 43
<211> LENGTH: 60
<212> TYPE: DNA
<213> ORGANISM: Artificial Sequence
<220> FEATURE:
<223> OTHER INFORMATION: Primer

<400> SEQUENCE: 43
caaggcaaaa atatcatcct gtttatctag gcggccgcgt cgacacgcaa aaaggccatc    60

```
<210> SEQ ID NO 44
<211> LENGTH: 60
<212> TYPE: DNA
<213> ORGANISM: Artificial Sequence
<220> FEATURE:
<223> OTHER INFORMATION: Primer

<400> SEQUENCE: 44
gacgaagttt tgttttcaa tgaagtgcat agtctgcgcg tctttcaggg cttcatcgac      60

<210> SEQ ID NO 45
<211> LENGTH: 60
<212> TYPE: DNA
<213> ORGANISM: Artificial Sequence
<220> FEATURE:
<223> OTHER INFORMATION: Primer

<400> SEQUENCE: 45
atggcctttt tgcgtgtcga cgcggccgct taattcgagc gggtaaagat cttcatcagg      60

<210> SEQ ID NO 46
<211> LENGTH: 60
<212> TYPE: DNA
<213> ORGANISM: Artificial Sequence
<220> FEATURE:
<223> OTHER INFORMATION: Primer

<400> SEQUENCE: 46
atggcctttt tgcgtgtcga cgcggccgct taattcgagc gggtaaagat cttcatcagg      60

<210> SEQ ID NO 47
<211> LENGTH: 60
<212> TYPE: DNA
<213> ORGANISM: Artificial Sequence
<220> FEATURE:
<223> OTHER INFORMATION: Primer

<400> SEQUENCE: 47
ctgatgaaga tctttacccg ctcgaattaa gcggccgcgt cgacacgcaa aaaggccatc      60

<210> SEQ ID NO 48
<211> LENGTH: 60
<212> TYPE: DNA
<213> ORGANISM: Artificial Sequence
<220> FEATURE:
<223> OTHER INFORMATION: Primer

<400> SEQUENCE: 48
cggggtacgc ttaatcaggt tatcaatcat agtctgcgcg tctttcaggg cttcatcgac      60

<210> SEQ ID NO 49
<211> LENGTH: 60
<212> TYPE: DNA
<213> ORGANISM: Artificial Sequence
<220> FEATURE:
<223> OTHER INFORMATION: Primer

<400> SEQUENCE: 49
gtcgatgaag ccctgaaaga cgcgcagact atgagcggtg aacactatgt cattagcctg      60
```

<210> SEQ ID NO 50
<211> LENGTH: 60
<212> TYPE: DNA
<213> ORGANISM: Artificial Sequence
<220> FEATURE:
<223> OTHER INFORMATION: Primer

<400> SEQUENCE: 50
gatggccttt ttgcgtgtcg acgcggccgc tcatttaaat tcgatgatca tcttgtcgtt    60

<210> SEQ ID NO 51
<211> LENGTH: 60
<212> TYPE: DNA
<213> ORGANISM: Artificial Sequence
<220> FEATURE:
<223> OTHER INFORMATION: Primer

<400> SEQUENCE: 51
aacgacaaga tgatcatcga atttaaatga gcggccgcgt cgacacgcaa aaaggccatc    60

<210> SEQ ID NO 52
<211> LENGTH: 60
<212> TYPE: DNA
<213> ORGANISM: Artificial Sequence
<220> FEATURE:
<223> OTHER INFORMATION: Primer

<400> SEQUENCE: 52
caggctaatg acatagtgtt caccgctcat agtctgcgcg tctttcaggg cttcatcgac    60

<210> SEQ ID NO 53
<211> LENGTH: 60
<212> TYPE: DNA
<213> ORGANISM: Artificial Sequence
<220> FEATURE:
<223> OTHER INFORMATION: Primer

<400> SEQUENCE: 53
gtcgatgaag ccctgaaaga cgcgcagact atggatgaaa tcaaactgtc ggtggttatg    60

<210> SEQ ID NO 54
<211> LENGTH: 60
<212> TYPE: DNA
<213> ORGANISM: Artificial Sequence
<220> FEATURE:
<223> OTHER INFORMATION: Primer

<400> SEQUENCE: 54
gatggccttt ttgcgtgtcg acgcggccgc tcattggcga cgccaatcga acgcaacgcg    60

<210> SEQ ID NO 55
<211> LENGTH: 60
<212> TYPE: DNA
<213> ORGANISM: Artificial Sequence
<220> FEATURE:
<223> OTHER INFORMATION: Primer

<400> SEQUENCE: 55
cgcgttgcgt tcgattggcg tcgccaatga gcggccgcgt cgacacgcaa aaaggccatc    60

<210> SEQ ID NO 56
<211> LENGTH: 60
<212> TYPE: DNA
<213> ORGANISM: Artificial Sequence
<220> FEATURE:
<223> OTHER INFORMATION: Primer

<400> SEQUENCE: 56
cataaccacc gacagtttga tttcatccat agtctgcgcg tctttcaggg cttcatcgac        60

<210> SEQ ID NO 57
<211> LENGTH: 60
<212> TYPE: DNA
<213> ORGANISM: Artificial Sequence
<220> FEATURE:
<223> OTHER INFORMATION: Primer

<400> SEQUENCE: 57
gtcgatgaag ccctgaaaga cgcgcagact atggaaaact atgtcgtctc tatccgcacc        60

<210> SEQ ID NO 58
<211> LENGTH: 60
<212> TYPE: DNA
<213> ORGANISM: Artificial Sequence
<220> FEATURE:
<223> OTHER INFORMATION: Primer

<400> SEQUENCE: 58
gatggccttt ttgcgtgtcg acgcggccgc tcatttgaac ggaacaatct ttttgtcatc        60

<210> SEQ ID NO 59
<211> LENGTH: 60
<212> TYPE: DNA
<213> ORGANISM: Artificial Sequence
<220> FEATURE:
<223> OTHER INFORMATION: Primer

<400> SEQUENCE: 59
gatgacaaaa agattgttcc gttcaaatga gcggccgcgt cgacacgcaa aaaggccatc        60

<210> SEQ ID NO 60
<211> LENGTH: 60
<212> TYPE: DNA
<213> ORGANISM: Artificial Sequence
<220> FEATURE:
<223> OTHER INFORMATION: Primer

<400> SEQUENCE: 60
ggtgcggata gagacgacat agttttccat agtctgcgcg tctttcaggg cttcatcgac        60

<210> SEQ ID NO 61
<211> LENGTH: 60
<212> TYPE: DNA
<213> ORGANISM: Artificial Sequence
<220> FEATURE:
<223> OTHER INFORMATION: Primer

<400> SEQUENCE: 61
gtcgatgaag ccctgaaaga cgcgcagact atgtcctcag ctttccatta cgtcattagc        60

<210> SEQ ID NO 62
<211> LENGTH: 60
<212> TYPE: DNA
<213> ORGANISM: Artificial Sequence
<220> FEATURE:
<223> OTHER INFORMATION: Primer

<400> SEQUENCE: 62
gatggccttt ttgcgtgtcg acgcggccgc tcattcaaat tcgataatca tggtgatttt    60

<210> SEQ ID NO 63
<211> LENGTH: 60
<212> TYPE: DNA
<213> ORGANISM: Artificial Sequence
<220> FEATURE:
<223> OTHER INFORMATION: Primer

<400> SEQUENCE: 63
aaaatcacca tgattatcga atttgaatga gcggccgcgt cgacacgcaa aaaggccatc    60

<210> SEQ ID NO 64
<211> LENGTH: 60
<212> TYPE: DNA
<213> ORGANISM: Artificial Sequence
<220> FEATURE:
<223> OTHER INFORMATION: Primer

<400> SEQUENCE: 64
gctaatgacg taatggaaag ctgaggacat agtctgcgcg tctttcaggg cttcatcgac    60

<210> SEQ ID NO 65
<211> LENGTH: 60
<212> TYPE: DNA
<213> ORGANISM: Artificial Sequence
<220> FEATURE:
<223> OTHER INFORMATION: Primer

<400> SEQUENCE: 65
gtcgatgaag ccctgaaaga cgcgcagact atgaacgtga ataagccgac caccgaaaag    60

<210> SEQ ID NO 66
<211> LENGTH: 60
<212> TYPE: DNA
<213> ORGANISM: Artificial Sequence
<220> FEATURE:
<223> OTHER INFORMATION: Primer

<400> SEQUENCE: 66
gatggccttt ttgcgtgtcg acgcggccgc tcagtattct tcaattttgt ccagttgata    60

<210> SEQ ID NO 67
<211> LENGTH: 60
<212> TYPE: DNA
<213> ORGANISM: Artificial Sequence
<220> FEATURE:
<223> OTHER INFORMATION: Primer

<400> SEQUENCE: 67
tatcaactgg acaaaattga agaatactga gcggccgcgt cgacacgcaa aaaggccatc    60

<210> SEQ ID NO 68
<211> LENGTH: 60
<212> TYPE: DNA
<213> ORGANISM: Artificial Sequence
<220> FEATURE:
<223> OTHER INFORMATION: Primer

<400> SEQUENCE: 68
cttttcggtg gtcggcttat tcacgttcat agtctgcgcg tctttcaggg cttcatcgac    60

<210> SEQ ID NO 69
<211> LENGTH: 60
<212> TYPE: DNA
<213> ORGANISM: Artificial Sequence
<220> FEATURE:
<223> OTHER INFORMATION: Primer

<400> SEQUENCE: 69
gtgatcaacg ccgccagcgg tcgtcagact gtcgatgaag ccctgaaaga cgcgcagact    60

<210> SEQ ID NO 70
<211> LENGTH: 60
<212> TYPE: DNA
<213> ORGANISM: Artificial Sequence
<220> FEATURE:
<223> OTHER INFORMATION: Primer

<400> SEQUENCE: 70
gcggccgcgt cgacacgcaa aaaggccatc catccgtcag gatggccttc tgcttaattt    60

<210> SEQ ID NO 71
<211> LENGTH: 60
<212> TYPE: DNA
<213> ORGANISM: Artificial Sequence
<220> FEATURE:
<223> OTHER INFORMATION: Primer

<400> SEQUENCE: 71
aaattaagca gaaggccatc ctgacggatg gatggccttt ttgcgtgtcg acgcggccgc    60

<210> SEQ ID NO 72
<211> LENGTH: 60
<212> TYPE: DNA
<213> ORGANISM: Artificial Sequence
<220> FEATURE:
<223> OTHER INFORMATION: Primer

<400> SEQUENCE: 72
agtctgcgcg tctttcaggg cttcatcgac agtctgacga ccgctggcgg cgttgatcac    60

<210> SEQ ID NO 73
<211> LENGTH: 66
<212> TYPE: DNA
<213> ORGANISM: Artificial Sequence
<220> FEATURE:
<223> OTHER INFORMATION: Primer

<400> SEQUENCE: 73
gtttaacttt aataaggaga tataccatgc tgacggaagt gcgcccggtc tctacgacga    60
aaccgc    66

<210> SEQ ID NO 74
<211> LENGTH: 66
<212> TYPE: DNA
<213> ORGANISM: Artificial Sequence
<220> FEATURE:
<223> OTHER INFORMATION: Primer

<400> SEQUENCE: 74
cgacctgcag gcgcgccgag ctcgaattca tttgatgtat ttgcaataga acacagaaaa    60
gaccgt                                                              66

<210> SEQ ID NO 75
<211> LENGTH: 66
<212> TYPE: DNA
<213> ORGANISM: Artificial Sequence
<220> FEATURE:
<223> OTHER INFORMATION: Primer

<400> SEQUENCE: 75
gtgttctatt gcaaatacat caaatgaatt cgagctcggc gcgcctgcag gtcgacaagc    60
ttgcgg                                                              66

<210> SEQ ID NO 76
<211> LENGTH: 69
<212> TYPE: DNA
<213> ORGANISM: Artificial Sequence
<220> FEATURE:
<223> OTHER INFORMATION: Primer

<400> SEQUENCE: 76
gagaccgggc gcacttccgt cagcatggta tatctcctta ttaaagttaa acaaaattat    60
ttctacagg                                                           69

<210> SEQ ID NO 77
<211> LENGTH: 62
<212> TYPE: DNA
<213> ORGANISM: Artificial Sequence
<220> FEATURE:
<223> OTHER INFORMATION: Primer

<400> SEQUENCE: 77
gtatggtgac cctgtggcgc aaatgagaat tcgagctcgg cgcgcctgca ggtcgacaag    60
ct                                                                  62

<210> SEQ ID NO 78
<211> LENGTH: 64
<212> TYPE: DNA
<213> ORGANISM: Artificial Sequence
<220> FEATURE:
<223> OTHER INFORMATION: Primer

<400> SEQUENCE: 78
gcgctgccct gtttgatttt atccatggta tatctcctta ttaaagttaa acaaaattat    60
ttct                                                                64

<210> SEQ ID NO 79
<211> LENGTH: 63
<212> TYPE: DNA
<213> ORGANISM: Artificial Sequence
<220> FEATURE:
<223> OTHER INFORMATION: Primer

<400> SEQUENCE: 79
cctgcaggcg cgccgagctc gaattctcat ttgcgccaca gggtcaccat acgtgccggc    60
agg    63

<210> SEQ ID NO 80
<211> LENGTH: 66
<212> TYPE: DNA
<213> ORGANISM: Artificial Sequence
<220> FEATURE:
<223> OTHER INFORMATION: Primer

<400> SEQUENCE: 80
gtttaacttt aataaggaga tataccatgg ataaaatcaa acagggcagc gcctctctgg    60
ttgtcg    66

<210> SEQ ID NO 81
<211> LENGTH: 57
<212> TYPE: DNA
<213> ORGANISM: Artificial Sequence
<220> FEATURE:
<223> OTHER INFORMATION: Primer

<400> SEQUENCE: 81
cagactcgag ggtaccgacg tcctaataag tagatgaata tttatcagga cgaagat    57

<210> SEQ ID NO 82
<211> LENGTH: 55
<212> TYPE: DNA
<213> ORGANISM: Artificial Sequence
<220> FEATURE:
<223> OTHER INFORMATION: Primer

<400> SEQUENCE: 82
aactaaaggt ttattttcca tatgtatatc tccttcttat acttaactaa tatac    55

<210> SEQ ID NO 83
<211> LENGTH: 64
<212> TYPE: DNA
<213> ORGANISM: Artificial Sequence
<220> FEATURE:
<223> OTHER INFORMATION: Primer

<400> SEQUENCE: 83
taaatattca tctacttatt aggacgtcgg taccctcgag tctggtaaag aaaccgctgc    60
tgcg    64

<210> SEQ ID NO 84
<211> LENGTH: 59
<212> TYPE: DNA
<213> ORGANISM: Artificial Sequence
<220> FEATURE:
<223> OTHER INFORMATION: Primer

<400> SEQUENCE: 84
gtataagaag gagatataca tatggaaaat aaacctttag tttcagtttt gatttgtgc    59

<210> SEQ ID NO 85
<211> LENGTH: 75
<212> TYPE: DNA
<213> ORGANISM: Artificial Sequence
<220> FEATURE:
<223> OTHER INFORMATION: Primer

<400> SEQUENCE: 85
taactttaag aaggagatat acaagagctc gagtcgaagg agatagaacc atggcaacag    60
catggtataa acaag                                                    75

<210> SEQ ID NO 86
<211> LENGTH: 82
<212> TYPE: DNA
<213> ORGANISM: Artificial Sequence
<220> FEATURE:
<223> OTHER INFORMATION: Primer

<400> SEQUENCE: 86
gcgtgtcgac gcgtttagag gccccaaggg gttatgctag tatcgattta tcatttagcc    60
acggatagtt tataaatttt ac                                            82

<210> SEQ ID NO 87
<211> LENGTH: 80
<212> TYPE: DNA
<213> ORGANISM: Artificial Sequence
<220> FEATURE:
<223> OTHER INFORMATION: Primer

<400> SEQUENCE: 87
ggttctatct ccttcgactc gagctcttgt atatctcctt cttaaagtta acaaaatta    60 tttctagatt tttgtcgaac                                              80

<210> SEQ ID NO 88
<211> LENGTH: 63
<212> TYPE: DNA
<213> ORGANISM: Artificial Sequence
<220> FEATURE:
<223> OTHER INFORMATION: Primer

<400> SEQUENCE: 88
taaatcgata ctagcataac cccttggggc ctctaaacgc gtcgacacgc aaaaaggcca    60
tcc                                                                63

<210> SEQ ID NO 89
<211> LENGTH: 80
<212> TYPE: DNA
<213> ORGANISM: Artificial Sequence
<220> FEATURE:
<223> OTHER INFORMATION: Primer

<400> SEQUENCE: 89
gttcgacaaa aatctagaaa taattttgtt taactttaag aaggagatat acaagagctc    60
gagtcgaagg agatagaacc                                              80

<210> SEQ ID NO 90
<211> LENGTH: 63
<212> TYPE: DNA
<213> ORGANISM: Artificial Sequence
<220> FEATURE:
<223> OTHER INFORMATION: Primer

<400> SEQUENCE: 90
ggatggcctt tttgcgtgtc gacgcgttta gaggccccaa ggggttatgc tagtatcgat     60
tta                                                                  63

<210> SEQ ID NO 91
<211> LENGTH: 34
<212> TYPE: DNA
<213> ORGANISM: Artificial Sequence
<220> FEATURE:
<223> OTHER INFORMATION: Primer

<400> SEQUENCE: 91
atatgacgtc tcattagcgg tttttcagga gacg                                 34

<210> SEQ ID NO 92
<211> LENGTH: 35
<212> TYPE: DNA
<213> ORGANISM: Artificial Sequence
<220> FEATURE:
<223> OTHER INFORMATION: Primer

<400> SEQUENCE: 92
atatcatatg ccgtccgaag cattccgtcg tcacc                                35

<210> SEQ ID NO 93
<211> LENGTH: 62
<212> TYPE: DNA
<213> ORGANISM: Artificial Sequence
<220> FEATURE:
<223> OTHER INFORMATION: Primer

<400> SEQUENCE: 93
taactttaat aaggagatat accatgacgc aatttaatcc cgttgatcat ccacatcgcc     60
gc                                                                   62

<210> SEQ ID NO 94
<211> LENGTH: 67
<212> TYPE: DNA
<213> ORGANISM: Artificial Sequence
<220> FEATURE:
<223> OTHER INFORMATION: Primer

<400> SEQUENCE: 94
attttcgcga atccggagtg taaaagcttg cggccgcata atgcttaagt cgaacagaaa     60
gtaatcg                                                              67

<210> SEQ ID NO 95
<211> LENGTH: 72
<212> TYPE: DNA
<213> ORGANISM: Artificial Sequence
<220> FEATURE:
<223> OTHER INFORMATION: Primer

<400> SEQUENCE: 95

```
aagcattatg cggccgcaag cttttacact ccggattcgc gaaaatggat atcgctgact    60
gcgcgcaaac gc                                                        72
```

<210> SEQ ID NO 96
<211> LENGTH: 68
<212> TYPE: DNA
<213> ORGANISM: Artificial Sequence
<220> FEATURE:
<223> OTHER INFORMATION: Primer

<400> SEQUENCE: 96

```
tcaacgggat taaattgcgt catggtatat ctccttatta agttaaaca aaattatttc     60 tacagggg                                                             68
```

<210> SEQ ID NO 97
<211> LENGTH: 57
<212> TYPE: DNA
<213> ORGANISM: Artificial Sequence
<220> FEATURE:
<223> OTHER INFORMATION: Primer

<400> SEQUENCE: 97

```
atggtgatgg ctgctgccca tttaaaccgc tttgactgcg tcggcaatac ggtgcgc       57
```

<210> SEQ ID NO 98
<211> LENGTH: 60
<212> TYPE: DNA
<213> ORGANISM: Artificial Sequence
<220> FEATURE:
<223> OTHER INFORMATION: Primer

<400> SEQUENCE: 98

```
gtttaacttt aataaggaga tataccatgc tgaacaacgc gatgtctgtt gttatcctgg    60
```

<210> SEQ ID NO 99
<211> LENGTH: 53
<212> TYPE: DNA
<213> ORGANISM: Artificial Sequence
<220> FEATURE:
<223> OTHER INFORMATION: Primer

<400> SEQUENCE: 99

```
cgcagtcaaa gcggtttaaa tgggcagcag ccatcaccat catcaccaca gcc           53
```

<210> SEQ ID NO 100
<211> LENGTH: 59
<212> TYPE: DNA
<213> ORGANISM: Artificial Sequence
<220> FEATURE:
<223> OTHER INFORMATION: Primer

<400> SEQUENCE: 100

```
tcgcgttgtt cagcatggta tatctcctta ttaaagttaa acaaaattat ttctacagg     59
```

```
<210> SEQ ID NO 101
<211> LENGTH: 35
<212> TYPE: DNA
<213> ORGANISM: Artificial Sequence
<220> FEATURE:
<223> OTHER INFORMATION: Primer

<400> SEQUENCE: 101
atatatcata tgtgcggtat cgttggtgct atcgc                              35

<210> SEQ ID NO 102
<211> LENGTH: 36
<212> TYPE: DNA
<213> ORGANISM: Artificial Sequence
<220> FEATURE:
<223> OTHER INFORMATION: Primer

<400> SEQUENCE: 102
atatatgacg tcttattcca cggtcacgga tttcgc                             36
```

PRODUCTION OF HUMAN MILK OLIGOSACCHARIDES IN MICROBIAL HOSTS WITH ENGINEERED IMPORT/EXPORT

CROSS-REFERENCE TO RELATED APPLICATIONS

This application is a National Stage entry of International Application No. PCT/EP2016/071420, filed Sep. 12, 2016, which claims priority to European Patent Application No. 15184968.4, filed Sep. 12, 2015.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "3000045-002000_Sequence_Listing_ST25.txt" created on 5 Mar. 2018, and 291,264 bytes in size) is submitted concurrently with the instant application, and the entire contents of the Sequence Listing are incorporated herein by reference.

BACKGROUND

Field

Human milk is regarded as the best diet for the development of infants. It is composed of fats, proteins, vitamins, minerals, trace elements and a complex carbohydrate mixture which comprises lactose and approximately 150 structurally diverse oligosaccharides (Human milk oligosaccharides, HMO).

Description of Related Art

Efforts to produce HMO chemically or by biotechnological approaches mainly attracted common attention due to their beneficial impact on the development of the gastrointestinal flora of infants, thus, advocating their use as nutritional additives. Besides these prebiotic properties, many other positive effects of HMO could be observed so far, expanding their field of application.

However, extensive scientific studies demand pure single compounds which are hardly achievable. This is especially true for complex free neutral and acidic oligosaccharides for which competitive large-scale production processes are still lacking. (e.g. lacto-N-tetraose (Gal($\beta$1-3)GlcNAc($\beta$1-3)Gal ($\beta$1-4)Gluc), lacto-N-neotetraose (Gal($\beta$1-4)GlcNAc($\beta$1-3) Gal($\beta$1-4)Gluc), lacto-N-fucopentaose I (Fuc($\alpha$1-2) Gal($\beta$1-3)GlcNAc($\beta$1-3)Gal($\beta$1-4)Gluc) lacto-N-neofucopenaose I (Fuc($\alpha$1-2) Gal($\beta$1-4)GlcNAc($\beta$1-3)Gal($\beta$1-4)Gluc) (Lacto-N-sialylpentaose a (LST-a; Neu5Ac($\alpha$2-3)Gal($\beta$1-3) GlcNAc($\beta$1-3)Gal($\beta$1-4)Gluc)) The metabolic engineering of a microorganism to produce these compounds represents the most promising approach since chemical methods are rather inefficient to produce these molecules at multi-ton scale.

Several fermentative approaches were already developed for the structural simpler HMOs such as 2'-fucosyllactose, 3-fucosyllactose or 3'-sialyllactose, using mainly metabolically engineered *Escherichia coli* strains.

However, large-scale quantities are only achievable through boosting the oligosaccharide export out of the bacterial cell, thus, (i) enhancing the productivity and (ii) allowing the recovering of the desired oligosaccharide from the culture broth. The need for solving the export problem seems to enlarge with the size of the produced sugar. Also, with the currently available fermentation processes, upon production of more complex oligosaccharides, the problem of an unwanted export of oligosaccharide precursors from the producing cell occurs, leading to an undesirable mix of product and precursor oligosaccharides in the fermentation medium. Whereas multiple transporter proteins are known to transfer mono- or disaccharides across the membrane, hardly any knowledge exists on the transport of larger oligosaccharides (e.g., trisaccharides and larger oligosaccharides).

For example, the genome of the often used fermentation model organism *E. coli* encodes more than 500 distinct transporter proteins (Busch and Saier, Crit Rev Biochem Mol Biol. 2002; 37(5):287-337). The classification of those membrane transport proteins is quite diverse and subgroups may vary in translocation mechanisms, protein structures or evolutionary origins.

Classically energy-driven active transporters perform substrate movement against its concentration or electrochemical gradient, while kinetics and direction of the substrate flow through channels primarily follows such gradients. Depending on the source of energy used for the translocation, pumps can be principally divided into primary active and secondary active transporters, exploiting metabolic energy like ATP or the electrochemical potential, respectively (Davidson and Maloney, Trends Microbiol. 2007 October; 15(10):448-55; Forrest et al, Biochim Biophys Acta. 2011 February; 1807(2):167-88). Although in-depth knowledge was achieved for several membrane proteins permitting energy generation, the import of carbohydrates and the efflux of proteins and antibacterial substances, however, keen insights into mechanistic processes or information on natural or probable substrates were gained only for a minor portion of annotated bacterial transporters so far.

The *E. coli* lactose permease LacY probably represents the most intensively characterized solute transporter (Guan and Kaback, Annu Rev Biophys Biomol Struct. 2006; 35:67-91) and is a member of the large and exceptionally diverse major facilitator superfamily (MFS) —that belongs to the secondary active transporter class-transporting sugars, drugs, hydrophobic molecules, peptides, organic ions, etc. by uniport, symport or antiport (Saier et al., J Mol Microbiol Biotechnol. 1999 November; 1(2):257-79). Apart from a few exceptions a common structural feature of MFS transporters are two six-helical subdomains that transverse the cytoplasmic membrane. The existence of functionally homologous amino acid positions between related $H^+$-coupled MFS symporters further suggests a similar kinetic mechanism as determined for the lactose permease (Madej and Kaback, Proc Natl Acad Sci USA. 2013 Dec. 10; 110(50):E4831-8).

Since decades, enormous knowledge about the import of carbohydrates into bacteria could be acquired. But regarding the export of carbohydrates, especially about molecules that are non-surface-associated, only little information is available. This is not unexpected since sugars actually depict a favourable carbon- and energy source, thus, once in the cell they shouldn't be released to a competitive environment.

However, the natural function of sugar exporters probably involve the reduction of osmotic or sugar-phosphate stress which might point to a flexible substrate spectrum. Interestingly, the export of a variety of galactosides like IPTG, TMG and lactose was shown for members of the so called sugar efflux transporter family (SET), which belong to the group of MFS transporters (Liu et al., J Biol Chem. 1999 Aug. 13; 274(33):22977-84; Liu et al., Mol Microbiol. 1999 March; 31(6):1845-51).

The *E. coli* transport protein SetA was even described to transfer the human milk oligosaccharide 3-fucosyllactose resulting in an improved production of said compound during fermentation of a recombinant *E. coli* strain overexpressing setA (see applicant's international patent application WO 2010/142305). Similarly, the expression of a sugar efflux transporter from *Yersinia* was shown to enable the export of the human milk oligosaccharide 2'-fucosyllactose out of an engineered *E. coli* production strain.

Apart from this, from a mechanistic and energetic point of view, only the ion-gradient-driven transport systems have the potential to translocate solutes in both directions across the membrane. This is exemplarily true for the above mentioned LacY, a galactoside/$H^+$ symporter, which is part of the bacterial lac operon that allows the metabolism of lactose in *E. coli*. This permease primarily imports lactose into the cell but it is also capable to transfer its substrate in the opposite direction.

Besides the major facilitator superfamily, which represents the largest group of transporters, bacteria possess further mechanisms to excrete solutes—often summarized in the classes of multidrug efflux pumps. Alike for the MFS, the activities of the small multidrug resistance superfamily (SMR), the multidrug and toxic compound extrusion superfamily (MATE) and the resistance-nodulation-cell division superfamily (RND) rely on the electrochemical gradient. The fifth class is the adenosine triphosphate (ATP)-binding cassette superfamily (ABC) which uses ATP as energy source to drive molecules from the cell. As for the MFS, members of SMR, MATE, RND and ABC transport structurally diverse molecules. Further, most of their so far identified substrates are not naturally occurring, and, thus, their preferences are hardly predictable.

Although chemical synthesizing processes are known for human milk oligosaccharides, these processes are very cost-intensive and do not lead to satisfying amounts. On the other hand, fermentation processes using genetically modified microorganisms still have the drawback that the export of larger oligosaccharides (tetra-, penta-, hexasaccharides) represents a major limitation for the establishment of cost effective production processes. As a consequence, there still is the need for improved processes for the production of large-scale human oligosaccharides.

SUMMARY

According to the invention, this and other objects are solved by the methods and microbial host cell(s) as claimed in the attached claims.

With the methods and host cells according to the invention it is possible to produce a desired oligosaccharide, preferably an oligosaccharide that is not produced in an unmodified host cell, and also preferably an oligosaccharide belonging to the human milk oligosaccharides, in large amounts obtainable from the medium. As such, the oligosaccharide is, so to say, obtainable in free from in the medium; it is not bound to a surface protein or membrane protein or other protein of the surface of the host cell.

According to the invention, a method for the production of a desired oligosaccharide by a genetically modified microbial host cell, comprising the steps of a) providing a genetically modified microbial host cell that comprises at least one recombinant glycosyltransferase, and that has the expression or activity of at least one endogenous sugar export protein modified such, that the expression or activity of the sugar export protein is either (i) increased or (ii) decreased or inactivated as compared to an genetically unmodified host cell, so that (i) the export of a oligosaccharide into the medium is either decreased or abolished, or (ii) the transport of a desired oligosaccharide is increased, respectively, as compared to an genetically unmodified host cell, b) cultivating the host cell in a medium under conditions permissive for the production of the desired oligosaccharide, whereby the desired oligosaccharide is transported into the medium. The method may further comprise the step of c) obtaining the desired oligosaccharide from the medium.

DETAILED DESCRIPTION OF A PREFERRED EMBODIMENT

Figure 1:
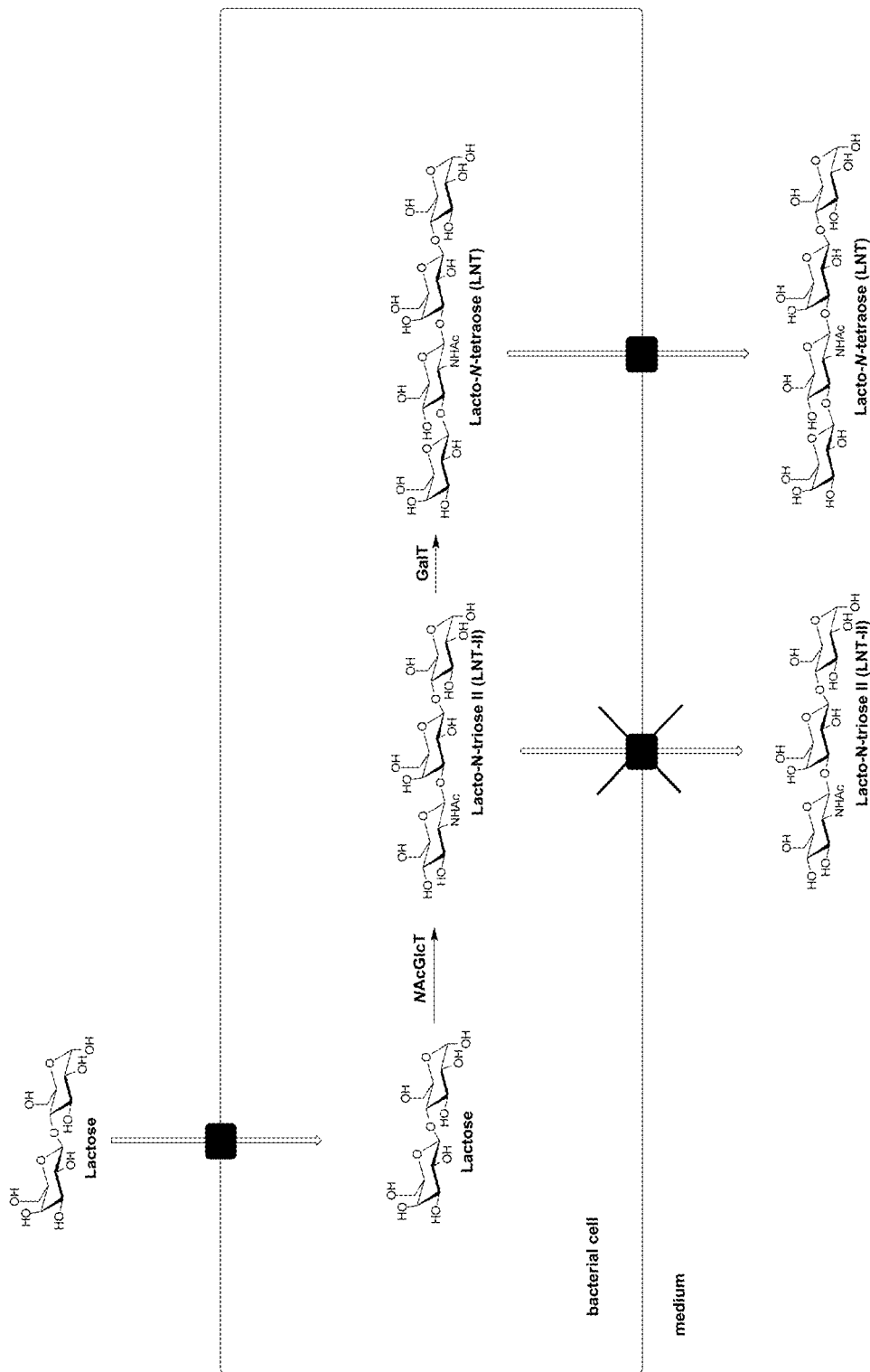
FIG. 1 shows a schematic illustration for the production of either lac-to-N-triose II or lacto-N-tetraose in a host cell cultivated in a medium.

In the method according to the invention, it is preferred if the desired oligosaccharide is a human milk oligosaccharide comprising a lacto-N-triose II (LNT-II; GlcNAc(β1-3)Gal (β1-4)Gluc) as a core trisaccharide. In this connection, an oligosaccharide having a "core trisaccharide" is meant to comprise the specific trisaccharide representing the reducing end of a desired oligosaccharide, and comprising, as the case may be, additional saccharide moieties, with the specific trisaccharide representing the major moiety.

Accordingly, in an embodiment of the method and the host cell according to the invention, the desired oligosaccharide is selected from the group consisting of: lacto-N-triose II, lacto-N-tetraose, lacto-N-neotetraose, lacto-N-fucopentaose I, lacto-N-fucopentaose II, lacto-N-fucopentaose III, lacto-N-fucopentaose V, lacto-N-difucosylhexose I, lacto-N-difucosylhexaose II, lacto-N-sialylpentaose LSTa, LSTb, LSTc, disialyllacto-N-tetraose, disialyllacto-N-neotetraose.

In order to overcome the above mentioned drawbacks of limited oligosaccharide export the object is further solved by a method according to the invention, wherein the host cell comprises: at least one homologous or heterologous nucleic acid sequence coding for a protein enabling the export of a desired oligosaccharide into the culture medium, wherein said host cell has been modified such, that the expression of the homologous or heterologous nucleic acid sequence is overexpressed or under control of a promoter enabling the overexpression of the nucleic acid sequence; and/or the deletion, disruption, diminishment or inactivation of at least one endogenous nucleic acid sequence coding for an exporter protein that exports precursors of the desired oligosaccharide outside the host cell; and/or at least one homologous or heterologous nuclei acid sequence coding for a protein mediating the import of a precursor of a desired oligosaccharide into said host cell, wherein preferably the nucleic acid sequence is overexpressed, and wherein preferably the precursor is larger than a disaccharide.

The genetically modified microbial host cell comprising the characteristics as set forth herein are cultured in the presence of glucose, sucrose, glycerin or a combination thereof—using these substrates as carbon- and energy sources—as well as in the presence of lactose or oligosaccharides larger than disaccharides, e.g., LNT-II.

In a preferred embodiment of this method and host cell, said protein enabling the export of a desired oligosaccharide belongs to the class of secondary active transporters, and more preferably effects the export of an oligosaccharide comprising at least three moieties.

According to preferred embodiments, for the export of desired oligosaccharides a suitable exporter is expressed in addition to the genes that are responsible for intracellular oligosaccharide biosynthesis.

According to one aspect of the method and host cell of the invention, the at least one nucleic acid sequence coding for a protein enabling the export of a desired oligosaccharide is an endogenous or a recombinant nucleic acid.

In a preferred embodiment of the method and the host cell of the invention, the nucleic acid sequence coding for a protein enabling the export of a desired oligosaccharide is of bacterial, archeal, plant, yeast or animal origin; preferably, the at least one nucleic acid sequence coding for a protein enabling the export of a desired oligosaccharide is a gene selected from the group consisting of yebQ and yjhB from *Escherichia coli*, proP from *Mannheimia succiniciproducens* and setA from *Cedecea neteri* or functional fragments thereof.

Preferably, the oligosaccharide exporter is a protein selected from at least one of the following: SetA, SetB, SetC, YdeA, Cmr, YnfM, MdtD, YfcJ, YhhS, EmrD, YdhC, YbdA, YdeE, MhpT, YebQ, YjhB, Bcr and YdeA of *E. coli*, or ProP from *Mannheimia succiniciproducens* and SetA from *Cedecea neteri* or variants or homologs thereof.

In yet another preferred embodiment, the recombinant glycosyltransferase is selected from at least one of the following: a galactosyltransferase, a sialyltransferase, an N-acetylglucosaminyltransferase and a fucosyltransferase, and is preferably selected from at least one of the following: β-1,3-N-acetylglucosaminyltransferase, β-1,3-galactosyltransferase, β-1,4-galactosyltransferase, β-1,6-galactosyltransferase, α-2,3-sialyltransferase, α-2,6-sialyltansferase, α-1,2-fucosyltransferase, or α-1,3-fucosyltransferase.

A preferred embodiment of the method and the host cell of the invention, concerns the a host cell or its provision, wherein the host cell comprises (i) a β-1,3-N-acetylglucosaminyltransferase, and (ii) a β-1,3-galactosyltransferase or a β-1,4-galactosyltransferase as glycosyltransferases. In this connection it is preferred, if said β-1,3-N-acetylglucosaminyltransferase has the activity of ligating N-acetylglucosamine to lactose generating lacto-N-triose II, and if said β-1,3-galactosyltransferase or said β-1,4-galactosyltransferase, respectively, have the activity to galactosylate lacto-N-triose II thus generating lacto-N-tetraose or lacto-N-neotetraose, respectively. The here developed system is easily adaptable to even more complex oligosaccharides by the expression of further glycosyltransferases.

With the microbial cell and the method according to the invention, it is possible to ferment a desired oligosaccharide in large quantities, especially an oligosaccharide comprising LNT-II as core structure, and to recover it from the culture broth.

In a preferred embodiment, said β-1,3-N-acetylglucosaminyltransferase belongs to the class of lgtA of *Neisseria meningitides* or PmnagT of *Pasteurella multocida*, or variants thereof.

Preferably, the glycosyltransferase is selected from a galactosyltransferase, a sialyltransferase, an N-acetylglucosaminyltransferase and a fucosyltransferase.

In yet another preferred embodiment, the lacto-N-tetraose generating β-1,3-galactosyltransferase is WbdO or a functional variant thereof. According to an aspect of the invention, the β-1,3-galactosyltransferase is a β-1,3-galactosyltransferase derived from *Salmonella enterica* (wbdO, acc. no. AY730594), and is preferably encoded by a gene selected from the group consisting of wbgO from *Escherichia coli* O55:H7 or furA from *Lutiella nitroferrum*, or a functional fragments thereof.

The invention also concerns a genetically modified microbial host cell, preferably a bacterial host cell, as described above in which the endogenous β-galactosidase gene is inactivated or deleted and in which a functional lactose permease gene is present.

Accordingly, in a preferred embodiment of the method and the host cell of the invention, a genetically modified host cell is provided, in which, where applicable, an endogenous β-galactosidase gene and a glucosamine-6-phosphate deaminase gene are inactivated or deleted, and wherein said genetically modified host cell comprises a nucleic acid sequence coding for a functional lactose permease protein, preferably LacY.

In a preferred embodiment, the genetically modified host cell comprises an increased UDP-N-acetylglucosamine and UDP-galactose, GDP-fucose or CMP-N-acetylneuraminic acid production capability as compared to a genetically unmodified host cell.

In a refinement of this embodiment of he method of and of the host cell of the invention, said increased UDP-N-acetylglucosamine and UDP-galactose production capability comprises the overexpression of one or more genes encoding for proteins comprising the following activities for a: L-glutamine: D-fructose-6-phosphate aminotransferase, N-acetyl glucosamine-1-phosphate uridyltransferase/glucosamine-1-phosphate acetyl transferase, phosphoglucosamine mutase, UDP-galactose-4-epimerase, phosphoglucomutase, glucose-1-phosphate uridylyltransferase.

For the synthesis of, e.g. LNT, UDP-galactose and UDP-N-acetylglucosamine are required. UDP-galactose can be obtained by feeding galactose to the HMO producing bacterial host cell via the fermentation medium. The galactose is then taken up by the cell, phosphorylated to galactose-1-phosphate and then converted to UDP-galactose. Genes encoding these enzymatic activities are well known in the literature (Grossiord et al., J. Bacteriol 2003 185(3) 870-878). The supply for UDP-galactose can be also obtained from the cells own metabolism, and the metabolism can be improved by further genetic modification, such as the overexpression of the UDP-galactose-4'-epimerase, or the UDP-galactose-4'-epimerase in combination with the glucose-1-phosphate-1-uridinyltransferase. UDP-N-acetylglucosamine can be also obtained from the bacterial host cell's own UDP-N-acetylglucosamine metabolism. The provision of UDP-N-acetylglucosamine for the synthesis of N-aectylglucosamine containing oligosaccharides can be improved by the inactivation of the N-acetylglucosamine catabolism within the producing cell.

According to one aspect of the invention, the genetically modified host cell is cultivated in the presence of glucose, sucrose, glycerol or a combination thereof, but neither by addition or in the presence of N-acetylglucosamine or galactose nor in a combination thereof.

In a preferred embodiment of the method and of the host cell of the invention, the desired oligosaccharide is lacto-N-triose II, which is produced by total fermentation from a simple carbon source in the host cell by the action of the heterologous expressed glycosyltransferases β-1,4-galactosyltransferase and β-1,3-N-acetylglucosaminyltransferase.

The present invention, as already mentioned above, also concerns a genetically modified host cell for the production of a desired oligosaccharide, the oligosaccharide comprising a lacto-N-triose II (LNT-II; GlcNAc(β1-3)Gal(β1-4)Gluc) as a core trisaccharid, wherein the host cell comprises at least one recombinant glycosyltransferase, the glycosyltransferase being preferably selected from a galactosyltransferase, a sialyltransferase, and an N-acetylglucosaminyltransferase, and has the expression or activity of at least one endogenous sugar transport protein modified such, that the expression or activity of the endogenous sugar transport protein is functionally inactivated for the export of a precursor of the desired oligosaccharide.

A preferred embodiment concerns a host cell as described above, comprising (i) a heterologous expressed β-1,3-N-acetylglucosaminyltransferase, and (ii) a heterologous expressed β-1,3-galactosyltransferase or a heterologous expressed β-1,4-galactosyltransferase as glycosyltransferases, wherein the host cell further preferably comprises at least one homologous or heterologous nucleic acid sequence coding for a protein enabling the export of the oligosaccharide into a culture medium the host cell is cultivated in, wherein said protein enabling the export of the desired oligosaccharide belongs to the class of secondary active transporters, wherein said host cell has been modified such, that the expression of the homologous or heterologous nucleic acid sequence is overexpressed or under control of a promoter enabling the overexpression of the nucleic acid sequence. In preferred embodiments of the host cell, said at least one nucleic acid sequence coding for a protein enabling the export of the desired oligosaccharide is an endogenous or a recombinant nucleic acid sequence.

As already outlined for the method according to the invention, it is also preferred in the host cell of the invention, if said nucleic acid sequence coding for a protein enabling the export of a desired oligosaccharide is of bacterial, archeal, plant, yeast or animal origin.

According to another aspect of the invention, the host cell as described above further comprises: the deletion, disruption, diminishment or inactivation of at least one endogenous nucleic acid sequence coding for an exporter protein that exports precursors of the desired oligosaccharide outside the host cell; and/or at least one homologous or heterologous nucleic acid sequence coding for a protein enabling the import of a precursor of a desired oligosaccharide into said host cell, wherein preferably the nucleic acid sequence is overexpressed, and wherein preferably the precursor is larger than a disaccharide.

With the overexpression of at least one homologous or heterologous nucleic acid sequence coding for a protein enabling the import of a precursor of a desired oligosaccharide into said host cell, it is possible to feed precursors of a desired oligosaccharide to the culture medium, which get imported into the host cell, such as, e.g., LNT-II.

According to one aspect of the invention, in the host cell said at least one nucleic acid sequence coding for a protein enabling the export of a desired oligosaccharide is a gene selected from the group consisting of yebQ and yjhB from *Escherichia coli*, proP from *Mannheimia succiniciproducens* and setA from *Cedecea neteri* or functional fragments thereof.

According to yet another preferred embodiment, the desired oligosaccharide is lacto-N-triose II, and the protein enabling the export of the oligosaccharide into a culture medium the host cell is cultivated in, is YjhB from *Escherichia coli*, ProP from *Mannheimia succiniciproducens* and SetA from *Cedecea neteri* or functional fragments thereof.

According to a preferred embodiment, the microbial host according to the invention is further modified not to express proteins exporting precursors of a desired oligosaccharide.

In a preferred embodiment of the host cell, the desired oligosaccharide is lacto-N-tetraose, the precursor is lacto-N-triose II, and the host cell has deleted, disrupted or inactivated at least one nucleic acid sequence coding for an exporter protein that is able to export lacto-N-triose II outside the host cell.

In this connection it is preferred, if the protein enabling the export of lacto-N-tetraose is selected from YebQ from *Escherichia coli* BL21(DE3), SpoVB of *Bacillus amyloliquefaciens*, YabM of *Erwinia pyrilfolia*, Bcr of *E. coli* MG1655, YdeA of *E. coli* MG1655, ProP2 of *Haemophilus parainfluenzae*, SetA of *Pectobacterium carotovorum*, FucP of *E. coli* MG1655, MdeA of *Staphylococcus aureus* Bmb9393, ImrA of *Lactococcus lactis*, SetA of *Pseudomonas* sp. MT-1 and SetA of *Beauveria bassiana* D1-5.

Preferably, the oligosaccharide exporter is a protein selected from at least one of the following: SetA, SetB, SetC, YdeA, Cmr, YnfM, MdtD, YfcJ, YhhS, EmrD, YdhC, YbdA, YdeE, MhpT, YebQ, YjhB, Bcr and YdeA of *E. coli*, or ProP from *Mannheimia succiniciproducens* and SetA from *Cedecea neteri* or variants or homologs thereof.

Presently, the term "nucleic acid" refers to a single- or double-stranded deoxyribonucleotide or ribonucleotide macromolecule and encompasses known analogues or natural or synthetically produced nucleotides that hybridize with the desired nucleic acid and that encode a certain polypeptide.

The term "recombinant" or "genetically modified", as used herein with reference to a microbial host cell indicates that the microbial host cell replicates a heterologous nucleic acid, or expresses a peptide or protein encoded by a heterologous nucleic acid (i.e., a sequence "foreign to said cell"). Recombinant cells can contain genes that are not found within the native (non-recombinant) form of the cell. Recombinant cells can also contain genes found in the native form of the cell wherein the genes are modified and reintroduced into the cell by artificial means. The term also encompasses cells that contain a nucleic acid endogenous to the cell that has been modified without removing the nucleic acid from the cell; such modifications include those obtained by gene replacement, site-specific mutation, and related techniques. Accordingly, a "recombinant polypeptide" is one which has been produced by a recombinant cell. A "heterologous sequence" or a "heterologous nucleic acid", as used herein, is one that originates from a source foreign to the particular host cell (e.g. from a different species), or, if from the same source, is modified from its original form. Thus, a heterologous nucleic acid operably linked to a promoter is from a source different from that from which the promoter was derived, or, if from the same source, is modified from its original form. The heterologous sequence may be stably introduced, e.g. by transfection, transformation, conjugation or transduction, into the genome of the host microbial host cell, thus representing a genetically modified host cell. Techniques may be applied which will depend on the host cell the sequence is to be introduced. Various techniques are known to a person skilled in the art and are, e.g., disclosed in Sambrook et al., Molecular Cloning: A Laboratory Manual, 2nd Ed., Cold Spring Harbor Laboratory Press, Cold Spring Harbor, N.Y. (1989).

Accordingly, a "microbial host cell" is presently understood as a microbial, preferably bacterial, cell which has been transformed or transfected, or is capable of transformation or transfection by an exogenous polynucleotide sequence.

Thus, the nucleic acid sequences as used in the present invention, may, e.g., be comprised in a vector which is to be stably transformed/transfected or otherwise introduced into host microorganism cells.

Presently, the term "operably linked" as used herein, shall mean a functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence. Accordingly, the term "Promoter" designates DNA sequences which usually "precede" a gene in a DNA polymer and provide a site for initiation of the transcription into mRNA. "Regulator" DNA sequences, also usually "upstream" of (i.e., preceding) a gene in a given DNA polymer, bind proteins that determine the frequency (or rate) of transcriptional initiation. Collectively referred to as "promoter/regulator" or "control" DNA sequence, these sequences which precede a selected gene (or series of genes) in a functional DNA polymer cooperate to determine whether the transcription (and eventual expression) of a gene will occur. DNA sequences which "follow" a gene in a DNA polymer and provide a signal for termination of the transcription into mRNA are referred to as transcription "terminator" sequences.

A great variety of expression systems can be used to produce the polypeptides of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and to synthesize a polypeptide in a host may be used for expression in this regard. The appropriate DNA sequence may be inserted into the expression system by any of a variety of well-known and routine techniques, such as, for example, those set forth in Sambrook et al., supra.

The art is rich in patent and literature publications relating to "recombinant DNA" methodologies for the isolation, synthesis, purification and amplification of genetic materials for use in the transformation of selected host organisms. Thus, it is common knowledge to transform host organisms with "hybrid" viral or circular plasmid DNA which includes selected exogenous (i.e. foreign or "heterologous") DNA sequences. The procedures known in the art first involve generation of a transformation vector by enzymatically cleaving circular viral or plasmid DNA to form linear DNA strands. Selected foreign DNA strands usually including sequences coding for desired protein product are prepared in linear form through use of the same/similar enzymes. The linear viral or plasmid DNA is incubated with the foreign DNA in the presence of ligating enzymes capable of effecting a restoration process and "hybrid" vectors are formed which include the selected exogenous DNA segment "spliced" into the viral or circular DNA plasmid.

As used herein, the term "cultivating" means growing a bacterial cell in a medium and under conditions permissive and suitable for the production of the desired oligosaccharide(s). A couple of suitable bacterial host cells as well as mediums and conditions for their cultivation will be readily available for one skilled in the art upon reading the disclosure of this invention in connection with the skilled person's technical and expert background.

As used herein, the term "recovering" or "obtaining" means isolating, harvesting, purifying, collecting or otherwise separating from the host cell culture the oligosaccharide produced by the host cell according to the invention.

A "microbial" host cell according to the invention, and as generally understood, means any microorganism, including bacteria, fungi and archaea, which is generally suitable for cultivation in large amounts, and which can be genetically modified according to the invention in order to produce a desired oligosaccharide. Preferred microorganisms are bacteria, e.g. *Escherichia coli, Corynebacterium glutamicum* and the yeast *Saccharomyces* sp., which have the advantage that these microorganisms can be grown easily and inexpensively in laboratory settings, and the bacteria and yeast have been intensively investigated for over many years Generally, and throughout the present invention, the term "glycosyltransferase activity" or "glycosyltransferase" designates and encompasses enzymes that are responsible for the biosynthesis of disaccharides, oligosaccharides and polysaccharides, and they catalyze the transfer of monosaccharide moieties from an activated nucleotide monosaccharide/sugar (the "glycosyl donor") to a glycosyl acceptor molecule.

Generally, and throughout the present invention, the terms "exporter" or "exporter protein" or "protein enabling the export of a desired oligosaccharide", which terms are presently being used synonymously, designates one or more polypeptides that solely or as part of a multi-protein complex transfers an oligosaccharide from the intracellular milieu of a bacterial cell into the periplasm of said cell or the culture supernatant, thus, enabling the oligosaccharide to pass the cellular membrane and/or the cell wall of said cell.

Within the scope of the present invention, also nucleic acid/polynucleotide and polypeptide polymorphic variants, alleles, mutants, and interspecies homologs are comprised by those terms, that have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to a polypeptide encoded by a wild type glycosyltransferase activity or oligosaccharide export displaying protein.

"Variant(s)" as the term is used herein, is a polynucleotide or polypeptide that differs from a reference polynucleotide or polypeptide, respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to the persons skilled in the art.

Accordingly, a "functional fragment" of any of the genes/proteins disclosed therein, is meant to designate sequence variants of the genes/proteins still retaining the same or somewhat lesser activity of the gene or protein the respective fragment is derived from.

In this connection, the term "nucleic acid sequence encoding . . . " generally refers to any polyribonucleotide or polydeoxyribonucleotide, which may be unmodified RNA or DNA or modified RNA or DNA, and generally represents a gene which encodes a certain polypeptide or protein.

In this context, the term "polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as "proteins". Polypeptides may contain amino acids other than the 20 gene encoded amino acids. "Polypeptide(s)" include those modified either by natural processes, such as processing and other post-translational modifications, but also by chemical modification techniques. It will be appreciated that the same type of modification may be present in the same or varying degree at several sites in a given polypeptide, without essentially altering the activity of the polypeptide. Also, a given polypeptide may contain many types of modifications. Modifications can occur anywhere in a polypeptide, including the peptide backbone, the amino acid side-chains, and the amino or carboxyl termini.

Further, with the expression "precursor" compounds are encompassed which are involved in the biosynthetic pathway of the oligosaccharide according to the invention or which are produced and naturally present in the host cell.

A "precursor that is larger than a disaccharide" is presently understood as a sugar moiety that comprises more than two monosaccharide residues.

The term "desired oligosaccharide" refers to a sugar polymer consisting of at least three moieties, thus, comprising trisaccharides, tetrasaccharides, pentasaccharides etc., preferably an oligosaccharide selected from at least one of the following: lacto-N-triose II, lacto-N-tetraose, lacto-N-neotetraose, lacto-N-fucopentaose I, lacto-N-fucopentaose II, lacto-N-fucopentaose III, lacto-N-fucopentaose V, lacto-N-difucosylhexose I, lacto-N-difucosylhexose II, lacto-N-sialylpentaose LSTa, LSTb, LSTc, disialyllacto-N-tetraose, disialyllacto-N-neotetraose.

Presently, and as generally understood in the relevant field, the expression "homologous" refers to a nucleic acid sequence that encodes for a specific product or products and is derived from the same species, in which said nucleic acid sequence is inserted. Accordingly, the term "heterologous" refers to a nucleic acid sequence encoding for a specific product or products and being derived from a species other than those in which said nucleic acid sequence is inserted.

The term "endogenous" herein and generally within the field means that the nucleic acid encoding for an enzyme of interest is originating from the bacterial host cell and has not been introduced into said host cell, whereas a "recombinant" nucleic acid has been introduced into said host cell and does not originates from said host cell.

The expression "overexpressed", or "overexpressing" or "under control of a promoter sequence enabling the overexpression of said nucleic acid sequence" presently, and generally in the art, means the expression of a gene in greater-than-normal amounts, i.e. in increased quantity thus leading to an increased amount of the protein the nucleic acid sequence is coding for.

In some embodiments, the nucleic acid sequence is placed under the control of an inducible promoter, which is a promoter that directs expression of a gene where the level of expression is alterable by environmental or developmental factors such as, for example, temperature, pH, anaerobic or aerobic conditions, light, transcription factors and chemicals. Such promoters are referred to herein as "inducible" promoters, which allow one to control the timing of expression of the proteins used in the present invention. For *E. coli*, and other microbial host cells, inducible promoters are known to those of skill in the art.

Further advantages are evident from the description and the drawings.

It is understood that the features mentioned above and those yet to be explained below can be used not only in the respective combinations indicated, but also in other combinations or in isolation, without leaving the context of the present invention.

Figure 2:
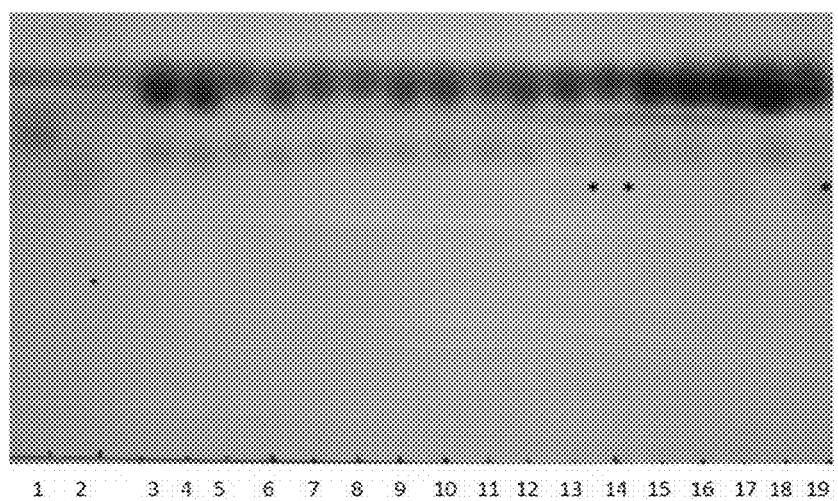
FIG. 2 shows the results of the TLC analysis of culture extracts of lacto-N-triose II (LNT II) producing *E. coli* BL21(DE3) strains overexpressing the β-1,3-N-acetyl glucosaminyltransferase gene PmnagT(13, 14)
Figure 3:
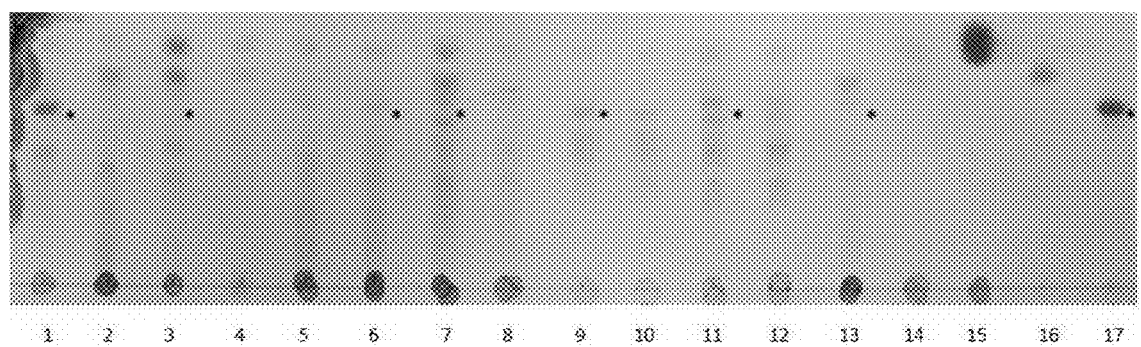
FIG. 3 shows the results of the TLC analysis of culture extracts of lacto-N-tetraose (LNT) producing *E. coli* BL21 (DE3) strains overexpressing the β-1,4-galactosyltransferase encoding genes BfgalT2 (1), PmgalT7 (3), MsgalT8 (6), gatD (7), lex1 (9), lgtB (11) or lsgD (13)
Figure 4:
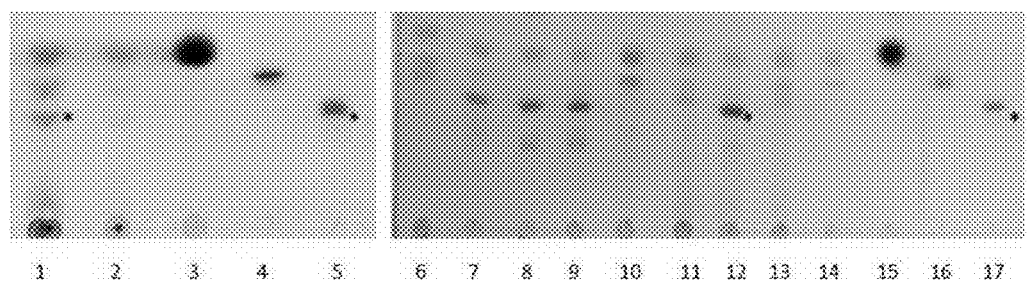
FIG. 4 shows the results of the TLC analysis of culture extracts of lacto-N-tetraose (LNT) producing *E. coli* BL21 (DE3) strains overexpressing the β-1,4-galactosyltransferase encoding genes KdgalT10 (1), cpsI14J (7), cpsIaJ (8, 9), HpgalT (12)
Figure 5:
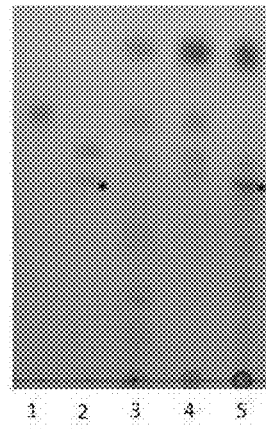
FIG. 5 shows the results of the TLC analysis of culture extracts of lacto-N-tetraose producing *E. coli* BL21(DE3) strains overexpressing the β-1,4-galactosyltransferase encoding gene waaX (5)
Figure 6:
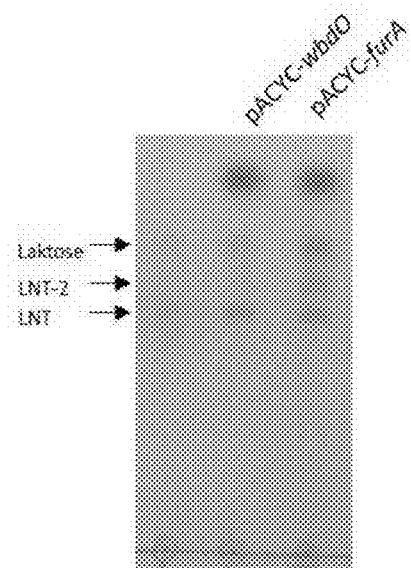
FIG. 6 shows the results of the TLC analysis of culture extracts of lacto-N-tetraose producing *E. coli* BL21(DE3) strains overexpressing the β-1,3-galactosyltransferase encoding genes wbdO or furA.
Figure 7:
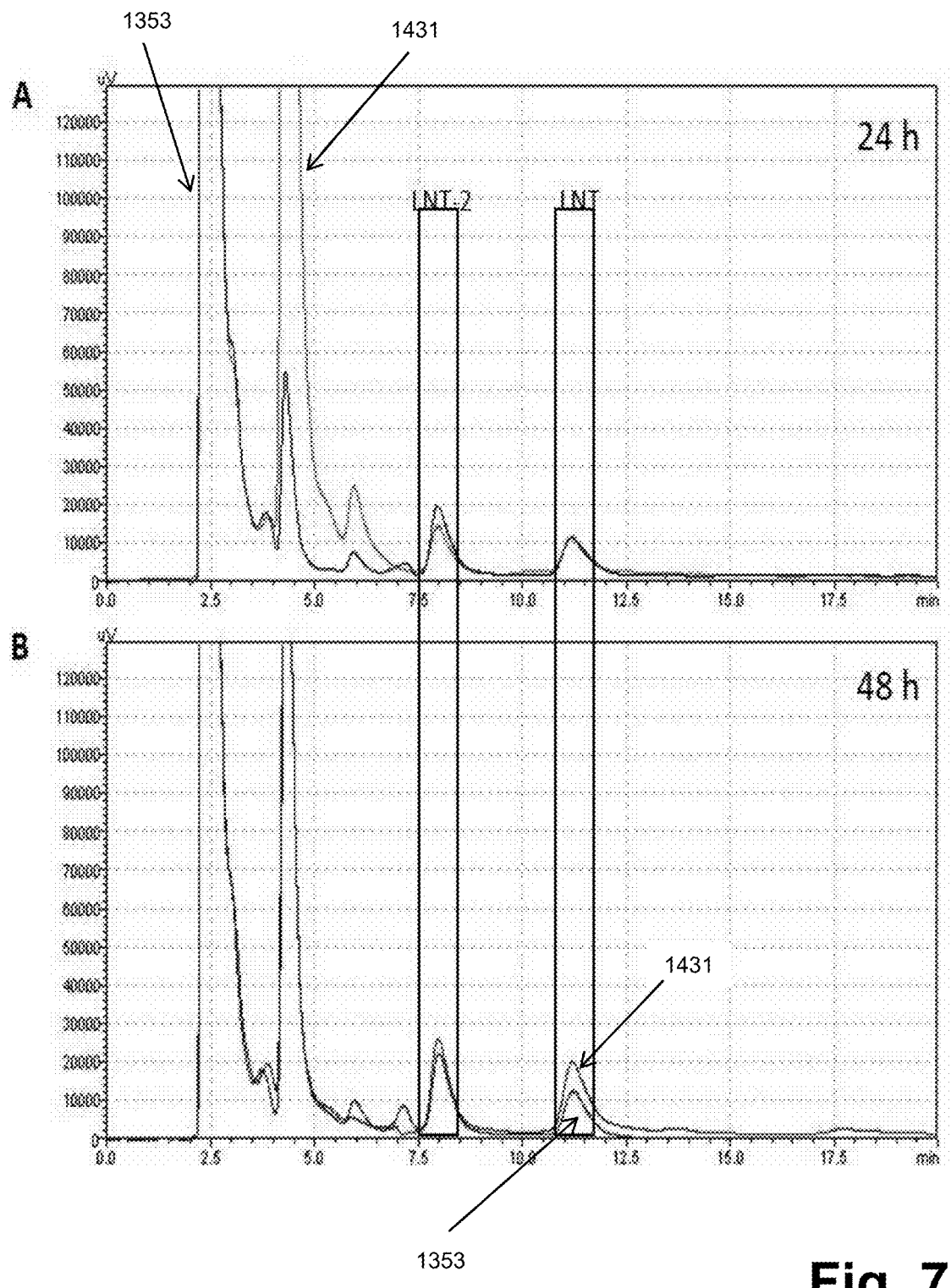
FIG. 7 shows the results of HPLC analyses of the culture superna-tant of lacto-N-tetraose producing *E. coli* BL21 (DE3) strain. (A) Supernatant of *E. coli* BL21(DE3) 1353 and 1431 grown in the presence of glucose and lactose after 24 h of incubation. (B) Supernatant of *E. coli* BL21(DE3) 1353 and 1431 grown in the presence of glucose and lactose after 48 h of incubation.
Figure 8:
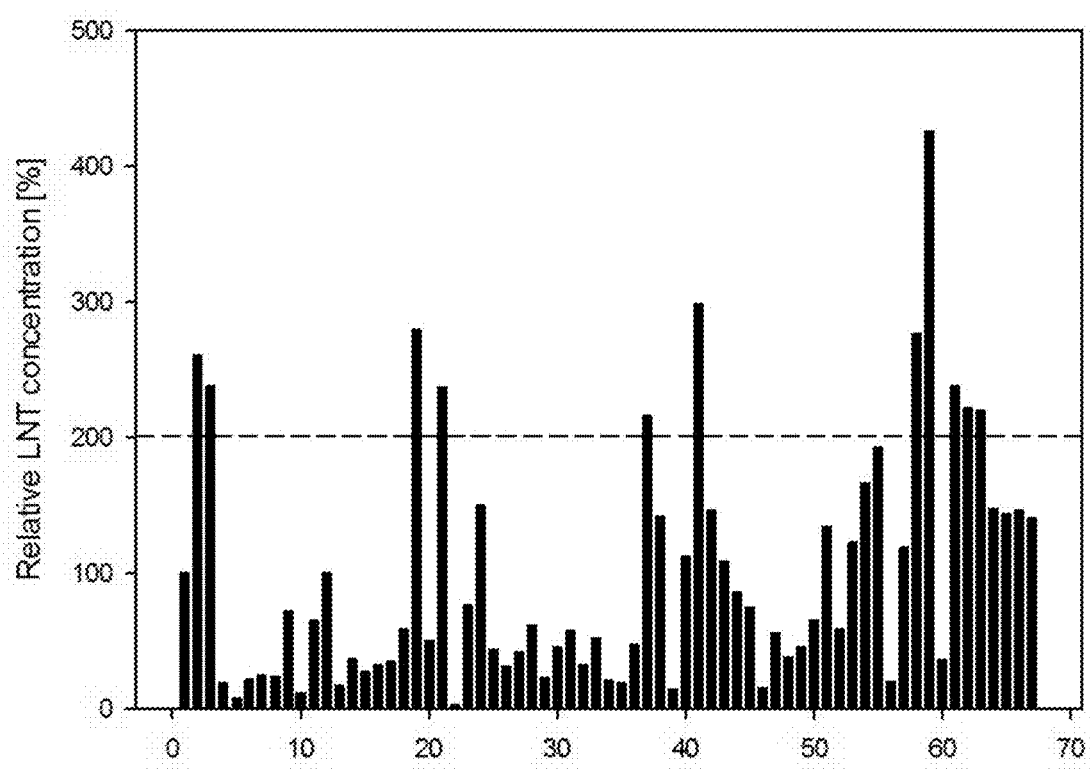
FIG. 8 shows a diagram depicting the relative concentration of lacto-N-tetraose in the supernatant of *E. coli* BL21 (DE3) strains overexpressing sugar efflux transporters compared to the control strain 1353.
Figure 9:
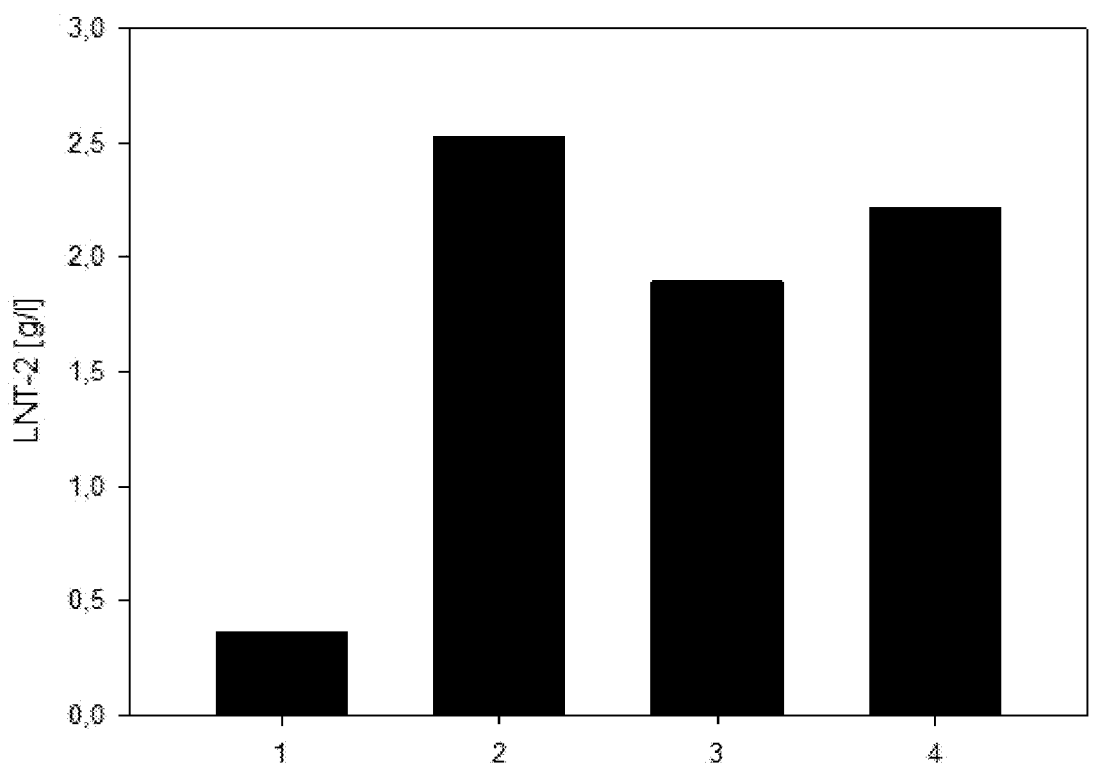
FIG. 9 shows a diagram depicting concentrations of lacto-N-triose II in the supernatant of *E. coli* BL21 (DE3) strains overexpressing the sugar efflux transport-ers TP11 (2), YjhB (3) or TP70 (4).

The invention will be described in more detail in the examples and the attached figures, in which FIG. 1 shows a schematic illustration for the production of either lacto-N-triose II or lacto-N-tetraose in a host cell cultivated in a medium;

FIG. 2 shows the results of the TLC analysis of culture extracts of lacto-N-triose II (LNT II) producing *E. coli* BL21(DE3) strains overexpressing the β-1,3-N-acetyl glucosaminyltransferase gene PmnagT(13, 14);

FIG. 3 shows the results of the TLC analysis of culture extracts of lacto-N-tetraose (LNT) producing *E. coli* BL21 (DE3) strains overexpressing the β-1,4-galactosyltransferase encoding genes BfgalT2 (1), PmgalT7 (3), MsgalT8 (6), gatD (7), lex1 (9), lgtB (11) or IsgD (13);

FIG. 4 shows the results of the TLC analysis of culture extracts of lacto-N-tetraose (LNT) producing *E. coli* BL21 (DE3) strains overexpressing the β-1,4-galactosyltransferase encoding genes KdgalT10 (1), cpsI14J (7), cpsIaJ (8, 9), HpgalT (12);

FIG. 5 shows the results of the TLC analysis of culture extracts of lacto-N-tetraose producing *E. coli* BL21(DE3) strains overexpressing the β-1,4-galactosyltransferase encoding gene waaX (5);

FIG. 6 shows the results of the TLC analysis of culture extracts of lacto-N-tetraose producing *E. coli* BL21(DE3) strains overexpressing the β-1,3-galactosyltransferase encoding genes wbdO or furA;

FIG. 7 shows the results of HPLC analyses of the culture supernatant of lacto-N-tetraose producing *E. coli* BL21 (DE3) strain. (A) Supernatant of *E. coli* BL21(DE3) 1353 and 1431 grown in the presence of glucose and lactose after 24 h of incubation. (B) Supernatant of *E. coli* BL21(DE3) 1353 and 1431 grown in the presence of glucose and lactose after 48 h of incubation;

FIG. 8 shows a diagram depicting the relative concentration of lacto-N-tetraose in the supernatant of *E. coli* BL21 (DE3) strains overexpressing sugar efflux transporters compared to the control strain 1353; and FIG. 9 shows a diagram depicting concentrations of lacto-N-triose II in the supernatant of *E. coli* BL21 (DE3) strains overexpressing the sugar efflux transporters TP11 (2), YjhB (3) or TP70 (4).

EXAMPLES

FIG. 1 shows a schematic drawing of an exemplary host cell 10 according to the invention, importing lactose and synthesizing lacto-N-triose II (LNT II) and lacto-N-tetraose (LNT). Lactose is imported from the medium the host cell is cultivated in into the cell via transporter 1. The enzyme N-acetylglucosaminyltransferase NacGlcT ligates N-acetylglucosamine to the acceptor substrate lactose, thus generating LNT-II. LNT-II is exported from the cell via exporter protein 20. Since LNT-II is a precursor of LNT or LNnT, the exporter exporting LNT-II represents an exporter protein exporting precursors of the latter oligosaccharides. As can further be seen from FIG. 1, the cell comprises a protein having β-1,3-galactosyltransferase activity enabling the galactosylation of LNT-II to intracellularly generate LNT; the cell may also and/or alternatively comprise or β-1,4-galactosyltransferase activity enabling the galactosylation of LNT-II to intracellularly generate lacto-N-neotetraose LNnt. LNT—or as the case may be LNnt—is then exported, via a oligosaccharide exporter from the cell into the culture medium the cell is cultivated in.

The exporters are membrane-bound, and their expression can be either overexpressed, which—in case of overexpression of the LNT-II exporter leads to an increased LNT-II export and to a decreased LNT export, whereas when the LNT-II exporting exporter protein is deleted or otherwise inactivated, this leads to an improved LNT-export. The LNT-II exporter preferably is an endogenous exporter protein, whereas the LNT-exporter protein preferably is a heterologous exporter protein.

Example 1

Development of an *E. coli* Lacto-N-Triose II Production Strain

*Escherichia coli* BL21(DE3) was used to construct a lacto-N-triose II (LNT-2) producing strain. Metabolic engineering included mutagenesis and deletions of specific genes, respectively, and genomic integrations of heterologous genes. The genes lacZ and araA were inactivated by mutagenesis using mismatch-oligonucleotides as described by Ellis et al., "High efficiency mutagenesis, repair, and engineering of chromosomal DNA using single-stranded oligonucleotides", Proc. Natl. Acad. Sci. USA 98: 6742-6746 (2001).

Genomic deletions were performed according to the method of Datsenko and Warner (Proc. Natl. Acad. Sci. USA 97:6640-6645 (2000)). To prevent intracellular degradation of N-acetylglucosamine, genes encoding N-acetylglucosamine-6-phosphate deacetylase (nagA) and glucosamine-6-phosphate deaminase (nagB) were deleted from the genome of the *E. coli* strain BL21 (DE3) strain. Also genes wzxC-wcaJ were deleted. WcaJ encodes an UDP-glucose:undecaprenyl phosphate glucose-1-phosphate transferase catalysing the first step in colanic acid synthesis (Stevenson et al., J. Bacteriol. 1996, 178:4885-4893). In addition the genes fucI and fucK, coding for L-fucose isomerase and L-fuculose kinase, respectively, were removed.

Genomic integration of heterologous genes was performed by transposition. Either the EZ-Tn5™ transposase (Epicentre, USA) was used to integrate linear DNA-fragments or the hyperactive C9-mutant of the mariner transposase Himar1 (Lampe et al., Proc. Natl. Acad. Sci. 1999, USA 96:11428-11433) was employed for transposition. To produce EZ-Tn5 transposomes the gene of interest together with a FRT-site flanked antibiotic resistance marker was amplified with primer 1119 and 1120 (all primer used are listed in table 3 below); the resulting PCR-product carried on both sites the 19-bp Mosaic End recognition sites for the EZ-Tn5 transposase. For integration using Himar1 transposase expression constructs (operons) of interest were similarly cloned together with a FRT-site flanked antibiotic resistance marker into the pEcomar vector. The pEcomar vector encodes the hyperactive C9-mutant of the mariner transposase Himar1 under the control of the arabinose inducible promoter $P_{araB}$. The expression fragment <$P_{tet}$-lacY-FRT-aadA-FRT> (SeqID1) was integrated by using the EZ-Tn5 transposase. After successful integration of the gene for the lactose importer LacY from *E. coli* K12 TG1 (acc. no. ABN72583) the resistance gene was eliminated from streptomycin resistant clones by the FLP recombinase encoded on plasmid pCP20 (Datsenko and Warner, Proc. Natl. Acad. Sci. 2000, USA 97:6640-6645). The N-acetylglucosaminyltransferase gene lgtA from *Neisseria meningitidis* MC58 (acc. no. NP_274923) was codon-optimized for expression in *E. coli* and prepared synthetically by gene synthesis. Together with the gene galT, encoding a galactose-1-phosphate uridylyltransferase from *E. coli* K-12 substr. MG1655 (acc. no. NP_415279) that was similarly obtained by gene synthesis, lgtA was inserted by transposition (SeqID2) using plasmid pEcomar-lgtA-galT. To enhance de novo synthesis of UDP-N-acetylglucosamine, genes encoding L-glutamine: D-fuctose-6-phosphate aminotransferase (glmS), phosphoglucosamine mutase from *E. coli* K-12 substr. MG1655 (glmM) and N-acetylglucosamine-1-phosphate uridyltransferase/glucosamine-1-phosphate acetyltransferase (glmU) from *E. coli* K-12 substr. MG1655 (acc. no. NP_418185, NP_417643, NP_418186, respectively) were codon-optimized and obtained by gene synthesis. The operon glmUM was cloned under the control of constitutive tetracyclin promoter $P_{tet}$ while glmS was cloned under the constitutive $P_{T5}$ promoter. The transposon cassette <$P_{tet}$-glmUM-$P_{T5}$-glmS-FRT-dhfr-FRT> (SeqID3), flanked by the inverted terminal repeats specifically recognized by the mariner-like element Himar1 transposase was inserted from pEcomar-glmUM-glmS revealing a lacto-N-triose II production strain. Additionally, the expression fragment <$P_{tet}$-lacY(6HIS)-FRT-aadA-FRT> (SeqID4) was integrated by using the EZ-Tn5 transposase.

The gal-operon (galETKM) was amplified from *E. coli* K12 TG1 (SeqID6) using primer 605 and 606 and inserted into the galM ybhJ locus of *E. coli* BL21 (DE3) strain by homologous recombination facilitated by using the red recombinase helper plasmid pKD46 (Datsenko and Warner, Proc. Natl. Acad. Sci. 2000, USA 97:6640-6645). Sequences of the heterologous genes and gene clusters are deposit in appendix 1.

Example 2

Batch Fermentation of *E. coli* BL21 (DE3) 707 Screening Various β-1,3-N-Acetyl-Glycosaminyltransferases The gene for the β-1,3-N-acetyl-glucosaminyltransferase PmnagT from *Pasteurella multocida* subsp. *multocida* str. HN06 (acc. no. PMCN06_0022) was codon-optimized and synthetically synthesized by GenScript Cooperation (Piscataway, USA). Cloning of the gene occurred by sequence and ligation-independent cloning into the plasmid pET-DUET (Merck KGaA, Darmstadt, Germany). All primer used for cloning are listed in table 3 below.

*E. coli* BL21(DE3) 707 (table 2 below) harbouring plamid pET-PmnagT coding for a β-1,3-N-acetyl glucosaminyl-transferase was grown at 30° C. in mineral salts medium (Samain et al., J. Biotech. 1999, 72:33-47) supplemented with 2% (wt/vol) glucose and ampicillin 100 μg ml$^{-1}$. When the cultures reached an OD660 nm of 0.1, gene expression was induced by addition of 0.3 mM IPTG. After four hours of incubation 1.5 mM lactose was added. After an additional incubation for 24 hours at 30° C. in shaking flasks cells were harvested. LNT-2 was detected by thin layer chromatography. Therefore, cells were mechanically disrupted in a defined volume using glass beads. Subsequently, samples were applied on TLC Silica Gel 60 $F_{254}$ (Merck KGaA, Darmstadt, Germany). The mobile phase was composed of acetone:butanol:acetic acid:water (35:35:7:23).

The result of the TLC analysis is shown in FIG. 2. The formation of a compound showing the same migration rate as the trisaccharide standard LNT-II could be observed when the gene PmnagT was overexpressed. The LNT-II production strain 724 served as a control (19). Standards for lactose (1) and LNT-II (2) are depicted. LNT-II product formation in the samples is marked by asterisks.

Example 3

Generation of an *E. coli* Lacto-N-Triose II Production Strain Overexpressing a Homologous Sugar Efflux Transporter The export of oligosaccharides produced in *E. coli* was proven to be a limiting factor during the fermentation process. However, trisaccharides like 2'-fucosyllactose and LNT-2 are translocated into the culture supernatant to some extent, thus probably encoding a working sugar efflux transporter. In order to improve the efflux of lacto-N-triose II (LNT-II; GluNAc(β1-3)Gal(β1-4)Glc), the *E. coli* BL21 (DE3) strain 1326 (table 2 below) was used for the screening of a library of sugar efflux transporters (SET). Putative SET proteins from *E. coli* were amplified from genomic DNA of *E. coli* BL21 (DE3) and integrated into vector pINT by sequence and ligation-independent cloning. Using the example of the gene yjhB, the primer 2567, 2568, 2526 and 2443 were used, generating the plasmid pINT-yjhB. The primer sequences used for cloning are listed in table 3 below.

*E. coli* BL21(DE3) 1326 harbouring plamids encoding for 20 different *E. coli* transporters were grown at 30° C. in mineral salts medium (Samain et al., J. Biotech. 1999, 72:33-47) supplemented with 2% (wt/vol) glucose, ampicillin 100 μg ml$^{-1}$ and zeocin 40 μg ml$^{-1}$. When the cultures reached an OD660 nm of 0.1, gene expression of the genes was induced by addition of 200 ng/ml anhydrotetracycline. After four hours of incubation 2.5 mM lactose was added. After an additional incubation for 24 and 48 hours at 30° C. in shaking flasks the LNT-II concentration in the supernatant was determined by LC-MS.

Mass analysis was performed by characteristic fragment ion detection using an LC Triple-Quadrupole MS detection system. Precursor ions are selected and analyzed in quadrupole 1, fragmentation takes place in the collision cell using nitrogen as CID gas, selection of fragment ions is performed in quadrupole 3.

Lacto-N-tetraose (LNT (Gal(β1-3)GlcNAc(β1-3)Gal(β1-4)Glc)), LNT-II and Maltotriose (internal standard for quantification) were analyzed in ESI positive ionization mode. LNT forms an ion of m/z 708.3 [M+H$^+$], LNT-II an ion of m/z 546.1 [M+H$^+$] and Maltotriose an ion of m/z 522.0 [M+NH$_4^-$]. Adduct formation of this carbohydrate [m/z 504.0] takes place with an ammonium ion (NH4$^+$), resulting in mass shift of +18. Thus for Maltotriose a precursor ion of m/z 522.0 was selected. The precursor ion was further fragmented in the collision cell into the characteristic fragment ions m/z 487.1, m/z 325.0 and m/z 163.2. The molecular ion of LNT (m/z 708.3) was fragmented into m/z 546.3, m/z 528.3, m/z 366.2 and m/z 204.0. LNT-II (m/z 546.1) was fragmented into m/z 204.2, 186.0, 138.0 and 126.0 (see method description).

Chromatographic separation of LNT and LNT-II was performed on a Luna NH$_2$ HPLC column (Phenomenex, Aschaffenburg, Germany). This was necessary due to partial fragmentation of LNT during ionization resulting in LNT-II signals affecting quantification results of the individual carbohydrates.

Only for the strain expressing the gene yjhB, an increased amount of LNT-2 in the culture supernatant was observed (see table 1 below).

TABLE 1

Calculated concentrations of LNT-II in the culture supernatant of an *E. coli* BL21 (DE3) strain overexpressing yjhB and the reference strain.

| Sample | Calc. conc. after 24 h of incubation [μM] | Calc. conc. after 48 h of incubation [μM] | Analyte RT |
|---|---|---|---|
| 1326 | 751 | 1265 | 0.616 |
| 1326 pINT-yjhB | 413 | 1975 | 0.609 |

Example 4

Batch Fermentations of *E. coli* BL21(DE3) 724 Screening Various β-1,4-Galactosyltransferases The genes for the β-1,4-galactosyltransferases lex1 from *Aggregatibacter aphrophilus* NJ8700 (acc. no. YP_003008647), PmgalT7 from *Pasteurella multocida* subsp. *multocida* str. HN06 (acc. No. PMCN06_0021), MsgalT8 from *Myxococcus stipitatus* DSM14675 (acc. no. MYSTI_04346), KdgalT10 from *Kingella denitrificans* ATCC 33394 (acc. no. HMPREF9098_2407), gatD from *Pasteurella multocida* M1404 (acc. no. GQ444331), BfgalT2 from *Bacterioidis fragilis* NCTC9343 (acc. no. BF9343_0585), IsgD from *Haemophilus influenza* (acc. no. AAA24981) and HpgalT from *Helicobacter pylori* (acc. no. AB035971) were codon-optimized and synthetically synthesized by GenScript Cooperation (Piscataway, USA). Cloning of the genes occurred by sequence and ligation-independent cloning (Li and Elledge, Nat Methods. 2007 March; 4(3):251-6.). Therefore, the plasmid pINT, harbouring the malE gene under control of an anhydrotetracyline-inducible promoter, was used, enabling the generation of a N-terminal fusion of the β-1,4-galactosyltransferase genes with malE. Solely, the β-1,4-galactosyltransferase encoding gene waaX from *Pectobacterium atrosepticum* JG10-08 (acc. no. ECA0154) was cloned into plasmid pACYC-Duet (Merck KGaA, Darmstadt, Germany). All primer used for cloning are listed in table 3 below.

*E. coli* BL21(DE3) 724 (table 2 below) harbouring plamid pCDF-galE and a plasmid coding for the gene fusion of malE with a β-1,4-galactosyltransferase was grown at 30° C. in mineral salts medium (Samain et al., J. Biotech. 1999, 72:33-47) supplemented with 2% (wt/vol) glucose, ampicillin 100 μg ml$^{-1}$ and zeocin 40 μg ml$^{-1}$. When the cultures reached an OD660 nm of 0.1, gene expression of the galE gene and the β-1,4-galactosyltransferase was induced by addition of 0.3 mM IPTG and 200 ng/ml anhydrotetracycline. *E. coli* BL21(DE3) 534 (table 2 below) harbouring plamids pET-lgtA, pCOLA-glmUM-glmS, pCDF-galT-galE and pACYC-waaX was grown at 30° C. in mineral salts medium supplemented with 2% (wt/vol) glucose, ampicillin 100 μg ml$^{-1}$, chloramphenicol 34 μg ml$^{-1}$, streptomycin 50 μg ml$^{-1}$ and kanamycin 30 μg ml$^{-1}$. When the cultures reached an OD660 nm of 0.1, gene expression was induced by addition of 0.3 mM IPTG. Four hours after induction of gene expression 2 mM lactose were added. After an additional incubation for 48 hours at 30° C. in shaking flasks, cells were harvested and mechanically disrupted. Lacto-N-neotetraose (LNnT (Gal(β1-4)GlcNAc(β1-3)Gal(β1-4)Glc)) was detected by thin layer chromatography. Therefore, cells were mechanically disrupted using glass beads. Subsequently, samples were applied on TLC Silica Gel 60 F$_{254}$ (Merck KGaA, Darmstadt, Germany). The mobile phase was composed of acetone:butanol:acetic acid:water (35:35:7:23).

The results of the TLC analyses are shown in FIGS. 3-5. FIG. 3 shows the TLC analysis of culture extracts of lacto-N-tetraose (LNT) producing *E. coli* BL21(DE3) strains overexpressing the β-1,4-galactosyltransferase encoding genes BfgalT2 (1), PmgalT7 (3), MsgalT8 (6), gatD (7), lex1 (9), lgtB (11) or IsgD (13). Standards for lactose (15), LNT-II (16) and LNnT (17) are depicted. LNnT product formation in the samples is marked by asterisks.

FIG. 4 shows the TLC analysis of culture extracts of lacto-N-tetraose (LNT) producing *E. coli* BL21(DE3) strains overexpressing the β-1,4-galactosyltransferase encoding genes KdgalT10 (1), cpsI14J (7), cpsIaJ (8, 9), HpgalT (12). Standards for lactose (3, 15), LNT-II (4, 16) and LNnT (5, 17) are depicted. LNnT product formation in the samples is marked by asterisks.

FIG. 5 shows the TLC analysis of culture extracts of lacto-N-tetraose producing *E. coli* BL21(DE3) strains overexpressing the β-1,4-galactosyltransferase encoding gene waaX (5). Standards for lactose (1), LNT-II and LNnT (2) are depicted. Again, LNnT product formation in the samples is marked by asterisks.

The formation of a compound showing the same migration rate as the tetrasaccharide standard LNnT could be observed when the following genes were overexpressed: lex1, PmgalT7, MsgalT8, BfgalT2, gatD, IsgD, KdgalT10, HpgalT, wax.

The β-1,4-galactosyltransferases cpsIaJ and cpsI14J, known from literature to produce LNnT (Watanabe et al., J Biochem. 2002 February; 131(2):183-91; Kolkman et J Bacteriol. 1996 July; 178(13):3736-41), were also included in the activity screening and served as positive control. Using the described expression system, the formation of LNnT could be observed by CpsIaJ and CpsI14J (FIG. 3). In total, 11 out of 30 tested genes were observed to produce LNnT from LNT-II and UDP-galactose.

Example 5

Batch Fermentations of *E. coli* BL21(DE3) 534 Screening Different β-1,3-Galactosyltransferases Using genomic DNA of *E. coli* K12 DH5a as template, galE was amplified using primer 1163 and 1162. The PCR product was purified, restricted with restriction endonucleases NdeI and XhoI and ligated into the second multiple cloning site of vector pCDFDuet (Merck KGaA, Darmstadt, Germany), which was cut with the same enzymes. GalE is expressed from the IPTG inducible T7 promoter. The *E. coli* K12 gene galT was amplified from genomic DNA and integrated into plasmid pCDF-galE by sequence and ligation-independent cloning using primer 991-994, producing the plasmid pCDF-galT-galE.

Using the codon-optimized gene of lgtA as template, amplification occurred using primer 688 and 689. The PCR product was purified, restricted with restriction endonucleases NdeI and AatII and ligated into the multiple cloning site of vector pETDuet (Merck KGaA, Darmstadt, Germany), which was cut with the same enzymes, producing the plasmid pET-lgtA.

Cloning of the codon-optimized gene construct of glmUM occurred by sequence and ligation-independent cloning into the plasmid pCOLA-Duet (Merck KGaA, Darmstadt, Germany) using primer 848-851. The codon-optimized form of glmS was amplified using primer 852 and 853. The PCR product was purified, restricted with restriction endonucleases NdeI and AatII and ligated into the second multiple cloning site of vector pCOLA-glmUM, which was cut with the same enzymes, producing the plasmid pCOLA-glmUM-glmS.

The genes for the β-1,3-galactosyltransferases wbdO from *Salmonella enterica* subsp. *salamae* serovar Greenside (acc. no. AY730594) and furA from *Lutiella nitroferrum* 2002 (FuraDRAFT_0419) were also codon-optimized and synthetically synthesized by GenScript Cooperation (Piscataway, USA). Cloning of the genes occurred by sequence and ligation-independent cloning into the plasmid pACYC-Duet (Merck KGaA, Darmstadt, Germany). All primer used for cloning are listed in table 3 below.

*E. coli* BL21(DE3) 534 harbouring plasmids pET-lgtA, pCOLA-glmUM-glmS, pCDF-galT-galE and a plasmid coding for a β-1,3-galactosyltransferase pACYC-furA or pACYC-wbdO was grown at 30° C. in mineral salts medium (Samain et al., J. Biotech. 1999, 72:33-47) supplemented with 2% (w/v) glucose, ampicillin 100 µg ml$^{-1}$, chloramphenicol 34 µg ml$^{-1}$, streptomycin 50 µg ml$^{-1}$ and kanamycin 30 µg ml$^{-1}$. When the cultures reached an OD660 nm of 0.1, gene expression was induced by addition of 0.3 mM IPTG. After four hours of incubation 2 mM lactose was added. After an additional incubation for 48 hours at 30° C. in shaking flasks, cells were harvested. LNT was detected by thin layer chromatography. Therefore, cells were mechanically disrupted using glass beads. Subsequently, samples were applied on TLC Silica Gel 60 F$_{254}$ (Merck KGaA, Darmstadt, Germany). The mobile phase was composed of acetone:butanol:acetic acid:water (35:35:7:23).

The results of the TLC analyses are shown in FIG. 6, showing TLC analysis of culture extracts of lacto-N-tetraose producing *E. coli* BL21(DE3) strains overexpressing the β-1,3-galactosyltransferase encoding genes wbdO or furA. LNT product formation in the samples is marked. Out of 12 tested putative β-1,3-galactosyltransferases, the formation of a compound showing the same migration rate as the tetrasaccharide standard LNT could only be observed when genes wbdO and furA were overexpressed.

Example 6

Development of an Improved Plasmid-Free *E. coli* Lacto-N-Tetraose Production Strain

*Escherichia coli* BL21(DE3) strain 724 was used to construct a lacto-N-tetraose (LNT) producing strain. Metabolic engineering included the genomic integration of the transposon cassettes <P$_{tet}$-wbdO-P$_{T5}$-galE-FRT-cat-FRT> (SeqID5), flanked by the inverted terminal repeats specifically recognized by the mariner-like element Himar1 transposase, which was inserted from pEcomar-wbdO-galE. The resulting strain 1353 was further metabolically engineered to exhibit an increased intracellular LNT-II pool resulting in the elevated production of LNT. Therefore, the mayor facilitator superfamily transporter yjhB (acc. no. YP_003001824) was deleted from the genome of the *E. coli* strain, generating strain 1431 (table 2 below).

Batch fermentation of the *E. coli* BL21(DE3) strains 1353 and 1431 was conducted for 48 hours at 30° C. in mineral salts medium (Samain et al., J. Biotech. 1999, 72:33-47) containing 2% (wt/vol) glucose as sole carbon and energy source. When the cultures reached an OD660 nm of 0.5, 2.5 mM lactose was added. The presence of LNT-II and LNT in the culture supernatant was detected by high performance liquid chromatography (HPLC).

Analysis by HPLC was performed using a refractive index detector (RID-10A) (Shimadzu, Duisburg, Germany) and a ReproSil Carbohydrate, 5 µm (250 mm×4.6 mm) (Dr. Maisch GmbH, Germany) connected to an HPLC system (Shimadzu, Duisburg, Germany). Elution was performed isocratically with acetonitril:H$_2$O (68/32 (v/v)) as eluent at 35° C. and a flow rate of 1.4 ml/min. 40 µl of the sample were applied to the column. Samples were filtered (0.22 µm pore size) and cleared by solid phase extraction on an ion exchange matrix (Strata ABW, Phenomenex, Aschaffenburg, Germany).

The results of the HPLC analyses are shown in FIG. 7, showing HPLC analyses of the culture supernatant of lacto-N-tetraose producing *E. coli* BL21 (DE3) strain. (A) Supernatant of *E. coli* BL21(DE3) 1353 (black graph) and 1431 (pink graph) grown in the presence of glucose and lactose after 24 h of incubation. (B) Supernatant of *E. coli* BL21 (DE3) 1353 (blue graph) and 1431 (brown graph) grown in the presence of glucose and lactose after 48 h of incubation. As can be seen from the HPLC analyses, the deletion of yjhB in a LNT producing strain resulted in an elevated accumulation of LNT in the culture supernatant.

Example 7

Generation of an *E. coli* Lacto-N-Tetraose Production Strain Overexpressing a Sugar Efflux Transporter Since an export of lacto-N-tetraose into the medium is only moderate for production strains, a screening of a sugar efflux transporter library was conducted. In accordance to example 3 putative SET proteins were either amplified from *E. coli* genomic DNA or were codon-optimized and synthetically synthesized by GenScript Cooperation (Piscataway, USA). Following amplification genes were integrated into vector pINT by sequence and ligation-independent cloning. The primer design for the cloning of *E. coli* genes was in accordance to example 3. Synthetic genes were synthesized with standardized nucleotide overhangs and likewise integrated into the expression vector using the primer 2527, 2444, 2526 and 2443. The primer sequences used for cloning are listed in table 3 below.

*E. coli* BL21(DE3) 1353 (table 2 below) harbouring plasmids encoding for 66 different transporters were grown at 30° C. in mineral salts medium (Samain et al., J. Biotech. 1999, 72:33-47) supplemented with 3% (w/v) glucose, 5 g l$^{-1}$ NH$_4$Cl$_2$, ampicillin 100 µg ml$^{-1}$ and kanamycin 15 µg ml$^{-1}$. Precultivation appeared in 96-well plates harbouring a total volume of 200 µl. After 24 h of incubation at 30° C. by continuous shaking, 50 µl per well was transferred into 96-well deep well plates harbouring a total volume of 400 µl mineral salts medium additionally supplemented with 200 ng ml$^{-1}$ anhydrotetracycline and 10 mM lactose. After a sustained incubation for 24 to 48 hours the LNT concentrations in the supernatant were determined by LC-MS. Mass analysis was performed as described in example 3.

FIG. 8 shows the relative concentration of lacto-N-tetraose in the supernatant of *E. coli* BL21 (DE3) strains overexpressing sugar efflux transporters compared to the control strain 1353. The LNT titer of strain 1353 was set to 100%. As shown in FIG. 8, the overexpression of 11 out of 66 genes resulted in a doubled LNT production. Among these, also a protein encoded in the genome of *E. coli* BL21 (DE3) proved to enhance the LNT export (TP37, yebQ, acc. no. NC_012971). YebQ is a predicted MFS transporter, putatively involved in multi drug efflux, which might represent a responsible transporter protein that realizes the observed basal efflux of LNT during fermentation of strain 1353.

Furthermore, the exporters encoded by the genes spoVB of *Bacillus amyloliquefaciens* (TP1, acc. no. AFJ60154), yabM of *Erwinia pyrifoliae* (TP2, acc. no. CAY73138), bcr of *E. coli* MG1655 (TP18, acc. no. AAC75243), ydeA of *E. coli* MG1655 (TP20, acc. no. AAC74601), proP2 of *Haemophilus parainfluenzae* (TP54, acc. no. EGC72107), setA of *Pectobacterium carotovorum* (TP55, acc. no. ZP_03829909), fucP of *E. coli* MG1655 (TP59, acc. no. AIZ90162), mdeA of *Staphylococcus aureus* Bmb9393 (TP61, acc. no. SABB_01261), lmrA of *Lactococcus lactis* (TP62, acc. no. L116532), setA of *Pseudomonas* sp. MT-1 (TP72, acc. no. BAP78849) and setA of *Beauveria bassiana* D1-5 (TP73, acc. no. KGQ13398) resulted in an increased LNT production when overexpressed in the *E. coli* production strain 1353.

Example 8

Generation of an *E. coli* Lacto-N-Triose II Production Strain by Overexpression of Heterologous Sugar Efflux Transporters The LNT exporter screening described in example 6 interestingly disclosed two proteins—TP11 from *Mannheimia succiniciproducens* MBEL55E (proP, acc. no. AAU37785) and TP70 from *Cedecea neteri* M006 (setA, acc. no. WP_039290253) —whose overexpression resulted in a significantly increased production of LNT-II and consequently in a decreased LNT production (data not shown). This observation was confirmed in an experimental setup as described in example 3. The overexpression of the sugar efflux transporter YjhB served as a positive control. The overexpression of TP11 as well as TP70 resulted in an approximately 4-fold increase in LNT-II production which was even slightly more than for YjhB: FIG. 9 shows a diagram displaying the concentrations of lacto-N-triose II in the supernatant of *E. coli* BL21 (DE3) strains overexpressing the sugar efflux transporters TP11 (2), YjhB (3) or TP70 (4). Strain 1326 harbouring an empty control plasmid served as a control (1). Thus, 3 sugar efflux transporters were identified which target LNT-II for export and whose overexpression might be useful to engineer a LNT-II production strain.

TABLE 2

Strains and plasmids

| Strain | Genotype | Ref. |
|---|---|---|
| *E. coli* BL21(DE3) | F– ompT hsdSB(rB–, mB–) gal dcm (DE3) | Merck KGaA, Darmstadt, Germany |
| *E. coli* BL21(DE3) 534 | *E. coli* BL21(DE3) ΔlacZ Δara ΔwcaJ ΔfuclK ΔnagAB harbouring genomic integrations of: galETKM, lacy | This study |
| *E. coli* BL21(DE3) 724 | *E. coli* BL21(DE3) ΔlacZ Δara ΔwcaJ ΔfuclK ΔnagAB harbouring genomic integrations of: galETKM, lacY, lgtA-galT-kanR, glmUM-glmS-dhfr | This study |
| *E. coli* BL21(DE3) 1326 | *E. coli* BL21(DE3) ΔlacZ Δara ΔwcaJ ΔfuclK ΔnagAB harbouring genomic integrations of: galETKM, lacY, lgtA-galT-kanR, glmUM-glmS-dhfr, lacy(6HIS)-aadA | This study |
| *E. coli* BL21(DE3) 707 | *E. coli* BL21(DE3) ΔlacZ Δara ΔwcaJ ΔfuclK ΔnagAB harbouring genomic integrations of: galETKM, lacY, glmUM-glmS-dhfr | This study |
| *E. coli* BL21(DE3) 1353 | *E. coli* BL21(DE3) ΔlacZ Δara ΔwcaJ ΔfuclK ΔnagAB harbouring genomic integrations of: galETKM, lacY, lgtA-galT-kanR, glmUM-glmS-dhfr, wbdO-galE-cat | This study |
| *E. coli* BL21(DE3) 1431 | *E. coli* BL21(DE3) ΔlacZ Δara ΔwcaJ ΔfuclK ΔnagAB harbouring genomic integrations of: galETKM, lacY, lgtA-galT-kanR, glmUM-glmS-dhfr, wbdO-galE-cat, ΔyjhB-aacC1 | This study |
| pCDF-galE | galE of *E. coli* K12 integrated into vector pCDFDuet | EP 14 162 869.3 |
| pET-lgtA (SeqID7) | lgtA of *Neisseria meningitidis* integrated into vector pETDuet | This study |
| pCDF-galT-galE (SeqID8) | galT and galE of *Escherichia coli* K12 integrated into vector pCDFDuet | This study |
| pCOLA-glmUM-glmS (SeqID9) | glmU, glmM and glmS of *Escherichia coli* K12 integrated into vector pCOLADuet | This study |
| pINT-malE-lex1 | Gene fusion of malE with lex-1 of *Aggregatibacter aphrophilus* NJ8700 integrated into vector pINT | EP 14 162 869.3 |
| pINT-malE-PmgalT7 (SeqID10) | Gene fusion of PmgalT7 of *Pasteurella multocida* subsp. *multocida* str. HN06 integrated into vector pINT | This study |
| pINT-malE-MsgalT8 (SeqID11) | Gene fusion of MsgalT8 of *Myxococcus stipitatus* DSM14675 integrated into vector pINT | This study |
| pINT-malE-KdgalT10 (SeqID12) | Gene fusion of KdgalT10 of *Kingella denitrificans* ATCC 33394 integrated into vector pINT | This study |
| pINT-malE-gatD (SeqID13) | Gene fusion of gatD of *Pasteurella multocida* M1404 integrated into vector pINT | This study |
| pINT-malE-BFgalT2 (SeqID14) | Gene fusion of BfgalT2 of *Bacterioidis fragilis* NCTC9343 integrated into vector pINT | This study |
| pINT-malE-lsgD (SeqID15) | Gene fusion of lsgD of *Haemophilus influenza* integrated into vector pINT | This study |
| pINT-malE-HPgalT (SeqID16) | Gene fusion of HpgalT of *Helicobacter pylori* integrated into vector pINT | This study |
| pACYC-waaX (SeqID17) | waaX of *Pectobacterium atrosepticum* JG10-08 integrated into vector pACYCDuet | This study |

TABLE 2-continued

Strains and plasmids

| Strain | Genotype | Ref. |
|---|---|---|
| pACYC-wbdO (SeqID18) | wbdO of *Salmonella enterica* subsp. *salamae* serovar Greenside integrated into vector pACYCDuet | This study |
| pACYC-furA (SeqID19) | furA of *Lutiella nitroferrum* 2002 integrated into vector pACYCDuet | This study |
| pET-PmnagT (SeqID20) | PmnagT of *Pasteurella multocida* subsp. *multocida* str. HN06 integrated into vector pETDuet | This study |
| pINT-yjhB (SeqID21) | yjhB of *E. coli* BL21 DE3 integrated into vector pINT | This study |
| pINT-yebQ (SeqID22) | yebQ of *E. coli* BL21 DE3 integrated into vector pINT | This study |
| pINT-proP (SeqID23) | proP of *Mannheimia succiniciproducens* MBEL55E integrated into vector pINT | This study |
| pINT-Cn-setA (SeqID24) | setA of *Cedecea neteri* M006 integrated into vector pINT | This study |
| pINT-spoVB (SeqID25) | spoVB of *Bacillus amyloliquefaciens* integrated into vector pINT | This study |
| pINT-yabM (SeqID26) | yabM of *Erwinia pyrifoliae* integrated into vector pINT | This study |
| pINT-ydeA (SeqID27) | ydeA of *E. coli* MG1655 integrated into vector pINT | This study |
| pINT-proP2 (SeqID28) | proP2 of *Haemophilus parainfluenzae* integrated into vector pINT | This study |
| pINT-Pc-setA (SeqID29) | setA of *Pectobacterium carotovorum* integrated into vector pINT | This study |
| pINT-fucP (SeqID30) | fucP of *Escherichia coli* BL21 (DE3) integrated into vector pINT | This study |
| pINT-mdeA (SeqID31) | mdeA of *Staphylococcus aureus* Bmb9393 integrated into vector pINT | This study |
| pINT-lmrA (SeqID32) | lmrA of *Lactococcus lactis* integrated into vector pINT | This study |
| pINT-Ps-setA (SeqID33) | setA of *Pseudomonas* sp. MT-1 integrated into vector pINT | This study |
| pINT-Bb-setA (SeqID34) | setA of *Beauveria bassiana* D1-5 integrated into vector pINT | This study |

TABLE 3

Oligonucleotides used for PCR

| Primer | Sequence 5'-3' |
|---|---|
| 605 KI gal fwd | TTACTCAGCAATAAACTGATATTCCGTCAGGCTGG (SeqID35) |
| 606 KI gal rev | TTGTAATCTCGCGCTCTTCACATCAGACTTTCCATATAGAGCGTAATTTC CGTTAACGTCGGTAGTGCTGACCTTGCCGGAGG (SeqID36) |
| 1119 ME-for | CTGTCTCTTATCACATCTCCTGAAATGGCCAGATGTAATTCCTAATTTTT GTTG (SeqID37) |
| 1120 ME rev | CTGTCTCTTATCACATCTCACATTACATCTGAGCGATTGTTAGG (SeqID38) |
| 1163 galE_NdeI-for | GATCACATATGAGAGTTCTGGTTACCGGTG (SeqID39) |
| 1164 galE_XhoI-rev | GATCACTCGAGTCATTAATCGGGATATCCCTGTGGATGGC (SeqID40) |
| 5176 lex1 pINT-f | GTCGATGAAGCCCTGAAAGACGCGCAGACTATGCACTTCATTGAAAAC AAAAACTTCGTC (SeqID41) |
| 5177 lex1 pINT-r | GATGGCCTTTTTGCGTGTCGACGCGGCCGCCTAGATAAACAGGATGAT ATTTTTGCCTIG (SeqID42) |
| 5178 pINT lex1-f | CAAGGCAAAAATATCATCCTGTTTATCTAGGCGGCCGCGTCGACACGC AAAAAGGCCATC (SeqID43) |
| 5179 pINT lex1-r | GACGAAGTTTTTGTTTTCAATGAAGTGCATAGTCTGCGCGTCTTTCAGG GCTTCATCGAC (SeqID44) |
| 5192 waaX pINT for | GTCGATGAAGCCCTGAAAGACGCGCAGACTATGATTGATAACCTGATTA AGCGTACCCCG (SeqID45) |

TABLE 3-continued

Oligonucleotides used for PCR

| Primer | Sequence 5'-3' |
|---|---|
| 5193 waaX pINT rev | ATGGCCTTTTTGCGTGTCGACGCGGCCGCTTAATTCGAGCGGGTAAAG ATCTTCATCAGG (SeqID46) |
| 5194 pINT waaX for | CTGATGAAGATCTTTACCCGCTCGAATTAAGCGGCCGCGTCGACACGC AAAAAGGCCATC (SeqID47) |
| 5195 pINT waaX rev | CGGGGTACGCTTAATCAGGTTATCAATCATAGTCTGCGCGTCTTTCAGG GCTTCATCGAC (SeqID48) |
| 5164 PmgalT7 pINT for | GTCGATGAAGCCCTGAAAGACGCGCAGACTATGAGCGGTGAACACTAT GTCATTAGCCTG (SeqID49) |
| 5165 PmgalT7 pINT rev | GATGGCCTTTTTGCGTGTCGACGCGGCCGCTCATTTAAATTCGATGATC ATCTTGTCGTT (SeqID50) |
| 5166 pINT PmgalT7 for | AACGACAAGATGATCATCGAATTTAAATGAGCGGCCGCGTCGACACGC AAAAAGGCCATC (SeqID51) |
| 5167 pINT PmgalT7 rev | CAGGCTAATGACATAGTGTTCACCGCTCATAGTCTGCGCGTCTTTCAGG GCTTCATCGAC (SeqID52) |
| 5168 MsgalT8 pINT for | GTCGATGAAGCCCTGAAAGACGCGCAGACTATGGATGAAATCAAACTG TCGGTGGTTATG (SeqID53) |
| 5169 MsgalT8 pINT rev | GATGGCCTTTTTGCGTGTCGACGCGGCCGCTCATTGGCGACGCCAATC GAACGCAACGCG (SeqID54) |
| 5170 pINT MsgalT8 for | CGCGTTGCGTTCGATTGGCGTCGCCAATGAGCGGCCGCGTCGACACG CAAAAAGGCCATC (SeqID55) |
| 5171 pINT MsgalT8 rev | CATAACCACCGACAGTTTGATTTCATCCATAGTCTGCGCGTCTTTCAGG GCTTCATCGAC (SeqID56) |
| 5561 KdgalT10 pINT for | GTCGATGAAGCCCTGAAAGACGCGCAGACTATGGAAAACTATGTCGTC TCTATCCGCACC (SeqID57) |
| 5562 KdgalT10 pINT-rev | GATGGCCTTTTTGCGTGTCGACGCGGCCGCTCATTTGAACGGAACAAT CTTTTTGTCATC (SeqID58) |
| 5563 pINT-KdgalT10 for | GATGACAAAAAGATTGTTCCGTTCAAATGAGCGGCCGCGTCGACACGC AAAAAGGCCATC (SeqID59) |
| 5564 pINT-KdgalT10 rev | GGTGCGGATAGAGACGACATAGTTTTCCATAGTCTGCGCGTCTTTCAG GCTTCATCGAC (SeqID60) |
| 5172 gatD pINT for | GTCGATGAAGCCCTGAAAGACGCGCAGACTATGTCCTCAGCTTTCCATT ACGTCATTAGC (SeqID61) |
| 5173 gatD pINT rev | GATGGCCTTTTTGCGTGTCGACGCGGCCGCTCATTCAAATTCGATAATC ATGGTGATTTT (SeqID62) |
| 5174 pINT gatD for | AAAATCACCATGATTATCGAATTTGAATGAGCGGCCGCGTCGACACGCA AAAAGGCCATC (SeqID63) |
| 5175 pINT gatD rev | GCTAATGACGTAATGGAAAGCTGAGGACATAGTCTGCGCGTCTTTCAG GCTTCATCGAC (SeqID64) |
| 5160 BfglaT2 pINT for | GTCGATGAAGCCCTGAAAGACGCGCAGACTATGAACGTGAATAAGCCG ACCACCGAAAAG (SeqID65) |
| 5161 BfgalT2 pINT rev | GATGGCCTTTTTGCGTGTCGACGCGGCCGCTCAGTATTCTTCAATTTTG TCCAGTTGATA (SeqID66) |
| 5162 pINT BfgalT2 for | TATCAACTGGACAAAATTGAAGAATACTGAGCGGCCGCGTCGACACGC AAAAAGGCCATC (SeqID67) |
| 5163 pINT BfgalT2 rev | CTTTTCGGTGGTCGGCTTATTCACGTTCATAGTCTGCGCGTCTTTCAGG GCTTCATCGAC (SeqID68) |
| 5746 | GTGATCAACGCCGCCAGCGGTCGTCAGACTGTCGATGAAGCCCTGAAA GACGCGCAGACT (SeqID69) |
| 5747 | GCGGCCGCGTCGACACGCAAAAAGGCCATCCATCCGTCAGGATGGCC TTCTGCTTAATTT (SeqID70) |

TABLE 3-continued

Oligonucleotides used for PCR

| Primer | Sequence 5'-3' |
|---|---|
| 5748 | AAATTAAGCAGAAGGCCATCCTGACGGATGGCCTTTTTGCGTGT CGACGCGGCCGC (SeqID71) |
| 5749 | AGTCTGCGCGTCTTTCAGGGCTTCATCGACAGTCTGACGACCGCTGGC GGCGTTGATCAC (SeqID72) |
| 1886 SLIC wbdO pACYC for | GTTTAACTTTAATAAGGAGATATACCATGCTGACGGAAGTGCGCCCGGT CTCTACGACGAAACCGC (SeqID73) |
| 1887 SLIC wbdO pACYC rev | CGACCTGCAGGCGCGCCGAGCTCGAATTCATTTGATGTATTTGCAATA GAACACAGAAAAGACCGT (SeqID74) |
| 1888 SLIC pACYC wbdo rev | GTGTTCTATTGCAAATACATCAAATGAATTCGAGCTCGGCGCGCCTGCA GGTCGACAAGCTTGCGG (SeqID75) |
| 1889 SLIC pACYC Wbd0 For | GAGACCGGGCGCACTTCCGTCAGCATGGTATATCTCCTTATTAAAGTTA AACAAAATTATTTCTACAGG (SeqID76) |
| 1890 SLIC pACYC furA rev | GTATGGTGACCCTGTGGCGCAAATGAGAATTCGAGCTCGGCGCGCCTG CAGGTCGACAAGCT (SeqID77) |
| 1891 SLIC pACYC furA for | GCGCTGCCCTGTTTGATTTTATCCATGGTATATCTCCTTATTAAAGTTAA ACAAAATTATTTCT (SeqID78) |
| 1892 SLIC furA pACYC rev | CCTGCAGGCGCGCCGAGCTCGAATTCTCATTTGCGCCACAGGGTCACC ATACGTGCCGGCAGG (SeqID79) |
| 1893 SLIC furA pACYC for | GITTAACTTTAATAAGGAGATATACCATGGATAAAATCAAACAGGGCAG CGCCTCTCTGGTTGTCG (SeqID80) |
| 3055 SLIC PmnagT pET rev | CAGACTCGAGGGTACCGACGTCCTAATAAGTAGATGAATATTTATCAGG ACGAAGAT (SeqID81) |
| 3056 SLIC pET PmnagT for | AACTAAAGGTTTATTTTCCATATGTATATCTCCTTCTTATACTTAACTAAT ATAC (SeqID82) |
| 3057 SLIC pET PmnagT rev | TAAATATTCATCTACTTATTAGGACGTCGGTACCCTCGAGTCTGGTAAA GAAACCGCTGCTGCG (SeqID83) |
| 3058 SLIC PmnagT pET for | GTATAAGAAGGAGATATACATATGGAAAATAAACCTTTAGTTTCAGTTTT GATTTGTGC (SeqID84) |
| 2567_SLIC_yjhB-for | TAACTTTAAGAAGGAGATATACAAGAGCTCGAGTCGAAGGAGATAGAAC CATGGCAACAGCATGGTATAAACAAG (SeqID85) |
| 2568_SLIC_yjhB-rev | GCGTGTCGACGCGTTTAGAGGCCCCAAGGGGTTATGCTAGTATCGATT TATCATTTAGCCACGGATAGTTTATAAATTTTAC (SeqID86) |
| 2526_SLIC_pINT_TP-rev | GGTTCTATCTCCTTCGACTCGAGCTCTTGTATATCTCCTTCTTAAAGTTA AACAAAATTATTTCTAGATTTTGTCGAAC (SeqID87) |
| 2443_SLIC_pINT_TP-forw | TAAATCGATACTAGCATAACCCCTTGGGGCCTCTAAACGCGTCGACAC GCAAAAAGGCCATCC (SeqID88) |
| 2527_SLIC_TP_pINT-forw | GTTCGACAAAAATCTAGAAATAATTTTGTTTAACTTTAAGAAGGAGATAT ACAAGAGCTCGAGTCGAAGGAGATAGAACC (SeqID89) |
| 2444_SLIC_TP_pINT-rev | GGATGGCCTTTTTGCGTGTCGACGCGTTTAGAGGCCCCAAGGGGTTAT GCTAGTATCGATTTA (SeqID90) |
| 688 IgtA AatII rev | ATATGACGTCTCATTAGCGGTTTTTCAGGAGACG (SeqID91) |
| 689 IgtA NdeI for | ATATCATATGCCGTCCGAAGCATTCCGTCGTCACC (SeqID92) |
| 991 galT-pCDF for | TAACTTTAATAAGGAGATATACCATGACGCAATTTAATCCCGTTGATCAT CCACATCGCCGC (SeqID93) |
| 992 pCDF-galT for | ATTTTCGCGAATCCGGAGTGTAAAAGCTTGCGGCCGCATAATGCTTAAG TCGAACAGAAAGTAATCG (SeqID94) |
| 993 galT-pCDF rev | AAGCATTATGCGGCCGCAAGCTTTTACACTCCGGATTCGCGAAAATGG ATATCGCTGACTGCGCGCAAACGC (SeqID95) |
| 994 pCDF-galT rev | TCAACGGGATTAAATTGCGTCATGGTATATCTCCTTATTAAAGTTAAACA AAATTATTTCTACAGGGG (SeqID96) |

TABLE 3-continued

Oligonucleotides used for PCR

| Primer | Sequence 5'-3' |
|---|---|
| 848 glmM pCOLA SLIC rev | ATGGTGATGGCTGCTGCCCATTTAAACCGCTTTGACTGCGTCGGCAATA CGGTGCGC (SeqID97) |
| 849 glmU pCOLA SLIC for | GTTTAACTTTAATAAGGAGATATACCATGCTGAACAACGCGATGTCTGTT GTTATCCTGG (SeqID98) |
| 850 pCOLA glmM SLIC rev | CGCAGTCAAAGCGGTTTAAATGGGCAGCAGCCATCACCATCATCACCA CAGCC (SeqID99) |
| 851 pCOLA glmU SLIC for | TCGCGTTGTTCAGCATGGTATATCTCCTTATTAAAGTTAAACAAAATTAT TTCTACAGG (SeqID100) |
| 852 glmSco pCOLA for NdeI | ATATATCATATGTGCGGTATCGTTGGTGCTATCGC (SeqID101) |
| 853 glmSco pCOLA rev AatII | ATATATGACGTCTTATTCCACGGTCACGGATTTCGC (SeqID102) |

The invention claimed is:

1. A method for production of an oligosaccharide comprising a lacto-N-triose II (LNT-II; GlcNAc(β1-3)Gal(β1-4)Gluc) as a core trisaccharide by a genetically modified microbial host cell, comprising
providing a genetically modified microbial host cell that comprises:
at least one recombinant glycosyltransferase;
increased expression or activity of at least one endogenous sugar export protein capable of exporting the oligosaccharide; and
decreased expression or inactivation of at least one export protein that exports precursors of the oligosaccharide from the host cell;
cultivating the host cell in a medium under conditions permissive for the production of the oligosaccharide, whereby the oligosaccharide is exported into the medium at an increased level compared to the unmodified host cell, and
obtaining the oligosaccharide from the medium.

2. The method of claim 1, wherein the oligosaccharide comprising a lacto-N-triose II (LNT-II; GlcNAc(β1-3)Gal (β1-4)Gluc) as a core trisaccharide is selected from the group consisting of: lacto-N-triose II, lacto-N-tetraose, lacto-N-neotetraose, lacto-N-fucopentaose I, lacto-N-fucopentaose II, lacto-N-fucopentaose III, lacto-N-fucopentaose V, lacto-N-difucosylheaxose I, lacto-N-difucosylhexaose II, lacto-N-sialylpentaose LSTa, LSTb, LSTc, disialyllacto-N-tetraose, and disialyllacto-N-neotetraose.

3. The method of claim 1, wherein the host cell comprises:
overexpression of at least one endogenous nucleic acid sequence coding for the sugar export protein capable of exporting the oligosaccharide into the culture medium; and
deletion, disruption, diminishment or inactivation of at least one endogenous nucleic acid sequence coding for an export protein that exports precursors of the oligosaccharide outside the host cell; and
overexpression of at least one homologous or heterologous sequence coding for a protein mediating import of a precursor of the oligosaccharide into said host cell, wherein the precursor is larger than a disaccharide.

4. The method of claim 3, wherein said sugar export protein capable of exporting the oligosaccharide belongs to the class of secondary active transporters.

5. The method of claim 3, wherein said at least one nucleic acid sequence coding for the sugar export protein capable of exporting the oligosaccharide is a gene selected from the group consisting of yebQ and yjhB from *Escherichia coli*, proP from *Mannheimia succiniciproducens* and setA from *Cedecea neteri*.

6. The method of claim 1, wherein said recombinant glycosyltransferase is selected from the group consisting of at least one of a galactosyltransferase, a sialyltransferase, an N-acetylglucosaminyltransferase and a fucosyltransferase, and is optionally selected from at least one of the following: β-1,3-N-acetylglucosaminyltransferase, β-1,3-galactosyltransferase, β-1,4-galactosyltransferase, β-1,6-galactosyltransferase, α-2,3-sialyltransferase, α-2,6-sialyltansferase, α-1,2-fucosyltransferase, and α-1,3-fucosyltransferase.

7. The method of claim 1, wherein the host cell comprises (i) a β-1,3-N-acetylglucosaminyltransferase, and (ii) a β-1,3-galactosyltransferase or a β-1,4-galactosyltransferase as the glycosyltransferase.

8. The method of claim 6, wherein said β-1,3-N-acetylglucosaminyltransferase belongs to the class of lgtA of *Neisseria meningitides* or PmnagT of *Pasteurella multocida*.

9. The method of claim 7, wherein the lacto-N-tetraose generating β-1,3-galactosyltransferase is WbdO.

10. The method of claim 1, wherein the genetically modified microbial host cell comprises an increased UDP-N-acetylglucosamine and UDP-galactose or GDP-fucose or CMP-N-acetylneuraminic acid production capability as compared to a genetically unmodified host cell, wherein optionally said increased UDP-N-acetylglucosamine and UDP-galactose production capability is by the overexpression of one or more genes encoding a protein selected from the group consisting of L-glutamine: D-fructose-6-phosphate aminotransferase, N-acetyl glucosamine-1-phosphate uridyltransferase/glucosamine-1-phosphate acetyl transferase, phosphoglucosamine mutase, UDP-galactose-4-epimerase, phosphoglucomutase, and glucose-1-phosphate uridylyltransferase.

11. The method according to claim 1, wherein said genetically modified microbial host cell is cultivated in the presence of glucose, sucrose, glycerol or a combination thereof.

12. The method according to claim 11, wherein the microbial host cell is cultured in the absence of N-acetyl-glucosamine and galactose.

* * * * *